(12) United States Patent
de los Rios et al.

(10) Patent No.: US 9,017,695 B2
(45) Date of Patent: Apr. 28, 2015

(54) CHIMERIC THERAPEUTICS, COMPOSITIONS, AND METHODS FOR USING SAME

(75) Inventors: Miguel de los Rios, Del Mar, CA (US); Stephanie de los Rios, Del Mar, CA (US)

(73) Assignee: Biomed Realty, L.P., San Diego, CA (US)

( * ) Notice: Subject to any disclaimer, the term of this patent is extended or adjusted under 35 U.S.C. 154(b) by 0 days.

(21) Appl. No.: 13/272,828

(22) Filed: Oct. 13, 2011

(65) Prior Publication Data

US 2012/0121713 A1    May 17, 2012

Related U.S. Application Data

(63) Continuation of application No. PCT/US2010/031023, filed on Apr. 14, 2010.

(60) Provisional application No. 61/169,124, filed on Apr. 14, 2009.

(51) Int. Cl.
| | |
|---|---|
| A61K 39/29 | (2006.01) |
| C12N 15/00 | (2006.01) |
| C07H 21/04 | (2006.01) |
| C12P 21/06 | (2006.01) |

(52) U.S. Cl.
CPC .................................. *A61K 39/292* (2013.01)

(58) Field of Classification Search
USPC ........................................................ 424/490
See application file for complete search history.

(56) References Cited

U.S. PATENT DOCUMENTS

| | | | |
|---|---|---|---|
| 5,133,961 | A | 7/1992 | Ellis et al. |
| 5,420,026 | A | 5/1995 | Payne |
| 5,439,686 | A | 8/1995 | Desai et al. |
| 5,498,421 | A | 3/1996 | Grinstaff et al. |
| 5,620,689 | A | 4/1997 | Allen et al. |
| 5,670,630 | A | 9/1997 | Thill |
| 5,714,316 | A | 2/1998 | Weiner et al. |
| 5,858,726 | A | 1/1999 | Payne |
| 5,863,541 | A | 1/1999 | Samulski et al. |
| 5,980,901 | A | 11/1999 | Shih et al. |
| 6,046,173 | A | 4/2000 | Forstova et al. |
| 6,063,370 | A | 5/2000 | Dadey |
| 6,096,331 | A | 8/2000 | Desai et al. |
| 6,204,059 | B1 | 3/2001 | Samulski et al. |
| 6,231,864 | B1 | 5/2001 | Birkett |
| 6,287,857 | B1 | 9/2001 | O'Riordan et al. |
| 6,387,662 | B1 | 5/2002 | Liang et al. |
| 6,420,160 | B1 | 7/2002 | Bloch |
| 6,506,405 | B1 | 1/2003 | Desai et al. |
| 6,506,559 | B1 | 1/2003 | Fire et al. |
| 6,537,579 | B1 | 3/2003 | Desai et al. |
| 6,573,009 | B1 | 6/2003 | Noda et al. |
| 6,593,308 | B2 | 7/2003 | Szoka, Jr. |
| 6,602,706 | B1 | 8/2003 | Fallaux et al. |
| 6,602,932 | B2 | 8/2003 | Feldheim et al. |
| 6,616,944 | B2 | 9/2003 | Kissel et al. |
| 6,620,617 | B2 | 9/2003 | Mathiowitz et al. |
| 6,627,202 | B2 | 9/2003 | Murray et al. |
| 6,696,038 | B1 | 2/2004 | Mahato et al. |
| 6,710,173 | B1 | 3/2004 | Binley et al. |
| 6,749,868 | B1 | 6/2004 | Desai et al. |
| 6,753,006 | B1 | 6/2004 | Desai et al. |
| 6,984,386 | B2 | 1/2006 | Douglas et al. |
| 7,056,704 | B2 | 6/2006 | Tuschl et al. |
| 7,078,194 | B2 | 7/2006 | Withers et al. |
| 7,101,995 | B2 | 9/2006 | Lewis et al. |
| 7,148,342 | B2 | 12/2006 | Tolentino et al. |
| 7,148,343 | B2 | 12/2006 | Bair, Jr. et al. |
| 7,282,199 | B2 | 10/2007 | Gao et al. |
| 7,332,321 | B2 | 2/2008 | Belcher et al. |
| 7,332,337 | B2 | 2/2008 | van Es et al. |
| 7,344,872 | B2 | 3/2008 | Gao et al. |
| 7,365,978 | B2 | 4/2008 | Chen et al. |
| 7,422,902 | B1 | 9/2008 | Wheeler et al. |
| 7,964,196 | B2 | 6/2011 | de los Rios et al. |
| 8,067,011 | B2 | 11/2011 | Davis et al. |
| 2003/0153081 | A1 | 8/2003 | Tagawa et al. |
| 2004/0005338 | A1 | 1/2004 | Bachmann et al. |
| 2004/0247660 | A1 | 12/2004 | Singh |
| 2005/0004002 | A1 | 1/2005 | Desai et al. |
| 2005/0089526 | A1 | 4/2005 | Moore et al. |

(Continued)

FOREIGN PATENT DOCUMENTS

| | | |
|---|---|---|
| EP | 0863987 A2 | 9/1998 |
| EP | 0920514 B1 | 6/1999 |

(Continued)

OTHER PUBLICATIONS

Boisgerault, et al., "Virus-like particles: a new family of delivery systems." Expert Rev. Vaccines 1(1):101-109, 2002.

Bottcher, et al., "Determination of the fold of the core protein of hepatitis B virus by electron cryomicroscopy." Nature 386:88-91, 1997.

Brumfield, "Heterologous expression of the modified coat protein of Cowpea chlorotic mottle bromovirus results in the assembly of protein cages with altered architecture and function." J. Gen. Virol. 85:1049-1053, 2004.

Crommelin, et al., "Nanotechnological approaches for the delivery of macromolecules." J Controlled Release 87:81-88, 2003.

Crowther, et al., "Three-dimensional structure of hepatitis B virus core particles determined by electron cryomicroscopy." Cell 77:943-50, 1994.

de Kruif, et al., "Biosynthetically lipid-modified human scFv fragments from phage display libraries as targeting molecules for immunoliposomes" FEBS Lett, 399(3):232-336, 1996.

(Continued)

*Primary Examiner* — Zachariah Lucas
*Assistant Examiner* — Barry A Chestnut
(74) *Attorney, Agent, or Firm* — Goodwin Procter LLP

(57) ABSTRACT

Chimeric therapeutics are disclosed that include a modified viral core protein comprising at least one mutation or modification in an immunogenic epitope and a therapeutic agent. The therapeutic agent may be associated with the modified viral core protein and may be a nucleic acid, a protein, or a small molecule. Also disclosed are particles and compositions that include the disclosed chimeric therapeutics.

8 Claims, 31 Drawing Sheets

(56) References Cited

U.S. PATENT DOCUMENTS

| | | |
|---|---|---|
| 2006/0292118 A1 | 12/2006 | Kuroda et al. |
| 2006/0292174 A1 | 12/2006 | de los Rios et al. |
| 2007/0248573 A1 | 10/2007 | Sturino |
| 2007/0249554 A1 | 10/2007 | Tuszynski |
| 2007/0258889 A1 | 11/2007 | Douglas et al. |
| 2007/0269370 A1 | 11/2007 | Davis et al. |
| 2007/0280962 A1 | 12/2007 | Murray |
| 2008/0050343 A1 | 2/2008 | Wilson et al. |
| 2008/0050345 A1 | 2/2008 | Wilson et al. |
| 2008/0069802 A1 | 3/2008 | Davis et al. |
| 2008/0075737 A1 | 3/2008 | Gao et al. |
| 2008/0075740 A1 | 3/2008 | Gao et al. |
| 2008/0090281 A1 | 4/2008 | Wilson et al. |
| 2008/0125385 A1 | 5/2008 | Hajjar et al. |
| 2008/0131928 A1 | 6/2008 | Handa et al. |
| 2009/0226525 A1 | 9/2009 | de los Rios et al. |
| 2011/0293725 A1 | 12/2011 | de los Rios et al. |
| 2011/0293726 A1 | 12/2011 | de los Rios et al. |
| 2011/0293727 A1 | 12/2011 | de los Rios et al. |
| 2011/0293733 A1 | 12/2011 | de los Rios et al. |
| 2012/0315335 A1 | 12/2012 | de los Rios et al. |
| 2013/0156818 A1 | 6/2013 | de los Rios et al. |
| 2014/0010885 A1 | 1/2014 | de los Rios et al. |

FOREIGN PATENT DOCUMENTS

| | | |
|---|---|---|
| EP | 1204761 B1 | 5/2002 |
| EP | 1219705 A1 | 7/2002 |
| EP | 1447079 A1 | 8/2004 |
| EP | 1563834 A1 | 8/2005 |
| EP | 1845163 A2 | 10/2007 |
| EP | 1849799 A1 | 10/2007 |
| EP | 1944043 A1 | 7/2008 |
| WO | WO-95/32706 A1 | 12/1995 |
| WO | WO-99/40214 A2 | 8/1999 |
| WO | WO-00/09158 A1 | 2/2000 |
| WO | WO-01/02551 A1 | 1/2001 |
| WO | WO-01/12235 A2 | 2/2001 |
| WO | WO-02/44204 A2 | 6/2002 |
| WO | WO-03/096990 | 11/2003 |
| WO | WO-2004/047812 A1 | 6/2004 |
| WO | WO-2006/033679 A2 | 3/2006 |
| WO | WO2006033679 * | 3/2006 |
| WO | WO-2006/066048 A2 | 6/2006 |
| WO | WO-2007/126764 A2 | 11/2007 |
| WO | WO-2007/136263 A1 | 11/2007 |
| WO | WO-2008/008881 A1 | 1/2008 |
| WO | WO-2008/010864 A2 | 1/2008 |
| WO | WO-2008/021908 A2 | 2/2008 |
| WO | WO-2008/024427 A2 | 2/2008 |
| WO | WO-2008/027084 A2 | 3/2008 |
| WO | WO-2008/037504 A1 | 4/2008 |
| WO | WO-2008/048288 A2 | 4/2008 |
| WO | WO-2008/051101 A1 | 5/2008 |
| WO | WO-2008/054826 A2 | 5/2008 |
| WO | WO-2008/124165 A2 | 10/2008 |
| WO | WO-2010/042749 A2 | 4/2010 |
| WO | WO-2010/042751 A2 | 4/2010 |
| WO | WO-2010/042755 A2 | 4/2010 |
| WO | WO-2010/120874 A2 | 10/2010 |

OTHER PUBLICATIONS

DeNardo, et al., "Efficacy and Toxicity of 67Cu-2IT-BAT-Lym-1 Radio-immunoconjugate in Mice Implanted with Human Burkitt's Lymphoma (Raji)," Clin. Cancer Res., 3:71-79, 1997.
Fasbender, et al., "Complexes of Adenovirus with Polycationic Polymers and Cationic Lipids Increase the Efficiency of Gene Transfer in Vitro and Vivo" J. Biol. Chem, 272(10):6479-6489, 1997.
Fernandez, et al., "Activated protein C Correlates Inversely with Thrombin Levels in Resting Healthy Individuals" Am. J. Hematol., 56:29-31, 1997.
Ganem and Schneider, "Hepadnaviridae: The Viruses and Their Replication," Chapter 35 of Fundamental Virology, 4th Ed., by David Knipe and Peter Howley, 2001, Published by Lippincott, Williams and Wilkins, Philadelphia, PA, pp. 1285, 1302, and 1303.
Haag, "Supramolecular drug-delivery systems based on polymeric core-shell architectures." Angew Chem. Int. Ed. 43:278-282, 2004.
Hashida, et al., "Fusion of HIV-1 Tat protein transduction domain to poly-lisine as a new DNA delivery tool" British J. of Cancer, 90(6):1252-1258, 2004.
International Preliminary Report on Patentability for PCT/US2010/31023, dated Oct. 18, 2011, (8 pages).
International Search Report for PCT/US2005/18456, dated Sep. 13, 2006, (4 pages).
International Search Report for PCT/US2008/04585, dated Mar. 17, 2009, (4 pages).
International Search Report for PCT/US2008/08938, dated Oct. 8, 2007, (4 pages).
International Search Report for PCT/US2010/31023, mailed Mar. 28, 2011, (7 pages).
Jenny, et al., "A critical review of the methods for cleavage of fusion proteins with thrombin and factor Xa." Prot. Express Purif. 31:1-11, 2003.
Kayser, et al., "Formulation and biopharmaceutical issues in the development of drug delivery systems for antiparasitic drugs." Parasitol Res. 90:S63-S70, 2003.
Lamprecht, et al., "Biodegradable nanoparticles for targeted drug delivery in treatment of inflammatory bowel disease." J. Pharmacol. Exp. Ther. 299:775-81, 2002.
Larsen, et al., "Lyumphoproliferative disorders: prospects for gene therapy" Pathology, 37(6):523-533, 2005.
Leng, et al., Nucleic Acids Research, 33(4): e40, pp. 1-9, 2005.
Liu, et al., "Nanostructured materials designed for cell binding and transduction." Biomacromolecules 2:362-368, 2001.
Lundstrom, et al., "Breakthrough in cancer therapy:encapsulation of drugs and viruses" Curr. Drug Disc. 19-23, 2002.
Maeda, "The enhanced permeability and retention (EPR) effect in tumor vasculature: the key role of tumor-selective macromolecular drug targeting." Adv. Enzyme Regul. 41:189-207, 2001.
Managit, et al., "Targeted and sustained drug delivery using PEGylated galatosylated liposomes." Int. J. Pharmaceutics 266:77-84, 2003.
Mansfield, et al., "recombinant RFB4 immunotoxins exhibit potent cytoxic activity for CD22-bearing cells and tumors". Blood, 90(5):2020-2026, 1997.
Martin, et al., "Immunospecific targeting of liposomes to cells: a novel and efficient method for covalent attachment of Fab' fragments via disulfide bonds." Biochemistry 20:4229-38, 1981.
Moghimi, et al., "Long-circulating and target-specific nanoparticles: theory to practice." Pharmacol Rev. 53:283-318, 2001.
Monsky, et al., "Augmentation of transvascular transport of macro-molecules and nanoparticles in tumors using vascular endothelial growth factor." Cancer Res. 59:4129-35, 1999.
Moreira, et al., "Use of the post-insertion technique to insert peptide ligands into pre-formed Stealth liposomes with retention of binding activity and cytotoxicity" Pharmaceutical Research 19(3):265-269, 2002.
Paddison, et al., "Stable Expression of Gene Suppression by RNAi in mammalian cells" PNAS, 99, (3):1443-1448, 2002.
Panyam, et al., "Biodegradable nanoparticles for drug and gene delivery to cells and tissue." Adv. Drug Del. Rev. 55:329-47, 2003.
Panyam, et al., "Fluorescence and electron microscopy probes for cellular and tissue uptake of poly(D,L-lactide-coglycolide) nanoparticles." Int. J. Pharm. 262:1-11, 2003.
Perales, et al., "An evaluation of receptor-mediated gene transfer using synthetic DNA-ligand complexes." European J. of Biochemistry, 226(2):255-266, 1994.
Roca, et al., "Social Implications of Nanoscience and Technology." National Science Foundation Report, 2001 (280 pages).
Rosenthal, et al., "Viral workhorses." Scientific American, pp. 1-4 ,2002.
Sahoo, et al., "Nanotech approaches to drug delivery and imaging." Drug Disc. Today 8:1112-1120, 2003.
Sahoo, et al., "Pegylated zinc protoporphyrin: a water-soluble heme oxygenase inhibitor with tumor targeting capacity." Bioconjugate Chem. 13:1031-1038, 2002.

(56) References Cited

OTHER PUBLICATIONS

Schmidt, et al., "Binding of external ligands onto an engineered virus capsid," Protein Eng. 14:769-774, 2001.
Schmidt, et al., "Protein and peptide delivery via engineered polyomavirus-like particles." FASEB J 15:1646-1648, 2001.
Scott, et al., "Chemical camouflage of antigenic determinants: stealth erythrocytes" Proc. Natl. Acad. Sci. U. S. A.94(14):7566-7571, (1997).
Sinha, et al., "Biodegradable microspheres for protein delivery." J. Controlled Rel. 90:261-280, 2003.
Stevens, "The cost and value of three-dimensional protein structure" Drug Disc. World 4, 4:35-48, 2003.
Wagner, et al., "Transferrin-polycation-DNA complexes: The effect of polycations on the structure of the complex and DNA delivery to cells" Proceedings of the National Academy of Science of USA, Nat'l Acad. of Sci.,88(10):4255-4259, 1991.
Wynne, et al., "The crystal structure of the human hepatitis B virus capsid." Molecular Cell 3:771-80, 1999.
Yamada, et al., "Nanoparticles for the Delivery of Genes and Drugs to Human Hepatocytes", Nature Biotechnology, 21(8):885-890, 2003.
Zhao, "Intracellular Cargo Delivery Using Tat Peptide and Derivatives," Medical Research Reviews 24(1):1-12, 2004.
Zlotnick, "Are weak protein-protein interactions the general rule in capsid assembly?" Virology, 315:269-274, 2003.
Zlotnick, et al., "Dimorphism of Hepatitis B Virus Capsids is Strongly Influenced by the C-Terminus of the Capsid Protein," Biochemistry, 35:7412-7421, 1996.
Zlotnick, et al., "Localization of the C Terminus of the Assembly Domain of Hepatitis B Virus Capsid Protein: Implications for Morphogenesis and Organization of Encapsidated RNA" Proc. Natl. Acad. Sci. USA, 94:9556-9561, 1997.
Ratner et al., "Biomaterials: Where We Have Been and Where We are Going," *Annu. Rev. Biomed. Eng.*, (2004), vol. 6, pp. 41-75.
Wingfield et al., "Hepatitis Core Antigen Produced in *Escherichia coli*: Subunit Composition, Conformational Analysis, and In Vitro Capsid Assembly," *Biochemistry* (1995), vol. 34, pp. 4919-4932.

* cited by examiner

SEQUENCE LISTING

```
<160> NUMBER OF SEQ ID NOS: 263

<210> SEQ ID NO 1
<211> LENGTH: 183
<212> TYPE: PRT
<213> ORGANISM: Hepatitis B virus

<400> SEQUENCE: 1

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 2
<211> LENGTH: 183
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80
```

```
Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 3
<211> LENGTH: 34
<212> TYPE: PRT
<213> ORGANISM: Hepatitis B virus

<400> SEQUENCE: 3

```
Arg Arg Arg Gly Arg Ser Pro Arg Arg Thr Pro Ser Pro Arg Arg
1               5                   10                  15

Arg Arg Ser Gln Ser Pro Arg Arg Arg Ser Gln Ser Arg Glu Ser
            20                  25                  30

Gln Cys
```

<210> SEQ ID NO 4
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (6)..(110)
<223> OTHER INFORMATION: This region may encompass 4 to 21 "Lys Lys Lys
      Lys Lys" repeating units
<220> FEATURE:
<221> NAME/KEY: misc_feature
<222> LOCATION: (113)..(122)
<223> OTHER INFORMATION: This region may encompass 0 to 10 "His"
      residues
<220> FEATURE:
<223> OTHER INFORMATION: see specification as filed for detailed
      description of substitutions and preferred embodiments

<400> SEQUENCE: 4

```
Lys Leu Ala Ala Ala Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
            35                  40                  45

Lys Lys Lys Lys Lys Lys Lys Lys Lys Lys Lys Lys Lys Lys Lys Lys
        50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys
                85                  90                  95
```

```
Lys Lys Lys Lys Lys Lys Lys Lys Lys Lys Lys Lys Lys Leu Glu
            100                 105                 110

His His His His His His His His
            115                 120

<210> SEQ ID NO 5
<211> LENGTH: 504
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg tgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtggac aagcttgcgg ccgcaaagaa gaaaaagaag     480
ctcgagcacc accaccacca ccac                                             504

<210> SEQ ID NO 6
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Leu Glu His His His His His His
                165
```

<210> SEQ ID NO 7
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg tgatccggcg      240 agccgcgatc tggttgtgaa ctatgtgaat accaacatgg gcctgaaaat tcgtcagctg     300
ctgtggtttc atatcagctg cctgaccttt ggcgcgaaa ccgtgctgga atatctggtg      360
agctttggcg tttggatccg taccccgccg gcgtatcgtc cgccgaatgc gccgattctg     420
agcaccctgc cggaaaccac cgttgtggac aagcttgcgg ccgcaaagaa gaagaaaaag     480
aagaagctcg agcaccacca ccaccaccac                                      510
```

<210> SEQ ID NO 8
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Leu Glu His His His His His His
                165                 170

<210> SEQ ID NO 9
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg tgatccggcg      240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtggac aagcttgcgg ccgcaaagaa aaagaagaag     480
aaaaagaaga agctcgagca ccaccaccac caccac                               516
```

<210> SEQ ID NO 10
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Asp Ile Asp Pro Tyr Lys Glu Phe Gly Ala Thr Val Glu Leu Leu
1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170
```

<210> SEQ ID NO 11
<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
atggatatcg atccgtataa agaatttggc gccaccgtgg aactgctgag ctttctgccg     60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg tgatccggcg    240
agccgcgatc tggttgtgaa ctatgtgaat accaacatgg gcctgaaaat tcgtcagctg    300
ctgtggtttc atatcagctg cctgaccttt ggcgcgaaa ccgtgctgga atatctggtg    360
agctttggcg tttggatccg taccccgccg gcgtatcgtc cgccgaatgc gccgattctg    420
agcaccctgc cggaaaccac cgttgtggac aagcttgcgg ccgcaaagaa aaagaagaag    480
aagaagaaga gaaactcga gcaccaccac caccaccac                           519
```

<210> SEQ ID NO 12
<211> LENGTH: 173
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Lys Leu Glu His His His His His His
                165                 170
```

<210> SEQ ID NO 13
<211> LENGTH: 522
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
atggatatcg atccgtataa agaatttggc gccaccgtgg aactgctgag ctttctgccg     60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
```

```
tgctggggtg aactgatgac cctggcgacc tgggttggca acaacctgtg tgatccggcg    240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtggac aagcttgcgg ccgcaaagaa gaagaaaaag    480
aagaagaaaa agaagaagct cgagcaccac caccaccacc ac                      522
```

<210> SEQ ID NO 14
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Lys Leu Glu His His His His His His
                165                 170
```

<210> SEQ ID NO 15
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg tgatccggcg    240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
```

```
agctttggcg tttggatccg taccccgccg gcgtatcgtc cgccgaatgc gccgattctg    420
agcaccctgc cggaaaccac cgttgtggac aagcttgcgg ccgcaaagaa aaagaagaag    480
aaaaagaaga gaaaaagaa gaagctcgag caccaccacc accaccac                  528
```

<210> SEQ ID NO 16
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Lys Lys Lys Leu Glu His His His His His
                165                 170                 175
```

<210> SEQ ID NO 17
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg tgatccggcg    240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtggac aagcttgcgg ccgcaaagaa aaagaagaag    480
aagaagaaga gaaaaagaa gaagaagaag aagaagaaga aaaagctcga gcaccaccac    540
``` caccaccac 549

<210> SEQ ID NO 18
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Lys Lys Lys Lys Lys Lys Lys Lys Lys Lys Lys Leu
                165                 170                 175

Glu His His His His His His
            180
```

<210> SEQ ID NO 19
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
tgctggggtg aactgatgac cctggcgacc tgggttggca acaacctgtg tgatccggcg   240
agccgcgatc tggttgtgaa ctatgtgaat accaacatgg gcctgaaaat cgtcagctg    300 ctgtggtttc atatcagctg cctgaccttt ggcgcgaaa ccgtgctgga atatctggtg    360
agctttggcg tttggatccg taccccgccg gcgtatcgtc cgccgaatgc gccgattctg   420
agcaccctgc cggaaaccac cgttgtggac aagcttgcgg ccgcaaaggc aaaggcaaag   480
gcgaaggcaa aggctaaggc gaaggctaag gcgaagctcg agcaccacca ccaccaccac   540
```

<210> SEQ ID NO 20
<211> LENGTH: 180
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Ala Lys Ala Lys
145                 150                 155                 160

Ala Lys Ala Lys Ala Lys Ala Lys Ala Lys Leu Glu His His
                165                 170                 175

His His His His
            180
```

<210> SEQ ID NO 21
<211> LENGTH: 540
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg tgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtggac aagcttgcgg ccgcaaaggg taagggcaag     480
ggtaagggca agggtaaggg caagggcaag ggtaagctcg agcaccacca ccaccaccac     540
```

<210> SEQ ID NO 22
<211> LENGTH: 180
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 22

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Lys Gly Lys Gly Lys
145                 150                 155                 160

Gly Lys Gly Lys Gly Lys Gly Lys Gly Lys Leu Glu His His
                165                 170                 175

His His His His
        180
```

<210> SEQ ID NO 23
<211> LENGTH: 528
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
tgctggggtg aactgatgac cctggcgacc tgggttggca caacctgtgt gatccggcg   240
agccgcgatc tggttgtgaa ctatgtgaat accaacatgg gcctgaaaat tcgtcagctg   300
ctgtggtttc atatcagctg cctgaccttt ggccgcgaaa ccgtgctgga atatctggtg   360
agctttggcg tttggatccg taccccgccg cgtatcgtc cgccgaatgc gccgattctg   420
agcaccctgc cggaaaccac cgttgtggac aagcttgcgg ccgcaaagaa aagaagagc   480
cagagcccga agaagaagaa gaaactcgag caccaccacc accaccac                528
```

<210> SEQ ID NO 24
<211> LENGTH: 176
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 24

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Lys Lys Lys Lys Lys Ser
145                 150                 155                 160

Gln Ser Pro Lys Lys Lys Lys Leu Glu His His His His His His
                165                 170                 175

<210> SEQ ID NO 25
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Leu Glu His His His His His His

<210> SEQ ID NO 26
<211> LENGTH: 170
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Leu Glu His His His His His His
                165                 170
```

<210> SEQ ID NO 27
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
```

```
                    115                 120                 125
Pro Pro Ala Tyr Arg Pro Pro Asn Ala Pro Ile Leu Ser Thr Leu Pro
        130                 135                 140

Glu Thr Thr Val Val Asp Lys Leu Ala Ala Lys Lys Lys Lys
145                 150                 155                 160

Lys Lys Lys Lys Leu Glu His His His His His His
                165                 170
```

<210> SEQ ID NO 28
<211> LENGTH: 173
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys
145                 150                 155                 160

Lys Lys Lys Lys Lys Leu Glu His His His His His
                165                 170
```

<210> SEQ ID NO 29
<211> LENGTH: 174
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
```

```
                65                  70                  75                  80
Ser Arg Glu Leu Val Val Ser Tyr Val Asn Val Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Ala Lys Lys Lys Lys Lys
145                 150                 155                 160

Lys Lys Lys Lys Lys Lys Leu Glu His His His His His
                165                 170

<210> SEQ ID NO 30
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
            50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Ala Lys Lys Lys Lys Lys
145                 150                 155                 160

Lys Lys Lys Lys Lys Lys Lys Leu Glu His His His His His His
                165                 170                 175

<210> SEQ ID NO 31
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
```

```
                20                  25                  30
Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Lys Lys Lys Lys Lys Lys
145                 150                 155                 160

Lys Lys Lys Lys Lys Lys Lys Lys Lys Lys Lys Lys Lys Lys Lys Leu
                165                 170                 175

Glu His His His His His
            180

<210> SEQ ID NO 32
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (6)..(29)
<223> OTHER INFORMATION: This region may encompass 5 to 12 "Ala Lys"
      repeating units
<220> FEATURE:
<221> NAME/KEY: misc_feature
<222> LOCATION: (32)..(41)
<223> OTHER INFORMATION: This region may encompass 0 to 10 "His"
<220> FEATURE:
<223> OTHER INFORMATION: see specification as filed for detailed
      description of substitutions and preferred embodiments

<400> SEQUENCE: 32

Asp Lys Leu Ala Ala Ala Lys Ala Lys Ala Lys Ala Lys Ala Lys Ala
1               5                   10                  15

Lys Ala Lys Ala Lys Ala Lys Ala Lys Ala Lys Ala Lys Leu Glu His
                20                  25                  30

His His His His His His His His
            35                  40

<210> SEQ ID NO 33
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
```

```
                    20                  25                  30
Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
            50                  55                  60

Leu Met Asn Leu Ala Thr Trp Val Gly Ser Asn Leu Glu Asp Pro Ala
 65                 70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Ala Lys Ala Lys Ala Lys
145                 150                 155                 160

Ala Lys Ala Lys Ala Lys Ala Lys Ala Lys Leu Glu His His
                165                 170                 175

His His His His
            180

<210> SEQ ID NO 34
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Asp Ile Asp Pro Tyr Lys Glu Phe Gly Ala Ser Val Glu Leu Leu
 1               5                  10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
            50                  55                  60

Leu Met Asn Leu Ala Thr Trp Val Gly Ser Asn Leu Glu Asp Pro Ala
 65                 70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Asp Lys Leu Ala Ala Ala Lys Gly Lys Gly Lys
145                 150                 155                 160

Gly Lys Gly Lys Gly Lys Gly Lys Gly Lys Leu Glu His His
                165                 170                 175

His His His His
            180
```

<210> SEQ ID NO 35
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Ser
145                 150                 155                 160

Gln Ser Pro Lys Lys Lys Lys Leu Glu His His His His His His
                165                 170                 175

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (7)..(27)
<223> OTHER INFORMATION: This region may encompass 4 to 21 "Arg"
      residues
<220> FEATURE:
<221> NAME/KEY: misc_feature
<222> LOCATION: (30)..(39)
<223> OTHER INFORMATION: This region may encompass 0 to 10 "His"
      residues
<220> FEATURE:
<223> OTHER INFORMATION: see specification as filed for detailed
      description of substitutions and preferred embodiments

<400> SEQUENCE: 36

Asp Lys Leu Ala Ala Ala Arg Arg Arg Arg Arg Arg Arg Arg Arg
1               5                   10                  15

Arg Arg Arg Arg Arg Arg Arg Arg Arg Arg Arg Leu Glu His His His
                20                  25                  30

His His His His His His
        35

<210> SEQ ID NO 37

<211> LENGTH: 504
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
tgctggggtg aactgatgac cctggcgacc tgggttggca acaacctgtg cgatccggcg   240
agccgcgatc tggttgtgaa ctatgtgaat accaacatgg gcctgaaaat cgtcagctg    300
ctgtggtttc atatcagctg cctgaccttt ggcgcgaaa ccgtgctgga atatctggtg   360
agctttggcg tttggatccg taccccgccg gcgtatcgtc cgccgaatgc gccgattctg   420
agcaccctgc cggaaaccac cgttgtcgac aagcttgcgg ccgcacgccg tcgccgtcgc   480
ctcgagcacc accaccacca ccac                                          504
```

<210> SEQ ID NO 38
<211> LENGTH: 168
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Arg Arg Arg Arg Arg
145                 150                 155                 160

Leu Glu His His His His His His
                165
```

<210> SEQ ID NO 39
<211> LENGTH: 510
<212> TYPE: DNA
<213> ORGANISM: Artificial Sequence
<220> FEATURE:
<223> OTHER INFORMATION: Description of Artificial Sequence: Synthetic polynucleotide -continued

```
<400> SEQUENCE: 39
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcacgccg tcgccgtcgc     480
cgtcgcctcg agcaccacca ccaccaccac                                     510

<210> SEQ ID NO 40
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Arg Arg Arg Arg Arg
145                 150                 155                 160

Arg Arg Leu Glu His His His His His His
                165                 170

<210> SEQ ID NO 41
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
```

```
gcgctggaaa gcccggaaca ttgtagcccg caccataccg ccctgcgtca ggcgattctg    180
tgctggggtg aactgatgac cctggcgacc tgggttggca acaacctgtg cgatccggcg    240
agccgcgatc tggttgtgaa ctatgtgaat accaacatgg gcctgaaaat tcgtcagctg    300
ctgtggtttc atatcagctg cctgaccttt ggccgcaaa ccgtgctgga atatctggtg     360
agctttggcg tttggatccg taccccgccg gcgtatcgtc cgccgaatgc gccgattctg    420
agcaccctgc cggaaaccac cgttgtcgac aagcttgcgg ccgcacgccg tcgccgtcgc    480
cgtcgccgtc gcctcgagca ccaccaccac caccac                              516
```

```
<210> SEQ ID NO 42
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Arg Arg Arg Arg Arg
145                 150                 155                 160

Arg Arg Arg Arg Leu Glu His His His His His His
                165                 170
```

```
<210> SEQ ID NO 43
<211> LENGTH: 522
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
```

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg cgatccggcg    240
agccgcgatc tggttgtgaa ctatgtgaat accaacatgg gcctgaaaat tcgtcagctg    300
```

```
ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtcgac aagcttgcgg ccgcacgccg tcgccgtcgc    480
cgtcgccgtc gccgtcgcct cgagcaccac caccaccacc ac                      522
```

<210> SEQ ID NO 44
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Arg Arg Arg Arg Arg
145                 150                 155                 160

Arg Arg Arg Arg Arg Arg Leu Glu His His His His His His
                165                 170
```

<210> SEQ ID NO 45
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg cgatccggcg    240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtcgac aagcttgcgg ccgcacgccg tcgccgtcgc    480
```
cgtcgccgtc gccgtcgccg tcgcctcgag caccaccacc accaccac 528

<210> SEQ ID NO 46
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Arg Arg Arg Arg Arg
145                 150                 155                 160

Arg Arg Arg Arg Arg Arg Arg Arg Leu Glu His His His His His His
                165                 170                 175
```

<210> SEQ ID NO 47
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
tgctggggtg aactgatgac cctggcgacc tgggttggca acaacctgtg cgatccggcg   240
agccgcgatc tggttgtgaa ctatgtgaat accaacatgg gcctgaaaat cgtcagctg   300 ctgtggtttc atatcagctg cctgaccttt ggccgcgaaa ccgtgctgga atatctggtg   360
agctttggcg tttggatccg taccccgccg gcgtatcgtc cgccgaatgc gccgattctg   420
agcaccctgc cggaaaccac cgttgtcgac aagcttgcgg ccgcacgccg tcgccgtcgc   480
cgtcgccgtc gccgtcgccg tcgccgtcgc cgtcgccgtc gccgcctcga gcaccaccac   540
caccaccac                                                           549

<210> SEQ ID NO 48
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Arg Arg Arg Arg Arg
145                 150                 155                 160

Arg Arg Arg Arg Arg Arg Arg Arg Arg Arg Arg Arg Arg Arg Arg Leu
                165                 170                 175

Glu His His His His His His
            180
```

<210> SEQ ID NO 49
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg tgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtgcgt cgccgtggtc gcagcctcga gcaccaccac     480
caccaccac                                                             489
```

<210> SEQ ID NO 50
<211> LENGTH: 163
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 50

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Leu Glu His His His
145                 150                 155                 160

His His His

<210> SEQ ID NO 51
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atggatatcg atccgtataa agaatttggc gccaccgtgg aactgctgag ctttctgccg     60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg tgatccggcg    240
agccgcgatc tggttgtgaa ctatgtgaat accaacatgg gcctgaaaat cgtcagctg     300 ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtgcgt cgccgtggtc gcagcccgcg ccgtcgtacc    480
ccgagcctcg agcaccacca ccaccaccac                                      510

<210> SEQ ID NO 52
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52
```

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Leu Glu His His His His His His
                165                 170

<210> SEQ ID NO 53
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
tgctggggtg aactgatgac cctggcgacc tgggttggca acaacctgtg tgatccggcg   240
agccgcgatc tggttgtgaa ctatgtgaat accaacatgg gcctgaaaat tcgtcagctg   300
ctgtggtttc atatcagctg cctgaccttt ggccgcgaaa ccgtgctgga atatctggtg   360
agctttggcg tttggatccg taccccgccg gcgtatcgtc cgccgaatgc gccgattctg   420
agcaccctgc cggaaaccac cgttgtgcgt cgccgtggtc gcagcccgcg ccgtcgtacc   480
ccgagcccgc gtcgtcgtcg tagccagagc ctcgagcacc accaccacca ccac         534

<210> SEQ ID NO 54
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

-continued

```
Thr Ala Ser Ala Leu Tyr Arg Glu Ala Leu Ser Pro Glu His Cys
             35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Leu Glu His His His His
                165                 170                 175

His His

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: This region may encompass 1 to 6 "Ser Ala Gly"
      repeating units

<400> SEQUENCE: 55

Ser Ala Gly Ser Ala Gly Ser Ala Gly Ser Ala Gly Ser Ala Gly Ser
1               5                   10                  15

Ala Gly

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: This region may encompass 1 to 6 "Thr Ala Gly"
      repeating units

<400> SEQUENCE: 56

Thr Ala Gly Thr Ala Gly Thr Ala Gly Thr Ala Gly Thr Ala Gly Thr
1               5                   10                  15

Ala Gly

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: misc_feature
<222> LOCATION: (1)..(18)
<223> OTHER INFORMATION: This region may encompass 1 to 6 "Gly Ala Gly"
      repeating units

<400> SEQUENCE: 57

Gly Ala Gly Gly Ala Gly Gly Ala Gly Gly Ala Gly Gly Ala Gly Gly
1               5                   10                  15

Ala Gly

<210> SEQ ID NO 58
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcagc gcgggcagcg ccggcaagaa aagaagaag      480 aaaaagaaga agctcgagca ccaccaccac caccac                               516

<210> SEQ ID NO 59
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140
```

```
Glu Thr Thr Val Val Ser Ala Gly Ser Ala Gly Lys Lys Lys Lys
145                 150                 155                 160

Lys Lys Lys Lys Leu Glu His His His His His
                165                 170

<210> SEQ ID NO 60
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg cgatccggcg      240 agccgcgatc tggttgtgaa ctatgtgaat accaacatgg gcctgaaaat tcgtcagctg     300 ctgtggttc atatcagctg cctgaccttt ggccgcgaaa ccgtgctgga atatctggtg      360
agctttggcg tttggatccg taccccgccg gcgtatcgtc cgccgaatgc gccgattctg     420
agcaccctgc cggaaaccac cgttgtcacc gcgggcaccg ccggcaagaa aaagaagaag     480
aaaaagaaga agctcgagca ccaccaccac caccac                               516

<210> SEQ ID NO 61
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Thr Ala Gly Thr Ala Gly Lys Lys Lys Lys Lys
145                 150                 155                 160

Lys Lys Lys Lys Leu Glu His His His His His
                165                 170
```

<210> SEQ ID NO 62
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
atggatatcg atccgtataa agaatttggc gccaccgtgg aactgctgag ctttctgccg 60
agcgatttct ttccgagcgt gcgtgatctg ctggataccg cgagcgcgct gtatcgcgaa 120
gcgctggaaa gcccggaaca ttgtagcccg caccataccg ccctgcgtca ggcgattctg 180
tgctggggtg aactgatgac cctggcgacc tgggttggca acaacctgtg cgatccggcg 240
agccgcgatc tggttgtgaa ctatgtgaat accaacatgg gcctgaaaat tcgtcagctg 300
ctgtggtttc atatcagctg cctgaccttt ggccgcgaaa ccgtgctgga atatctggtg 360
```

```
agctttggcg tttggatccg taccccgccg gcgtatcgtc cgccgaatgc gccgattctg 420
agcaccctgc cggaaaccac cgttgtcggc gcgggcggcg ccggcaagaa aaagaagaag 480
aaaaagaaga agctcgagca ccaccaccac caccac 516
```

<210> SEQ ID NO 63
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Met Asp Ile Asp Pro Tyr Lys Glu Phe Gly Ala Thr Val Glu Leu Leu
1 5 10 15

Ser Phe Leu Pro Ser Asp Phe Phe Pro Ser Val Arg Asp Leu Leu Asp
20 25 30

Thr Ala Ser Ala Leu Tyr Arg Glu Ala Leu Glu Ser Pro Glu His Cys
35 40 45

Ser Pro His His Thr Ala Leu Arg Gln Ala Ile Leu Cys Trp Gly Glu
50 55 60

Leu Met Thr Leu Ala Thr Trp Val Gly Asn Asn Leu Cys Asp Pro Ala
65 70 75 80

Ser Arg Asp Leu Val Val Asn Tyr Val Asn Thr Asn Met Gly Leu Lys
85 90 95

Ile Arg Gln Leu Leu Trp Phe His Ile Ser Cys Leu Thr Phe Gly Arg
100 105 110

Glu Thr Val Leu Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Gly Ala Gly Gly Ala Gly Lys Lys Lys Lys Lys
145 150 155 160

Lys Lys Lys Lys Leu Glu His His His His His His
165 170

<210> SEQ ID NO 64
<211> LENGTH: 525
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 64

```
atggatatcg atccgtataa agaatttggc gccaccgtgg aactgctgag ctttctgccg     60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca caacctgtg cgatccggcg     240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtcagc gcgggcagcg ccggcagcgc gggcaagaaa    480
aagaagaaga aaagaagaa gctcgagcac caccaccacc accac                     525
```

<210> SEQ ID NO 65
<211> LENGTH: 175
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 65

```
Met Asp Ile Asp Pro Tyr Lys Glu Phe Gly Ala Thr Val Glu Leu Leu
1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Ser Ala Gly Ser Ala Gly Ser Ala Gly Lys Lys
145                 150                 155                 160

Lys Lys Lys Lys Lys Lys Leu Glu His His His His His
                165                 170                 175
```

<210> SEQ ID NO 66
<211> LENGTH: 525
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 66

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggcgcgaaa  ccgtgctgga atatctggtg     360
agctttggcg tttggatccg taccccgccg gcgtatcgtc cgccgaatgc gccgattctg     420
agcaccctgc cggaaaccac cgttgtcacc gcgggcaccg ccggcaccgc gggcaagaaa     480
aagaagaaga aaaagaagaa gctcgagcac caccaccacc accac                    525
```

<210> SEQ ID NO 67
<211> LENGTH: 175
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 67

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Thr Ala Gly Thr Ala Gly Thr Ala Gly Lys Lys
145                 150                 155                 160

Lys Lys Lys Lys Lys Lys Leu Glu His His His His His His
                165                 170                 175
```

<210> SEQ ID NO 68
<211> LENGTH: 525
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
```

-continued

```
tgctggggtg aactgatgac cctggcgacc tgggttggca acaacctgtg cgatccggcg      240
agccgcgatc tggttgtgaa ctatgtgaat accaacatgg gcctgaaaat tcgtcagctg      300
ctgtggtttc atatcagctg cctgaccttt ggccgcgaaa ccgtgctgga atatctggtg      360
agctttggcg tttggatccg taccccgccg gcgtatcgtc cgccgaatgc gccgattctg      420
agcaccctgc cggaaaccac cgttgtcggc gcgggcggcg ccggcggcgc gggcaagaaa      480
aagaagaaga aaaagaagaa gctcgagcac caccaccacc accac                     525
```

```
<210> SEQ ID NO 69
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69
```

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Gly Ala Gly Gly Ala Gly Gly Ala Gly Lys Lys
145                 150                 155                 160

Lys Lys Lys Lys Lys Lys Leu Glu His His His His His His
                165                 170                 175

```
<210> SEQ ID NO 70
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atggatatcg atccgtataa agaatttggc gccaccgtgg aactgctgag ctttctgccg       60
agcgatttct ttccgagcgt gcgtgatctg ctggataccg cgagcgcgct gtatcgcgaa      120
gcgctggaaa gcccggaaca ttgtagcccg caccataccg ccctgcgtca ggcgattctg      180
tgctggggtg aactgatgac cctggcgacc tgggttggca acaacctgtg cgatccggcg      240
agccgcgatc tggttgtgaa ctatgtgaat accaacatgg gcctgaaaat tcgtcagctg      300
ctgtggtttc atatcagctg cctgaccttt ggccgcgaaa ccgtgctgga atatctggtg      360
```

```
agctttggcg tttggatccg taccccgccg gcgtatcgtc cgccgaatgc gccgattctg    420
agcaccctgc cggaaaccac cgttgtcagc gcgggcagcg ccggcagcgc gggcagcgcc    480
ggcaagaaaa agaagaagaa aaagaagaag ctcgagcacc accaccacca ccac          534
```

<210> SEQ ID NO 71
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Ser Ala Gly Ser Ala Gly Ser Ala Gly Ser Ala
145                 150                 155                 160

Gly Lys Lys Lys Lys Lys Lys Lys Lys Leu Glu His His His His
                165                 170                 175

His His
```

<210> SEQ ID NO 72
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg cgatccggcg    240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtcacc gcgggcaccg ccggcaccgc gggcaccgcc    480
```
ggcaagaaaa agaagaagaa aaagaagaag ctcgagcacc accaccacca ccac      534

<210> SEQ ID NO 73
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Thr Ala Gly Thr Ala Gly Thr Ala Gly Thr Ala
145                 150                 155                 160

Gly Lys Lys Lys Lys Lys Lys Lys Leu Glu His His His His
                165                 170                 175

His His

<210> SEQ ID NO 74
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggcgcgaaa ccgtgctgga atatctggtg      360
agctttggcg tttggatccg taccccgccg gcgtatcgtc cgccgaatgc gccgattctg     420
agcaccctgc cggaaaccac cgttgtcggc gcgggcggcg ccggcggcgc gggcggcgcc     480
ggcaagaaaa agaagaagaa aaagaagaag ctcgagcacc accaccacca ccac           534

<210> SEQ ID NO 75

<211> LENGTH: 178
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Gly Ala Gly Gly Ala Gly Gly Ala Gly Gly Ala
145                 150                 155                 160

Gly Lys Lys Lys Lys Lys Lys Lys Lys Leu Glu His His His
                165                 170                 175

His His

<210> SEQ ID NO 76
<211> LENGTH: 492
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggcgcgaaa ccgtgctgga atatctggtg     360
agctttggcg tttggatccg taccccgccg gcgtatcgtc cgccgaatgc gccgattctg     420
agcacccctg cggaaaccac cgttgtcgac aagcttgcgg ccgcaaagaa aagaagaag     480 aaaaagaaga ag                                                         492

<210> SEQ ID NO 77
<211> LENGTH: 164
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 77

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys
```

<210> SEQ ID NO 78
<211> LENGTH: 149
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (18)..(18)
<223> OTHER INFORMATION: Phe or His
<220> FEATURE:
<221> NAME/KEY: MOD_RES
<222> LOCATION: (23)..(23)
<223> OTHER INFORMATION: Phe or Cys
<220> FEATURE:
<221> NAME/KEY: MOD_RES
<222> LOCATION: (29)..(29)
<223> OTHER INFORMATION: Asp or Cys
<220> FEATURE:
<221> NAME/KEY: MOD_RES
<222> LOCATION: (33)..(33)
<223> OTHER INFORMATION: Thr or Cys
<220> FEATURE:
<221> NAME/KEY: MOD_RES
<222> LOCATION: (37)..(37)
<223> OTHER INFORMATION: Leu or Cys
<220> FEATURE:
<221> NAME/KEY: MOD_RES
<222> LOCATION: (48)..(48)
<223> OTHER INFORMATION: Cys or Ala
<220> FEATURE:
<221> NAME/KEY: MOD_RES
<222> LOCATION: (61)..(61)
<223> OTHER INFORMATION: Cys or Ala
<220> FEATURE:
<221> NAME/KEY: MOD_RES
<222> LOCATION: (107)..(107)
<223> OTHER INFORMATION: Cys or Ala
<220> FEATURE:
<221> NAME/KEY: MOD_RES

```
<222> LOCATION: (121)..(121)
<223> OTHER INFORMATION: Ser or Cys
<220> FEATURE:
<221> NAME/KEY: MOD_RES
<222> LOCATION: (124)..(124)
<223> OTHER INFORMATION: Val or Cys
<220> FEATURE:
<221> NAME/KEY: MOD_RES
<222> LOCATION: (127)..(127)
<223> OTHER INFORMATION: Arg or Cys
<220> FEATURE:
<221> NAME/KEY: MOD_RES
<222> LOCATION: (132)..(132)
<223> OTHER INFORMATION: Tyr, Ala, Val, Ile, Phe or Cys
<220> FEATURE:
<221> NAME/KEY: MOD_RES
<222> LOCATION: (139)..(139)
<223> OTHER INFORMATION: Ile or Ala
<220> FEATURE:
<221> NAME/KEY: MOD_RES
<222> LOCATION: (141)..(141)
<223> OTHER INFORMATION: Ser or Cys

<400> SEQUENCE: 78

Met Asp Ile Asp Pro Tyr Lys Glu Phe Gly Ala Thr Val Glu Leu Leu
1               5                   10                  15

Ser Xaa Leu Pro Ser Asp Xaa Phe Pro Ser Val Arg Xaa Leu Leu Asp
            20                  25                  30

Xaa Ala Ser Ala Xaa Tyr Arg Glu Ala Leu Glu Ser Pro Glu His Xaa
        35                  40                  45

Ser Pro His His Thr Ala Leu Arg Gln Ala Ile Leu Xaa Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Xaa Leu Thr Phe Gly Arg
            100                 105                 110

Glu Thr Val Leu Glu Tyr Leu Val Xaa Phe Gly Xaa Trp Ile Xaa Thr
        115                 120                 125

Pro Pro Ala Xaa Arg Pro Pro Asn Ala Pro Xaa Leu Xaa Thr Leu Pro
    130                 135                 140

Glu Thr Thr Val Val
145

<210> SEQ ID NO 79
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Asp Ile Asp Pro Tyr Lys Glu Phe Gly Ala Thr Val Glu Leu Leu
1               5                   10                  15

Ser Phe Leu Pro Ser Asp Cys Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
```

```
                65                   70                  75                  80
Ser Arg Asp Leu Val Val Asn Tyr Val Asn Thr Asn Met Gly Leu Lys
                        85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Cys Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 80
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Met Asp Ile Asp Pro Tyr Lys Glu Phe Gly Ala Ser Val Glu Leu Leu
1               5                   10                  15

Ser Phe Leu Pro Ser Asp Cys Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Cys Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 81
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 82
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Cys Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

```
Pro Ser Pro Arg Arg Arg Arg Ser Gln Ser Pro Arg Arg Arg Ser
            165                 170                 175

Gln Ser Arg Glu Ser Gln Cys
            180

<210> SEQ ID NO 83
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Cys Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Cys Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Ser
            165                 170                 175

Gln Ser Arg Glu Ser Gln Cys
            180

<210> SEQ ID NO 84
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Cys Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80
```

```
Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Cys Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 85
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Cys Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Cys Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 86
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86
```

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Cys Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Cys Ser Phe Gly Val Trp Ile Arg Thr
            115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
                180

<210> SEQ ID NO 87
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atggatatcg atccgtataa agaatttggc gccaccgtgg aactgctgag ccatctgccg      60
agcgatttct ttccgagcgt gcgtgatctg ctggataccc gagcgcgct gtatcgcgaa     120 gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                              516

<210> SEQ ID NO 88
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Asp Ile Asp Pro Tyr Lys Glu Phe Gly Ala Thr Val Glu Leu Leu
1               5                   10                  15
```

Ser His Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Val Val Asp Lys Leu Ala Ala Ala Lys Lys Lys Lys Lys Lys
145                 150                 155                 160

Lys Lys Lys Lys Leu Glu His His His His His His
                165                 170

<210> SEQ ID NO 89
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg cggctcgtc cgccgaatgc gccgattctg     420
agcaccctgc cggaaaccac cgttgtcgac aagcttgcgg ccgcaaagaa aagaagaag      480 aaaaagaaga agctcgagca ccaccaccac caccac                               516

<210> SEQ ID NO 90
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
            50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
                    85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Ala Arg Pro Pro Asn Ala Pro Ile Leu Ser Thr Leu Pro
            130                 135                 140

Glu Thr Thr Val Val Asp Lys Leu Ala Ala Lys Lys Lys Lys
145                 150                 155                 160

Lys Lys Lys Lys Leu Glu His His His His His
                165                 170

<210> SEQ ID NO 91
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg cgatccggcg      240 agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcggttcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                               516

<210> SEQ ID NO 92
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Thr Leu Ala Thr Trp Val Gly Asn Asn Leu Cys Asp Pro Ala
 65                  70                  75                  80

Ser Arg Asp Leu Val Val Asn Tyr Val Asn Thr Asn Met Gly Leu Lys
            85                  90                  95

Ile Arg Gln Leu Leu Trp Phe His Ile Ser Cys Leu Thr Phe Gly Arg
        100                 105                 110

Glu Thr Val Leu Glu Tyr Leu Val Ser Phe Gly Val Trp Ile Arg Thr
    115                 120                 125

Pro Pro Ala Val Arg Pro Asn Ala Pro Ile Leu Ser Thr Leu Pro
130             135                 140

Glu Thr Thr Val Val Asp Lys Leu Ala Ala Lys Lys Lys Lys
145             150                 155                 160

Lys Lys Lys Lys Leu Glu His His His His His His
            165                 170

<210> SEQ ID NO 93
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggcgcgaaa ccgtgctgga atatctggtg     360
agctttggcg tttggatccg taccccgccg gcgattcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                              516

<210> SEQ ID NO 94
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65              70                  75                  80

Ser Arg Asp Leu Val Val Asn Tyr Val Asn Thr Asn Met Gly Leu Lys
            85                  90                  95

Ile Arg Gln Leu Leu Trp Phe His Ile Ser Cys Leu Thr Phe Gly Arg
        100                 105                 110

Glu Thr Val Leu Glu Tyr Leu Val Ser Phe Gly Val Trp Ile Arg Thr
            115                 120                 125

Pro Pro Ala Ile Arg Pro Pro Asn Ala Pro Ile Leu Ser Thr Leu Pro
        130                 135                 140

Glu Thr Thr Val Val Asp Lys Leu Ala Ala Lys Lys Lys Lys
145                 150                 155                 160

Lys Lys Lys Lys Leu Glu His His His His His His
                165                 170

<210> SEQ ID NO 95
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtttcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                               516

<210> SEQ ID NO 96
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Phe Arg Pro Pro Asn Ala Pro Ile Leu Ser Thr Leu Pro
    130                 135                 140

```
Glu Thr Thr Val Val Asp Lys Leu Ala Ala Ala Lys Lys Lys Lys
145                 150                 155                 160

Lys Lys Lys Lys Leu Glu His His His His His His
                165                 170
```

<210> SEQ ID NO 97
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
tgctggggtg aactgatgac cctggcgacc tgggttggca acaacctgtg cgatccggcg   240
agccgcgatc tggttgtgaa ctatgtgaat accaacatgg gcctgaaaat cgtcagctg    300
ctgtggtttc atatcagctg cctgaccttt ggcgcgaaa ccgtgctgga atatctggtg    360
agctttggcg tttggatccg taccccgccg gcgtatcgtc cgccgaatgc gccggctctg   420
agcaccctgc cggaaaccac cgttgtcgac aagcttgcgg ccgcaaagaa aaagaagaag   480
aaaaagaaga agctcgagca ccaccaccac caccac                              516
```

<210> SEQ ID NO 98
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ala Leu Ser Thr Leu Pro
130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170
```

<210> SEQ ID NO 99
<211> LENGTH: 516
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 99
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
tgctttggcg tttggatccg taccccgccg gcgtatcgtc cgccgaatgc gccgattctg     420
tgcaccctgc cggaaaccac cgttgtcgac aagcttgcgg ccgcaaagaa aaagaagaag     480
aaaaagaaga agctcgagca ccaccaccac caccac                              516

<210> SEQ ID NO 100
<211> LENGTH: 172
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 100

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Tyr Arg Pro Pro Asn Ala Pro Ile Leu Cys Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170

<210> SEQ ID NO 101
<211> LENGTH: 516
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 101

```
atggatatcg atccgtataa agaatttggc gccaccgtgg aactgctgag ccatctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
tgctttggcg tttggatccg taccccgccg gcgtatcgtc cgccgaatgc gccgattctg     420
tgcaccctgc cggaaaccac cgttgtcgac aagcttgcgg ccgcaaagaa aaagaagaag     480
aaaaagaaga agctcgagca ccaccaccac caccac                              516
```

<210> SEQ ID NO 102
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Met Asp Ile Asp Pro Tyr Lys Glu Phe Gly Ala Thr Val Glu Leu Leu
1               5                   10                  15

Ser His Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Tyr Arg Pro Pro Asn Ala Pro Ile Leu Cys Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170
```

<210> SEQ ID NO 103
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
atggatatcg atccgtataa agaatttggc gccaccgtgg aactgctgag ctttctgccg      60
```

```
agcgatttct tccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg cgatccggcg    240
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
tgctttggcg tttggatccg taccccgccg gcgtttcgtc cgccgaatgc gccgattctg    420
tgcaccctgc cggaaaccac cgttgtcgac aagcttgcgg ccgcaaagaa aaagaagaag    480
aaaaagaaga agctcgagca ccaccaccac caccac                              516
```

<210> SEQ ID NO 104
<211> LENGTH: 172
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 104

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Phe Arg Pro Pro Asn Ala Pro Ile Leu Cys Thr Leu Pro
    130                 135                 140

Glu Thr Thr Val Val Asp Lys Leu Ala Ala Lys Lys Lys Lys
145                 150                 155                 160

Lys Lys Lys Lys Leu Glu His His His His His His
                165                 170
```

<210> SEQ ID NO 105
<211> LENGTH: 516
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 105

```
atggatatcg atccgtataa agaatttggc gccaccgtgg aactgctgag ctttctgccg     60
agcgatttct tccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca acaacctgtg cgatccggcg    240
```

```
agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
tgctttggcg tttggatccg taccccgccg gcgtatcgtc cgccgaatgc gccggctctg    420
tgcaccctgc cggaaaccac cgttgtcgac aagcttgcgg ccgcaagaa aagaagaag     480 aaaaagaaga agctcgagca ccaccaccac caccac                              516

<210> SEQ ID NO 106
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Ile Arg Pro Pro Asn Ala Pro Ala Leu Cys Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170

<210> SEQ ID NO 107
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atggatatcg atccgtataa agaatttggc gccaccgtgg aactgctgag ctttctgccg     60
agcgatttct ttccgagcgt gcgtgatctg ctggataccg cgagcgcgct gtatcgcgaa    120
gcgctggaaa gcccggaaca ttgtagcccg caccataccg ccctgcgtca ggcgattctg    180
tgctggggtg aactgatgac cctggcgacc tgggttggca caacctgtg cgatccggcg    240 agccgcgatc tggttgtgaa ctatgtgaat accaacatgg gcctgaaaat tcgtcagctg    300
ctgtggtttc atatcagctg cctgaccttt ggccgcgaaa ccgtgctgga atatctggtg    360
tgctttggcg tttggatccg taccccgccg gcggttcgtc cgccgaatgc gccgattctg    420
```

```
tgcaccctgc cggaaaccac cgttgtcgac aagcttgcgg ccgcaaagaa aagaagaag      480 aaaaagaaga agctcgagca ccaccaccac caccac                              516
```

<210> SEQ ID NO 108
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Val Arg Pro Pro Asn Ala Pro Ile Leu Cys Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170
```

<210> SEQ ID NO 109
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca tgcgagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggcgcgaaa ccgtgctgga atatctggtg      360
agctttggcg tttggatccg taccccgccg gcgtatcgtc cgccgaatgc gccgattctg     420
agcaccctgc cggaaaccac cgttgtcgac aagcttgcgg ccgcaaagaa aagaagaag      480 aaaaagaaga agctcgagca ccaccaccac caccac                              516
```

<210> SEQ ID NO 110
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Ala
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170
```

<210> SEQ ID NO 111
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
gcgtggggtg aactgatgac cctggcgacc tgggttggca acaacctgtg cgatccggcg   240
agccgcgatc tggttgtgaa ctatgtgaat accaacatgg gcctgaaaat tcgtcagctg   300
ctgtggtttc atatcagctg cctgaccttt ggccgcgaaa ccgtgctgga atatctggtg   360
agctttggcg tttggatccg taccccgccg gcgtatcgtc cgccgaatgc gccgattctg   420
agcaccctgc cggaaaccac cgttgtcgac aagcttgcgg ccgcaaagaa aaagaagaag   480
aaaaagaaga agctcgagca ccaccaccac caccac                              516
```

<210> SEQ ID NO 112
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Ala Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Lys Lys Lys Lys Lys
145                 150                 155                 160

Lys Lys Lys Lys Leu Glu His His His His His His
                165                 170

<210> SEQ ID NO 113
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagcgc gctgaccttt ggccgcgaaa ccgtgctgga atatctggtg     360
agctttggcg tttggatccg taccccgccg gcgtatcgtc cgccgaatgc gccgattctg     420
agcacgctgc cggaaaccac cgttgtcgac aagcttgcgg ccgcaaagaa aaagaagaag     480
aaaaagaaga agctcgagca ccaccaccac caccac                              516

<210> SEQ ID NO 114
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
 50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Ala Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Asp Lys Leu Ala Ala Lys Lys Lys Lys Lys
145                 150                 155                 160

Lys Lys Lys Lys Leu Glu His His His His His
            165                 170

<210> SEQ ID NO 115
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca tgcgagcccg caccataccg ccctgcgtca ggcgattctg     180
gcgtggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagctg cctgaccttt ggcgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                              516

<210> SEQ ID NO 116
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Ala
        35                  40                  45

Ser Pro His His Thr Ala Leu Arg Gln Ala Ile Leu Ala Trp Gly Glu
     50                   55                   60

Leu Met Thr Leu Ala Thr Trp Val Gly Asn Asn Leu Cys Asp Pro Ala
 65                   70                   75                   80

Ser Arg Asp Leu Val Val Asn Tyr Val Asn Thr Asn Met Gly Leu Lys
                 85                   90                   95

Ile Arg Gln Leu Leu Trp Phe His Ile Ser Cys Leu Thr Phe Gly Arg
             100                  105                  110

Glu Thr Val Leu Glu Tyr Leu Val Ser Phe Gly Val Trp Ile Arg Thr
         115                  120                  125

Pro Pro Ala Tyr Arg Pro Pro Asn Ala Pro Ile Leu Ser Thr Leu Pro
     130                  135                  140

Glu Thr Thr Val Val Asp Lys Leu Ala Ala Ala Lys Lys Lys Lys Lys
145                  150                  155                  160

Lys Lys Lys Lys Leu Glu His His His His His His
                 165                  170

<210> SEQ ID NO 117
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca tgcgagcccg caccataccg ccctgcgtca ggcgattctg     180
tgctggggtg aactgatgac cctggcgacc tgggttggca acaacctgtg cgatccggcg     240
agccgcgatc tggttgtgaa ctatgtgaat accaacatgg gcctgaaaat tcgtcagctg     300
ctgtggtttc atatcagcgc gctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                              516

<210> SEQ ID NO 118
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Asp Ile Asp Pro Tyr Lys Glu Phe Gly Ala Thr Val Glu Leu Leu
 1               5                   10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Ala
             35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Cys Asp Pro Ala
 65                  70                  75                  80

```
Ser Arg Asp Leu Val Val Asn Tyr Val Asn Thr Asn Met Gly Leu Lys
            85                  90                  95

Ile Arg Gln Leu Leu Trp Phe His Ile Ser Ala Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Asp Lys Leu Ala Ala Lys Lys Lys Lys
145                 150                 155                 160

Lys Lys Lys Lys Leu Glu His His His His His His
                165                 170
```

<210> SEQ ID NO 119
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
atggatatcg atccgtataa agaatttggc gccaccgtgg aactgctgag ctttctgccg    60
agcgatttct ttccgagcgt gcgtgatctg ctggataccg cgagcgcgct gtatcgcgaa   120
gcgctggaaa gcccggaaca ttgtagcccg caccataccg ccctgcgtca ggcgattctg   180
gcgtggggtg aactgatgac cctggcgacc tgggttggca caacctgtg cgatccggcg    240
agccgcgatc tggttgtgaa ctatgtgaat accaacatgg gcctgaaaat cgtcagctg    300
ctgtggtttc atatcagcgc gctgaccttt ggcgcgaaa ccgtgctgga atatctggtg    360
agctttggcg tttggatccg taccccgccg gcgtatcgtc cgccgaatgc gccgattctg   420
agcaccctgc cggaaaccac cgttgtcgac aagcttgcgg ccgcaaagaa aaagaagaag   480
aaaaagaaga agctcgagca ccaccaccac caccac                             516
```

<210> SEQ ID NO 120
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Ala Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
            85                  90                  95

Ile Arg Gln Leu Leu Trp Phe His Ile Ser Ala Leu Thr Phe Gly Arg
            100                 105                 110
```

```
Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
130                 135                 140

Glu Thr Thr Val Val Asp Lys Leu Ala Ala Ala Lys Lys Lys Lys Lys
145                 150                 155                 160

Lys Lys Lys Lys Leu Glu His His His His His His
                165                 170

<210> SEQ ID NO 121
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
atggatatcg atccgtataa agaatttggc gccaccgtgg aactgctgag ctttctgccg     60
agcgatttct ttccgagcgt gcgtgatctg ctggataccg cgagcgcgct gtatcgcgaa    120
gcgctggaaa gcccggaaca tgcgagcccg caccataccg ccctgcgtca ggcgattctg    180
gcgtggggtg aactgatgac cctggcgacc tgggttggca acaacctgtg cgatccggcg    240
agccgcgatc tggttgtgaa ctatgtgaat accaacatgg gcctgaaaat tcgtcagctg    300
ctgtggtttc atatcagcgc gctgaccttt ggccgcgaaa ccgtgctgga atatctggtg    360
agctttggcg tttggatccg taccccgccg gcgtatcgtc cgccgaatgc gccgattctg    420
agcaccctgc cggaaaccac cgttgtcgac aagcttgcgg ccgcaaagaa aaagaagaag    480
aaaaagaaga agctcgagca ccaccaccac caccac                              516

<210> SEQ ID NO 122
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Ala
            35                  40                  45

Ser Pro His His Thr Ala Leu Arg Gln Ala Ile Leu Ala Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Ala Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
130                 135                 140
```

Glu Thr Thr Val Val Asp Lys Leu Ala Ala Ala Lys Lys Lys Lys
145                 150                 155                 160

Lys Lys Lys Lys Leu Glu His His His His His His
                165                 170

<210> SEQ ID NO 123
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca tgcgagcccg caccataccg ccctgcgtca ggcgattctg     180
gcgtggggtg aactgatgac cctggcgacc tgggttggca caacctgtg cgatccggcg      240 agccgcgatc tggttgtgaa ctatgtgaat accaacatgg gcctgaaaat tcgtcagctg     300
ctgtggtttc atatcagcgc gctgaccttt ggccgcgaaa ccgtgctgga atatctggtg     360
tgctttggcg tttggatccg taccccgccg gcgtatcgtc cgccgaatgc gccgattctg     420
tgcaccctgc cggaaaccac cgttgtcgac aagcttgcgg ccgcaaagaa aaagaagaag     480
aaaaagaaga agctcgagca ccaccaccac caccac                              516

<210> SEQ ID NO 124
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Ala
            35                  40                  45

Ser Pro His His Thr Ala Leu Arg Gln Ala Ile Leu Ala Trp Gly Glu
        50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Ala Leu Thr Phe Gly Arg
            100                 105                 110

Glu Thr Val Leu Glu Tyr Leu Val Cys Phe Gly Val Trp Ile Arg Thr
        115                 120                 125

Pro Pro Ala Tyr Arg Pro Pro Asn Ala Pro Ile Leu Cys Thr Leu Pro
    130                 135                 140

Glu Thr Thr Val Val Asp Lys Leu Ala Ala Ala Lys Lys Lys Lys
145                 150                 155                 160

Lys Lys Lys Lys Leu Glu His His His His His His
                165                 170

<210> SEQ ID NO 125
<211> LENGTH: 12
<212> TYPE: PRT
<213> ORGANISM: Unknown
<220> FEATURE:
<223> OTHER INFORMATION: Description of Unknown: Thrombin peptide

<400> SEQUENCE: 125

Gly Pro Gly Ala Pro Gly Leu Val Pro Arg Gly Ser
1               5                   10

<210> SEQ ID NO 126
<211> LENGTH: 12
<212> TYPE: PRT
<213> ORGANISM: Unknown
<220> FEATURE:
<223> OTHER INFORMATION: Description of Unknown: Factor Xa peptide

<400> SEQUENCE: 126

Gly Pro Ala Ser Gly Pro Gly Ile Glu Gly Arg Ala
1               5                   10

<210> SEQ ID NO 127
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg cgatggcccg      240 ggtgcgccgg tcttgttcc gcgtggtagc agccgcgatc tggttgtgaa ctatgtgaat      300
accaacatgg cctgaaaat tcgtcagctg ctgtggtttc atatcagctg cctgaccttt      360
ggccgcgaaa ccgtgctgga atatctggtg agctttggcg tttggatccg taccccgccg     420
gcgtatcgtc cgccgaatgc gccgattctg agcacccctgc cggaaaccac cgttgtcgac     480
aagcttgcgg ccgcaaagaa aagaagaag aaaagaaga agctcgagca ccaccaccac       540
caccac                                                                 546

<210> SEQ ID NO 128
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu

```
Leu Met Thr Leu Ala Thr Trp Val Gly Asn Asn Leu Cys Asp Gly Pro
 65                  70                  75                  80

Gly Ala Pro Gly Leu Val Pro Arg Gly Ser Ser Arg Asp Leu Val Val
                 85                  90                  95

Asn Tyr Val Asn Thr Asn Met Gly Leu Lys Ile Arg Gln Leu Leu Trp
            100                 105                 110

Phe His Ile Ser Cys Leu Thr Phe Gly Arg Glu Thr Val Leu Glu Tyr
                115                 120                 125

Leu Val Ser Phe Gly Val Trp Ile Arg Thr Pro Ala Tyr Arg Pro
        130                 135                 140

Pro Asn Ala Pro Ile Leu Ser Thr Leu Pro Glu Thr Thr Val Val Asp
145                 150                 155                 160

Lys Leu Ala Ala Ala Lys Lys Lys Lys Lys Lys Lys Lys Leu Glu
                165                 170                 175

His His His His His His
            180

<210> SEQ ID NO 129
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg tcgatggccg      240 gcgagcggtc cgggtattga aggtcgtgcg agccgcgatc tggttgtgaa ctatgtgaat     300
accaacatgg gcctgaaaat tcgtcagctg ctgtggtttc atatcagctg cctgaccttt     360
ggccgcgaaa ccgtgctgga atatctggtg agctttggcg tttggatccg tacccgccg     420 gcgtatcgtc cgccgaatgc gccgattctg agcaccctgc cggaaaccac cgttgtcgac     480
aagcttgcgg ccgcaaagaa aaagaagaag aaaaagaaga agctcgagca ccaccaccac     540
caccac                                                               546

<210> SEQ ID NO 130
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60
```

```
Leu Met Thr Leu Ala Thr Trp Val Gly Asn Asn Leu Cys Asp Gly Pro
 65                  70                  75                  80

Ala Ser Gly Pro Gly Ile Glu Gly Arg Ala Ser Arg Asp Leu Val Val
                 85                  90                  95

Asn Tyr Val Asn Thr Asn Met Gly Leu Lys Ile Arg Gln Leu Leu Trp
            100                 105                 110

Phe His Ile Ser Cys Leu Thr Phe Gly Arg Glu Thr Val Leu Glu Tyr
        115                 120                 125

Leu Val Ser Phe Gly Val Trp Ile Arg Thr Pro Pro Ala Tyr Arg Pro
    130                 135                 140

Pro Asn Ala Pro Ile Leu Ser Thr Leu Pro Glu Thr Thr Val Val Asp
145                 150                 155                 160

Lys Leu Ala Ala Lys Lys Lys Lys Lys Lys Lys Lys Leu Glu
                165                 170                 175

His His His His His His
            180

<210> SEQ ID NO 131
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgga aagcccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                               516

<210> SEQ ID NO 132
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Ser Pro Ala
 65                  70                  75                  80
```

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Asp Lys Leu Ala Ala Lys Lys Lys Lys
145                 150                 155                 160

Lys Lys Lys Lys Leu Glu His His His His His His
                165                 170

<210> SEQ ID NO 133
<211> LENGTH: 516
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 133
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgga agaaccggcg     240
agccgcgatc tggttgtgaa ctatgtgaat accaacatgg gcctgaaaat cgtcagctg      300 ctgtggtttc atatcagctg cctgaccttt ggcgcgaaa ccgtgctgga atatctggtg      360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                              516

<210> SEQ ID NO 134
<211> LENGTH: 172
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 134

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Glu Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Val Val Asp Lys Leu Ala Ala Ala Lys Lys Lys Lys
145                 150                 155                 160

Lys Lys Lys Lys Leu Glu His His His His His His
            165                 170

<210> SEQ ID NO 135
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 136
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Cys Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 137
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Cys
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 138
<211> LENGTH: 183
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 138

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Cys Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Ser Gln Cys
            180
```

<210> SEQ ID NO 139
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Cys Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
```

```
                130              135             140
Glu Thr Thr Val Val Arg Arg Arg Gly Arg Ser Pro Arg Arg Arg Thr
145                 150             155                 160

Pro Ser Pro Arg Arg Arg Arg Ser Gln Ser Pro Arg Arg Arg Ser
                165             170             175

Gln Ser Arg Glu Ser Gln Cys
            180

<210> SEQ ID NO 140
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Cys
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150             155                 160

Pro Ser Pro Arg Arg Arg Arg Ser Gln Ser Pro Arg Arg Arg Ser
                165             170             175

Gln Ser Arg Glu Ser Gln Cys
            180

<210> SEQ ID NO 141
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Ala Arg Gly Ala Arg Gly Ala Arg Gly Ala Arg Gly Ile Leu Gly
1               5                   10                  15

Val Phe Ile Leu Leu Tyr Met
                20

<210> SEQ ID NO 142
<211> LENGTH: 570
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 142

```
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca acaacctgtg tgatccggcg     240
agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtgcgt cgccgtggtc gcagcccgcg ccgtcgtacc     480
ccgagcccgc gtcgtcgtcg tagccagagc ccgcgtcgtc gccgcagcca gagccgcgaa     540
agccagctcg agcaccacca ccaccaccac                                      570
```

<210> SEQ ID NO 143
<211> LENGTH: 190
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Cys Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Leu Glu His His His His His His
            180                 185                 190
```

<210> SEQ ID NO 144
<211> LENGTH: 492
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 144
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg  cgatccggcg     240 agccgcgatc tggttgtgaa ctatgtgaat accaacatgg gcctgaaaat tcgtctgctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcactcga gcaccaccac     480
caccaccact ga                                                         492

<210> SEQ ID NO 145
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
atggatatcg atccgtataa agaatttggc gccaccgtgg aactgctgag ctttctgccg      60
agcgatttct ttccgagcgt gcgtgatctg ctggataccg cgagcgcgct gtatcgcgaa     120
gcgctggaaa gcccggaaca ttgtagcccg caccataccg ccctgcgtca ggcgattctg     180
tgctggggtg aactgatgac cctggcgacc tgggttggca caacctgtg  cgatccggcg     240 agccgcgatc tggttgtgaa ctatgtgaat accaacatgg gcctgaaaat tcgtcagctg     300
ctgtggtttc atatcagctg cctgaccttt ggccgcgaaa ccgtgctgga atatctggtg     360
agctttggcg tttggatccg taccccgccg gcgtatcgtc cgccgaatgc gccgattctg     420
agcaccctgc cggaaaccac cgttgtcgac aagcttgcgg ccgcaaagaa aaagaagaag     480
aaaaagaaga agctcgagca ccaccaccac caccac                               516

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cgactcacta tagggaatt gtgagcgg                                          28

<210> SEQ ID NO 147
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ggcctcgagc ttcttttct ctttgcggc cgcaagcttg tcgac                        45
```

<210> SEQ ID NO 148
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
ggcctcgagc ttcttctttt tcttcttctt tgcggccgca agcttgtcga c      51

<210> SEQ ID NO 149
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
ggcctcgagc ttcttctttt tcttcttctt tttctttgcg gccgcaagct tgtcgac      57

<210> SEQ ID NO 150
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
ggcctcgagt ttcttcttct tcttcttctt cttttctttt gcggccgcaa gcttgtcgac      60

<210> SEQ ID NO 151
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
ggcctcgagc ttcttctttt tcttcttctt tttcttcttc tttgcggccg caagcttgtc      60
gac      63

<210> SEQ ID NO 152
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
ggcctcgagc ttcttctttt tcttcttctt tttcttcttc ttttctttg cggccgcaag      60 cttgtcgac      69

<210> SEQ ID NO 153
<211> LENGTH: 90
<212> TYPE: DNA
<213> ORGANISM: Artificial Sequence
<220> FEATURE:
<223> OTHER INFORMATION: Description of Artificial Sequence: Synthetic primer

<400> SEQUENCE: 153

```
ggcctcgagc tttttcttct tcttcttctt cttcttcttt ttcttcttct tcttcttctt    60 cttttcttt gcggccgcaa gcttgtcgac                                      90
```

<210> SEQ ID NO 154
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154

```
ggcctcgagc ttcgccttag ccttcgcctt agcctttgcc ttcgccttag cctttgcctt    60
tgcggccgca agcttgtcga c                                              81
```

<210> SEQ ID NO 155

<400> SEQUENCE: 155

000

<210> SEQ ID NO 156
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156

```
ggcctcgagt ttcttcttct tcttcgggct ctggctcttc tttttctttg cggccgcaag    60
cttgtcgac                                                            69
```

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157

```
attctcgagg ctgcgaccac ggcgacgcac                                     30
```

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158

```
attctcgagg ctcggggtac gacggcgcgg                                     30
```

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159

```
attctcgagg ctctggctac gacgacgacg cgggctcggg gt                        42
```

<210> SEQ ID NO 160
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160

```
ggcctcgagc ttcttctttt tcttcttctt tttcttgccg gcgctgcccg cgctgacaac    60
ggtggtttcc ggcag                                                      75
```

<210> SEQ ID NO 161
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161

```
ggcctcgagc ttcttctttt tcttcttctt tttcttgccg gcggtgcccg cggtgacaac    60
ggtggtttcc ggcag                                                      75
```

<210> SEQ ID NO 162
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162

```
ggcctcgagc ttcttctttt tcttcttctt tttcttgccg gcgccgcccg cgccgacaac    60
ggtggtttcc ggcag                                                      75
```

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163

```
aactgctgag ccatctgccg agcgattt                                        28
```

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164

```
taccccgccg gcggctcgtc cgccgaat                                        28
```

<210> SEQ ID NO 165
<211> LENGTH: 28
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 165
taccccgccg gcggttcgtc cgccgaat                                       28

<210> SEQ ID NO 166
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
taccccgccg gcgattcgtc cgccgaat                                       28

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
taccccgccg gcgtttcgtc cgccgaat                                       28

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tccgccgaat gcgccggctc tgagcaccct                                     30

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tggaatatct ggtgtgcttt ggcgttt                                        27

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
atgcgccgat tctgtgcacc ctgccggaaa                                     30

<210> SEQ ID NO 171
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 171
agcccggaac atgcgagccc gcaccat                                        27

<210> SEQ ID NO 172
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
aggcgattct ggcgtggggt gaact                                          25

<210> SEQ ID NO 173
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tttcatatca gcgcgctgac ctttggccgc ga                                  32

<210> SEQ ID NO 174
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tggcaacaac ctggaaagcc cggcgagccg cga                                 33

<210> SEQ ID NO 175
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ttggcaacaa cctggaagaa ccggcgagcc gcgat                               35

<210> SEQ ID NO 176
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aaatcgctcg gcagatggct cagcagtt                                       28

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
attcggcgga cgagccgccg gcggggta								28

<210> SEQ ID NO 178
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
attcggcgga cgaaccgccg gcggggta								28

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
attcggcgga cgaatcgccg gcggggta								28

<210> SEQ ID NO 180
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
attcggcgga cgaaacgccg gcggggta								28

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
agggtgctca gagccggcgc attcggcgga								30

<210> SEQ ID NO 182
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
aaacgccaaa gcacaccaga tattcca								27

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tttccggcag ggtgcacaga atcggcgcat                              30

<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
atggtgcggg ctcgcatgtt ccgggct                                 27

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
agttcacccc acgccagaat cgcct                                   25

<210> SEQ ID NO 186
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tcgcggccaa aggtcagcgc gctgatatga aa                           32

<210> SEQ ID NO 187
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tcgcggctcg ccgggctttc caggttgttg cca                          33

<210> SEQ ID NO 188
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
atcgcggctc gccggttctt ccaggttgtt gccaa                        35

<210> SEQ ID NO 189
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189

-continued

```
aagaaaaaga agaagtgaga tccggct                                          27

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
agcagccgga tctcacttct tcttttctt                                        30

<210> SEQ ID NO 191
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ggaaagacug uuccaaaaau uuccuuucu gacaagguuu uu                          42

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192
gcugacccug aaguucauct t                                                21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
gaugaacuuc agggucagct t                                                21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 194
gcugacccug aaguucauct t                                                21

<210> SEQ ID NO 195
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gucaucacac ugaauaccaa u                                                    21

<210> SEQ ID NO 196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
auugguauuc agugugauga cac                                                  23

<210> SEQ ID NO 197
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (1)..(1)
<223> OTHER INFORMATION: 2'-o-methyl-C
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: misc_feature
<222> LOCATION: (8)..(9)
<223> OTHER INFORMATION: Phosphorothioate linkage
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: MOD_RES
<222> LOCATION: (11)..(11)
```

<223> OTHER INFORMATION: 2'-o-methyl-G

<400> SEQUENCE: 197
cagtctgctc g                                                          11

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: MOD_RES
<222> LOCATION: (4)..(4)
<223> OTHER INFORMATION: 2'-F-u
<220> FEATURE:
<221> NAME/KEY: MOD_RES
<222> LOCATION: (5)..(5)
<223> OTHER INFORMATION: 2'-F-c
<220> FEATURE:
<221> NAME/KEY: MOD_RES
<222> LOCATION: (7)..(7)
<223> OTHER INFORMATION: 2'-F-u
<220> FEATURE:
<221> NAME/KEY: MOD_RES
<222> LOCATION: (8)..(8)
<223> OTHER INFORMATION: 2'-F-c
<220> FEATURE:
<221> NAME/KEY: MOD_RES
<222> LOCATION: (9)..(9)
<223> OTHER INFORMATION: 2'-F-u
<220> FEATURE:
<221> NAME/KEY: MOD_RES
<222> LOCATION: (10)..(10)
<223> OTHER INFORMATION: 2'-F-c
<220> FEATURE:
<221> NAME/KEY: MOD_RES
<222> LOCATION: (14)..(14)
<223> OTHER INFORMATION: 2'-F-u
<220> FEATURE:
<221> NAME/KEY: MOD_RES
<222> LOCATION: (15)..(15)
<223> OTHER INFORMATION: 2'-F-c
<220> FEATURE:
<221> NAME/KEY: MOD_RES
<222> LOCATION: (16)..(17)
<223> OTHER INFORMATION: 2'-F-u
<220> FEATURE:
<221> NAME/KEY: MOD_RES
<222> LOCATION: (19)..(19)
<223> OTHER INFORMATION: 2'-F-c
<220> FEATURE:
<221> NAME/KEY: misc_feature
<222> LOCATION: (20)..(21)
<223> OTHER INFORMATION: Phosphorothioate linkage

<400> SEQUENCE: 198
ggaucaucuc aagucuuact t                                               21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: MOD_RES

```
<222> LOCATION: (2)..(2)
<223> OTHER INFORMATION: 2'-F-u
<220> FEATURE:
<221> NAME/KEY: MOD_RES
<222> LOCATION: (7)..(7)
<223> OTHER INFORMATION: 2'-F-c
<220> FEATURE:
<221> NAME/KEY: MOD_RES
<222> LOCATION: (8)..(9)
<223> OTHER INFORMATION: 2'-F-u
<220> FEATURE:
<221> NAME/KEY: MOD_RES
<222> LOCATION: (14)..(14)
<223> OTHER INFORMATION: 2'-F-u
<220> FEATURE:
<221> NAME/KEY: MOD_RES
<222> LOCATION: (17)..(17)
<223> OTHER INFORMATION: 2'-F-u
<220> FEATURE:
<221> NAME/KEY: MOD_RES
<222> LOCATION: (18)..(19)
<223> OTHER INFORMATION: 2'-F-c
<220> FEATURE:
<221> NAME/KEY: misc_feature
<222> LOCATION: (20)..(21)
<223> OTHER INFORMATION: Phosphorothioate linkage

<400> SEQUENCE: 199
guaagacuug agaugaucct t                                          21

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
ugguuuacau gucgacuaa                                             19

<210> SEQ ID NO 201
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uguuguucag auuugccucc gcacc                                      25

<210> SEQ ID NO 202
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
acaacaaguc uaaacggagg cgugg                                      25

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 203

Lys Lys Lys Lys Lys
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Lys Lys Lys Lys Lys Lys Lys
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Lys Lys Lys Lys Lys Lys Lys Lys Lys
1               5

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Lys Lys Lys Lys Lys Lys Lys Lys Lys Lys
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Lys Lys Lys Lys Lys Lys Lys Lys Lys Lys Lys
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Lys Lys Lys Lys Lys Lys Lys Lys Lys Lys Lys Lys Lys
1               5                   10

<210> SEQ ID NO 209
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 209

Lys Lys Lys Lys Lys Lys Lys Lys Lys Lys Lys Lys Lys Lys Lys Lys
1               5                   10                  15

Lys Lys Lys Lys
            20

<210> SEQ ID NO 210
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Lys Ala Lys Ala Lys Ala Lys Ala Lys Ala Lys Ala Lys Ala Lys Ala
1               5                   10                  15

Lys Ala

<210> SEQ ID NO 211
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Lys Gly Lys Gly Lys Gly Lys Gly Lys Gly Lys Gly Lys Gly Lys Gly
1               5                   10                  15

Lys Gly

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(8)
<223> OTHER INFORMATION: Any amino acid

<400> SEQUENCE: 212

Lys Lys Lys Lys Xaa Xaa Xaa Xaa Lys Lys Lys Lys Lys
1               5                   10

<210> SEQ ID NO 213
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Gln Ser Pro
1

<210> SEQ ID NO 214
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Arg Arg Arg Arg Arg
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Arg Arg Arg Arg Arg Arg Arg
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Arg Arg Arg Arg Arg Arg Arg Arg
1               5

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Arg Arg Arg Arg Arg Arg Arg Arg Arg Arg
1               5                   10

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Arg Arg Arg Arg Arg Arg Arg Arg Arg Arg Arg Arg
1               5                   10

<210> SEQ ID NO 219
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219
```

Arg Arg Arg Arg Arg Arg Arg Arg Arg Arg Arg Arg Arg Arg Arg Arg
1               5                   10                  15

Arg Arg Arg Arg
        20

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gaagaugcaa cucgauuca                                                19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
acagucgcuu cuucaguga                                                19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ugaaugcacg ggcaaugaa                                                19

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cgggagaagu ggagcagua                                                19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
agaagcagga ccuuaucua                                                19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ggacaugggu uccaaauua							19

<210> SEQ ID NO 226
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ccaatgctgg actttataa							19

<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gcatgcttac tgatataaa							19

<210> SEQ ID NO 228
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
caaccagtgt acccttaaa							19

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
gaagaugcaa cucgauuca							19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
acagucgcuu cuucaguga							19

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 231
gucaucacac ugaauaccaa u                                              21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
cuuuacaagc cuugguucag u                                              21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ggaaucuuau auuugaucca a                                              21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
uagaagggaa ucuuauauuu g                                              21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
gccccaucac uuuacaagcc u                                              21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
aaauagaagg gaaucuuaua u                                              21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
```
agguguaugg cuucaacccu g                                              21

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
gucaucacac ugaauaccaa u                                              21

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
gaacaccaac uucuuccacg a                                              21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
gauaccgugu auggaaacug c                                              21

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cagccccauc acuuuacaag c                                              21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gauugauuga ccuguccauu c                                              21

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
agguguaugg cuucaacccu g								21

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gaaugugggu ggcaacuuua g								21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gucaucacac ugaauaccaa u								21

<210> SEQ ID NO 246
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
auugguauuc agugugauga cac							23

<210> SEQ ID NO 247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
acugaaccaa ggcuuguaaa gug							23

<210> SEQ ID NO 248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uuggaucaaa uauaagauuc ccu							23

<210> SEQ ID NO 249
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
caaauauaag auucccuucu auu							23

```
<210> SEQ ID NO 250
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
aggcuuguaa agugaugggg cug                                             23

<210> SEQ ID NO 251
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
auauaagauu cccuucuauu uug                                             23

<210> SEQ ID NO 252
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
caggguugaa gccauacacc ucu                                             23

<210> SEQ ID NO 253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
auugguauuc agugugauga cac                                             23

<210> SEQ ID NO 254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ucguggaaga aguugguguu cau                                             23

<210> SEQ ID NO 255
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gcaguuucca uacacgguau cca                                             23
```

<210> SEQ ID NO 256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gcuuguaaag ugauggggcu gga                                              23

<210> SEQ ID NO 257
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gaauggacag gucaaucaau cuu                                              23

<210> SEQ ID NO 258
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
caggguugaa gccauacacc ucu                                              23

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
aaaguugcca cccacauuca g                                                21

<210> SEQ ID NO 260
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
auugguauuc agugugauga cac                                              23

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 261

His His His His His His
1               5

```
<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This region may encompass 4 to 5 "Lys" residues

<400> SEQUENCE: 262

Lys Lys Lys Lys Lys
1               5

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This region may encompass 4 to 5 "Arg" residues

<400> SEQUENCE: 263

Arg Arg Arg Arg Arg
1               5
```

CHIMERIC THERAPEUTICS, COMPOSITIONS, AND METHODS FOR USING SAME

CROSS-REFERENCE TO RELATED APPLICATIONS

This application is a continuation of International (PCT) Patent Application Serial No. PCT/US2010/031023, filed Apr. 14, 2010, which claims the benefit of and priority to U.S. Provisional Application No. 61/169,124, filed Apr. 14, 2009; the disclosures of each application are hereby incorporated by reference in their entirety.

BACKGROUND

Nucleic acid-based and protein-based therapeutic agents represent promising new drugs for the treatment of various diseases and disorders including cancer, infectious diseases, neurological disorders, inflammation and immune disorders, and cardiovascular disease. However, many proposed nucleic acid-based and protein-based therapeutic agents have not been successful because of a limited ability for these agents to reach the target tissue and exert a therapeutic effect. The challenges in developing effective nucleic acid-based and protein-based therapeutic agents include degradation, rapid clearance through the kidneys, short-half lives, low stability, the generation of neutralizing antibodies to the foreign antigen, and rapid clearance of these therapeutic agents from the immune system. Efforts to increase efficacy of these therapeutics have included chemical modifications, e.g., pegylation of proteins and phosphorothioate modifications of nucleic acids. Such chemical modifications improve stability, increase half-lives, and decrease the likelihood of triggering an immune response. However, the success of these chemical modifications in improving therapeutic efficacy is dependent on the drug, e.g., the nucleic acid sequence, and can vary depending on the route of drug delivery.

As such, there is an on-going need for nucleic acid-based and protein-based therapeutics that are long-lasting and provide effective treatment for diseases and disorders.

SUMMARY

The present disclosure is generally directed, at least in part, to therapeutic chimerics, e.g., chimeric proteins that may include a protein and a polynucleotide, and/or particles and/or compositions that include the disclosed therapeutic chimerics that are capable of evading the immune system. Such therapeutic chimerics may be referred to as stealth therapeutics because of their ability to evade immune clearance and exert a therapeutic effect at the desired target location.

In an embodiment, a chimeric therapeutic is provided that comprises a modified viral core protein comprising at least one mutation or modification in an immunogenic epitope or domain compared to a wild type viral core protein, and a therapeutic agent. An immunogenic epitope or domain refers to any antigenic determinant or subunit thereof that is capable of inducing an immune response. A mutation or modification in an immunogenic epitope of a viral core protein may reduce the immunogenicity of the viral core protein. In some embodiments, a mutation or modification in an immunogenic epitope reduces the immunogenicity of the viral core protein by down-regulating an immune response (e.g., a humoral immune response, a cell-mediated immune response, and/or other immune response). In certain embodiments, a chimeric therapeutic mutated or modified in at least one immunogenic epitope may escape immune clearance by evading the immune system. In some embodiments, the immunogenic epitope that is mutated or modified is a T cell epitope (for example, a T helper cell epitope, a cytotoxic T cell epitope, or a minor T cell epitope), a B cell epitope, and/or an HLA-peptide binding site. In certain embodiments, the modified viral core protein comprising at least one mutation or modification in an immunogenic domain is substantially non-immunogenic compared to a wild type viral core protein.

The modified viral core protein may comprise a mutation, e.g., a deletion, a substitution, and/or an insertion, in an immunogenic domain as compared to a wild type core protein. In some embodiments, a modified viral core protein of a disclosed chimeric therapeutic may comprise a deletion of at least 1, 2, 3, 4, 5, 6, 7, 8, 9, 10 or more amino acids in an immunogenic domain. In other embodiments, a modified viral core protein of a disclosed chimeric therapeutic may comprise a substitution of at least 1, 2, 3, 4, 5, 6, 7, 8, 9, 10 or more amino acids in an immunogenic domain. In still other embodiments, a modified viral core protein of a disclosed chimeric therapeutic may comprise an insertion of at least 1, 2, 3, 4, 5, 6, 7, 8, 9, 10 or more amino acids in an immunogenic domain.

The modified viral core protein may comprise a modification or alteration in an immunogenic domain as compared to a wild type core protein. Exemplary modifications include chemical modifications, e.g., covalent modifications (e.g., conjugation to another protein, protein domain, lipid, polysaccharide including synthetic or natural polysaccharides, or polymer including synthetic or natural polymers) or non-covalent modifications. Chemical modifications may include polymer modified viral core proteins, lipid modified viral core proteins, peptide modified viral core proteins, or saccharide modified viral core proteins, such as phosphatidyl ethanolamine-maleimide (PE-maleimide or PE-mal), polyethylene glycol (PEG), poly-alanine, N-ethylmaleimide (NEM), fluorescein-maleimide (FL-maleimide or FL-Mal), and gamma-maleimide-butrylamide (GMBA). In some embodiments, a modified viral core protein may comprise a modification of at least 1, 2, 3, 4, 5, 6, 7, 8, 9, 10 or more amino acids in an immunogenic domain. In some embodiments, a modified viral core protein may comprise at least one mutation in an immunogenic domain and at least one modification in an immunogenic domain.

Disclosed modified viral core proteins may be a modified hepatitis virus core protein, for example, a modified hepatitis B core protein. A mutation in an immunogenic domain of a modified hepatitis B core protein may be mutated such that at least one amino acid of SEQ ID NO. 1 or SEQ ID NO. 2 is independently selected from the group consisting of asparagine 21, alanine 21, valine 21, alanine 27, isoleucine 27, valine 60, and leucine 97.

In some embodiments, a chimeric therapeutic is provided that comprises a modified viral core protein comprising at least one mutation or modification in an immunogenic epitope, a structural core portion and/or a tail portion; and a therapeutic agent associated with the modified viral core protein. In certain embodiments, the therapeutic agent may be bound to the modified viral core protein. The structural core protein of a disclosed modified viral core protein may be a modified structural core protein. The tail portion of a disclosed modified viral core portion may be a modified C-terminal tail portion of a disclosed viral core portion, for example.

In some embodiments, the therapeutic agent is a nucleic acid bound to a modified tail portion of a disclosed therapeutic is substantially less immunogenic as compared to an identical unbound nucleic acid. In other embodiments, a nucleic acid bound to the modified viral core protein is bound with a binding affinity that allows release of the nucleic acid when the chimeric therapeutic is administered in vivo. A disclosed nucleic acid bound to a disclosed modified viral core protein may be, e.g., resistant in an aqueous solution to degradation with a nuclease.

The nucleic acid bound to a modified viral core protein of a disclosed chimeric therapeutic may have a binding affinity of about 50 nM to about 500 nM, at 20 mM NaHCO$_3$, and a pH of 9.5, or about 55 nM to about 400 nM, at 20 mM NaHCO$_3$, and a pH of 9.5, and/or about 50 nM to about 500 nM, at 20 mM (CH$_2$OH)$_3$CNH$_2$, and a pH of 7.7. In some embodiments, the nucleic acid of a disclosed chimeric therapeutic is substantially bound to the modified viral core protein by Coulombic interactions.

The disclosed chimeric therapeutics, compositions, and/or particles may be substantially free of nuclease and/or substantially free of endogenous nucleic acids.

In some embodiments, a disclosed chimeric therapeutic and/or particle having a nucleic acid bound to a viral core protein may be substantially protected from serum degradation when administered in vivo, for example, a nucleic acid bound to a viral core protein may be substantially protected from serum degradation for at least two weeks when a disclosed therapeutic chimeric and/or particle and/or composition is exposed at 37° C. to a composition comprising a 1:1 weight ratio of human serum to water.

Disclosed modified viral core proteins may include a modified structural core portion comprises a conjugation site allowing attachment of a chemical linker moiety and/or a modified structural core portion may comprise one or more stability modifications. In some embodiments, a modified structural core portion may include about 149 or about 138 amino acids. Disclosed modified viral core proteins may be a modified hepatitis virus core protein, for example, modified hepatitis B core protein.

Disclosed modified hepatitis B core proteins may include at least one mutation in an immunogenic epitope (e.g., a mutation such that at least one amino acid of SEQ ID NO. 1 or SEQ. ID NO. 2 is independently selected from the group consisting of asparagine 21, alanine 21, valine 21, alanine 27, isoleucine 27, valine 60, and leucine 97) and at least one mutation in a structural core protein (e.g., a mutation such that at least one amino acid of SEQ ID NO. 1 or SEQ. ID NO. 2 is independently selected from the group consisting of phenylalanine 23, aspartic acid 29, threonine 33, leucine 37, valine 120, valine 124, arginine 127, tyrosine 132, glutamic acid 77, aspartic acid 78 and alanine 80 is changed to a cysteine). Disclosed modified hepatitis B core proteins may further comprise a protease recognition site replacing amino acids 79 and 80 of said HBV core proteins of SEQ ID NO. 1 or SEQ ID NO. 2. In an exemplary embodiment, said protease recognition site is a thrombin recognition site or a factor Xa recognition site.

Disclosed modified viral core proteins may include a modified tail portion that comprises about 10 to about 35 amino acids. In some embodiments, a modified tail portion comprises truncations, substitutions and/or additions of amino acids as compared to a wild type tail portion. For example, a modified tail portion may include about 4 to about 30 lysines, e.g., may include a lysine domain of about 5 to about 20 lysines, e.g., about 9 lysines. In some embodiments, a disclosed modified tail portion may comprise a histidine tag of about 1 to about 10 histidines, e.g., about 5 to about 6 histidines. Disclosed modified tail portions may further comprise a linker segment comprising about 1 to about 20 amino acids.

The disclosed therapeutic agents may be a nucleic acid, a protein, or a small molecule. Exemplary chimeric therapeutics disclosed herein may include a nucleic acid that is e.g., an inhibiting nucleic acid, and/or is chemically modified, e.g., has a thiophosphate linkage. Contemplated nucleic acids that may, e.g., form part of disclosed chimeric therapeutics, particles and/or compositions include double stranded RNA, antisense nucleic acid, hairpin RNA, and microRNA. In some embodiments, a contemplated nucleic acid may be about 25 to about 45 bases in length, or about 25 to about 35 bases in length, or about 25 to about 30 bases in length. In another embodiment, a contemplated nucleic acid may be about 10 to about 30 bases in length, or about 15 to about 25 bases in length, or about 19 to about 23 bases in length.

Disclosed herein are compositions that include disclosed particles and/or chimeric therapeutics and a pharmaceutically acceptable carrier.

For example, disclosed herein is a therapeutic composition that includes a particle formed from a plurality of disclosed chimeric therapeutics, wherein the particle further comprises a coating; and a pharmaceutically acceptable excipient. In another embodiment, a therapeutic composition is provided that comprises: a particle formed from at least: i) a first discrete number of modified viral core proteins; and ii) a second discrete number of nucleic acids each bound to one of said modified viral core proteins. In some embodiments, the nucleic acids bound to said modified viral core proteins may be substantially nonimmunogenic. In other embodiments, disclosed particles may include optionally, a coating associated with said particle and/or a pharmaceutically acceptable excipient. The first discrete number may be about, for example, 180 to about 250, or about 150 to about 190. The second discrete number may be about, for example, 2 to about 60, or about 8 to about 20, or about 14 to about 18.

In another embodiment, a therapeutic particle is provided that includes a plurality of viral core proteins each comprising a structural core portion comprising at least one mutation or modification in an immunogenic epitope and a modified tail portion, wherein the structural core portions form a capsid; and the modified tail portions are substantially disposed within said capsid; and a plurality of nucleic acids, bound to said modified tail portion, wherein the nucleic acids are resistant to degradation with a nuclease when said particle is placed in an aqueous solution. For example, a particle comprises about 180 to about 250 viral core proteins, or about 170 to about 190 viral core proteins. In another embodiment, the particle includes about 3 to about 50 nucleic acids, or about 6 to about 28 nucleic acids. A chemical linker moiety, in some embodiments, may be bound to the capsid, e.g., a chemical linker moiety may be formed by contacting said capsid with PE-maleimide.

A coating may be provided, in some embodiments, that is, e.g., associated with a disclosed particle, and may include one or more lipids. For example, in an embodiment, at least one lipid molecule may be covalently bound through lipid linker moiety to one of the viral core proteins that form, e.g., the particle Disclosed coatings may include, cholesterol or one or more neutral lipids. In some embodiments, the coating comprises HSPC and/or POPG.

Also provided herein are methods for targeting expression in a cell comprising administering to the cell, a chimeric therapeutic, a therapeutic particle or composition disclosed herein. Claims appended to this disclosure are incorporated by reference and form part of this disclosure.

DETAILED DESCRIPTION

Figure 1:
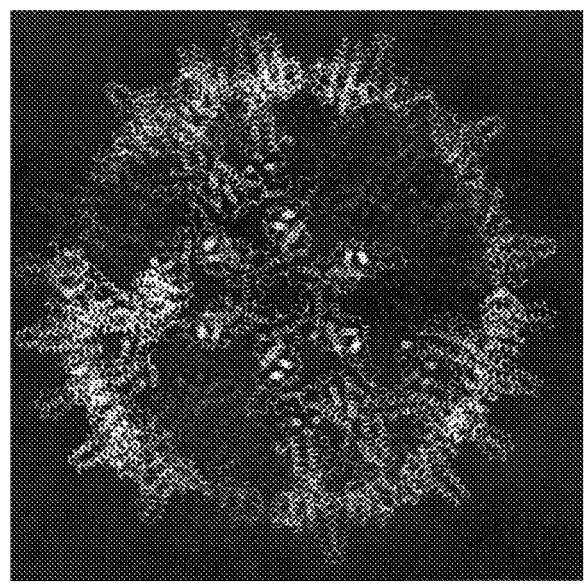
FIG. 1 is a computational reconstruction depicting wild-type Hepatitis B Virus (HBV) capsid reconstructed from electron density maps of the full size HBV dimer from the perspective of looking down at the 6-fold axis.

The present disclosure is generally directed, at least in part, to chimeric therapeutics, e.g., a therapeutic that comprises a modified viral core protein comprising at least one mutation or modification in an immunogenic epitope and a therapeutic agent, e.g., a nucleic acid associated with the modified viral core protein, and particles and/or compositions that include such chimeric therapeutics. The disclosed modified viral core protein comprises at least one mutation or modification in an immunogenic epitope that reduces the immunogenicity of the modified viral core protein compared to a wild type viral core protein. Thus, the disclosed modified viral core proteins may be capable of evading the immune system and, therefore, the disclosed chimeric therapeutics may be referred to as stealth therapeutic agents.

Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine such as egg phosphatidylcholine or hydrogenated soy phosphatidylcholine, phosphatidylethanolamine, phosphatidylserine, phosphatidylinositol, phosphatidic acid, pahnitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, phosphatidyl glycerol, monosialoganlgolioside, spingomyelin, dimyristoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipid described above can be mixed with other lipids including triglycerides and sterols.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). Examples of cationic lipids include, but are not limited to, N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 1,2-dilinoleyloxy-N,N-dimethylaminopropane (DLinDMA), 1,2-dilinolenyloxy-N,N-dimethylaminopropane (DLenDMA), and mixtures thereof. In certain embodiments, anionic lipids can be neutral on the surface with an internal negative charge.

An "effective amount" or "therapeutically effective amount" of a therapeutic, composition or particle contemplated herein is an amount sufficient to produce a desired effect, e.g., inhibition of expression of a target in comparison to the normal expression level detected in the absence of administration. The therapeutically effective amount will vary depending upon the subject and disease condition being treated, the rate of target transcript turnover, the weight and age of the subject, the severity of the disease condition, the manner of administration and the like. For example, certain compositions of the present invention may be administered in a sufficient amount to produce a reasonable benefit/risk ratio applicable to such treatment.

The term "gene" refers to a nucleic acid (e.g., DNA or RNA) sequence that comprises partial length or entire length coding sequences necessary for the production of a polypeptide or precursor polypeptide.

The term "inhibitory nucleic acid" refers to a single-stranded or double-stranded RNA, siRNA (small interfering RNA), shRNA (short hairpin RNA), or antisense RNA, or a portion thereof, or an analog or mimetic thereof, that when administered to a mammal results in a decrease (e.g., by 10%, 25%, 50%, 75%, 90%, 95%, or 100%) in the expression of a target. Typically, an inhibitory nucleic acid comprises or corresponds to at least a portion of a target nucleic acid or gene, or an ortholog thereof, or comprises at least a portion of the complementary strand of a target nucleic acid or gene. An inhibitory nucleic acid typically has substantial or complete identity or homology (e.g., 60%, 70%, 80%, 85%, 90%, 95%, 99% or 100%) to the target nucleic acid.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "modulation" is art-recognized and refers to up regulation (i.e., activation or stimulation), down regulation (i.e., inhibition or suppression) of a response, or the two in combination or apart.

The term "reduce" refers to any reduction, decrease, inhibition, or suppression of a response, e.g., an immune response.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chromosomal DNA, or derivatives and combinations of these groups. RNA may be in the form of inhibitory RNA, mRNA, tRNA, rRNA, tRNA, vRNA, and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). "Nucleotides" contain a deoxyribose (DNA) or ribose (RNA), a sugar, a nitrogenous base, and a phosphate group or analog thereof. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

A "patient," "subject" or "host" to be treated by a disclosed method may mean either a human or non-human animal.

The term "pharmaceutically acceptable excipient" is art-recognized and refers to a pharmaceutically-acceptable material, composition or vehicle, such as a liquid or solid filler, diluent, excipient, or solvent, involved in carrying or transporting any subject composition or component thereof from one organ, or portion of the body, to another organ, or portion of the body. Each excipient must be "acceptable" in the sense of being compatible with the subject composition and its components and not injurious to the patient. Some examples of materials which may serve as pharmaceutically acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "portion" when used in reference to a protein refers to fragments of that protein.

"Target" refers to a nucleic acid or variants thereof required for expression of a polypeptide that is the site or potential site of therapeutic intervention by a therapeutic agent; or a non-peptide entity including a microorganism, virus, bacterium, or single cell parasite (wherein the entire genome of a virus may be regarded as a target); and/or a naturally occurring interfering RNA or microRNA or precursor thereof. For example, target may refer to the sequence of nucleotides corresponding to the portion of a gene's coding mRNA.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

Chimeric Therapeutics

The chimeric therapeutics disclosed herein may be capable of forming a particle, which may be a nanoparticle, for example, a plurality of disclosed chimeric therapeutics may self-assemble in to a particle or capsid. Such therapeutic chimerics may include a modified viral core protein comprising at least one mutation or modification in an immunogenic domain with a therapeutic agent associated with, e.g., bound to, the modified viral core protein. The therapeutic agent may be bound to the modified viral core protein by Coulombic forces or covalent bonding.

Nucleic acids associated with a disclosed viral core protein may be, e.g., substantially homologous to a target, e.g., a target gene. In some embodiments, the nucleic acid, when bound to the modified viral core protein, may be substantially non-immunogenic. For example, a nucleic acid bound to a modified viral core protein may be substantially less immunogenic as compared to an identical unbound nucleic acid.

In another embodiment, a chimeric therapeutic is provided that includes an, e.g., modified viral core protein and a nucleic acid bound to the modified viral core protein (e.g., to a modified tail portion of the viral core protein) with a binding affinity that allows release of the nucleic acid when the chimeric therapeutic is administered in vivo.

The nucleic acid of a chimeric therapeutic, wherein bound to a disclosed modified viral core protein, may be resistant in an aqueous solution to degradation with a nuclease, e.g., benzoase. For example, a nucleic acid bound to a disclosed modified viral core protein at 1.9 units/nmole, 100 unit/nmole, 500 units/nmole or 945 units/nmole and incubated for 1 hour at room temperature does not substantially degrade as compared to an identical, but unbound, nucleic acid. In other embodiments, a nucleic acid bound to a disclosed modified viral core protein is substantially protected from serum degradation in vivo or in vitro, for example, when a chimeric therapeutic is exposed at 37° C. to a composition comprising a 1:1 weight ratio of human serum to water.

Disclosed chimeric therapeutics may be substantially free of nuclease and/or may be substantially free of endogenous nucleic acids.

Viral Core Protein

Any viral core protein that is capable, either alone or with another viral core protein, of self-assembling into a capsid is suitable for use in the disclosed therapeutics. Exemplary viral core proteins include hepatitis core proteins such as human and duck Hepatitis B Virus core protein, Hepatitis C Virus core protein, and may also include Human Papilloma Virus type 6 L1 and L2 protein and cowpea chlorotic mottle virus coat protein. An exemplary viral core protein is Hepatitis B Virus (HBV) core protein (C-protein). It may be appreciated that different strains of HBV may have slight variations in the sequence of C-protein, and that any strain of HBV C-protein can be utilized. Exemplary sequences of HBV-C include SEQ ID NO: 1 and 2, with amino acid sequence 1 to 183 include NCBI Protein Database Accession Number BAD86623 and AY741795.

```
                                             (SEQ ID NO: 1)
MDIDPYKEFGASVELLSFLPSDFFPSIRDLLDTASALYREALESPEHCSP

HHTALRQAILCWGELMNLATWVGSNLEDPASRELVVSYVNVNMGLKIRQL

LWFHISCLTFGRETVLEYLVSFGVWIRTPPAYRPPNAPILSTLPETTVVR

RRGRSPRRRTPSPRRRRSQSPRRRRSQSRESQC (SEQ ID NO: 2)
MDIDPYKEFGATVELLSFLPSDFFPSVRDLLDTASALYREALESPEHCSP

HHTALRQAILCWGELMTLATWVGNNLEDPASRDLVVNYVNTNMGLKIRQL

LWFHISCLTFGRETVLEYLVSFGVWIRTPPAYRPPNAPILSTLPETTVVR

RRGRSPRRRTPSPRRRRSQSPRRRRSQSRESQC
```

Modified viral core proteins contemplated herein comprise at least one mutation or modification in an immunogenic epitope compared to a wild type viral core protein. An immunogenic epitope refers to any antigenic determinant or subunit thereof that is capable of inducing an immune response. As described herein, at least one mutation or modification in an immunogenic epitope reduces the immunogenicity of the viral core protein. For example, at least one mutation or modification in an immunogenic epitope may down regulate a humoral immune response (e.g., B cell activation), a cell mediated immune response (e.g., T cell activation), or both. In some embodiments, a mutation or modification in an immunogenic epitope reduces the binding capacity of a T cell receptor or B cell receptor to bind the viral core protein. In other embodiments, a mutation or modification in an immunogenic epitope may result in the modified viral core protein not being recognized by a B cell or a T cell. A mutation or modification in an immunogenic epitope may also reduce the affinity of a MHC (also referred to as HLA in humans) class I or class II molecule for peptide or antigen thereby reducing an immune response. In other embodiments, a mutation or modification in an immunogenic epitope may reduce the production of neutralizing antibodies thus preventing the inhibition and/or destruction of a modified viral core protein. In certain embodiments, a mutation or modification in an immunogenic epitope may result in the modified viral core protein not being recognized by other immune cells (e.g., phagocytes (macrophages, neutrophils, and dendritic cells), natural killer cells, mast cells, and/or eosinophils). In another embodiment, a mutation or modification in an immunogenic epitope may result in the viral core protein not being capable of inducing an inflammation response (e.g., cytokine production). A mutation and/or modification in an immunogenic epitope may allow the viral core protein to escape immune clearance. Further, modified viral core proteins as described herein may be referred to as stealth viral core proteins because they down regulate an immune response(s) and may evade the immune system.

Immunogenic epitopes that may be mutated and/or modified on a viral core protein include any antigenic determinant or subunit thereof that is capable of induing an immune response. Exemplary immunogenic epitopes that may be mutated or modified on a viral core protein include T cell epitopes, B cell epitopes, and HLA-peptide binding sites. Exemplary T cell epitopes include T helper cell epitopes, cytotoxic T cell epitopes, and minor T cell sites. Mutations in an immunogenic epitope may include deletions, substitutions and/or insertions of amino acids as compared to the wild type viral core protein. Modifications in an immunogenic epitope may include chemical modifications of amino acids as compared to the wild type viral core protein.

Viral core proteins as described herein may be mutated or modified to comprise at least 1, 2, 3, 4, 5, 6, 7, 8, 9, 10 or more mutations and/or modifications in an immunogenic epitope. In certain embodiments, modified viral core proteins may be mutated and/or modified in only a B cell epitope. In other embodiments, modified viral core proteins may be mutated and/or modified in only a T cell epitope. In still other embodiments, modified viral core proteins may be mutated and/or modified in at least one B cell epitope and at least one T cell epitope.

In certain embodiments, the HBV core protein is mutated or modified in at least one immunogenic epitope. Immunogenic epitopes that may be mutated in the hepatitis B core protein to reduce immunogenicity of the viral core protein may include T helper cell epitopes, cytotoxic T cell epitopes, minor T cell sites, and B cell epitopes. Exemplary T helper cell epitopes that may be mutated in the hepatitis B core protein comprise amino acids 1-20 of SEQ ID NO. 1 or SEQ ID NO. 2 and amino acids 50-69 of SEQ ID NO. 1 or SEQ ID NO. 2. Exemplary cytotoxic T cell epitopes that may be mutated in the hepatitis B core protein comprise amino acids 18-27 of SEQ ID NO. 1 or SEQ ID NO. 2, amino acids 117-131 of SEQ ID NO. 1 or SEQ ID NO. 2, and amino acids 141-151 of SEQ ID NO. 1 or SEQ ID NO. 2. Exemplary minor T cell sites that may be mutated in the hepatitis B core protein comprise amino acids 20-34, 28-47, 70-89, 82-101, 100-119, 140-155, and 169-183 of SEQ ID NO. 1 or SEQ ID NO. 2. Exemplary B cell epitopes that may be mutated in the hepatitis B core protein comprise amino acids 74-89 of SEQ ID NO. 1 or SEQ ID NO. 2, amino acids 107-118 of SEQ ID NO. 1 or SEQ ID NO. 2, and amino acids 130-138 of SEQ ID NO. 1 or SEQ ID NO. 2.

In certain embodiments, the hepatitis B core protein is mutated to reduce immunogenicity of the viral core protein (e.g., down regulating a T cell response to the viral core protein) such that at least one amino acid of SEQ ID NO. 1 or SEQ. ID NO. 2 is independently selected from the group consisting of histidine 5, threonine 5, tyrosine 9, proline 11, alanine 13, cysteine 17, asparagine 21, alanine 21, valine 21, alanine 26, proline 26, alanine 27, isoleucine 27, glutamine 52, valine 53, valine 54, isoleucine 55, valine 55, leucine 57, isoleucine 57, threonine 59, phenylalanine 59, valine 60, isoleucine 60, valine 63, lysine 64, isoleucine 65, valine 65, glutamine 66, isoleucine 66, isoleucine 68, valine 68, leucine 97, cysteine 146, isoleucine 148, isoleucine 149, leucine 149, and cysteine 151.

One of skill in the art understands that hepatitis B viral core proteins may refer to many different amino acid sequences. It is appreciated that in some embodiments, a hepatitis B viral core protein may include an amino acid mutation that in a disclosed different HBV viral core protein would be considered wild type. For example, an isoleucine at amino acid position 27 in SEQ ID NO: 1 is typically considered wild type, but an isoleucine at amino acid position 27 in SEQ ID NO: 2 may be considered a mutation.

In other embodiments, the hepatitis B core protein is mutated to reduce immunogenicity of the viral core protein (e.g., to down regulate a B cell response to the viral core protein) such that at least one amino acid of SEQ ID NO. 1 or SEQ. ID NO. 2 is independently selected from the group consisting of glutamine 77, alanine 84, serine 84, glutamine 84, serine 87, glycine 87, tyrosine 107, arginine 108, aspartic acid 113, proline 120, threonine 130, valine 131, proline 131, glutamine 135, serine 135, and proline 137.

In an exemplary embodiment, the hepatitis B core protein is mutated to reduce immunogenicity of the viral core protein such that at least one amino acid of SEQ ID NO. 1 or SEQ. ID NO. 2 is independently selected from the group consisting of asparagine 21, alanine 21, valine 21, alanine 27, isoleucine 27, valine 60, and leucine 97.

In another embodiment, the hepatitis B core protein may be mutated or modified at amino acid 44, 71, 72, 73, 74, 75, 76, 77, 78, 81, 82, 83, 84, 85, 92, 149, and/or 150 of SEQ ID NO. 1 or SEQ ID NO. 2. A mutation at any of these positions includes deletions, substitutions and/or insertions of amino acids as compared to the wild type viral core protein. In another embodiment, the mutation is an insertion of at least 1, 2, 3, 4, 5, 10 or more amino acids. Insertion of an amino acid sequence may be made in any immunogenic domain such as a B cell epitope or a T cell epitope to reduce or inhibit recognition of the epitope by the immune system.

In another embodiment, the mutation is a deletion of at least 1, 2, 3, 4, 5, 10 or more amino acids in an immunogenic epitope. Deletion of an amino acid sequence may be made in any immunogenic domain such as a B cell epitope or a T cell epitope to reduce or inhibit recognition of the epitope by the immune system.

Hepatitis B core proteins may be mutated at amino acid 44, 71, 72, 73, 74, 75, 76, 77, 78, 81, 82, 83, 84, 85, 92, 149, and/or 150 of SEQ ID NO. 1 or SEQ ID NO. 2 by substitution of an amino acid. Substitutions may be conservative or non-conservative amino acid changes. Mutations at these positions (e.g., insertions, deletions, or substitutions) may be alone or in combination with another mutation or modification that reduces immunogenicity of the viral core protein.

Modified viral core proteins, such as a modified hepatitis B core protein, may be also be modified by a chemical modification. Chemical modifications may include covalent modifications (e.g., conjugation to another protein, protein domain, lipid, polysaccharide, or polymer including synthetic or natural polymers) or non-covalent modifications. Exemplary chemical modifications may include polymer modified viral core proteins, lipid modified viral core proteins, peptide modified viral core proteins, or saccharide modified viral core proteins (e.g., branched and unbranched polysaccharides), such as phosphatidyl ethanolamine-maleimide (PE-maleimide or PE-mal), polyethylene glycol (PEG), poly-alanine, N-ethylmaleimide (NEM), fluorescein-maleimide (FL-maleimide or FL-Mal), gamma-maleimide-butrylamide (GMBA).

Exemplary polymers suitable for use include, but are not limited to, natural polymers, synthetic polymers, branched polymers, and co-polymers such as polyethylene glycol (PEG), polystyrene, poly-methyl-methacrylate, poly-vinyl acetate, and poly-vinyl ethyl ether, poly-aspartic acid, poly-aspartic acid hydrazide, poly-glutamic acid, poly-glutamic acid hydrazide, polyserine, polyglycine, poly-cytidylic acid, poly-asparagine, poly-glutamine, poly-acrylic acid, poly-acrylic acid hydrazide, poly-N-(2-hydroxypropyl) methacrylamide (poly-HPMA) and derivatives thereof.

Exemplary lipids suitable for use include, but are not limited to, a neutral lipid, an anionic lipid, and/or a cationic lipid such as those discussed above. For example, a neutral lipid and/or an amphipathic lipid, for example, a phospholipid such as phophatidyl serine, may be covalently bonded to a lipid linker moiety. Exemplary phospholipids suitable for use include, but are not limited to, hydrogenated soy phosphatidylcholine (HSPC), egg phosphatidylcholine (EPC), phosphatidyl ethanolamine (PE), phosphatidyl glycerol (PG), phosphatidyl inositol (PI), monosialogangolioside, spingomyelin (SPM), distearoylphosphatidylcholine (DSPC), dimyristoylphosphatidylcholine (DMPC), or dimyristoylphosphatidylglycerol (DMPG).

Exemplary proteins, peptides and peptide domains suitable for use include, but are not limited to, immunoglobulin domains, fibronectin domains, albumin, poly-serine-alanine (poly-ser-ala) domains, and poly-threonine-alanine (poly-thr-ala) domains. Exemplary poly-serine-alanine domains and/or poly-threonine-alanine domains (e.g., serine-alanine or threonine-alanine dipeptide repeats) may include about 10 to about 1000 amino acids, or about 30 to about 800 amino acids, or about 50 to about 500 amino acids, e.g., at least 50, 100, 150, 200, 250, 300, 350, 400, 450, 500 or more amino acids.

Exemplary saccharides (e.g., sugars) suitable for use include, but are not limited to, natural sugars or synthetic sugars such as monosaccharides, disaccharides, polysaccharides, amino sugars, sulfosugars, sugar acids, and sugar alcohols. Exemplary monosaccharides suitable for use include, but are not limited to glucose, mannose, galactose, glyceraldehyde, erythrose, threose, ribose, arabinose, xylose, lyxose, allose, altrose, gulose, idose, talose, dihydroxyacteone, erythrulose, ribulose, xylulose, fructose, sobose, tagatose, piscose, ketoheptoses, mannopetulose, and sedoheptulose. Sugars may be in the D or L configuration. Exemplary disaccharides suitable for use include, but are not limited to sucrose, lactose, maltose, trehalose, cellobiose, kojiboise, nigerose, isomaltose, β,β-trehalose, sophorose, laminaribiose, gentiobiose, turanose, matulose, palatinose, gentiobiulose, mannobiose, melibiose, rutiose, rutinulose, and xylobiose. Exemplary polysaccharides suitable for use include, but are not limited to glucose polymers (e.g., starches), glycogen, and cellulose. Exemplary amino sugars suitable for use include, but are not limited to galactosamine, glucosamine, sialic acid and N-acetylglucosamine. Exemplary sulfosugars suitable for use include, but are not limited to sulfoguinovose. Exemplary sugar acids suitable for use include, but are not limited to ascorbic acid, gluconic acid, neuraminic acid, ketodeoxyoctulosconic acid, glucuronic acid, galacturonic acid, mesogalactaric acid (Mucic acid) and D-glucaric acid (Saccharic acid). Exemplary sugar alcohols suitable for use include, but are not limited to glycol, glycerol, arabitol, mannitol, sorbitol, ribitol, lactitol, and maltitol.

In certain embodiments, at least 1, 2, 3, 4, 5, 6, 7, 8, 9, or 10 or more amino acids in an immunogenic epitope may be chemically modified. The at least one chemical modification may be covalently bound through a chemical linker moiety, e.g, a bifunctional linker or a lipid linker moiety, to a viral core protein, e.g., an immunogenic domain of a disclosed viral core protein. Exemplary chemical linkers include moieties such as those formed by contacting a cysteine residue with a maleimide containg compound such as phosphatidylethanolamine-maleimide (PE-maleimide or PE-mal). Exemplary lipid linker moieties may be formed from contacting, e.g., a succinimidyl derivative such as succinimidyl-4-(p-maleimidophenyl)butyrate (SMPB) or m-maleimidobenzoyl-N-hydroxysuccinimide ester with an immunogenic domain of the viral core protein.

Viral core proteins as described herein may also be modified to include at least one mutation in an immunogenic epitope and at least one chemical modification in an immunogenic epitope.

A modified viral core protein comprising at least one mutation or modification in an immunogenic region contemplated herein may include a structural core protein and a tail portion. Such a modified viral core protein or stealth viral core protein may include a modified structural core as compared to the wild type structural core, and/or a modified tail portion as compared to the wild type tail portion. For example, a modified viral core protein for use in the disclosed therapeutics may include a modified structural core portion and a tail portion, e.g., a carboxyl terminal tail portion and/or a N-terminal tail portion, or may include a structural core portion and a modified tail portion, or may include a modified structure core portion and a modified tail portion. In some embodiments, the structural core portions of modified viral core proteins may form a capsid, and the tail portion of the modified viral core proteins may be substantially disposed within the capsid. For example, a modified viral core protein, e.g., a modified HBV C protein may include a modified structural core portion and a modified C-terminal tail portion. In other embodiments, an inward facing surface of formed capsid may act as a modification location. Such modifications can include alterations, truncations and/or mutations, etc. to the structural core portion and/or the modified tail portion of the viral core protein. Such modifications may enhance the structural and functional characteristics of the HBV C-protein and may provide more effective therapeutics, e.g., a modified viral core protein is bound to a nucleic acid, e.g., an inhibitory nucleic acid. In other embodiments, a modified, e.g., C-terminal tail portion of a viral core protein (e.g., HBV) may provide a therapeutic that is substantially free of endogenous nucleic acids and/or substantially free of nuclease. These modifications to the HBV C-protein can be made or engineered according to any method known in the art, including without limitation genetic engineering, chemical modifications, etc.

Modification to the viral core protein, for example, a viral core protein with a modified tail portion, may also optimize binding and release of a nucleic acid bound to a viral core protein. For example, the binding affinity of a nucleic acid bound to a disclosed modified viral core protein may be about 50 nM to about 500 nM, or about 55 nM to about 400 nM, at 20 mM NaHCO$_3$, and a pH of 9.5, or may be about 50 nM to about 500 nM, or about 55 nM to about 400 nM, at 20 mM (CH$_2$OH)$_3$CNH$_2$, and a pH of 7.7.

Disclosed viral core proteins can be expressed and purified using common molecular biology and biochemistry techniques. For example, recombinant expression vectors can be used which can be engineered to carry a viral core protein gene into a host cell to provide for expression of the viral core protein. Such vectors, for example, can be introduced into a host cell by transfection means including, but not limited to, heat shock, calcium phosphate, DEAE-dextran, electroporation or liposome-mediated transfer. Recombinant expression vectors include, but are not limited to, *Escherichia coli* based expression vectors such as BL21 (DE3) pLysS, COS cell-based expression vectors such as CDM8 or pDC201, or CHO cell-based expression vectors such as pED vectors. A C-protein gene coding region, for example, can be linked to one of any number of promoters in an expression vector that can be activated in the chosen cell line. In an embodiment, a cassette (capsid gene and promoter) is carried by a vector that contains a selectable marker such that cells receiving the vector can be identified.

For example, promoters to express the capsid proteins within a cell line can be drawn from those that are functionally active within the host cell. Such promoters can include, but are not limited to, a T7 promoter, a CMV promoter, a SV40 early promoter, a herpes TK promoter, and others known in recombinant DNA technology. Inducible promoters can be used, and include promoters such as metallothionine promoter (MT), mouse mammary tumor virus promoter (MMTV), and others known to those skilled in the art. Exemplary selectable markers and their attendant selection agents can be drawn, for example, from the group including, but not limited to, ampicillin, kanamycin, aminoglycoside phosphotransferase/G418, hygromycin-B phosphotransferase/hygromycin-B, and amplifiable selection markers such as dihydrofolate reductase/methotrexate and others known to skilled practitioners.

A variety of eukaryotic, prokaryotic, insect, plant and yeast expression vector systems (e.g., vectors which contain the necessary elements for directing the replication, transcription, and translation of viral core protein coding sequences) can be utilized by those skilled in the art to express viral core protein coding sequences. These include but are not limited to microorganisms such as bacteria transformed with recombinant bacteriophage DNA, plasmid DNA or cosmid DNA expression vectors containing the capsid protein coding sequences; yeast transformed with recombinant yeast expression vectors containing the capsid protein coding sequences; insect cell systems infected with recombinant virus expression vectors (e.g., baculovirus) containing the capsid protein coding sequences; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the capsid protein coding sequences.

The wildtype HBV C protein is 183 amino acids of which the first 149 amino acids form a globular fold followed by a 35 amino acid C-terminal tail. In some embodiments, the first 149 amino acids of a hepatitis B core protein, e.g., a modified viral core protein, may substantially form a structural core portion, which may be modified, as discussed below. When a viral core protein includes a structural core portion of about 149 amino acids, combined with a tail portion as discussed below, a capsid or cage structure with e.g., a substantial T=4 geometry may be formed from e.g., a plurality of viral core proteins. In another embodiment, a structural core portion includes the first 138 amino acids of a modified hepatitis B core protein, e.g., a modified viral core protein, and combined with a tail portion below, of which a plurality of such viral core proteins may form a capsid with e.g., a substantial T=3 geometry. Both types of structural core portion are contemplated.

A. Modified Tail Portions

Various modifications of the terminal tails of the disclosed viral core protein are contemplated. For example, the C-terminal tail of a hepatitis B core protein, can be engineered to, for example, provide appropriate properties for binding a nucleic acid to the modified viral core protein. For example, a therapeutic chimeric is provided that includes a viral core protein with a modified tail portion and a nucleic acid associated with, e.g., bound to the modified tail portion.

The 35 amino C-terminal tail of the wild type HBV-C protein is presumed to hang inside the fully formed viral capsid and bind the viral nucleic acid, and is shown below:

SEQ ID NO: 3: C-terminal tail amino acid sequence 150 to 183

RRRGRSPRRRTPSPRRRRSQSPRRRRSQSRESQC

This wild type tail can be modified, truncated, and/or mutated to provide a modified tail portion, that, together with a structural core portion, provides a complete viral core protein for use in the disclosed therapeutic chimerics, particles, and compositions.

Poly-Lysine Tail

In some embodiments, a modified tail portion, e.g., a modified C-terminal tail portion, may include a modification that includes one or more poly-lysines. For example, the modified tail portion may include about 4 to about 30 lysines, or about 5 to about 20 lysines, e.g., about 7, 8, 9, or 10 lysines.

In some embodiments, the modified tail portion may include one or more lysine domains. For example, each poly-lysine domain may comprise about one to about thirty lysine residues. In some embodiments the poly-lysine domain may comprise about 5 lysine residues to about 20 lysine residues. When more than one polylysine domain is present, the poly-lysine domains can be separated by about 1 to about 20 amino acid residues. In some embodiments, where more than one polylysine domain is present the each poly-lysine domain can comprise about 4 lysine residues to about 20 lysine residues (or any specific amino acid length disposed with the range). In some embodiments, at least four or at least five consecutive lysine residues are included in a modified C-terminal tail.

Polylysines and poly-lysine domains and/or a polyhistidine tag can form part of a modified C-terminal tails separately or in combination. A polyhistidine tag may, in some embodiments, facilitate purification of the proteins.

Exemplary C-terminal tail portions include those having e.g., 5 lysines (K5), 7 lysines (K7), 9 lysines (K9), 10 lysines (K10), 11 lysines (K11), 13 lysines (K13), 20 lysines (K20). Other exemplary C-terminal tail portions include those with a poly-lysine region with nine lysines alternating with a poly-alanine region with nine alanines (KA9), a poly-lysine region with nine lysines alternating with a poly-glycine region with nine glycines (KG9) and a poly-lysine region with nine lysines interrupted by a sequence of at least four amino acids between the fourth and fifth lysines (K4-5). In some embodiments, an about four amino acid stretch between the fourth and fifth lysines of the K4-5 tail may be amino acids Ser-Gln- Ser-Pro. For example, a modified tail portion may be represented by:

KLAAA[KKKKK]$_i$LE[H]$_j$     SEQ ID NO: 4 wherein i is an integer from 4 to 21, and j is an integer from 0 to 10. For example, i may be 5, 6, 7, 8, 9, 10, 11, 12, 13, 14, 15, 16, 17, 18, 19 or 20; j may be 0, 1, 2, 3, 4, 5 or more. Such modified tail portion may form part of a modified viral core protein as shown below together with the corresponding nucleic acid sequences. The viral core proteins are contemplated for use in the therapeutic chimerics, particles, and compositions disclosed herein. Exemplary modified tail portions (and associated nucleic acids include:

```
K5
                                                        (SEQ ID NO: 5)
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAG AAA AAG AAG CTC GAG

CAC CAC CAC CAC CAC CAC

K5 (contains E77C}
                                                        (SEQ ID NO: 6)
MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKLEHHHHHH

K7
                                                        (SEQ ID NO: 7)
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAG AAG AAA AAG AAG AAG

CTC GAG CAC CAC CAC CAC CAC CAC

K7 (contains E77C)
                                                        (SEQ ID NO: 8)
MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKKKLEHHHHHH

K9
                                                        (SEQ ID NO: 9)
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT
```

-continued

```
ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAA AAG AAG AAG AAA AAG

AAG AAG CTC GAG CAC CAC CAC CAC CAC CAC
```

K9 (contains E77C)
(SEQ ID NO: 10)

MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKKKKLEHHHHHH

K10
(SEQ ID NO: 11)

```
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAA AAG AAG AAG AAG AAG

AAG AAG AAA CTC GAG CAC CAC CAC CAC CAC CAC
```

K10
(SEQ ID NO: 12)

MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKKKKKLEHHHHHH

K11
(SEQ ID NO: 13)

```
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAG AAG AAA AAG AAG AAG

AAA AAG AAG AAG CTC GAG CAC CAC CAC CAC CAC CAC
```

K11
(SEQ ID NO: 14)

MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKKKKKKLEHHHHHH

K13

(SEQ ID NO: 15)

ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAA AAG AAG AAG AAA AAG

AAG AAG AAA AAG AAG AAG CTC GAG CAC CAC CAC CAC CAC CAC

K13

(SEQ ID NO: 16)

MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKKKKKKKLEHHHHHH

K20

(SEQ ID NO: 17)

ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG AAA AAG AAG AAG AAG AAG

AAG AAG AAA AAG AAG AAG AAG AAG AAG AAG AAA AAG CTC GAG CAC CAC CAC

CAC CAC CAC

K20

(SEQ ID NO: 18)

MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKKKKKKKKKKKKKKKKKKLEHHH

HHH

In other embodiments, a modified tail portion may be formed from alternating lysines. For example, in one embodiment, a modified tail portion can be represented by:

DKLAA[AK]$_p$LE[H]$_j$   SEQ ID NO: 32 wherein p is an integer from 5 to 12, and j is an integer from 0 to 10. For example, p may be 5, 6, 7, 8, 9, 10, 11, or 12; j may be 0, 1, 2, 3, 4, 5 or more.

For example, a viral core protein may be represented by a viral core protein selected from:

KA9 (SEQ ID NO: 19)

ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

```
CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG GCA AAG GCA AAG GCG AAG

GCA AAG GCT AAG GCG AAG GCT AAG GCG AAG CTC GAG CAC CAC CAC CAC CAC CAC
```

KA9 (SEQ ID NO: 20)

```
MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKAKAKAKAKAKAKAKLEHHHHHH
```

KG9 (SEQ ID NO: 21)

```
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG GAC AAG CTT GCG GCC GCA AAG GGT AAG GGC AAG GGT AAG

GGC AAG GGT AAG GGC AAG GGC AAG GGT AAG CTC GAG CAC CAC CAC CAC CAC CAC
```

KG9 (SEQ ID NO: 22)

```
MDIDPYKEFGATVELLSFLPSDFFPSVRDLLDTASALYREALESPEHCSPHHTALRQAIL

CWGELMTLATWVGNNLCDPASRDLVVNYVNTNMGLKIRQLLWFHISCLTFGRETVLEYLV

SFGVWIRTPPAYRPPNAPILSTLPETTVVDKLAAAKGKGKGKGKGKGKGKGKLEHHHHHH
```

K4-5 (SEQ ID NO: 23)

```
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG
```

```
GAA ACC ACC GTT GTG GAC AAG CTT GCG GCC GCA AAG AAA AAG AAG AGC CAG AGC
CCG AAG AAG AAG AAG AAA CTC GAG CAC CAC CAC CAC CAC CAC
```

K4-5 (SEQ ID NO: 24)

MDIDPYKEFGATVELLSFLPSDFFPSVRDLLDTASALYREALESPEHCSPHHTALRQAIL
CWGELMTLATWVGNNLCDPASRDLVVNYVNTNMGLKIRQLLWFHISCLTFGRETVLEYLV
SFGVWIRTPPAYRPPNAPILSTLPETTVVDKLAAAKKKKSQSPKKKKKLEHHHHHH

It is understood that the above mutations can also be modified within wildtype HBV C-protein variant 1 (SEQ ID NO: 1).

For example, a modification identified with K5 and based on a modified structural core of SEQ ID NO: 1 can be represented by (SEQ ID NO: 25)

MDIDPYKEFGASVELLSFLPSDFFPSIRDLLDTASALYREALESPEHCSPHHTALRQAIL
CWGELMNLATWVGSNLEDPASRELVVSYVNVNMGLKIRQLLWFHISCLTFGRETVLEYLV
SFGVWIRTPPAYRPPNAPILSTLPETTVVDKLAAAKKKKKLEHHHHHH

K7: (SEQ ID NO: 26)

MDIDPYKEFGASVELLSFLPSDFFPSIRDLLDTASALYREALESPEHCSPHHTALRQAIL
CWGELMNLATWVGSNLEDPASRELVVSYVNVNMGLKIRQLLWFHISCLTFGRETVLEYLV
SFGVWIRTPPAYRPPNAPILSTLPETTVVDKLAAAKKKKKKKLEHHHHHH

K9: (SEQ ID NO: 27)

MDIDPYKEFGASVELLSFLPSDFFPSIRDLLDTASALYREALESPEHCSPHHTALRQAIL
CWGELMNLATWVGSNLEDPASRELVVSYVNVNMGLKIRQLLWFHISCLTFGRETVLEYLV
SFGVWIRTPPAYRPPNAPILSTLPETTVVDKLAAAKKKKKKKKKLEHHHHHH

K10: (SEQ ID NO: 28)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVDKLAAAKKKKKKKKKLEHHHHHH

K11: (SEQ ID NO: 29)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVDKLAAAKKKKKKKKKLEHHHHHH

K13: (SEQ ID NO: 30)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVDKLAAAKKKKKKKKKKKLEHHHHHH

K20: (SEQ ID NO: 31)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSEGVWIRTPPAYRPPNAPILSTLP
ETTVVDKLAAAKKKKKKKKKKKKKKKLEHHHHHH

KA9 (SEQ ID NO: 33)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVDKLAAAKAKAKAKAKAKAKAKLEHHHHHH

KG9: (SEQ ID NO: 34)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVDKLAAAKGKGKGKGKGKGKGKLEHHHHHH

K4-5 (SEQ ID NO: 35)

MDIDPYKEFGASVELLSFLPSDFFPSIRDLLDTASALYREALESPEHC
SPHHTALRQAILCWGELMNLATWVGSNLEDPASRELVVSYVNVNMGLK
IRQLLWFHISCLTFGRETVLEYLVSFGVWIRTPPAYRPPNAPILSTLP
ETTVVDKLAAAKKKKSQSPKKKKKLEHHHHHH

In some embodiments, mutations creating, e.g., various poly-lysine domains of differing lengths after, e.g., first 149 amino acids, or the first 138 amino acids, of HBV core protein can be engineered using any methods known in the art. In one embodiment, the core protein gene can be amplified via PCR up to amino acid 149 and various numbers of lysine (or other) residues can be added to amino acids 1-149.

Poly-Arginine Tail

In some embodiments, a modified tail portion includes one or more poly-arginines. For example, the modified tail portion may include about 4 to about 30 arginines, or about 5 to about 20 arginines, e.g., about 7, 8, 9, or 10 arginines.

In some embodiments, the modified tail portion may include one or more arginine domains. When more than one poly-arginine domain is present, the poly-arginine domains can be separated by about 1 to about 20 amino acid residues. For example, each poly-arginine domain may comprise about one to about thirty arginine residues. In some embodiments, when more than one poly-arginine domain is present, the each poly-arginine domain can comprise about 4 arginine residues to about 20 arginine residues (or any specific amino acid length disposed with the range). In some embodiments, a modified C-terminal tail includes at least four or at least five consecutive arginine residues. In another embodiment, a modified C-terminal tail may have mixtures of arginines and lysines, e.g., one or more arginine domains and one or more lysine domains.

Poly-arginine domains and/or a poly-histidine tag can be added to the C-terminal tails separately or in combination. A poly-histidine tag may, in some embodiments, facilitate purification of the proteins. Exemplary C-terminal tail portions may include 5 arginines (R5), 7 arginines (R7), 9 arginines (R9), 11 arginines (R11), 13 arginines (R13), and 20 arginines (R20). Such modified tail portions that include poly-arginine domains may be represented by:

DKLAAA[R]$_q$LE[H]$_j$          SEQ ID NO: 36 wherein q is an integer from 4 to 21 or more, and j is an integer from 0 to 10. For example, q may be 5, 6, 7, 8, 9, 10, 11, 12, 13, 14, 15, 16, 17, 18, 19 or 20; j may be 0, 1, 2, 3, 4, 5 or more.

For example, exemplary modified viral core proteins and corresponding nucleic acid that include a arginine modified tail portion include the following (together with associated nucleic acids):

R5 (SEQ ID NO: 37)

ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC GAC AAG CTT GCG GCC GCA CGC
CGT CGC CGT CGC CTC GAG CAC CAC CAC CAC CAC CAC

R5 (SEQ ID NO: 38)

MDIDPYKEFGATVELLSFLPSDFFPSVRDLLDTASALYREALESPEHC
SPHHTALRQAILCWGELMTLATWVGNNLCDPASRDLVVNYVNTNMGLK
IRQLLWFHISCLTFGRETVLEYLVSFGVWIRTPPAYRPPNAPILSTLP
ETTVVDKLAAARRRRRLEHHHHHH

R7 (SEQ ID NO: 39)

ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC GAC AAG CTT GCG GCC GCA CGC
CGT CGC CGT CGC CGT CGC CTC GAG CAC CAC CAC CAC
CAC CAC

R7 (SEQ ID NO: 40)

MDIDPYKEFGATVELLSFLPSDFFPSVRDLLDTASALYREALESPEHC
SPHHTALRQAILCWGELMTLATWVGNNLCDPASRDLVVNYVNTNMGLK
IRQLLWFHISCLTFGRETVLEYLVSFGVWIRTPPAYRPPNAPILSTLP
ETTVVDKLAAARRRRRRRLEHHHHHH

R9 (SEQ ID NO: 41)

ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC GAC AAG CTT GCG GCC GCA CGC
CGT CGC CGT CGC CGT CGC CGT CGC CTC GAG CAC CAC
CAC CAC CAC CAC

R9 (SEQ ID NO: 42)

MDIDPYKEFGATVELLSFLPSDFFPSVRDLLDTASALYREALESPEHC
SPHHTALRQAILCWGELMTLATWVGNNLCDPASRDLVVNYVNTNMGLK
IRQLLWFHISCLTFGRETVLEYLVSFGVWIRTPPAYRPPNAPILSTLP
ETTVVDKLAAARRRRRRRRLEHHHHHH

R11 (SEQ ID NO: 43)

ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC GAC AAG CTT GCG GCC GCA CGC
CGT CGC CGT CGC CGT CGC CGT CGC CGT CGC CTC GAG
CAC CAC CAC CAC CAC CAC

R11 (SEQ ID NO: 44)

MDIDPYKEFGATVELLSFLPSDFFPSVRDLLDTASALYREALESPEH
CSPHHTALRQAILCWGELMTLATWVGNNLCDPASRDLVVNYVNTNMG
LKIRQLLWFHISCLTFGRETVLEYLVSFGVWIRTPPAYRPPNAPILS
TLPETTVVDKLAAARRRRRRRRRRLEHHHHHH

R13 (SEQ ID NO: 45)

ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC GAC AAG CTT GCG GCC GCA CGC
CGT CGC CGT CGC CGT CGC CGT CGC CGT CGC CGT CGC
CTC GAG CAC CAC CAC CAC CAC CAC

R13 (SEQ ID NO: 46)

MDIDPYKEFGATVELLSFLPSDFFPSVRDLLDTASALYREALESPEH
CSPHHTALRQAILCWGELMTLATWVGNNLCDPASRDLVVNYVNTNMG
LKIRQLLWFHISCLTFGRETVLEYLVSFGVWIRTPPAYRPPNAPILS
TLPETTVVDKLAAARRRRRRRRRRRRLEHHHHHH

R20 (SEQ ID NO: 47)

ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG

```
GTT GTG AAC TAT GTG AAT ACC AAC ATG GGC CTG AAA

ATT CGT CAG CTG CTG TGG TTT CAT ATC AGC TGC CTG

ACC TTT GGC CGC GAA ACC GTG CTG GAA TAT CTG GTG

AGC TTT GGC GTT TGG ATC CGT ACC CCG CCG GCG TAT

CGT CCG CCG AAT GCG CCG ATT CTG AGC ACC CTG CCG

GAA ACC ACC GTT GTC GAC AAG CTT GCG GCC GCA CGT

CGC CGT CGC CGT CGC CGT CGC CGT CGC CGT CGC

CGT CGC CGT CGC CGT CGC CGC CTC GAG CAC CAC CAC

CAC CAC CAC
```

R20 (SEQ ID NO: 48)

```
MDIDPYKEFGATVELLSFLPSDFFPSVRDLLDTASALYREALESPEH
CSPHHTALRQAILCWGELMTLATWVGNNLCDPASRDLVVNYVNTNMG
LKIRQLLWFHISCLTFGRETVLEYLVSFGVWIRTPPAYRPPNAPILS
TLPETTVVDKLAAARRRRRRRRRRRRRRRRRRRRRLEHHHHHH
```

Truncation Mutations

In some embodiments, a modified tail portion includes one or more truncation mutations. For example, such modified tail portions may form part of a viral core protein as provided below, together with the corresponding nucleic acids. The modified tail portion is underlined for ease of identification. Some modified tail portions may or may not include a histidine tag.

Exemplary truncation mutants include a mutation at CP155 with the following nucleic acid sequence: (SEQ ID NO: 49)

```
ATG GAT ATC GAT CCG TAT AAA GAA TTT GGC GCC ACC

GTG GAA CTG CTG AGC TTT CTG CCG AGC GAT TTC TTT

CCG AGC GTG CGT GAT CTG CTG GAT ACC GCG AGC GCG

CTG TAT CGC GAA GCG CTG GAA AGC CCG GAA CAT TGT

AGC CCG CAC CAT ACC GCC CTG CGT CAG GCG ATT CTG

TGC TGG GGT GAA CTG ATG ACC CTG GCG ACC TGG GTT

GGC AAC AAC CTG TGT GAT CCG GCG AGC CGC GAT CTG

GTT GTG AAC TAT GTG AAT ACC AAC ATG GGC CTG AAA

ATT CGT CAG CTG CTG TGG TTT CAT ATC AGC TGC CTG

ACC TTT GGC CGC GAA ACC GTG CTG GAA TAT CTG GTG

AGC TTT GGC GTT TGG ATC CGT ACC CCG CCG GCG TAT

CGT CCG CCG AAT GCG CCG ATT CTG AGC ACC CTG CCG

GAA ACC ACC GTT GTG CGT CGC CGT GGT CGC AGC CTC

GAG CAC CAC CAC CAC CAC CAC
```

CP155 has the following amino acid sequence, with the modified tail portion underlined: (SEQ ID NO: 50)

```
MDIDPYKEFGATVELLSFLPSDFFPSVRDLLDTASALYREALESPEH
CSPHHTALRQAILCWGELMTLATWVGNNLCDPASRDLVVNYVNTNMG
LKIRQLLWFHISCLTFGRETVLEYLVSFGVWIRTPPAYRPPNAPILS
TLPETTVVRRRGRSLEHHHHHH
```

Other modified viral core proteins (and associated nucleic acids) include: CP162 (SEQ ID NO: 51)

```
ATG GAT ATC GAT CCG TAT AAA GAA TTT GGC GCC ACC

GTG GAA CTG CTG AGC TTT CTG CCG AGC GAT TTC TTT

CCG AGC GTG CGT GAT CTG CTG GAT ACC GCG AGC GCG

CTG TAT CGC GAA GCG CTG GAA AGC CCG GAA CAT TGT

AGC CCG CAC CAT ACC GCC CTG CGT CAG GCG ATT CTG

TGC TGG GGT GAA CTG ATG ACC CTG GCG ACC TGG GTT

GGC AAC AAC CTG TGT GAT CCG GCG AGC CGC GAT CTG

GTT GTG AAC TAT GTG AAT ACC AAC ATG GGC CTG AAA

ATT CGT CAG CTG CTG TGG TTT CAT ATC AGC TGC CTG

ACC TTT GGC CGC GAA ACC GTG CTG GAA TAT CTG GTG

AGC TTT GGC GTT TGG ATC CGT ACC CCG CCG GCG TAT

CGT CCG CCG AAT GCG CCG ATT CTG AGC ACC CTG CCG

GAA ACC ACC GTT GTG CGT CGC CGT GGT CGC AGC CCG

CGC CGT CGT ACC CCG AGC CTC GAG CAC CAC CAC CAC

CAC CAC
```

CP162 (SEQ ID NO: 52)

```
MDIDPYKEFGATVELLSFLPSDFFPSVRDLLDTASALYREALESPEHC
SPHHTALRQAILCWGELMTLATWVGNNLCDPASRDLVVNYVNTNMGLK
IRQLLWFHISCLTFGRETVLEYLVSFGVWIRTPPAYRPPNAPILSTLP
ETTVVRRRGRSPRRRTPSLEHHHHHH
```

CP170 (SEQ ID NO: 53)

```
ATG GAT ATC GAT CCG TAT AAA GAA TTT GGC GCC ACC

GTG GAA CTG CTG AGC TTT CTG CCG AGC GAT TTC TTT

CCG AGC GTG CGT GAT CTG CTG GAT ACC GCG AGC GCG

CTG TAT CGC GAA GCG CTG GAA AGC CCG GAA CAT TGT

AGC CCG CAC CAT ACC GCC CTG CGT CAG GCG ATT CTG

TGC TGG GGT GAA CTG ATG ACC CTG GCG ACC TGG GTT

GGC AAC AAC CTG TGT GAT CCG GCG AGC CGC GAT CTG

GTT GTG AAC TAT GTG AAT ACC AAC ATG GGC CTG AAA

ATT CGT CAG CTG CTG TGG TTT CAT ATC AGC TGC CTG

ACC TTT GGC CGC GAA ACC GTG CTG GAA TAT CTG GTG

AGC TTT GGC GTT TGG ATC CGT ACC CCG CCG GCG TAT

CGT CCG CCG AAT GCG CCG ATT CTG AGC ACC CTG CCG

GAA ACC ACC GTT GTG CGT CGC CGT GGT CGC AGC CCG
```

-continued

```
CGC CGT CGT ACC CCG AGC CCG CGT CGT CGT CGT AGC

CAG AGC CTC GAG CAC CAC CAC CAC CAC CAC
```

CP170 (SEQ ID NO: 54)

```
MDIDPYKEFGATVELLSFLPSDFFPSVRDLLDTASALYREALESPEHC
SPHHTALRQAILCWGELMTLATWVGNNLCDPASRDLVVNYVNTNMGLK
IRQLLWFHISCLTFGRETVLEYLVSFGVWIRTPPAYRPPNAPILSTLP
ETTVVRRRGRSPRRRTPSPRRRRSQSLEHHHHHH
```

Linker Segment Mutations

A linker segment may be optionally present between, e.g., a modified core portion and a modified tail portion, for example between the amino acid residue 149 and another modified tail portion domain. In some embodiments, the linker segment is about 3 amino acids to about 15 amino acids in length (or any specific amino acid length disposed with the range) and can link, e.g., a modified tail portion including a poly-lysine domain and/or a poly-arginine domain to, e.g., amino acid 149 of the HBV core protein, for example, to provide flexibility to the C-terminal tail. In some embodiments, an, e.g., poly-lysine domain can be followed by a poly histidine tag and/or followed by an XhoI restriction site. In some embodiments, a poly histidine tag can include at least six histidine residues added to the C-terminal tail. For example, such linker segments may be represented by

[SAG]<sub>s</sub>  SEQ ID NO. 55

[TAG]<sub>r</sub>  SEQ ID NO. 56

[GAG]<sub>r</sub>  SEQ ID NO. 57 wherein r, s and t are, each independently, integers from 1 to 6 or more.

Exemplary viral core proteins that include a linker segment (with corresponding nucleic acids) are provided below:

Linker 1 K9 (SEQ ID NO: 58)

```
ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC AGC GCG GGC AGC GCC GGC AAG
AAA AAG AAG AAG AAA AAG AAG AAG CTC GAG CAC CAC
CAC CAC CAC CAC
```

Linker 1 K9: (SEQ ID NO: 59)

```
MDIDPYKEFGATVELLSFLPSDFFPSVRDLLDTASALYREALESPEH
CSPHHTALRQAILCWGELMTLATWVGNNLCDPASRDLVVNYVNTNMG
LKIRQLLWFHISCLTFGRETVLEYLVSFGVWIRTPPAYRPPNAPILS
TLPETTVVSAGSAGKKKKKKKKKLEHHHHHH
```

Linker 2 K9 has the following nucleic acid sequence: (SEQ ID NO: 60)

```
ATG GAT ATC GAT CCG TAT AAA GAA TTT GGC GCC ACC
GTG GAA CTG CTG AGC TTT CTG CCG AGC GAT TTC TTT
CCG AGC GTG CGT GAT CTG CTG GAT ACC GCG AGC GCG
CTG TAT CGC GAA GCG CTG GAA AGC CCG GAA CAT TGT
AGC CCG CAC CAT ACC GCC CTG CGT CAG GCG ATT CTG
TGC TGG GGT GAA CTG ATG ACC CTG GCG ACC TGG GTT
GGC AAC AAC CTG TGC GAT CCG GCG AGC CGC GAT CTG
GTT GTG AAC TAT GTG AAT ACC AAC ATG GGC CTG AAA
ATT CGT CAG CTG CTG TGG TTT CAT ATC AGC TGC CTG
ACC TTT GGC CGC GAA ACC GTG CTG GAA TAT CTG GTG
AGC TTT GGC GTT TGG ATC CGT ACC CCG CCG GCG TAT
CGT CCG CCG AAT GCG CCG ATT CTG AGC ACC CTG CCG
GAA ACC ACC GTT GTC ACC GCG GGC ACC GCC GGC AAG
AAA AAG AAG AAG AAA AAG AAG AAG CTC GAG CAC CAC
CAC CAC CAC CAC
```

Linker 2 K9 (SEQ ID NO: 61)

```
MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVTAG
TAGKKKKKKKKKLEHHHHHH
```

Linker 3 K9 (SEQ ID NO: 62)

```
ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
```

-continued

```
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GGC GCG GGC
GGC GCC GGC AAG AAA AAG AAG AAG AAA AAG AAG AAG CTC GAG CAC CAC CAC CAC CAC
CAC
```

15

Linker 3 K9 (SEQ ID NO: 63)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVGAG
GAGKKKKKKKKLEHHHHHH

Linker 4 K9 (SEQ ID NO: 64)

```
ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC AGC GCG GGC
AGC GCC GGC AGC GCG GGC AAG AAA AAG AAG AAG AAA AAG AAG AAG CTC GAG CAC CAC
CAC CAC CAC CAC
```

Linker 4 K9 (SEQ ID NO: 65)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVSAG
SAGSAGKKKKKKKKLEHHHHHH

Linker 5 K9 (SEQ ID NO: 66)

```
ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC ACC GCG GGC
```

ACC GCC GGC ACC GCG GGC AAG AAA AAG AAG AAG AAA AAG AAG AAG CTC GAG CAC CAC
CAC CAC CAC CAC

Linker 5 K9 (SEQ ID NO: 67)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVTAG
TAGTAGKKKKKKKKKLEHHHHHH

Linker 6 K9 (SEQ ID NO: 68)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GGC GCG GGC
GGC GCC GGC GGC GCG GGC AAG AAA AAG AAG AAG AAA AAG AAG AAG CTC GAG CAC CAC
CAC CAC CAC CAC

Linker 6 K9 (SEQ ID NO: 69)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVGAG
GAGGAGKKKKKKKKKLEHHHHHH

Linker 7 K9 (SEQ ID NO: 70)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC AGC GCG GGC
AGC GCC GGC AGC GCG GGC AGC GCC GGC AAG AAA AAG AAG AAG AAA AAG AAG AAG CTC
GAG CAC CAC CAC CAC CAC CAC

Linker 7 K9 (SEQ ID NO: 71)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVSAG
SAGSAGSAGKKKKKKKKKLEHHHHHH

Linker 8 K9 (SEQ ID NO: 72)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC ACC GCG GGC
ACC GCC GGC ACC GCG GGC ACC GCC GGC AAG AAA AAG AAG AAG AAA AAG AAG AAG CTC
GAG CAC CAC CAC CAC CAC CAC

Linker 8 K9: (SEQ ID NO: 73)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVTAG
TAGTAGTAGKKKKKKKKKLEHHHHHH

Linker 9 K9 (SEQ ID NO: 74)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GGC GCG GGC
GGC GCC GGC GGC GCG GGC GGC GCC GGC AAG AAA AAG AAG AAG AAA AAG AAG AAG CTC
GAG CAC CAC CAC CAC CAC CAC

Linker 9 K9 (SEQ ID NO: 75)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVGAG
GAGGAGGAGKKKKKKKKKLEHHHHHH

An exemplary non-His tagged K9 has the following nucleic acid sequence: (SEQ ID NO: 76)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG

```
AAA ATT CGT CAG CTG CTG TGG TTT CAT ATC AGC TGC CTG ACC TTT GGC CGC GAA ACC

GTG CTG GAA TAT CTG GTG AGC TTT GGC GTT TGG ATC CGT ACC CCG CCG GCG TAT CGT

CCG CCG AAT GCG CCG ATT CTG AGC ACC CTG CCG GAA ACC ACC GTT GTC GAC AAG CTT

GCG GCC GCA AAG AAA AAG AAG AAG AAA AAG AAG AAG
```

Non-His tagged K9 viral core protein has the following amino acid sequence: (SEQ ID NO: 77)

MDIDPYKEFGATVELLSFLPSDFFPSVRDLLDTASALYREALESPEHCSPHHTALRQAILCWGELMTLATWVGNNL

CDPASRDLVVNYVNTNMGLKIRQLLWFHISCLTFGRETVLEYLVSFGVWIRTPPAYRPPNAPILSTLPETTVVDKL

AAAKKKKKKKK

In some embodiments, the modification of the tail portion may allow a nucleic acid to bind to the tail portion with a binding affinity that may allow release of the nucleic acid when the chimeric therapeutic (e.g., viral core protein bound to a nucleic acid) is administered e.g., in vivo. For example, a modified tail portion that includes lysine, e.g., lysine domains, may bind a nucleic acid using substantially Coulombic forces only, such that the nucleic acid may, in some embodiments, be easily released when exposed to a ionic solution e.g., a salt solution. Without being bound by any theory, it is believed that the wild type HBV binds to a nucleic acid with both hydrogen bonding and Coulombic forces. In some embodiments, a tail portion is provided that includes, e.g., both lysine and arginine in portions that optimize binding and/or release of the nucleic acid.

In another embodiment, the disclosed chimeric therapeutics, e.g., that do not include a modified tail portion with a substantial number of arginines such as those arranged as in the wild type tail portion, may be substantially free of endogenous nucleic acids.

B. Modified Structural Core

A structural core portion of a viral core protein may be modified to for example, (a) strengthen and promote assembly of the viral core protein, e.g., HBV C-protein monomers, into a capsid; (b) enhance and promote the coating of one or more capsids with a layer comprising a lipid or lipid/cholesterol; (c) facilitate the attachment of other moieties, e.g., chemical modifiers and/or targeting agents; and/or (d) facilitate the disassembly of the entire capsid in the bloodstream following administration.

The wild type HBV C-protein is typically 183 amino acids. The first 149 amino acids typically form a globular fold or structural core. It is noted that in some embodiments, a structural core portion includes the first 138 amino acids of, e.g., a wild type HBV protein. Provided herein, for example, is a structural core portion of a viral core protein based on amino acids 1-149 of SEQ ID NO: 1 or SEQ ID NO: 2, that may include one or more modifications. It will be appreciated that a contemplated modified structural portion of a viral core protein may include amino acids 1-138 of SEQ ID NO: 1 or SEQ ID NO: 2, and that such a structural portion may include any one or more of the modifications indicated below.

For simplicity, the embodiments described below exemplify modifications of the HBV C-protein variant (SEQ ID NO: 2). It is appreciated that the same modifications can be engineered within HBV C-protein (SEQ ID NO: 1). An exemplary modified structural core protein can be, in some embodiments, represented by SEQ ID NO: 78, where X, independently for each occurrence, represents an amino acid. It is understood that a contemplated viral core protein may include a structural portion represented by, e.g., SEQ ID NO: 78 and may additionally include a modified or unmodified tail portion, e.g., a modified C-terminal tail portion such as those described above.

SEQ ID. NO: 78
MDIDPYKEFGATVELLSXLPSDXFPSVRXLLDXASAXYREALESPEHXSPHHTALRQAIL

XWGELMTLATWVGNNLEDPASRDLVVNYVNTNMGLKIRQLLWFHISXLTFGRETVLEYLV

XFGXWIXTPPAXRPPNAPXLXTLPETTVV wherein the X, at a given location, is selected from:
X at 18: X=F, H
X at 23: X=F, C
x at 29: X=D, C
X at 33: X=T, C
X at 37: X=L, C
X at 48: X=C, A
X at 61: X=C, A
X at 77: X=E, C,
X at 78: X=D, C, S, E
X at 80: X=A, C
X at 107: X=C, A
X at 121: X=S, C
X at 124: X=V, C
X at 127: X=R, C
X at 132: X=Y, A, V, I, F, C
X at 139: X=I, A
X at 141: X=S, C Capsid Assembly Modifications In an embodiment, a HBV capsid may be formed from protein dimers. For example, intermolecular interactions between dimers may stabilize the assembly and may be formed by disulfide bonds, salt bridges, and hydrophobic interactions between proteins. In some embodiments, a structural core portion may include mutation of interacting amino acid side chains to either stabilize or destabilize the interactions and therefore, the capsid or particle assembly. For example, destabilizing mutations may be introduced at Phe18, Tyr132, and/or Ile139. In another embodiment, a disulfide bond may be introduced at Ser121 and/or Ser141, which may, for example, stabilize inter-dimer associations between viral core proteins. In other embodiments, the native cysteine residues at positions 48, 61, and/or 107 may also be mutated, (for example to an alanine), without substantially affecting the ability of the core protein to form a capsid or particle.

Modifications of the structural core portion of a viral core protein can include the introduction of, e.g., a pair of cysteines into a spike area of a formed dimer or the interface between dimers. For example, a first cysteine (e.g., amino acid 23) is introduced in the first position in order to form a disulfide bond with a second cysteine (amino acid 132 in this case) in a neighboring molecule. Similarly, the second position may also participate in a disulfide bond, allowing the dimer to participate in four disulfide bridges and a total of 180 stabilizing covalent interactions. At least four different types of disulfide bonds may be created:

In some embodiments, such mutations may affect the long-term stability of a capsid or particle formed from viral core proteins that include such viral structural portions. Such stabilizing and destabilizing mutations can be introduced, e.g., singly and/or in combination.

For example, exemplary modified viral core proteins, that include a modified structural core portion, include the following:

HBV C-protein variant of SEQ ID NO: 2 comprising mutation 1: phenylalanine 23 to cysteine; tyrosine 132 to cysteine. (SEQ ID NO: 79)

MDIDPYKEFGATVELLSFLPSDCFPSVRDLLDTASALYREALESPEHCSPHHTALRQAIL

CWGELMTLATWVGNNLEDPASRDLVVNYVNTNMGLKIRQLLWFHISCLTFGRETVLEYLV

SFGVWIRTPPACRPPNAPILSTLPETTVVRRRGRSPRRRTPSPRRRRSQSPRRRRSQSRE

SQC

HBV C-protein SEQ ID NO: 1 comprising mutation 1: phenylalanine 23 to cysteine; tyrosine 132 to cysteine. (SEQ ID NO: 80)

MDIDPYKEFGASVELLSFLPSDCFPSIRDLLDTASALYREALESPEHCSPHHTALRQAIL

CWGELMNLATWVGSNLEDPASRELVVSYVNVNMGLKIRQLLWFHISCLTFGRETVLEYLV

SFGVWIRTPPACRPPNAPILSTLPETTVVRRRGRSPRRRTPSPRRRRSQSPRRRRSQSRE

SQC

HBV C-protein variant SEQ ID NO: 2 comprising mutation 2: aspartic acid 29 to cysteine; arginine 127 to cysteine. (SEQ ID NO: 81)

MDIDPYKEFGATVELLSFLPSDFFPSVRCLLDTASALYREALESPEHCSPHHTALRQAIL

CWGELMTLATWVGNNLEDPASRDLVVNYVNTNMGLKIRQLLWFHISCLTFGRETVLEYLV

SFGVWICTPPAYRPPNAPILSTLPETTVVRRRGRSPRRRTPSPRRRRSQSPRRRRSQSRE

SQC

Exemplary HBV C-protein SEQ ID NO: 1 comprising mutation 2: aspartic acid 29 to cysteine; arginine 127 to cysteine. (SEQ ID NO: 82)

MDIDPYKEFGASVELLSFLPSDFFPSIRCLLDTASALYREALESPEHCSPHHTALRQAIL

CWGELMNLATWVGSNLEDPASRELVVSYVNVNMGLKIRQLLWFHISCLTFGRETVLEYLV

SFGVWICTPPAYRPPNAPILSTLPETTVVRRRGRSPRRRTPSPRRRRSQSPRRRRSQSRE

SQC

HBV C-protein variant SEQ ID NO: 2 comprising mutation 3: threonine 33 to cysteine; valine 124 to cysteine. (SEQ ID NO: 83)

MDIDPYKEFGATVELLSFLPSDFFPSVRDLLDCASALYREALESPEHCSPHHTALRQAIL

CWGELMTLATWVGNNLEDPASRDLVVNYVNTNMGLKIRQLLWFHISCLTFGRETVLEYLV

SFGCWIRTPPAYRPPNAPILSTLPETTVVRRRGRSPRRRTPSPRRRRSQSPRRRRSQSRE

SQC

HBV C-protein SEQ ID NO: 1 comprising mutation 3: threonine 33 to cysteine; valine 124 to cysteine. (SEQ ID NO: 84)

MDIDPYKEFGASVELLSFLPSDFFPSIRDLLDCASALYREALESPEHCSPHHTALRQAIL

CWGELMNLATWVGSNLEDPASRELVVSYVNVNMGLKIRQLLWFHISCLTFGRETVLEYLV

SFGCWIRTPPAYRPPNAPILSTLPETTVVRRRGRSPRRRTPSPRRRRSQSPRRRRSQSRE

SQC

HBV C-protein variant SEQ ID NO: 2 comprising mutation 4: leucine 37 to cysteine; valine 120 to cysteine. (SEQ ID NO: 85)

MDIDPYKEFGATVELLSFLPSDFFPSVRDLLDTASACYREALESPEHCSPHHTALRQAIL

CWGELMTLATWVGNNLEDPASRDLVVNYVNTNMGLKIRQLLWFHISCLTFGRETVLEYLC

SFGVWIRTPPAYRPPNAPILSTLPETTVVRRRGRSPRRRTPSPRRRRSQSPRRRRSQSRE

SQC

HBV C-protein SEQ ID NO: 1 comprising mutation 4: leucine 37 to cysteine; valine 120 to cysteine. (SEQ ID NO: 86)

MDIDPYKEFGASVELLSFLPSDFFPSIRDLLDTASACYREALESPEHCSPHHTALRQAIL

CWGELMNLATWVGSNLEDPASRELVVSYVNVNMGLKIRQLLWFHISCLTFGRETVLEYLC

SFGVWIRTPPAYRPPNAPILSTLPETTVVRRRGRSPRRRTPSPRRRRSQSPRRRRSQSRE

SQC

Exemplary modified viral core proteins, that include a modified structural core portion, include the following viral core proteins together with corresponding nucleic acid sequences:

F18H K9 (SEQ ID NO: 87)

ATG GAT ATC GAT CCG TAT AAA GAA TTT GGC GCC ACC GTG GAA CTG CTG AGC CAT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT TGT AGC CCG CAC CAT ACC GCC CTG CGT CAG

GCG ATT CTG TGC TGG GGT GAA CTG ATG ACC CTG GCG ACC TGG GTT GGC AAC AAC CTG

TGC GAT CCG GCG AGC CGC GAT CTG GTT GTG AAC TAT GTG AAT ACC AAC ATG GGC CTG

AAA ATT CGT CAG CTG CTG TGG TTT CAT ATC AGC TGC CTG ACC TTT GGC CGC GAA ACC

GTG CTG GAA TAT CTG GTG AGC TTT GGC GTT TGG ATC CGT ACC CCG CCG GCG TAT CGT

CCG CCG AAT GCG CCG ATT CTG AGC ACC CTG CCG GAA ACC ACC GTT GTC GAC AAG CTT

GCG GCC GCA AAG AAA AAG AAG AAG AAA AAG AAG AAG CTC GAG CAC CAC CAC CAC CAC

CAC

F18H K9 (SEQ ID NO: 88)

MDIDPYKEFGATVELLSHLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVDKL
AAAKKKKKKKKKLEHHHHHH

Y132A K9 (SEQ ID NO: 89)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG GCT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

Y132A K9 (SEQ ID NO: 90)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAARPPNAPILSTLPETTVVDKL
AAAKKKKKKKKKLEHHHHHH

Y132V K9 (SEQ ID NO: 91)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG GTT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

Y132V K9 (SEQ ID NO: 92)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAVRPPNAPILSTLPETTVVDKL
AAAKKKKKKKKKLEHHHHHH

Y1321 K9 (SEQ ID NO: 93)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG ATT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

Y1321 K9 (SEQ ID NO: 94)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAIRPPNAPILSTLPETTVVDKL
AAAKKKKKKKKKLEHHHHHH

Y132F K9 (SEQ ID NO: 95)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TTT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

Y132F K9 (SEQ ID NO: 96)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAFRPPNAPILSTLPETTVVDKL
AAAKKKKKKKKKLEHHHHHH

I139A K9 (SEQ ID NO: 97)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG

```
                       -continued
AAA ATT CGT CAG CTG CTG TGG TTT CAT ATC AGC TGC CTG ACC TTT GGC CGC GAA ACC

GTG CTG GAA TAT CTG GTG AGC TTT GGC GTT TGG ATC CGT ACC CCG CCG GCG TAT CGT

CCG CCG AAT GCG CCG GCT CTG AGC ACC CTG CCG GAA ACC ACC GTT GTC GAC AAG CTT

GCG GCC GCA AAG AAA AAG AAG AAG AAA AAG AAG AAG CTC GAG CAC CAC CAC CAC CAC

CAC
```

I139A K9 (SEQ ID NO: 98)

```
MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVSFGVWIRTPPAYRPPNAPALSTLPETTVVDKL
AAAKKKKKKKKKLEHHHHHH
```

S121C S141C K9 (SEQ ID NO: 99)

```
ATG GAT ATC GAT CCG TAT AAA GAA TTT GGC GCC ACC GTG GAA CTG CTG AGC TTT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT TGT AGC CCG CAC CAT ACC GCC CTG CGT CAG

GCG ATT CTG TGC TGG GGT GAA CTG ATG ACC CTG GCG ACC TGG GTT GGC AAC AAC CTG

TGC GAT CCG GCG AGC CGC GAT CTG GTT GTG AAC TAT GTG AAT ACC AAC ATG GGC CTG

AAA ATT CGT CAG CTG CTG TGG TTT CAT ATC AGC TGC CTG ACC TTT GGC CGC GAA ACC

GTG CTG GAA TAT CTG GTG TGC TTT GGC GTT TGG ATC CGT ACC CCG CCG GCG TAT CGT

CCG CCG AAT GCG CCG ATT CTG TGC ACC CTG CCG GAA ACC ACC GTT GTC GAC AAG CTT

GCG GCC GCA AAG AAA AAG AAG AAG AAA AAG AAG AAG CTC GAG CAC CAC CAC CAC CAC

CAC
```

S121C S141C K9 (SEQ ID NO: 100)

```
MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVCFGVWIRTPPAYRPPNAPILCTLPETTVVDKL
AAAKKKKKKKKKLEHHHHHH
```

F18H S121C S141C K9 (SEQ ID NO: 101)

```
ATG GAT ATC GAT CCG TAT AAA GAA TTT GGC GCC ACC GTG GAA CTG CTG AGC CAT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT TGT AGC CCG CAC CAT ACC GCC CTG CGT CAG

GCG ATT CTG TGC TGG GGT GAA CTG ATG ACC CTG GCG ACC TGG GTT GGC AAC AAC CTG

TGC GAT CCG GCG AGC CGC GAT CTG GTT GTG AAC TAT GTG AAT ACC AAC ATG GGC CTG

AAA ATT CGT CAG CTG CTG TGG TTT CAT ATC AGC TGC CTG ACC TTT GGC CGC GAA ACC

GTG CTG GAA TAT CTG GTG TGC TTT GGC GTT TGG ATC CGT ACC CCG CCG GCG TAT CGT

CCG CCG AAT GCG CCG ATT CTG TGC ACC CTG CCG GAA ACC ACC GTT GTC GAC AAG CTT

GCG GCC GCA AAG AAA AAG AAG AAG AAA AAG AAG AAG CTC GAG CAC CAC CAC CAC CAC

CAC
```

F18H S121C S141C K9 (SEQ ID NO: 102)

MDIDPYKEFGATVELLSHLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVCFGVWIRTPPAYRPPNAPILCTLPETTVVDKL
AAAKKKKKKKKKLEHHHHHH

Y132F S121C S141C K9 (SEQ ID NO: 103)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG TGC TTT GGC GTT TGG ATC CGT ACC CCG CCG GCG TTT CGT
CCG CCG AAT GCG CCG ATT CTG TGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

Y132F S121C S141C K9: (SEQ ID NO: 104)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVCFGVWIRTPPAFRPPNAPILCTLPETTVVDKL
AAAKKKKKKKKKLEHHHHHH

35

I139A S121C S141C K9 (SEQ ID NO: 105)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG TGC TTT GGC GTT TGG ATC CGT ACC CCG CCG GCG TAT CGT
CCG CCG AAT GCG CCG GCT CTG TGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

I139A S121C S141C K9 (SEQ ID NO: 106)

MDIDPYKEFGATVELLSFLPSDFFPSVRDLLDTASALYREALESPEHCSPHHTALRQAILCWGELMTLATWVGNNL

CDPASRDLVVNYVNTNMGLKIRQLLWFHISCLTFGRETVLEYLVCFGVWIRTPPAIRPPNAPALCTLPETTVVDKL

AAAKKKKKKKKKLEHHHHHH

Y132V S121C S141C K9 (SEQ ID NO: 107)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG TGC TTT GGC GTT TGG ATC CGT ACC CCG CCG GCG GTT CGT
CCG CCG AAT GCG CCG ATT CTG TGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

Y132V S121C S141C K9 (SEQ ID NO: 108)

MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISCLTFGRETVLEYLVCFGVWIRTPPAVRPPNAPILCTLPETTVVDKL
AAAKKKKKKKKKLEHHHHHH

C48A K9 (SEQ ID NO: 109)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT GCG AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

C48A K9 (SEQ ID NO: 110)

MDIDPYKEFGATVELLSFLPSDFFPSVRDLLDTASALYREALESPEHASPHHTALRQAILCWGELMTLATWVGNNL
CDPASRDLVVNYVNTNMGLKIRQLLWFHISCLTFGRETVLEYLVSFGVWIRTPPAYRPPNAPILSTLPETTVVDKL
AAAKKKKKKKKKLEHHHHHH

C61A K9 (SEQ ID NO: 111)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG GCG TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG

-continued

```
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC
```

C61A K9 (SEQ ID NO: 112)

```
MDIDPYKEFGATVELLSFLPSDFFPSVRDLLDTASALYREALESPEHCSPHHTALRQAILAWGELMTLATWVGNNL
CDPASRDLVVNYVNTNMGLKIRQLLWFHISCLTFGRETVLEYLVSFGVWIRTPPAYRPPNAPILSTLPETTVVDKL
AAAKKKKKKKKKLEHHHHHH
```

C107A K9 (SEQ ID NO: 113)

```
ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC GCG CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC
```

C107A K9 (SEQ ID NO: 114)

```
MDIDPYKEFGATVELLSFLPSDFFPSVRDLLDTASALYREALESPEHCSPHHTALRQAILCWGELMTLATWVGNNL
CDPASRDLVVNYVNTNMGLKIRQLLWFHISALTFGRETVLEYLVSFGVWIRTPPAYRPPNAPILSTLPETTVVDKL
AAAKKKKKKKKKLEHHHHHH
```

C48A C61A K9 (SEQ ID NO: 115)

```
ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT GCG AGC CCG CAC CAT ACC GCC CTG CGT CAG
GCG ATT CTG GCG TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC
```

C48A C61A K9 (SEQ ID NO: 116)

MDIDPYKEFGATVELLSFLPSDFFPSVRDLLDTASALYREALESPEHASPHHTALRQAILAWGELMTLATWVGNNL
CDPASRDLVVNYVNTNMGLKIRQLLWFHISCLTFGRETVLEYLVSFGVWIRTPPAYRPPNAPILSTLPETTVVDKL
AAAKKKKKKKKKLEHHHHHH

C48A C107A K9 (SEQ ID NO: 117)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT GCG AGC CCG CAC CAT ACC GCC CTG CGT CAG
GCG ATT CTG TGC TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC GCG CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

C48A C107A K9 (SEQ ID NO: 118)

MDIDPYKEFGATVELLSFLPSDFFPSVRDLLDTASALYREALESPEHASPHHTALRQAILCWGELMTLATWVGNNL
CDPASRDLVVNYVNTNMGLKIRQLLWFHISALTFGRETVLEYLVSFGVWIRTPPAYRPPNAPILSTLPETTVVDKL
AAAKKKKKKKKKLEHHHHHH

C61A C107A K9 (SEQ ID NO: 119)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG GCG TGG GGT GAA CTG ATG ACC CTG GCG ACC TGG GTT GGC AAC AAC CTG
TGC GAT CCG GCG AGC CGC GAT CTG GTT GTG AAC TAT GTG AAT ACC AAC ATG GGC CTG
AAA ATT CGT CAG CTG CTG TGG TTT CAT ATC AGC GCG CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

C61A C107A K9 (SEQ ID NO: 120)

MDIDPYKEFGATVELLSFLPSDFFPSVRDLLDTASALYREALESPEHCSPHHTALRQAILAWGELMTLATWVGNNL
CDPASRDLVVNYVNTNMGLKIRQLLWFHISALTFGRETVLEYLVSFGVWIRTPPAYRPPNAPILSTLPETTVVDKL
AAAKKKKKKKKKLEHHHHHH

C48A C61A C107A K9 (SEQ ID NO: 121)

```
ATG GAT ATC GAT CCG TAT AAA GAA TTT GGC GCC ACC GTG GAA CTG CTG AGC TTT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT GCG AGC CCG CAC CAT ACC GCC CTG CGT CAG

GCG ATT CTG GCG TGG GGT GAA CTG ATG ACC CTG GCG ACC TGG GTT GGC AAC AAC CTG

TGC GAT CCG GCG AGC CGC GAT CTG GTT GTG AAC TAT GTG AAT ACC AAC ATG GGC CTG

AAA ATT CGT CAG CTG CTG TGG TTT CAT ATC AGC GCG CTG ACC TTT GGC CGC GAA ACC

GTG CTG GAA TAT CTG GTG AGC TTT GGC GTT TGG ATC CGT ACC CCG CCG GCG TAT CGT

CCG CCG AAT GCG CCG ATT CTG AGC ACC CTG CCG GAA ACC ACC GTT GTC GAC AAG CTT

GCG GCC GCA AAG AAA AAG AAG AAG AAA AAG AAG AAG CTC GAG CAC CAC CAC CAC CAC

CAC
```

C48A C61A C107A K9 (SEQ ID NO: 122)

MDIDPYKEFGATVELLSFLPSDFFPSVRDLLDTASALYREALESPEHASPHHTALRQAILAWGELMTLATWVGNNL
CDPASRDLVVNYVNTNMGLKIRQLLWFHISALTFGRETVLEYLVSFGVWIRTPPAYRPPNAPILSTLPETTVVDKL
AAAKKKKKKKKKLEHHHHHH

C48A C61A C107A S121C S141C K9 (SEQ ID NO: 123)

```
ATG GAT ATC GAT CCG TAT AAA GAA TTT GGC GCC ACC GTG GAA CTG CTG AGC TTT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT GCG AGC CCG CAC CAT ACC GCC CTG CGT CAG

GCG ATT CTG GCG TGG GGT GAA CTG ATG ACC CTG GCG ACC TGG GTT GGC AAC AAC CTG

TGC GAT CCG GCG AGC CGC GAT CTG GTT GTG AAC TAT GTG AAT ACC AAC ATG GGC CTG

AAA ATT CGT CAG CTG CTG TGG TTT CAT ATC AGC GCG CTG ACC TTT GGC CGC GAA ACC

GTG CTG GAA TAT CTG GTG TGC TTT GGC GTT TGG ATC CGT ACC CCG CCG GCG TAT CGT

CCG CCG AAT GCG CCG ATT CTG TGC ACC CTG CCG GAA ACC ACC GTT GTC GAC AAG CTT

GCG GCC GCA AAG AAA AAG AAG AAG AAA AAG AAG AAG CTC GAG CAC CAC CAC CAC CAC

CAC
```

C48A C61A C107A S121C S141C K9 (SEQ ID NO: 124)

MDIDPYKEFGATVELLSFLPSDFFPSVRDLLDTASALYREALESPEHASPHHTALRQAILAWGELMTLATWVGNNL
CDPASRDLVVNYVNTNMGLKIRQLLWFHISALTFGRETVLEYLVCFGVWIRTPPAYRPPNAPILCTLPETTVVDKL
AAAKKKKKKKKKLEHHHHHH

Capsid Disassembly Modifications

Alterations or mutations may be made on, e.g., a viral structural core that may, for example, facilitate disassembly of a capsid or particle formed disclosed viral core proteins after, for example, administering in vivo. For example, mutations are contemplated that may introduce blood protease recognition sequences, e.g., protease recognition sites at hinge and loop regions. Such sequences can be inserted, for example, into the spike region of the HBV C-protein (e.g., replacing amino acids 79 and 80 with these 12 amino acid insertion loops. In some embodiments, a viral core protein may include up to a further about 40, or about 46 residues and may still, in some embodiments, be capable of forming a particle or capsid.

Exemplary blood protease recognition sequences include for example, thrombin (SEQ ID NO: 125) and factor Xa (SEQ ID NO: 126.)

```
GPGAPGLVPRGS           (SEQ ID NO: 125)

GPASGPGIEGRA           (SEQ ID NO: 126)
```

For example, contemplated HBV C-proteins from SEQ ID NO:2 (and associated nucleic acids) that comprise such a blood protease recognition sequence can be represented by:

(SEQ ID NO: 127)

ATG GAT ATC GAT CCG TAT AAA GAA TTT GGC GCC ACC GTG GAA CTG CTG AGC TTT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT TGT AGC CCG CAC CAT ACC GCC CTG CGT CAG

GCG ATT CTG TGC TGG GGT GAA CTG ATG ACC CTG GCG ACC TGG GTT GGC AAC AAC CTG

TGC GAT GGC CCG GGT GCG CCG GGT CTT GTT CCG CGT GGT AGC AGC CGC GAT CTG GTT

GTG AAC TAT GTG AAT ACC AAC ATG GGC CTG AAA ATT CGT CAG CTG CTG TGG TTT CAT

ATC AGC TGC CTG ACC TTT GGC CGC GAA ACC GTG CTG GAA TAT CTG GTG AGC TTT GGC

GTT TGG ATC CGT ACC CCG CCG GCG TAT CGT CCG CCG AAT GCG CCG ATT CTG AGC ACC

CTG CCG GAA ACC ACC GTT GTC GAC AAG CTT GCG GCC GCA AAG AAA AAG AAG AAG AAA

AAG AAG AAG CTC GAG CAC CAC CAC CAC CAC CAC (SEQ ID NO: 128)

MDIDPYKEFGATVELLSFLPSDFFPSVRDLLDTASALYREALESPEHCSPHHTALRQAILCWGELMTLATWVGNNL
CDGPGAPGLVPRGSSRDLVVNYVNTNMGLKIRQLLWFHISCLTFGRETVLEYLVSFGVWIRTPPAYRPPNAPILST
LPETTVVDKLAAAKKKKKKKKLEHHHHHH (SEQ ID NO: 129)

ATG GAT ATC GAT CCG TAT AAA GAA TTT GGC GCC ACC GTG GAA CTG CTG AGC TTT CTG

CCG AGC GAT TTC TTT CCG AGC GTG CGT GAT CTG CTG GAT ACC GCG AGC GCG CTG TAT

CGC GAA GCG CTG GAA AGC CCG GAA CAT TGT AGC CCG CAC CAT ACC GCC CTG CGT CAG

GCG ATT CTG TGC TGG GGT GAA CTG ATG ACC CTG GCG ACC TGG GTT GGC AAC AAC CTG

TGC GAT GGT CCG GCG AGC GGT CCG GGT ATT GAA GGT CGT GCG AGC CGC GAT CTG GTT

GTG AAC TAT GTG AAT ACC AAC ATG GGC CTG AAA ATT CGT CAG CTG CTG TGG TTT CAT

ATC AGC TGC CTG ACC TTT GGC CGC GAA ACC GTG CTG GAA TAT CTG GTG AGC TTT GGC

GTT TGG ATC CGT ACC CCG CCG GCG TAT CGT CCG CCG AAT GCG CCG ATT CTG AGC ACC

CTG CCG GAA ACC ACC GTT GTC GAC AAG CTT GCG GCC GCA AAG AAA AAG AAG AAG AAA

AAG AAG AAG CTC GAG CAC CAC CAC CAC CAC CAC (SEQ ID NO: 130)

MDIDPYKEFGATVELLSFLPSDFFPSVRDLLDTASALYREALESPEHCSPHHTALRQAILCWGELMTLATWVGNNL
CDGPASGPGIEGRASRDLVVNYVNTNMGLKIRQLLWFHISCLTFGRETVLEYLVSFGVWIRTPPAYRPPNAPILST
LPETTVVDKLAAAKKKKKKKKLEHHHHHH

Capsid Conjugate Site Modifications

In some embodiments, a structural core portion of the viral core protein may be modified to include a conjugation site that allows the attachment of a moiety, e.g., a chemical linker moiety such as a lipid linker moiety. For example, either of the amino acids cysteine or lysine may be placed in the structural core in such a way so that when formed in a capsid or particle these modifications may protrude away from the capsid surface, e.g., toward a plasma membrane.

In an embodiment, such modifications may permit the addition of one or more lipid linker moieties which can serve to promote or facilitate a lipid layer. In another embodiment, such a modification may permit the addition (e.g., the attachment of) one or more targeting agents, as described below.

For example, three positions on a structural core portion of a viral core protein may be used for the introduction of one or more cysteines and/or lysines, e.g., site 77, glutamic acid to cysteine; 78, aspartic acid to cysteine; and/or site 80, alanine to cysteine on a HBV C protein. Such cysteine modifications, for example, may be further functionalized. Cysteine mutations can also be introduced at other locations in the C-protein. Exemplary modified viral core proteins and associated nucleic acids include:

C77E D78S K9 (SEQ ID NO: 131)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
GAA AGC CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

C77E D78S K9 (SEQ ID NO: 132)

MDIDPYKEFGATVELLSFLPSDFFPSVRDLLDTASALYREALESPEHCSPHHTALRQAILCWGELMTLATWVGNNL
ESPASRDLVVNYVNTNMGLKIRQLLWFHISCLTFGRETVLEYLVSFGVWIRTPPAYRPPNAPILSTLPETTVVDKL
AAAKKKKKKKKKLEHHHHHH

C77E D78E K9 (SEQ ID NO: 133)

ATG GAT ATC GAT CCG TAT AAA GAA TTT GGC GCC ACC GTG GAA CTG CTG AGC TTT CTG
CCG AGC GAT TTC TTT CCG AGC GTG CGT GAT CTG CTG GAT ACC GCG AGC GCG CTG TAT
CGC GAA GCG CTG GAA AGC CCG GAA CAT TGT AGC CCG CAC CAT ACC GCC CTG CGT CAG
GCG ATT CTG TGC TGG GGT GAA CTG ATG ACC CTG GCG ACC TGG GTT GGC AAC AAC CTG
GAA GAA CCG GCG AGC CGC GAT CTG GTT GTG AAC TAT GTG AAT ACC AAC ATG GGC CTG
AAA ATT CGT CAG CTG CTG TGG TTT CAT ATC AGC TGC CTG ACC TTT GGC CGC GAA ACC
GTG CTG GAA TAT CTG GTG AGC TTT GGC GTT TGG ATC CGT ACC CCG CCG GCG TAT CGT
CCG CCG AAT GCG CCG ATT CTG AGC ACC CTG CCG GAA ACC ACC GTT GTC GAC AAG CTT
GCG GCC GCA AAG AAA AAG AAG AAG AAA AAG AAG AAG CTC GAG CAC CAC CAC CAC CAC
CAC

C77E D78E K9 (SEQ ID NO: 134)

MDIDPYKEFGATVELLSFLPSDFFPSVRDLLDTASALYREALESPEHCSPHHTALRQAILCWGELMTLATWVGNNL
EEPASRDLVVNYVNTNMGLKIRQLLWFHISCLTFGRETVLEYLVSFGVWIRTPPAYRPPNAPILSTLPETTVVDKL
AAAKKKKKKKKKLEHHHHHH

E77C (SEQ ID NO: 135)

MDIDPYKEFGATVELLSFLPSDFFPSVRDLLDTASALYREALESPEHCSPHHTALRQAIL
CWGELMTLATWVGNNLCDPASRDLVVNYVNTNMGLKIRQLLWFHISCLTFGRETVLEYLV
SFGVWIRTPPAYRPPNAPILSTLPETTVVRRRGRSPRRRTPSPRRRRSQSPRRRRSQSRE
SQC

D78C (SEQ ID NO: 136)

MDIDPYKEFGATVELLSFLPSDFFPSVRDLLDTASALYREALESPEHCSPHHTALRQAIL

CWGELMTLATWVGNNLECPASRDLVVNYVNTNMGLKIRQLLWFHISCLTFGRETVLEYLV

SFGVWIRTPPAYRPPNAPILSTLPETTVVRRRGRSPRRRTPSPRRRRSQSPRRRRSQSRE

SQC

A80C (SEQ ID NO: 137)

MDIDPYKEFGATVELLSFLPSDFFPSVRDLLDTASALYREALESPEHCS

PHHTALRQAILCWGELMTLATWVGNNLEDPCSRDLVVNYVNTNMGLKIR

QLLWFHISCLTFGRETVLEYLVSFGVWIRTPPAYRPPNAPILSTLPETT

VVRRRGRSPRRRTPSPRRRRSQSPRRRRSQSRESQC

It is understood that such conjugate site modifications may also be generated in a HBV C-protein variant 1 (SEQ ID NO:1). For example, E77C generated within HBV C-protein variant 1 has the following amino acid sequence: (SEQ ID NO: 138)

MDIDPYKEFGASVELLSFLPSDFFPSIRDLLDTASALYREALESPEHCS

PHHTALRQAILCWGELMNLATWVGSNLCDPASRELVVSYVNVNMGLKIR

QLLWFHISCLTFGRETVLEYLVSFGVWIRTPPAYRPPNAPILSTLPETT

VVRRRGRSPRRRTPSPRRRRSQSPRRRRSQSRESQC

D78C generated within HBV C-protein variant 1 has the following amino acid sequence: (SEQ ID NO: 139)

MDIDPYKEFGASVELLSFLPSDFFPSIRDLLDTASALYREALESPEHCS

PHHTALRQAILCWGELMNLATWVGSNLECPASRELVVSYVNVNMGLKIR

QLLWFHISCLTFGRETVLEYLVSFGVWIRTPPAYRPPNAPILSTLPETT

VVRRRGRSPRRRTPSPRRRRSQSPRRRRSQSRESQC

A80C generated within HBV C-protein variant 1 has the following amino acid sequence: (SEQ ID NO: 140)

MDIDPYKEFGASVELLSFLPSDFFPSIRDLLDTASALYREALESPEHCS

PHHTALRQAILCWGELMNLATWVGSNLEDPCSRELVVSYVNVNMGLKIR

QLLWFHISCLTFGRETVLEYLVSFGVWIRTPPAYRPPNAPILSTLPETT

VVRRRGRSPRRRTPSPRRRRSQSPRRRRSQSRESQC

In a one embodiment, a chemical linker, e.g., a bifunctional linker, may bind another moiety to a particle formed from viral core proteins that include a modified structure core portion, e.g., that include one or more cysteine residues. Exemplary chemical linkers include moieties such as those formed by contacting a cysteine residue with a maleimide containing compound such as phosphatidylethanolamine-maleimide (PE-maleimide or PE-mal). Phospholipids, for example, may be directly linked through a chemical linker to a modified structural core portion, e.g., to link a lipid molecule and/or a targeting agent.

In another embodiment, cysteine residues may be engineered into the structural core portion region to provide a covalent linker to a modified Hepatitis B Virus S-protein. In some embodiments, a S-protein may guide the coating of the lipid layer or lipid/cholesterol layer. Contemplated S-proteins for attaching to a disclosed capsid or particle may be modified to have cysteines as well to complement the disulfide bridge formation between C-protein monomers. Alternatively, a S-protein can be replaced by a peptide such as a transmembrane engineered peptide. An exemplary transmembrane engineered peptide may have, e.g., a flexible region that ends with a cysteine so as to form disulfide bridges with the cage, with the opposite end comprising primarily of hydrophobic residues. A non-limiting example of such a HBV S-protein transmembrane engineered peptide has the amino acid sequence:

CARGARGARGARGILGVFILLYM   (SEQ ID NO: 141)

One of skill in the art recognizes that nucleic acid and amino acid sequences of the specific modified viral core proteins, e.g., about 75% to about 99% identical, about 80% to about 95% identical, about 85% to about 90% identical, or about 95% to about 99% identical, or any specific percent identity disposed within these ranges, to disclosed viral core proteins capable of forming a capsid and capable of binding a nucleic acid are within the scope of the present invention.

Compositions and Particles

Provided herein are therapeutic compositions that include particles formed from a plurality of chimeric therapeutics as described above. Such particles may include a coating, or alternatively, a set of particles may be associated with each other, and such set of particles may include a coating over the set. Therapeutic compositions may include a pharmaceutically acceptable excipient.

For example, provided herein is a therapeutic composition comprising a particle formed from at least: i) a first discrete number of modified viral core proteins; and ii) a second discrete number of nucleic acids each bound to one of said modified viral core proteins. For example, not all of the first discrete number of modified viral core proteins may be associated or bound to a nucleic acid. In some embodiments, only a portion of modified viral core proteins that form part of a particle are bound to a nucleic acid. For example, within a disclosed particle, only some viral core proteins are associated or bound to a nucleic acid. It will be appreciated that in some embodiments, a particle may include different modified viral core proteins, e.g., those with different modified tail portions, or a particle may be, e.g., formed from all the same modified viral core proteins. Contemplated particles may include a coating associated with a given particle or may include a coating associated with or surrounding several particles.

In some embodiments, for example, when the modified structural core portion of the viral core protein is about 149 amino acid residues in length, the first discrete number of modified viral core proteins is about 180 to about 250, about 200 to about 245, e.g., about 240 modified viral core proteins. In other embodiments, for example, when the modified structural core portion of the viral core protein is about 138 amino acid residues in length, the first discrete number of modified viral core proteins is about 160 to about 250, e.g., about 180 modified viral core proteins.

The second discrete number of nucleic acids, wherein each nucleic acid is bound to one of the viral core proteins, is about 2 to about 60, about 8 to about 20, or about 14 to about 18, e.g., about 15, 16, or 17 nucleic acids. For example, in an exemplary embodiment, if a disclosed particle is formed from 240 modified viral core proteins, about 14 to about 18 of those modified viral core proteins are bound to a nucleic acid. In an embodiment, a given particle can include e.g., about 8 to about 20 of the same nucleic acid, or one or more nucleic acids may be substantially different, e.g., directed to a different area of a gene target or to a different gene target.

Also contemplated herein is a therapeutic particle that includes a plurality of viral core proteins each comprising a structural core portion and a modified tail portion, wherein said structural core portions form a capsid; and said modified tail portions are substantially disposed within said capsid; and a plurality of nucleic acids, bound to a modified tail portion of one of the viral core proteins. In some embodiments, the number of nucleic acids bound to a modified tail portion is less than that number of viral core proteins present in the particle. For example, disclosed herein are particles formed from a plurality of disclosed viral core proteins and comprise about 8 to about 20 nucleic acids, e.g., about 14 to about 18, e.g., about 15, 16, or 17 nucleic acids each substantially homologous to a given target.

It will be appreciated that in some embodiments, a disclosed particle may include two or more different modified viral core proteins, e.g., those with different modified tail portions, or a particle may be, e.g., formed from all the same modified viral core proteins.

In an embodiment, this disclosure also provided for therapeutic multiplexes comprising two or more disclosed particles, e.g., a plurality of particles, and a coating at least partially surrounding the particles. For example, a disclosed multiplex may have about 3 to about 12 particles, or about 4 to about 8 particles, e.g., about 12 particles. In some embodiments, a disclosed multiplex has about 6 capsids, e.g., associated with each other, and a coating at least partially, or substantially, surrounding, e.g., 6 capsids.

In some embodiments, contemplated particles formed from, e.g., disclosed chimeric therapeutics are about 20 to about 25 nm in diameter, or about 30 to about 35 nm in diameter. Particles contemplated herein may be substantially spherical and/or may be icosahedral in form.

Throughout the specification, particles contemplated herein may be referred to as "capsids," "particles," "therapeutic particles," and "therapeutic chimeric particles."

Disclosed particles may further, in some embodiments, comprise a partial or substantially complete coating disposed on the particle that includes one or more lipids. For example, at least one lipid molecule may covalently bound through a chemical linker moiety, e.g., a lipid linker moiety, to a viral core protein, e.g., to a structural core portion of a disclosed viral core protein. For example, the lipid may be attached via bond or chemical linker moiety, to an engineered location on the structural core portion of the viral core protein, for example at position 77, 78 or 80 of a hepatitis B structural core portion, as described above.

Contemplated lipid linker moieties may include those discussed above. Exemplary lipid linker moities may be formed from contacting e.g., a succinimidyl derivative such as succinimidyl-4-(p-maleimidophenyl)butyrate (SMPB) or m-maleimidobenzoyl-N-hydroxysuccinimide ester with a modified structural core portion of the viral core protein.

A disclosed particle (or set of particles) may have a layer or coating comprising one or more lipids, e.g., a neutral lipid, an anionic lipid, and/or a cationic lipid. For example, a neutral lipid and/or an amphipathic lipid, for example, a phospholipid such as phophatidyl serine, may be covalently bonded to a lipid linker moiety. Such covalently bound lipid molecules may guide the placement of a coating, e.g., that may include one more neutral lipids, and/or may include an anionic lipid that is surface neutral, such as POPG.

Exemplary phospholipids suitable for use include, but are not limited to, hydrogenated soy phosphatidylcholine (HSPC), egg phosphatidylcholine (EPC), phosphatidyl ethanolamine (PE), phosphatidyl glycerol (PG), phosphatidyl inositol (PI), monosialogangolioside, spingomyelin (SPM), distearoylphosphatidylcholine (DSPC), dimyristoylphosphatidylcholine (DMPC), or dimyristoylphosphatidylglycerol (DMPG).

In some embodiments, particles contemplated herein include one or more lipids including one, two, or more of lipids such as palmitoyloleoylphosphatidylglycerol (POPG), hydrogenated soy phosphatidylcholine (HSPC). Contemplated lipids include PEG-phospholipids, including poly(ethylene glycol)-derivatized distearoylphosphatidylethanolamine (PEG-DSPE) and/or poly(ethylene glycol)-derivatized ceramides (PEG-CER).

Provided herein are particles that may include a coating comprising one or more lipids and cholesterol, for example, may include various amounts of cholesterol, HSPC or POPG. The lipid coating may include about 5% to about 40% cholesterol, about 10% to about 80% HSPC and/or about 5% to about 80% POPG, or any specific percentage within said ranges. In some embodiments, a coating may comprise, for example, (a) about 20% cholesterol and about 80% HSPC; (b) about 50% cholesterol and about 50% HSPC; (c) about 20% cholesterol and about 20% HSPC and about 60% POPG; (d) about 50% cholesterol and about 50% POPG; (e) 20% cholesterol and 80% POPG; or (f) about 10% cholesterol and about 15% HSPC and about 65% POPG. In an embodiment, a coating may include about 20% cholesterol, about 20% HSPC and about 60% POPG.

A coating composition may have a mass value of the particle of about 10% to about 60%, about 10% to about 50%, about 15 to about 40%, about 20% to about 35% of the total protein (w/w), or any specific percentage with the recited ranges. For example, a lipid coating composition may coat a particle at a mass value of about 30% to about 100% (w/w).

Suitable ratios of protein:lipid for the coating process may range, in an embodiment, from approximately 1:1 protein:lipid (w:w) to approximately 1:30 protein:lipid (w:w).

Figure 4:
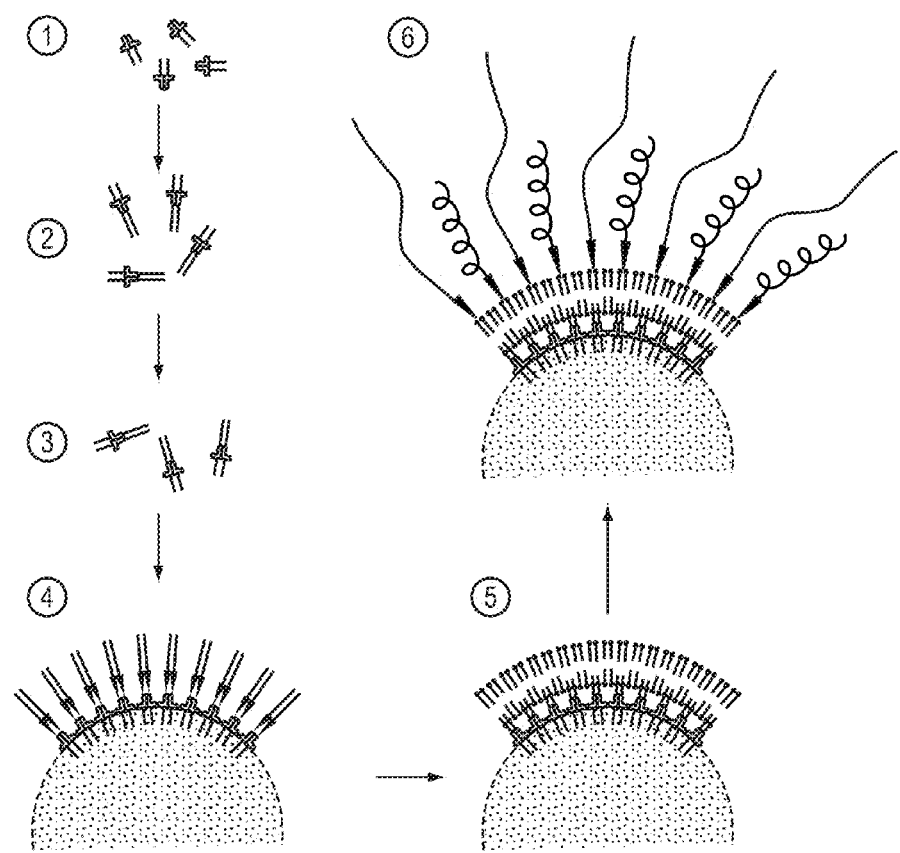
FIG. 4 is a flow diagram depicting the construction of a therapeutic particle.

In an exemplary embodiment, a disclosed particle that includes a lipid coating may be generally prepared by 1) first mixing a modified viral core protein with an nucleic acid of choice; 2) placing the core protein in a buffered solution, e.g., phosphate, citrate, tris, sodium buffer, causing particles to be formed that substantially encapsulate the nucleic acid; 3) adding sonicated phospholipids solution to the mixture which may bind with modified sites on the viral core protein; 4) adding cholesterol or lipid-tagged polyethylene glycol to the mixture; and 5) purifying the system by centrifugation or size exclusion chromatography. In a exemplary embodiment, formation of a disclosed particle is shown pictorially in FIG. 4.

To prevent premature formation of a capsid or particle, the viral core proteins may be maintained in any suitable chemical denaturant or denaturing agent known in the art (e.g., urea, guanidine hydrochloride (GuHCl), sodium dodecyl sulfate (SDS)) in a concentration of about 1M to about 6M, about 1.5M to about 5M, about 1.75M to about 4.5M, or any integer disposed within said ranges. For example, the chemical denaturant may be urea, which may be present in, e.g., a concentration of about 2M to about 6M, about 3M to about 5M, about 3.5M to about 4.5M, e.g., about 4M, or any integer disposed within said ranges. To trigger a self-assembly reaction of a capsid or particle, the ionic strength of a solution of viral core proteins can be raised to a final concentration of about 50 mM to about 600 mM using e.g., a salt, e.g., NaCl. The final concentration can be about 100 mM to about 550 mM, about 150 mM to about 500 mM, about 200 to about 450 mM, about 250 mM to about 400 mM or about 300 mM to about 350 mM, or any integer disposed within said ranges. The final ionic concentration of the solution may be directly related to the amount of chemical denaturant present in the solution. In addition to salt and chemical denaturant concentrations, temperature may facilitate self-assembly of the capsid. A temperature of about 25° C. to about 105° C., about 40° C. to about 90° C. or about 55° C. to about 75° C. (or any specific temperature within the recited ranges) may trigger self-assembly of the capsid. In another embodiment, reducing agents such as DTT or beta-mercaptoethanol may also be used to facilitate self-assembly of the capsid.

After incubating the mixture, the presence of fully formed particles may be verified using standard biochemical analyses known in the art.

Particles disclosed herein may be substantially non-replicating. For example, the viral core proteins may be designed so that once the particle starts to disintegrate, they are degraded quickly so as to limit any potential immune response. Disclosed particles do not substantially incorporate any attenuated wild type virus.

Targeting Agents

Various targeting agents can be incorporated into, e.g., a coating layer of the disclosed particles, e.g., incorporated or bound to a lipid layer or lipid/cholesterol layer coat to direct the particle to a tissue or cell target. Alternatively, a targeting agent may be bound directly, e.g., chemically linked, directly or through a chemical linker moiety, to a disclosed particle.

An exemplary targeting agent may be an antibody. For example, exposed sulfhydryl groups on the heavy chain of an antibody can be used to link the antibody to, e.g., a free sulfate group on a coating comprising one or more lipids. Alternatively, a lipid can be attached to antibodies through different chemical means, such as reacting an activated lipid such as PE-maleimide to activated free amines of an antibody with agents such as Traut's Reagent.

A reduced antibody heavy chain-light chain complex above can also be attached directly to the naked particle. For example, the modified viral core protein may incorporate cysteine residues with reactive sulfhydryl groups as described above which then can be linked with the partially disassociated antibody chains.

Antibodies suitable for use as targeting agents include antibodies directed to cell surface antigens which cause the antibody-nanoparticle complex to be internalized, either directly or indirectly. Specific non-limiting examples of suitable antibodies include antibodies to CD19, CD20, CD22, CD33 and CD74. CD33 and CD22 are over-expressed on lymphomas and binding to these antigens caused endocytosis and thereby internalization of the antibody-nanoparticle complex. Methods for incorporating incorporation of monoclonal antibodies to CD22 into the lipid coating can be found in U.S. Patent Publication No. 20070269370.

In some embodiments, a coating of a particle, or the particle itself, may be modified, to enhance, e.g., the ability of the particles to enter target cells and/or to at least partially evade the immune system in vivo. For example, a large polymer (e.g., PEG), cholesterol-tagged or lipid-tagged polyethylene glycol (PEG) and/or protein transduction domains (PTD) may form part of a coating, and/or may be covalently linked through a bond or a chemical linker moiety to the coating and/or to specific site(s) (e.g., cysteine sites) on the modified structural core portion of the viral core protein. Non-limiting examples of suitable PTDs are the Human Immunodeficiency Virus (HIV) transactivator of transcription (Tat) peptide and/ or poly-arginine (poly-Arg). In an embodiment, the particles and/or coatings may be modified by attaching a PEG. For example, one or more cholesterol-tagged PEGs may be anchored into a lipid coating or particle, and/or one or more cholesterol tagged PTD may be anchored into a coating or particle. In some embodiments, a particle and/or coating may be modified, e.g., covalently bonded through a chemical linker, to a carbohydrate and/or a sugar, e.g., a branched sugar, moiety. PTD amino acid sequence may be engineered into, e.g., the spike region (e.g., position 77 or 78) of the structure portion of a viral core protein.

Antibody mimetics and/or peptide mimetics that include complementarity determining region (CDR) subunits may also be, in some embodiments, associated with or bound to (e.g., via linker) to a coating or particle disclosed herein.

In another embodiment, an targeting agent that binds FcRN, s-protein or other moiety can be bound or associated with either a coating, e.g., a lipid coating, or may be bound directly to a modified viral core. Such targeting agents include those in US Patent Application 20070254831.

Nucleic Acids

The therapeutic chimerics, particles and compositions disclosed here include at least one nucleic acid substantially homologous to a particular target bound to, or associated with, a viral core protein. In certain embodiments, an nucleic acid, when bound to a viral core protein, is "substantially non-immunogenic" i.e., does not elicit, induce, or invoke a substantial immune response, for example, a humoral and/or a cellular immune response in a mammalian subject, such as a human subject. In other embodiments, a nucleic acid molecule, e.g., an inhibitory nucleic acid that is not bound to the viral core protein, e.g., when substantially released in vivo from a therapeutic disclosed herein, may be substantially non-immunogenic, or may have immunogenic properties.

Exemplary nucleic acids that may form part of the, e.g., disclosed therapeutics, particles and/or compositions disclosed herein include inhibitory nucleic acids. Other exemplary nucleic acids contemplated for use include double stranded RNA, antisense nucleic acid, hairpin RNA, and microRNA.

Inhibitory nucleic acid include an inhibitory double-stranded RNA, i.e., a "interfering RNA" or "iRNA" of about 10 to about 60, about 15 to about 50, about 15 to about 40, about 15 to about 30, or about 15 to about 20 nucleotides in length. In some embodiments, an inhibitory double stranded RNA is about 25 to about 45, about 25 to about 40, about 25 to about 35, about 27 to about 40, about 30 to about 40, about 33 to about 40, or about 36 to about 40 nucleotides in length. For example, an inhibitory double stranded RNA is about 25, 26, 27, 28, 29, 30, 31, 32, or 33 bases or nucleotides in length. In other embodiments, an inhibitory double stranded RNA is about 15 to about 30, about 15 to about 25, about 19 to about 25, about 19 to about 23, or about 19 to about 21 nucleotides in length. In yet other embodiments, an inhibitory double stranded RNA is about 20 to about 24 or about 21 to about 22 or to about 23 nucleotides in length. An inhibitory double stranded RNA may be transcribed from a transcriptional cassette in a DNA plasmid. Such inhibitory double stranded RNA reduces, inhibits or silences expression of a target gene by mediating the degradation of mRNAs, which are complementary to the sequence of an inhibitory RNA, by the process of RNA interference.

RNA interference (RNAi) is a process by which double-stranded RNA (dsRNA) is used to silence gene expression. While not wanting to be bound by theory, RNAi begins with the cleavage of longer dsRNAs into smaller inhibitory dsRNAs by an RNaseIII-like enzyme, dicer Inhibitory dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the inhibitory dsRNA is incorporated into a ribonucleoprotein complex known as the RNA-induced silencing complex (RISC). RISC uses this RNA strand to identify mRNA molecules that are at least partially complementary to the incorporated RNA strand, and then cleaves these target mRNAs or inhibits their translation. Therefore, the RNA strand that is incorporated into RISC is known as the guide strand or the antisense strand. The other RNA strand, known as the passenger strand or the sense strand, is eliminated from the RNA and is at least partially homologous to the target mRNA. Those of skill in the art will recognize that, in principle, either strand of a dsRNA can be incorporated into RISC and function as a guide strand. However, inhibitory dsRNA design (e.g., decreased dsRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include hairpin RNAs, single-stranded RNAs, microRNAs, and dicer-substrate 27-mer duplexes.

An inhibitory double stranded RNA can be formed by two complementary strands or by a single, self-complementary strand. The relationship between a target mRNA and the sense strand of an inhibitory RNA is that of identity. The sense strand of an inhibitory RNA is also called a passenger strand, if present. The relationship between a target mRNA (a sense strand) and the antisense strand of an inhibitory RNA is that of complementarity. The antisense strand of an inhibitory RNA is also called a guide strand. Exemplary inhibitory double stranded RNA duplex may comprise 3' overhangs of about 1 to about 4 nucleotides, for example of about 2 to about 3 nucleotides, and 5' phosphate termini. In other embodiments, an inhibitory double stranded RNA duplex may have no overhangs on one or both ends (blunt ends). Some exemplary inhibitory double stranded RNAs may lack a terminal phosphate.

Examples of inhibitory double stranded RNA molecules include, without limitation, a double-stranded polynucleotide molecule assembled from two separate oligonucleotides, wherein one strand is the sense strand and the other is the complementary antisense strand; a double-stranded polynucleotide molecule assembled from a single oligonucleotide, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide may be processed in vivo or in vitro to generate an active inhibitory double-stranded RNA molecule.

The sequence of an inhibitory double-stranded RNA to be delivered by the present invention must have a sufficient identity to a target nucleic acid in order to mediate target-specific RNA interference. In an embodiment, an inhibitory double-stranded RNA has an identity of at least about 85%, 90%, 95%, or 100% to the desired target nucleic acid. The identity of a double-stranded RNA molecule to a predetermined nucleic acid target molecule, e.g., an mRNA target molecule, may be determined as follows: $I=n/L \times 100$: wherein I is the identity in percent, n is the number of identical nucleotides in the double-stranded portion of the dsRNA and the target and L is the length of the sequence overlap of the double-stranded portion of the dsRNA and the target.

Alternatively, the identity of a double-stranded RNA molecule to the target sequence may also be defined to include a 3' overhang, particularly an overhang having a length from 1-3 nucleotides, with a sequence identity of at least about 50%, about 70%, or about 85% or more to the target sequence. For example, the nucleotides from the 3' overhang and up to 2 nucleotides from the 5' and/or 3' terminus of the double strand may be modified without significant loss of activity.

Inhibitory nucleic acids may include one or more mismatch motifs or mismatch regions, which refer to a portion of an nucleic acid sequence that does not have 100% complementary to its target sequence. A nucleic acid may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

Inhibitory double stranded RNA contemplated herein may be sufficiently identical or sufficiently complementary, e.g., substantially homologous to a target nucleic acid, e.g., a target mRNA, such that the inhibitory double stranded RNA silences production of protein encoded by the target mRNA. In one embodiment, a contemplated inhibitory double stranded RNA may be identical or exactly complementary (excluding the RRMS containing subunit(s)) to a target RNA, e.g., the target RNA and the inhibitory double stranded RNA anneal, e.g., to form a hybrid made of Watson-Crick base pairs in the region of exact identity or complementarity. For example, a sufficiently identical or sufficiently complementary target RNA may include an internal region (e.g., of at least 10 nucleotides) that is exactly identical or complementary to a target. Moreover, in some instances, an inhibitory double stranded RNA may specifically discriminate a single-nucleotide difference, for example, mediating RNA interference if exact identity or complementary is found in the region of the single-nucleotide difference (e.g., within 7 nucleotides of the single nucleotide difference).

Selecting and Optimizing Inhibitory Nucleic Acid Molecule Sequences

Suitable inhibitory double stranded RNA sequences that target a gene of interest may be identified using any means known in the art. Typically, methods such as gene walking or the methods described in Elbashir et al., Nature 411:494-498 (2001) and Elbashir et al., EMBO J 20: 6877-6888 (2001) are combined with rational design rules set forth in Reynolds et al., Nature Biotech. 22:326-330 (2004), each of which are incorporated herein by reference.

Typically, a sequence within about 50 to about 100 nucleotides 3' of the AUG start codon of a transcript from the target gene of interest is scanned for dinucleotide sequences (e.g., AA, CC, GG, or UU) (see, e.g., Elbashir, et al., EMBO J 20: 6877-6888 (2001)). The nucleotides immediately 3' to the dinucleotide sequences are identified as potential inhibitory double stranded RNA target sequences. Typically, the 19, 21, 23, 25, 27, 29, 31, 33, 35, 38, 40, 42, or more nucleotides immediately 3' to the dinucleotide sequences are identified as potential inhibitory double stranded RNA target sites. The dinucleotide sequence may be, for example, an AA sequence and the 19 to about 40 nucleotides immediately 3' to the AA dinucleotide are identified as a potential inhibitory double stranded RNA target site. Typically, inhibitory double stranded RNA target sites are spaced at different positions along the length of the target gene. To further enhance silencing efficiency of an inhibitory double stranded RNA sequences, potential inhibitory double stranded RNA target sites may be analyzed to identify sites that do not contain regions of homology to other coding sequences. For example, in some embodiments, a suitable inhibitory double stranded RNA target site of about 21 base pairs may not have more than 16-17 contiguous base pairs of homology to other coding sequences. If inhibitory double stranded RNA sequences are to be expressed from an RNA Pol III promoter, inhibitory double stranded RNA target sequences lacking more than 4 contiguous A's or T's may be selected.

Once a potential inhibitory double stranded RNA sequence has been identified, the sequence may be analyzed using a variety of criteria known in the art. For example, to enhance their silencing efficiency, inhibitory double stranded RNA sequences may be analyzed by a rational design algorithm to identify sequences that have one or more of the following features: (1) G/C content of about 25% to about 60% G/C; (2) at least 2 or 3 A/Us at positions 15-19 of the sense strand; (3) no internal repeats; (4) an A at position 19 of the sense strand; (5) an A at position 3 of the sense strand; (6) a U at position 10 of the sense strand; (7) an A at position 14 of the sense strand; (8) no G/C at position 19 of the sense strand; and (9) no G at position 13 of the sense strand. Inhibitory double stranded RNA design tools that incorporate algorithms that assign suitable values of each of these features and are useful for selection of inhibitory double stranded RNA can be found at, e.g., the website boz094.ust.hk/RNAi/siRNA. One of skill in the art will appreciate that sequences with one or more of the foregoing characteristics may be selected for further analysis and testing as potential inhibitory double stranded RNA sequences. Inhibitory RNA sequences complementary to target sites may also be designed. Techniques for selecting target sequences for inhibitory RNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. For example, initial search parameters can include G/C contents between 35% and 55% and siRNA lengths between 19 and 27 nucleotides. The target sequence may be located in the coding region or in the 5' or 3' untranslated regions of the mRNA.

Additionally, potential inhibitory double stranded RNA target sequences with one or more of the following criteria can often be eliminated as inhibitory double stranded RNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequence comprising direct repeats of 4 or more bases within the candidates resulting in internal fold-back structures. However, one of skill in the art will appreciate that sequences with one or more of the foregoing characteristics may still be selected for further analysis and testing as potential inhibitory double stranded RNA sequences. The importance of various criteria can vary greatly. For instance, a C base at position 10 of the sense strand may make a minor contribution to duplex functionality. In contrast, the absence of a C at position 3 of the sense strand is may be very important.

With respect to criteria for selecting an inhibitory double stranded RNA, GC content, as well as a high number of AU in positions 15-19 of the sense strand, may be important for easement of the unwinding of an inhibitory double stranded RNA duplex. Duplex unwinding has been shown to be crucial for inhibitory double stranded RNA functionality in vivo. The internal structure is measured in terms of the melting temperature (Tm) of the single strand of inhibitory double stranded RNA, which is the temperature at which 50% of the molecules will become denatured.

It should be noted that all of the aforementioned criteria regarding sequence position specifics are with respect to the 5' end of the sense strand. Reference is made to the sense strand, because most databases contain information that describes the information of the mRNA. An inhibitory nucleic acid molecule contemplated herein may be a variety of lengths. The aforementioned criteria may assume an inhibitory nucleic acid molecule of at least 19 nucleotides in length so that it is important to keep the aforementioned criteria applicable to the correct bases. It is understood that a person skilled in the art will know how to apply the aforementioned criteria to inhibitory nucleic acid molecules of varying lengths.

In addition to gene walking and sequence analysis and optimization, as described above, various algorithms well-known in the art can be utilized to select an inhibitory dsRNA sequence. Exemplary algorithms for selecting inhibitory RNA sequences are disclosed in Naito et al., Nucleic Acids Res 33: W589-591, 2005, Henschel et al., Nucleic Acids Res 32: W113-120, 2004, Naito et al., Nucleic Acids Res 32: W124-129, 2004 (for mammalian-specific interfering RNAs) and Naito et al., Nucleic Acids Res 34: W448-450, 2006 (for viral-specific interfering RNAs), each of which is incorporated herein by reference. In some embodiments, a person skilled in the art may use one or more algorithms to select an inhibitory RNA sequence. Further, a person skilled in the art will appreciate the use of multiple parameters and algorithms in selecting and optimizing an inhibitory RNA sequence.

Inhibitory double stranded RNA selected according to the aforementioned criteria or one of the aforementioned algorithms are also, for example, useful in the simultaneous screening and functional analysis of multiple genes and gene families using high throughput strategies, as well as in direct gene suppression or silencing. Useful applications for inhibitory nucleic acid molecules include, but are not limited to, target validation, gene functional analysis, research and drug discovery, gene therapy and therapeutics. Methods for using inhibitory nucleic acid molecules including inhibitory double-stranded RNA molecules in these applications are well known to persons of skill in the art.

Inhibitory double stranded RNA molecules contemplated herein may be applicable across a broad range of species, including but not limited to all mammalian species, such as humans, dogs, horses, cats, cows, mice, hamsters, chimpanzees and gorillas, as well as other species and organisms such as bacteria, viruses, insects, plants and C. elegans.

Also contemplated herein are nucleic acids applicable for use for silencing a broad range of genes, including but not limited to the roughly 45,000 genes of a human genome. For example, contemplated herein are nucleic acids that target to genes are associated with diseases such as the gene targets discussed herein.

Analysis of Inhibitory Nucleic Acid Molecules

Potential inhibitory double stranded RNA target sequences may be further analyzed based on inhibitory double stranded RNA duplex asymmetry as described in, e.g., Khvorova et al., Cell, 115:209-216 (2003); and Schwarz et al., Cell, 115:199-208 (2003). Potential inhibitory double stranded RNA target sequences may be further analyzed based on secondary structure at the mRNA target site as described in, e.g., Luo et al., Biophys. Res. Commun., 318:303-310 (2004). For example, mRNA secondary structure may be modeled using the Mfold algorithm (available at www.bioinfo.rpi.edu/applications/mfold/rna/forml.cgi) to select inhibitory double stranded RNA sequences which favor accessibility at the mRNA target site where less secondary structure in the form of base-pairing and stem-loops is present.

Once a potential inhibitory double stranded RNA sequence has been identified, the sequence may be analyzed for the presence of any immunostimulatory properties, e.g., using an in vitro cytokine assay or an in vivo animal model. Motifs in the sense and/or antisense strand of the inhibitory double stranded RNA sequence such as GU-rich motifs (e.g., 5'-GU-3',5'-UGU-3',5'-GUGU-3',5'-UGUGU-3', etc.) may also provide an indication of whether the sequence may be immunostimulatory. If an inhibitory double stranded RNA molecule is found to be immunostimulatory, it may, in certain embodiments, be modified to decrease its immunostimulatory properties. The detectable immune response may comprise production of a cytokine or growth factor such as, e.g., TNF-α, IFN-α, IFN-β, IFN-γ, IL-6, IL-12, or a combination thereof. As a non-limiting example, an inhibitory double stranded RNA identified as being immunostimulatory can be modified to decrease its immunostimulatory properties by replacing at least one (but less than about 30%) of the nucleotides on the sense and/or antisense strand with modified nucleotides such as 2'OMe nucleotides (e.g., 2'OMe-guanosine, 2'OMe-uridine, 2'OMe-cytosine, and/or 2'OMe-adenosine), as described in further detail herein.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem. 255:4980-4983 (1980)); enzyme-linked immunosorbent assays (ELISA) as described, for example, by Raines et al., J. Biol. Chem. 257:5154-5160 (1982); immunocytochemical techniques, including the use of fluorochromes (Brooks et al., Clin. Exp. Immunol. 39:477 (1980)); and neutralization of activity (Bowen-Pope et al., Proc. Natl. Acad. Sci. USA 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

Generating Inhibitory Nucleic Acid Molecules

Inhibitory nucleic acid molecules may be provided in several forms including, e.g., as one or more isolated RNA duplexes, e.g., siRNA, longer double-stranded RNA (dsRNA) or RNA transcribed from a transcriptional cassette in a DNA plasmid Inhibitory nucleic acid molecules, such as inhibitory double stranded RNAs may also be chemically synthesized. The inhibitory double stranded RNA sequences may have overhangs (e.g., 3' or 5' overhangs as described in Elbashir et al., Genes Dev. 15:188 (2001) or Nykanen et al., Cell 107:309 (2001), or may lack overhangs (i.e., to have blunt ends).

Exemplary RNA population may be used to provide long precursor RNAs, or long precursor RNAs that have substantial or complete identity to a selected target sequence may be used to make the inhibitory dsRNA. For example, the RNAs can be isolated from cells or tissue, synthesized, and/or cloned according to methods well known to those of skill in the art. The RNA may be a mixed population (obtained from cells or tissue, transcribed from cDNA, subtracted, selected etc.), or may e.g., represent a single target sequence. RNA may be naturally occurring, (e.g., isolated from tissue or cell samples), synthesized in vitro (e.g., using T7 or SP6 polymerase and PCR products or a cloned cDNA), or chemically synthesized.

For example, to form a long dsRNA, for synthetic RNAs, the complement is transcribed in vitro and hybridized to form a dsRNA. If a naturally occurring RNA population is used, the RNA complements are also provided (e.g., to form dsRNA for digestion by E. coli RNAse III or Dicer), e.g., by transcribing cDNAs corresponding to the RNA population, or by using RNA polymerases. The precursor RNAs are then hybridized to form double stranded RNAs for digestion.

Alternatively, one or more DNA plasmids encoding one or more inhibitory dsRNA templates are used to provide the inhibitory dsRNA. Inhibitory dsRNA can, in some embodiments, be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., Science 296:550 (2002); Donze, et al., Nucleic Acids Res. 30:e46 (2002); Paddison, et al., Genes Dev. 16:948 (2002); Yu, et al., PNAS USA 99:6047 (2002); Lee, et al., Nat. Biotech. 20:500 (2002); Miyagishi, et al., Nat. Biotech. 20:497 (2002); Paul, et al., Nat. Biotech. 20:505 (2002); and Sui, et al., PNAS USA 99:5515 (2002)). Typically, a transcriptional unit or cassette will contain an RNA transcript promoter sequence, such as an H1-RNA or a U6 promoter, operably linked to a template for transcription of a desired inhibitory dsRNA sequence and a termination sequence, comprised of 2-3 uridine residues and a polythymidine (T5) sequence (polyadenylation signal) (Brummelkamp, Science, supra). The selected promoter may e.g., provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488, and such plasmids may provide for transient or stable delivery of a target cell. It will be apparent to those of skill in the art that plasmids originally designed to express desired gene sequences may be modified to contain a transcriptional unit cassette for transcription of inhibitory dsRNA.

Methods for isolating RNA, synthesizing RNA, hybridizing nucleic acids, making and screening cDNA libraries, and performing PCR are well known in the art (see, e.g., Gubler and Hoffman, Gene 25:263-269 (1983); Sambrook et al., supra; Ausubel et al., supra), as are PCR methods (see U.S.

Pat. Nos. 4,683,195 and 4,683,202; PCR Protocols: A Guide to Methods and Applications (Innis et al., eds, 1990)). Expression libraries are also well known to those of skill in the art. Additional basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

In an exemplary embodiment, contemplated inhibitory nucleic acid molecules are chemically synthesized. The single stranded molecules that comprise a modified inhibitory nucleic acid molecule may be synthesized using any of a variety of techniques known in the art, such as those described in Usman et al., J. Am. Chem. Soc. 109:7845 (1987); Scaringe et al., Nuc. Acids Res. 18:5433 (1990); Wincott et al., Nuc. Acids Res. 23:2677-2684 (1995); and Wincott et al., Methods Mol. Bio. 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses may be conducted on an Applied Biosystems synthesizer using a 0.2 µmol scale protocol with a 2.5 min. coupling step for 2'-O-methylated nucleotides. Alternatively, syntheses at the 0.2 µmol scale may be performed on a 96-well plate synthesizer from Protogene (Palo Alto, Calif.). However, a larger or smaller scale of synthesis is also within the scope of the present invention. Suitable reagents for oligonucleotide synthesis, methods for RNA deprotection, and methods for RNA purification are known to those of skill in the art.

Alternatively, an inhibitory dsRNA may be synthesized via a tandem synthesis technique, wherein both strands are synthesized as a single continuous oligonucleotide fragment or strand separated by a cleavable linker that is subsequently cleaved to provide separate fragments or strands that hybridize to form the inhibitory dsRNA duplex. For example, a linker can be a polynucleotide linker or a non-nucleotide linker. A tandem synthesis of modified inhibitory dsRNA may be readily adapted to both multiwell/multiplate synthesis platforms as well as large scale synthesis platforms employing batch reactors, synthesis columns, and the like. Alternatively, the modified inhibitory dsRNA can be assembled from two distinct oligonucleotides, wherein one oligonucleotide comprises the sense strand and the other comprises the antisense strand of the inhibitory dsRNA. For example, each strand can be synthesized separately and joined together by hybridization or ligation following synthesis and/or deprotection. In certain other instances, the modified inhibitory dsRNA can be synthesized as a single continuous oligonucleotide fragment, wherein the self-complementary sense and antisense regions hybridize to form an inhibitory dsRNA duplex having hairpin secondary structure.

Modifying Inhibitory Nucleic Acid Molecule Sequences

Inhibitory dsRNAs described herein may comprise at least one modified nucleotide in the sense and/or antisense strand. Exemplary contemplated modifications include the introduction of phosphorothioate linkages and 2'-substitutions on the ribose unit, e.g., 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-O—N-methylacetamido (2'-O-NMA) substitutions, 5-C-methyl, 2'-methoxyethyl, 4'-thio, 2'-amino, or 2'-C-allyl group. Modified nucleotides having a Northern conformation such as those described in, e.g., Saenger, Principles of Nucleic Acid Structure, Springer-Verlag Ed. (1984), are also suitable for use in an inhibitory dsRNA of the present invention. Such modified nucleotides include, without limitation, locked nucleic acid (LNA) nucleotides (e.g., 2'-O, 4'-C-methylene-(D-ribofuranosyl) nucleotides), 2'-methoxyethoxy (MOE) nucleotides, 2'-methylthio-ethyl nucleotides, 2'-deoxy-2'-fluoro nucleotides, 2'-deoxy-2'-chloro nucleotides, and 2'-azido nucleotides. In certain instances, the inhibitory dsRNA includes one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., J. Am. Chem. Soc. 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, Nucl. Acids Res. 29:2437-2447 (2001)) can be incorporated into the inhibitory dsRNA.

In an embodiment, a cholesterol moiety (e.g., on the 3'-end of the sense strand), a 2'-modification (e.g., a 2'-O-methyl or 2'-deoxy-2'-fluoro-modification), and a phosphorothioate (e.g., on the 3'-most one or two nucleotides of the sense and antisense strands) may be present in the same inhibitory dsRNA.

In an embodiment, 2'-substitutions may be made to the 5' nucleotide of a 5'-UA-3' dinucleotide, a 5'-UG-3' dinucleotide, a 5'-CA-3' dinucleotide, a 5'-UU-3' dinucleotide, or a 5'-CC-3' dinucleotide on the sense strand and, optionally, also on the antisense strand of the inhibitory dsRNA, or to all pyrimidine-base comprising nucleotides. For example, the 5'-most pyrimidines in substantially occurrences of the sequence motifs 5'-UA-3',5'-CA-3',5'-UU-3', and 5'-UG-3' may be 2'-modified nucleotides, or for example, substantially all pyrimidines in the sense strand are 2'-modified nucleotides, and 5'-most pyrimidines in substantially all occurrences of the sequence motifs 5'-UA-3' and 5'-CA-3', e.g., all pyrimidines in the sense strand are 2'-modified nucleotides, and the 5'-most pyrimidines in all occurrences of the sequence motifs 5'-UA-3',5'-CA-3',5'-UU-3', and 5'-UG-3' are 2'-modified nucleotides in the antisense strand.

Inhibitory dsRNA may include one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., Tetrahedron 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., Nucleic Acid Analogues: Synthesis and Properties, in Modern Synthetic Methods, VCH, 331-417 (1995); Mesmaeker et al., Novel Backbone Replacements for Oligonucleotides, in Carbohydrate Modifications in Antisense Research, ACS, 24-39 (1994)). Such exemplary chemical modifications can occur e.g., at the 5'-end and/or 3'-end of the sense strand, antisense strand, or both strands of the inhibitory dsRNA.

The sense and/or antisense strand may include, for example, a 3'-terminal overhang having about 1 to about 4 (e.g.,. 1, 2, 3, or 4) 2'-deoxy ribonucleotides and/or any combination of modified and unmodified nucleotides. Additional examples of modified nucleotides and types of chemical modifications that can be introduced into the modified inhibitory dsRNA are described, e.g., in UK Patent No. GB 2,397, 818 B and U.S. Patent Publication Nos. 20040192626 and 20050282188.

Modified inhibitory dsRNA described herein may include one or more non-nucleotides in one or both strands of the inhibitory dsRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

Chemical modification of the inhibitory dsRNA may include attaching a conjugate to the chemically-modified inhibitory dsRNA. The conjugate may be attached at the 5' and/or 3'-end of the sense and/or antisense strand of the chemically-modified inhibitory dsRNA via a covalent attachment such as, e.g., a biodegradable linker. The conjugate may also be attached to the chemically-modified inhibitory dsRNA, e.g., through a carbamate group or other linking group (see, e.g., U.S. Patent Publication Nos. 20050074771, 20050043219, and 20050158727). In certain instances, the conjugate is a molecule that facilitates the delivery of the chemically-modified inhibitory dsRNA into a cell. Examples of conjugate molecules suitable for attachment to a chemically-modified inhibitory dsRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the chemically-modified inhibitory dsRNA molecule may be evaluated for improved pharmacokinetic profiles, bioavailability, and/or stability of the inhibitory dsRNA. As such, one skilled in the art can screen chemically-modified inhibitory dsRNA having various conjugates attached thereto to identify ones having improved properties using any of a variety of well-known in vitro cell culture or in vivo animal models.

In some embodiments, the introduction of modifications into inhibitory dsRNAs may enhance stabilization towards degradation in biological environments and may improve pharmacological properties, e.g., pharmacodynamic properties. Other suitable modifications to a sugar, base, or backbone of an inhibitory dsRNA are described in PCT Publication No. WO 2004/064737. For example, an inhibitory dsRNA may include a non-naturally occurring base, such as the bases described in PCT Publication No. WO 2004/094345 and/or may include a non-naturally occurring sugar, such as a non-carbohydrate cyclic carrier molecule. Exemplary features of non-naturally occurring sugars for use in inhibitory dsRNAs are described in PCT Publication No. WO 2004/094595.

An inhibitory dsRNA may include, in some embodiments, an internucleotide linkage (e.g., the chiral phosphorothioate linkage) useful for increasing nuclease resistance. In addition, or in the alternative, an inhibitory dsRNA may include, for example, a ribose mimic for increased nuclease resistance. An inhibitory dsRNA may include ligand-conjugated monomer subunits and monomers for oligonucleotide synthesis, and/or may be complexed with an amphipathic moiety. The sense and antisense sequences of an inhibitory dsRNA may be palindromic, and/or may have non-canonical pairings, such as between the sense and antisense sequences of the iRNA duplex. Examples of these modifications are described in PCT Publication No. WO 2004/080406 and U.S. Patent Publication No. 2005/0107325.

Enhanced Nuclease Resistance

An inhibitory dsRNA, e.g., an inhibitory dsRNA that targets a gene of interest, may be modified to enhance resistance to nucleases. For example, increased resistance may include identifying cleavage sites and modifying such sites to inhibit cleavage. For example, the dinucleotides 5'-UA-3',5'-UG-3', 5'-CA-3',5'-UU-3', or 5'-CC-3' can serve as cleavage sites, as described in PCT Publication No. WO 2005/115481.

For increased nuclease resistance and/or binding affinity to the target, an inhibitory dsRNA, e.g., the sense and/or antisense strands of the inhibitory dsRNA, may include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino) It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification. The integer n may may any integer, e.g., 0 to 10.

"Deoxy" modifications include hydrogen (i.e. deoxyribose sugars, which are of particular relevance to the overhang portions of partially dsRNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; n=0 to 10), alkylamino, dialkylamino, heterocyclyl, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Exemplary substitutents include 2'-methoxyethyl, 2'-$OCH_3$, 2'-O-allyl, 2'-C-allyl, and 2'-fluoro.

In an exemplary embodiment, 2' modifications may be used in combination with one or more phosphate linker modifications (e.g., phosphorothioate).

In some embodiments, all the pyrimidines of an inhibitory dsRNA may carry a 2'-modification which may have enhanced resistance to endonucleases. In some embodiments, enhanced nuclease resistance may also be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The inhibitory dsRNA may include, in some embodiments, at least 2, at least 3, at least 4 or at least 5 of such dinucleotides. For example, 5'-most pyrimidines in substantially all occurrences of the sequence motifs 5'-UA-3',5'-CA-3',5'-UU-3', and 5'-UG-3' may be 2'-modified.

The inclusion of furanose sugars in the oligonucleotide backbone may, in some embodiments, decrease endonucleolytic cleavage. For example, an inhibitory dsRNA may be further modified by including a 3' cationic group, or by inverting the nucleoside at the 3'-terminus with a 3'-3' linkage. In another alternative, the 3'-terminus may be blocked with an aminoalkyl group, e.g., a 3' C5-aminoalkyl dT, or other 3' conjugates such as naproxen or ibuprofen, small alkyl chains, aryl groups, or heterocyclic conjugates or modified sugars (D-ribose, deoxyribose, glucose etc.). In another embodiment, a 5' conjugate may be included, such as naproxen or ibuprofen, may inhibit exonucleolytic cleavage by sterically blocking the exonuclease from binding to the 5'-end of oligonucleotide.

In some embodiments, an inhibitory dsRNA may have increased resistance to nucleases when a duplexed inhibitory dsRNA includes a single-stranded nucleotide overhang on at least one end. In exemplary instances, the nucleotide overhang includes 1 to 4, e.g., about 2 to 3, unpaired nucleotides. For example, an unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further instances, a nucleotide overhang may have 1 or 2 unpaired nucleotides, and in an exemplary instance a nucleotide overhang is 5'-GC-3', for example on the 3'-end of the antisense strand. In one instance, the inhibitory dsRNA includes the motif 5'-CGC-3' on the 3'-end of the antisense strand, such that a 2-nt overhang 5'-GC-3' is formed.

For example, an inhibitory dsRNA may include monomers which have been modified so as to inhibit degradation, e.g., by nucleases, e.g., endonucleases or exonucleases, found in the body of a subject. These monomers are referred to herein as NRMs, or Nuclease Resistance promoting Monomers or modifications. In many cases these modifications will modulate other properties of the inhibitory dsRNA as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

Modifications that may be useful for producing inhibitory dsRNA that invoke nuclease resistance may include one or more of the following chemical and/or stereochemical modifications of the sugar, base, and/or phosphate backbone:

(1) chiral (Sp) thioates, e.g., that include nucleotide dimers with a particular chiral form of a modified phosphate group containing a heteroatom at the nonbridging position, e.g., Sp or Rp, at the position X, where this is the position normally occupied by the oxygen. The atom at X may be for example, selected from S, Se, Nr2, or Br3. For example, when X is S, the linkage may be an enriched or chirally pure Sp linkage.

(2) attachment of one or more cationic groups to the sugar, base, and/or the phosphorus atom of a phosphate or modified phosphate backbone moiety, for example, NRMs including monomers at the terminal position derivatized at a cationic group. In an embodiment, a 5'-end of an antisense sequence has a terminal —OH or phosphate group so that a NRM is not used at the 5'-end of an antisense sequence. The group should be attached at a position on the base which minimizes interference with H bond formation and hybridization, e.g., away form the face which interacts with the complementary base on the other strand, e.g., at the 5' position of a pyrimidine or a 7-position of a purine.

(3) nonphosphate linkages at the termini, for example a NRM that includes non-phosphate linkages, e.g., a linkage of 4 atoms which confers greater resistance to cleavage than does a phosphate bond. Examples include 3' $CH_2$—$NCH_3$—O—$CH_2$-5' and 3' $CH_2$—NH—(O=)—$CH_2$-5'.

(4) 3'-bridging thiophosphates and 5'-bridging thiophosphates.

(5) L-RNA, 2'-5' linkages, inverted linkages, a-nucleosides, e.g., L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(6) conjugate groups, e.g., a targeting moiety or a conjugated ligand described herein conjugated with the monomer, e.g., through the sugar, base, or backbone;

(7) abasic linkages, e.g., an abasic monomer as described herein (e.g., a nucleobaseless monomer); an aromatic or heterocyclic or polyheterocyclic aromatic monomer as described herein; and (8) 5'-phosphonates and 5'-phosphate prodrugs. For example, NRM's may include monomers, e.g., at the terminal position, e.g., the 5' position, in which one or more atoms of the phosphate group is derivatized with a protecting group, which protecting group or groups, may be removed as a result of the action of a component in the subject's body, e.g., a carboxyesterase or an enzyme present in the subject's body.

In some embodiments, one or more different NRM modifications may be introduced into an inhibitory dsRNA or into a sequence of an inhibitory dsRNA. An NRM modification may be used more than once in a sequence or in an inhibitory dsRNA. As some NRMs interfere with hybridization the total number incorporated should be such that acceptable levels of inhibitory dsRNA duplex formation are maintained. For example, NRM modifications may be introduced into the terminal cleavage site or in the cleavage region of a sequence (a sense strand or sequence) which does not target a desired sequence or gene in the subject, which may reduce off-target silencing.

Nuclease resistant modifications may include those placed only at the terminus and others which may be placed at any position. Such modifications may inhibit hybridization, and in some embodiments, modifications are used only in terminal regions. A NRM may be used anywhere in a sense sequence, provided that sufficient hybridization between the two sequences of the inhibitory dsRNA is maintained. In some instances it is desirable to put a NRM at the cleavage site or in the cleavage region of a sequence which does not target a subject sequence or gene, as it may minimize off-target silencing.

In most cases, any nuclease-resistance promoting modifications will be distributed differently depending on whether the sequence will target a sequence in the subject (often referred to as an antisense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Such modifications may be introduced into the terminal regions, e.g., at the terminal position or within 2, 3, 4, or 5 positions of the terminus, of a sequence which targets or a sequence which does not target a sequence in the subject.

Inhibitory dsRNA may, in some embodiments, include a 5' phosphorylate or include a phosphoryl analog at the 5' prime terminus Possible 5'-phosphate modifications of the antisense strand include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—P-5'); 5'-guanosine cap (7-methylated or non-methylated) (7m-G-O-5'-(HO)(O)P—O—(HP)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$ (S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g., RP(OH)(O)—O-5'-).

In some embodiments, a sense strand can be modified in order to inactivate the sense strand and prevent formation of an active RISC, thereby potentially reducing off-target effects, for example, by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation may also be used, e.g., simply substituting the 5'-OH by H rather than O-Me. Alternatively, a large bulky group may be added to the 5'-phosphate turning it into a phosphodiester linkage.

More detailed and specific modifications for an inhibitory dsRNA, such as phosphate group and/or sugar group modifications, replacement of the phosphate group and/or ribophosphate backbone, terminal modifications or base modifications, as well as preferred inhibitory dsRNA formula, can be found in U.S. Patent Publication No. 2007/0275914.

Evaluation of Candidate Inhibitory Nucleic Acid Molecule

A candidate inhibitory dsRNA may be evaluated for its ability to down-regulate target gene expression. For example, a candidate inhibitory dsRNA may be contacted with a cell that expresses the target gene either endogenously or because it has been transfected with a construct from which the gene can be expressed. The level of target gene expression prior to and following contact with the candidate inhibitory dsRNA can be compared, e.g., on an mRNA or protein level. If it is determined that the amount of RNA or protein expressed from the target gene is lower following contact with the inhibitory dsRNA, then it may be concluded that the inhibitory dsRNA downregulates target gene expression. The level of target RNA or protein in the cell may be determined by any method desired. For example, the level of target RNA may be determined by Northern blot analysis, reverse transcription coupled with polymerase chain reaction (RT-PCR), or RNAse protection assay. The level of protein can be determined, for example, by Western blot analysis.

A functional assay may also be used in some embodiments, to evaluate a modified candidate inhibitory dsRNA. A functional assay may be applied to determine if the modification alters the ability of the molecule to silence gene expression. For example, a cell, e.g., a mammalian cell, such as a mouse or human cell, can be co-transfected with a plasmid expressing a fluorescent protein, e.g., GFP, and a candidate inhibitory dsRNA homologous to the transcript encoding the fluorescent protein (see, e.g., WO 00/44914). For example, a modified inhibitory dsRNA homologous to the GFP mRNA can be assayed for the ability to inhibit GFP expression by monitoring for a decrease in cell fluorescence, as compared to a control cell, in which the transfection did not include the candidate inhibitory dsRNA, e.g., controls with no inhibitory dsRNA added and/or controls with a non-modified inhibitory dsRNA added. Efficacy of the candidate inhibitory dsRNA on gene expression may be assessed by comparing cell fluorescence in the presence of the modified and unmodified inhibitory dsRNA molecules.

Stability Testing, Modification, and Retesting of Inhibitory Nucleic Acid Molecules A candidate inhibitory dsRNA may be evaluated with respect to stability, e.g., its susceptibility to cleavage by an endonuclease or exonuclease, such as when the inhibitory dsRNA is introduced into the body of a subject. For example, methods can be employed to e.g., identify sites that are susceptible to modification, particularly cleavage, e.g., cleavage by a component found in the body of a subject.

When sites susceptible to cleavage are identified, a further inhibitory dsRNA may be designed and/or synthesized wherein the potential cleavage site is made resistant to cleavage, e.g., by introduction of a 2'-modification on the site of cleavage, e.g., a 2'-O-mathyl group. This further inhibitory dsRNA may be retested for stability, and this process may be iterated until an inhibitory dsRNA is found exhibiting the desired stability.

For example, a candidate inhibitory dsRNA, e.g., a modified inhibitory dsRNA, may be scanned for a selected property by, e.g., exposing the inhibitory dsRNA or modified inhibitory dsRNA and a control molecule to the appropriate conditions and evaluating for the presence of the selected property. For example, resistance to a degradent may be evaluated as follows. A candidate modified inhibitory dsRNA (e.g., a control molecule, usually the unmodified form) may be exposed to degradative conditions, e.g., exposed to a milieu, which includes a degradative agent, e.g., a nuclease. For example, one may use a biological sample, e.g., one that is similar to a milieu, which might be encountered, in therapeutic use, e.g., blood or a cellular fraction, e.g., a cell-free homogenate or disrupted cells. The candidate and control could then be evaluated for resistance to degradation by any of a number of approaches. For example, the candidate and control may be labeled, e.g., prior to exposure, with, e.g., a radioactive or enzymatic label, or a fluorescent label, such as Cy3 or Cy5. Control and modified inhibitory dsRNA may be incubated with the degradative agent, and optionally a control, e.g., an inactivated, e.g., heat inactivated, degradative agent. A physical parameter, e.g., size, of the modified and control molecules are then determined, and may be determined by a physical method, e.g., by polyacrylamide gel electrophoresis or a sizing column, to assess whether the molecule has maintained its original length, or assessed functionally. Alternatively, Northern blot analysis may be used to assay the length of an unlabeled modified molecule.

In Vivo Testing

An inhibitory dsRNA identified as being capable of inhibiting target gene expression may be tested for functionality in vivo in an animal model (e.g., in a mammal, such as in mouse or rat). For example, the inhibitory dsRNA may be administered to an animal, and the inhibitory dsRNA evaluated with respect to its biodistribution, stability, and its ability to inhibit target gene expression.

For example, an inhibitory dsRNA may be administered directly to the target tissue, such as by injection, or an inhibitory dsRNA may be administered to the animal model in the same manner that it would be administered to a human. An inhibitory dsRNA can also be evaluated for its intracellular distribution. Such evalution may include determining whether the inhibitory dsRNA was taken up into the cell and/or may include determining the stability (e.g., the half-life) of the inhibitory dsRNA. In an exemplary embodiment, an evaluation of an inhibitory dsRNA in vivo can be facilitated by use of an inhibitory dsRNA conjugated to a traceable marker (e.g., a fluorescent marker such as fluorescein; a radioactive label, such as $^{35}S$, $^{32}P$, $^{33}P$, or $^{3}H$; gold particles; or antigen particles for immunohistochemistry) or by using real-time PCR to quantitatively amplify the dsRNA directly.

In some embodiments, an inhibitory dsRNA useful for monitoring biodistribution may lack gene silencing activity in vivo. For example, the inhibitory dsRNA may target a gene not present in the animal (e.g., an inhibitory dsRNA injected into mouse may target luciferase), or an inhibitory dsRNA may have a non-sense sequence, which does not target any gene, e.g., any endogenous gene). Localization/biodistribution of the inhibitory dsRNA may be monitored, e.g., by a traceable label attached to the inhibitory dsRNA, such as a traceable agent described above.

Inhibitory dsRNA may be evaluated with respect to its ability to modulate, e.g., down regulate the gene expression of a particular target. Levels of target gene expression in vivo may be measured, for example, by in situ hybridization, or by the isolation of RNA from tissue prior to and following exposure to the inhibitory dsRNA. Where the animal needs to be sacrificed in order to harvest the tissue, an untreated control animal may serve for comparison. Target mRNA can be detected by any desired method, including but not limited to RT-PCR, Northern blot, branched-DNA assay, or RNAase protection assay. Alternatively, or additionally, target gene expression can be monitored by performing Western blot analysis on tissue extracts treated with the inhibitory dsRNA.

In one example, a candidate inhibitory dsRNA homologous to an endogenous mouse gene, e.g., a maternally expressed gene, such as c-mos, can be injected into an immature mouse oocyte to assess the ability of the inhibitory dsRNA to inhibit gene expression in vivo (see, e.g., WO 01/36646). A phenotype of the oocyte, e.g., the ability to maintain arrest in metaphase II, can be monitored as an indicator that the inhibitory dsRNA is inhibiting expression. For example, cleavage of c-mos mRNA by the inhibitory dsRNA may cause the oocyte to exit metaphase arrest and initiate parthenogenetic development (Colledge et al. Nature 370: 65-68, 1994; Hashimoto et al. Nature, 370:68-71, 1994). The effect of a modified inhibitory dsRNA on target RNA levels may be verified by, for example, a Northern blot to assay for a decrease in the level of target mRNA, or by Western blot to assay for a decrease in the level of target protein, as compared to a negative control. Such controls may include, e.g., cells in which no inhibitory dsRNA is added and/or cells in which a non-modified inhibitory dsRNA is added.

Targets

Disclosed chimeric therapeutics, particles and/or compositions include a nucleic acid, for example, a RNA, as described above. In one embodiment, a disclosed chimeric therapeutic, particles and/or composition includes a nucleic acid targeted to, e.g., substantially homologous with ApoB. For example, a provided nucleic acid is substantially homologous to a region of the ApoB gene, for example, a mammalian (e.g., human or mouse) ApoB gene.

Provided herein are methods for delivering, in-vivo or in-vitro, a nucleic acid targeting Apo B to a cell, e.g., by contacting a composition, therapeutic or particle disclosed herein with a cell. Also provided here are in vitro and in vivo methods for modulating, e.g., downregulating or silencing the transcription and translation of Apo B. In some embodiments, administered compositions, particles or therapeutics disclosed herein may, upon administration to a patient, localize in the liver or to the gut, e.g., the intestine, such as to the jejunum of the intestine.

Also provided herein are methods of treating a disease or disorder characterized by e.g., ApoB expression, e.g., ApoB misexpression, including, but not limited to, atherosclerosis, angina pectoris, high blood pressure, diabetes, hypothyroidism, hypercholesterolemia (e.g. statin-resistant hypercholesterolemia, atherosclerosis, angina pectoris, high blood pressure, elevated or otherwise unwanted levels of cholesterol, a lipid-mediated vascular disorder, and/or disregulation of lipid metabolism, that include administering to a patient in need thereof an effective amount of a disclosed composition, therapeutic, or particle. Such methods may further include administration (e.g., concurrently or consecutively) with conventional agents used to treat, e.g., a disease or disorder involving hypercholesterolemia, including for example, statins (e.g., atorvastatin, lovastatin, simvastin, fluvastatin, rosuvastatin), niacin, ACE inhibitors, beta-blockers, and the like.

Exemplary nucleic acids targeting ApoB that may be used in the chimeric therapeutic, particles and compounds disclosed herein include:

| Sense 5'-3' | Anti-Sense 3'-5' |
|---|---|
| GAA GAU GCA ACU CGA UUC A (SEQ ID NO: 300) | |
| ACA GUC GCU UCU UCA GUG A (SEQ ID NO: 301) | |
| UGA AUG CAC GGG CAA UGA A (SEQ ID NO: 302) | |
| CGG GAG AAG UGG AGC AGU A (SEQ ID NO: 303) | |
| AGA AGC AGG ACC UUA UCU A (SEQ ID NO: 304) | |
| GGA CAU GGG UUC CAA AUU A (SEQ ID NO: 305) | |
| CCA ATG CTG GAC TTT ATA A (SEQ ID NO: 306) | |
| GCA TGC TTA CTG ATA TAA A (SEQ ID NO: 307) | |
| CAA CCA GTG TAC CCT TAA A (SEQ ID NO: 308) | |
| GAA GAU GCA ACU CGA UUC A (SEQ ID NO: 309) | |
| ACA GUC GCU UCU UCA GUG A (SEQ ID NO: 310) | |
| GUC AUC ACA CUG AAU ACC AAU (SEQ ID NO: 311) | AUU GGU AUU CAG UGU GAU GAC AC (SEQ ID NO: 326) |
| CUU UAC AAG CCU UGG UUC AGU (SEQ ID NO: 312) | ACU GAA CCA AGG CUU GUA AAG UG (SEQ ID NO: 327) |
| GGA AUC UUA UAU UUG AUC CAA (SEQ ID NO: 313) | UUGGAU CAA AUA UAA GAU UCC CU (SEQ ID NO: 328) |
| UAG AAG GGA AUC UUA UAU UUG (SEQ ID NO: 314) | CAA AUA UAA GAU UCC CUU CUA UU (SEQ ID NO: 329) |
| GCC CCA UCA CUU UAC AAG CCU (SEQ ID NO: 315) | AGG CUU GUA AAG UGA UGG GGC UG (SEQ ID NO: 330) |
| AAA UAG AAG GGA AUC UUA UAU (SEQ ID NO: 316) | AUA UAA GAU UCC CUU CUA UUU UG (SEQ ID NO: 331) |
| AGG UGU AUG GCU UCA ACC CUG (SEQ ID NO: 317) | CAG GGU UGA AGC CAU ACA CCU CU (SEQ ID NO: 332) |
| GUC AUC ACA CUG AAU ACC AAU (SEQ ID NO: 318) | AUU GGU AUU CAG UGU GAU GAC AC (SEQ ID NO: 333) |
| GAA CAC CAA CUU CUU CCA CGA (SEQ ID NO: 319) | UCG UGG AAG AAG UUG GUG UUC AU (SEQ ID NO: 334) |
| GAU ACC GUG UAU GGA AAC UGC (SEQ ID NO: 320) | GCA GUU UCC AUA CAC GGU AUC CA (SEQ ID NO: 335) |
| CAG CCC AUC ACU UUA CAA GC (SEQ ID NO: 321) | GCU UGU AAA GUG AUG GGC UG GA (SEQ ID NO: 336) |
| GAU UGA UUG ACC UGU CCA UUC (SEQ ID NO: 322) | GAA UGG ACA GGU CAA UCA AUC UU (SEQ ID NO: 337) |
| AGG UGU AUG GCU UCA ACC CUG (SEQ ID NO: 323) | CAG GGU UGA AGC CAU ACA CCU CU (SEQ ID NO: 338) |
| GAA UGU GGG UGG CAA CUU UAG (SEQ ID NO: 324) | AAA GUU GCC ACC CAC AUU CAG (SEQ ID NO: 339) |

-continued

| Sense 5'-3' | Anti-Sense 3'-5' |
|---|---|
| GUC AUC ACA CUG AAU ACC AAU (SEQ ID NO: 325) | AUU GGU AUU CAG UGU GAU GAC AC (SEQ ID NO: 340) |

Also included are those nucleic acids targeting ApoB disclosed in U.S. Patent Publication No. 2007/0275914.

Various methodologies, such as those described herein (gene walks, algorithm computation) can be utilized to select candidate nucleic acids, as described above. For example, other nucleic acids targeting, for example, Apolipoprotein B can identified using the methods set forth herein, e.g., by scanning and mouse ApoB (XM_137955) and human ApoB (NM_000384) sequences to identify AA dinucleotide motifs and nucleotides 3' of the motif For example, sequences can be indentified that target human ApoB and are derived from GenBank Accession No. NM_000384, GenBank Accession No. NM_137955, or from GenBank Accession No. NM_000384.

In other embodiments, chimeric therapeutics, particles and/or compositions include a nucleic acid targeted to one or more of: prothrombin, FIX, angiotensinogen, renin (see US20070270365), TFPI (see U.S. Pat. No. 7,022,672), CCR5, HCV (see US20070149470), SYK (see U.S. Pat. No. 7,173,015), RANKL, IL-23 (see WO2004/094636), Complement C3 (see US20070178068), Factor H, IL-4Ralpha (see US 2005014333), RBP4, glucagon/glucagon receptor (see US2008/0113372), ghrelin (see US20080140056), GOAT, gastrin, PTP1B, leptin, PCSK-9, IGF-1R, cMet, DR4, DR5, VEGF-A, HGF, sclerostin, and/or myostatin.

In yet other embodiments, comtemplated nucleic acids, e.g., RNAs targeting specific gene targets include those recited in the following patents and patent applications, hereby incorporated by reference, and targeting the following genes: VEGF (see U.S. Pat. No. 7,176,304), HIF1 (see U.S. Patent Publication No. 20080188430), SARS (see U.S. Patent Publication No. 20070270360), HDAC (see U.S. Patent Publication No. 20070185049); Nogo and Nogo Receptor (see U.S. Patent Publication No. 20070185043), WHN (see U.S. Patent Publication No. 20070179104), PCSK9 (see U.S. Patent Publication No. 20070173473), CETP (see U.S. Patent Publication No. 20070173467), XIAP (see U.S. Patent Publication No. 20070093437), CHK-1 (see U.S. Patent Publication No. 20060216747), HR (see U.S. Patent Publication No. 20060160757), CDK2 (see U.S. Patent Publication No. 20060142225), PGF (see U.S. Patent Publication No. 20050267058), PTP-1B (see U.S. Patent Publication No. 20060025361), TGF-beta and TGF-beta Receptor (see U.S. Patent Publication No. 20050287128), STAT3 (see U.S. Patent Publication No. 20050196781), GAB2 (see U.S. Patent Publication No. 20050196767), ICAM (see U.S. Patent Publication No. 20050187174), BCL-2 (see U.S. Patent Publication No. 20050176025), ADAM33 (see U.S. Patent Publication No. 20050164968), EZH2 (see U.S. Patent Publication No. 20050159382), PCNA (see U.S. Patent Publication No. 20050158735), c-SRC (see U.S. Patent Publication No. 20040101850), Notch2 (see U.S. Patent Publication No. 20040101847), IL22 (see U.S. Patent Publication No. 20040097447), ADAMS (see U.S. Patent Publication No. 20040092466), PIM-1 (see U.S. Patent Publication No. 20040092463), TNFSF14 (see U.S. Patent Publication No. 20040096835), MAGE-D1 (see U.S. Patent Publication No. 20040110702), CD1D (see U.S. Patent Publication No. 20040110700), SEDL (see U.S. Patent Publication No. 20040110160), NRF (see U.S. Patent Publication No. 20040110156), BAF53 (see U.S. Patent Publication No. 20040110147), MALT1 (see U.S. Patent Publication No. 20040110145), CDK9 (see U.S. Patent Publication No. 20040110140), PAK1 (see U.S. Patent Publication No. 20040102623), KU86 (see U.S. Patent Publication No. 20040102404), and PPM1B (see U.S. Patent Publication No. 20040102397).

Contemplated nucleic acids include those targeting targets associated with viral infections, for example, those nucleic acids targeting the following viruses and recited in the following patent applications: Influenza Virus (see U.S. Patent Publication No. 20070197460), HVC (see U.S. Patent Publication No. 20080207542), RSV (see U.S. Patent Publication No. 20060287267), and HIV (see U.S. Patent Publication No. 20050191618), wherein each patent and patent application is incorporated by reference.

Nucleic acid sequences disclosed herein are written in a 5' to 3' direction unless otherwise indicated. The target sequences disclosed typically show the sense strand for a double stranded inhibitory nucleic acid molecule (e.g., an RNA). It is understood that the present methods and compositions encompass the complement sequence (or antisense strand) of any of the above identified sequences. Further, it is understood that uracil ("U") is substituted for thymine ("T") when the identified sequences are RNA sequences.

Administration and Dosage

Disclosed chimeric therapeutics, compositions and/or particles may be administered to a patient by any conventional route. These include, but are not limited to, the systemic routes, e.g., subcutaneous, intradermal, intramuscular or intravenous route, and mucosal routes, e.g., oral, nasal, pulmonary or anogenital route. For example, an intratumoral route may be used in, e.g., the treatment of solid tumors. When the treatment of genetic diseases is involved, the choice of the route of administration will depend on the nature of the disease; for example, particles and/or compositions may be administered via a pulmonary route in the case of cystic fibrosis (e.g., wherein the particles are formulated in aerosol form) or, e.g., via intravenous route in the case of hemophilia.

For example, disclosed particles may be administered a composition that comprises a pharmaceutically acceptable excipient and/or a biocompatible aqueous solution. Contemplated solutions may include water and/or saline, and may optionally contain pharmaceutical excipients known to those skilled in the art, for example, buffers, stabilizing molecules, preservatives, sugars, amino acids, proteins, carbohydrates and vitamins, and the like.

The administration of disclosed particles or compositions can be carried out at a single dose or at a dose repeated once or several times after a certain time interval. The appropriate dosage varies according to various parameters, for example the therapeutically effective dosage is dictated by and directly dependent on the individual treated, the mode of administration, the unique characteristics of the nucleic acid and the particular therapeutic effect to be achieved, and the limitations inherent in the art of compounding such an active compound for the treatment of individuals. Appropriate doses can be established by persons skilled in the art of pharmaceutical dosing such as physicians. The nanoparticles can be included in a container, pack, or dispenser together with instructions for administration.

In some embodiments, the particles and compositions disclosed herein may allow for sustained release of a nucleic acid, e.g., an inhibitory nucleic acid, to, e.g., a specific body target site, e.g., the liver. For example, in some embodiments, the disclosed compositions and/or particles may allow for release of a nucleic acid over about 1 day to about 7 days or more, e.g., about 1 day to about 3 days or more, or about 1 day to about 3 weeks or more.

In an embodiment, long-term storage stability of disclosed particles may be increased and/or enhanced by for example, freezing and lyophilizing particles disclosed herein in the presence of one or more protective agents such as sucrose, mannitol, trehalose or the like. Upon rehydration of the lyophilized particles, the suspension may, for example, retain essentially all nucleic acid previously encapsulated and/or may retain substantially the same particle size. Rehydration may be accomplished by, e.g., adding purified or sterile water or 0.9% sodium chloride injection or 5% dextrose solution followed by gentle swirling of the suspension.

EXAMPLES

The examples which follow are intended in no way to limit the scope of the invention but are provided to illustrate different features of the present invention, including preparation and use of the therapeutics contemplated herein. Many other embodiments of this invention will be apparent to one skilled in the art.

Example 1

A. 77C His-Tagged Core Protein

77C His-tagged core protein is cloned into the NdeI/XhoI restriction sites of vector pET21b (Novagen). This plasmid is transformed into *E. coli* BL21 (DE3) PlysS cells (Stratagene) for protein expression. The nucleic acid and corresponding amino acid sequences of the 77C His-tagged Core protein are depicted below:

```
                                                        (SEQ ID NO: 142)
ATG GAT ATC GAT CCG TAT AAA GAA TTT GGC GCC ACC GTG GAA CTG CTG AGC TTT

CTG CCG AGC GAT TTC TTT CCG AGC GTG CGT GAT CTG CTG GAT ACC GCG AGC GCG

CTG TAT CGC GAA GCG CTG GAA AGC CCG GAA CAT TGT AGC CCG CAC CAT ACC GCC

CTG CGT CAG GCG ATT CTG TGC TGG GGT GAA CTG ATG ACC CTG GCG ACC TGG GTT

GGC AAC AAC CTG TGT GAT CCG GCG AGC CGC GAT CTG GTT GTG AAC TAT GTG AAT

ACC AAC ATG GGC CTG AAA ATT CGT CAG CTG CTG TGG TTT CAT ATC AGC TGC CTG

ACC TTT GGC CGC GAA ACC GTG CTG GAA TAT CTG GTG AGC TTT GGC GTT TGG ATC

CGT ACC CCG CCG GCG TAT CGT CCG CCG AAT GCG CCG ATT CTG AGC ACC CTG CCG

GAA ACC ACC GTT GTG CGT CGC CGT GGT CGC AGC CCG CGC CGT CGT ACC CCG AGC

CCG CGT CGT CGT CGT AGC CAG AGC CCG CGT CGT CGC CGC AGC CAG AGC CGC GAA

AGC CAG CTC GAG CAC CAC CAC CAC CAC CAC (SEQ ID NO: 143)
MDIDPYKEFGATVELLSFLPSDFFPSVRDLLDTASALYREALESPEHCSPHHTALRQAILCWGELMTLATWVGN

NLCDPASRDLVVNYVNTNMGLKIRQLLWFHISCLTFGRETVLEYLVSFGVWIRTPPAYRPPNAPILSTLPETTV

VRRRGRSPRRRTPSPRRRRSQSPRRRRSQSRESQLEHHHHHH
```

B. Poly-Lysine Tail Mutants

DNA fragments containing the genes for K5, K7, K9, K10, K11, K13, K20, KA9, KG9 and K4-5 core protein mutants described previously are synthesized via PCR using the Cassette1 template and the primer sequences described in Table 1. Each PCR reaction is composed of 12.5 µl of 5×GC polymerase buffer (Finnzyme), 1.25 µl of a 10 mM dNTP mixture, 1.5 µl of 5 µM forward primer, 1.5 µl of 5 µM reverse primer, 0.6 µl of Stratagene mini-prepped template, 0.8 µl of 2 unit/µl Phusion Hot Start polymerase (Finnzyme), and 44.25 µl of water. The PCR reaction consist of a one-time incubation at 98° C. for 1 minute, followed by incubation at 98° C. for 25 seconds, incubation at 70° C. for 30 seconds, and incubation at 72° C. for 1 minute and 10 seconds. These last three steps are repeated 24 times followed by a final incubation at 72° C. for 7 minutes.

The Cassette1 template consists of the following nucleic acid sequence inserted into the NdeI/XhoI restriction sites of vector pET22b:

(SEQ ID NO: 144)
ATGGATATCGATCCGTATAAAGAATTTGGCGCCACCGTGGAACTGCTGAGCTTTCTGCCGAGCGATTTCTTTCC

GAGCGTGCGTGATCTGCTGGATACCGCGAGCGCGCTGTATCGCGAAGCGCTGGAAAGCCCGGAACATTGTAGCC

CGCACCATACCGCCCTGCGTCAGGCGATTCTGTGCTGGGGTGAACTGATGACCCTGGCGACCTGGGTTGGCAAC

AACCTGTGCGATCCGGCGAGCCGCGATCTGGTTGTGAACTATGTGAATACCAACATGGGCCTGAAAATTCGTCT

GCTGCTGTGGTTTCATATCAGCTGCCTGACCTTTGGCCGCGAAACCGTGCTGGAATATCTGGTGAGCTTTGGCG

TTTGGATCCGTACCCCGCCGGCGTATCGTCCGCCGAATGCGCCGATTCTGAGCACCCTGCCGGAAACCACCGTT

GTCGACAAGCTTGCGGCCGCACTCGAGCACCACCACCACCACCACTGA

The PCR products and a pET22b vector are both digested with restriction enzymes NdeI and XhoI at 37° C. for 2 hours. The digested products are run on an agarose gel. The bands are excised and purified via gel extraction (Stratagene). Ligation reactions are composed of 5 µl of digested and purified PCR product, 1 µl of digested and purified pET22b vector, 1 µl of T4 DNA ligase buffer (NEB), 1 µl of T4 DNA ligase (NEB), and 2 µl of water and are incubated at room temperature for 12 hours.

The ligation reactions are transformed into XLI Blue E. coli cells (Stratagene) and the resulting colonies are grown in IX LB broth. The plasmids are purified via mini-prep (Stratagene). The purified plasmids are sequenced (see below) and transformed into E. coli BL21 (DE3) PlysS cells (Stratagene) for protein expression. This strategy can be used for proteins containing from 0 to 30 lysine residues.

C. Modified Structural Core Mutants

DNA fragments containing point mutations of the K9 construct are synthesized via PCR using the K9 template (or in the case of double or triple mutants, the appropriate single or double mutant K9 template) and the primer sequences described in Table 2. Each PCR reaction consists of 5 µl of 10×Pfu Turbo polymerase buffer (Stratagene), 1 µl of a 10 mM dNTP mixture, 1.5 µl of 5 µM forward primer, 1.5 µl of 5 µM reverse primer, 1 µl of Stratagene mini-prepped template, 1 µl of 2.5 unit/µl Pfu Turbo polymerase (Stratagene), and 39 µl of water. The PCR reaction consists of a one-time incubation at 98° C. for 1 minute, followed by incubation at 98° C. for 30 seconds, incubation at 64-72° C. (depending on primer $T_m$) for 1 minute, and incubation at 72° C. for 6 minutes. These last three steps are repeated 20 times.

The K9 template consists of the following nucleic acid sequence inserted into the NdeI/XhoI restriction sites of vector pET22b:

(SEQ ID NO: 145)
ATGGATATCGATCCGTATAAAGAATTTGGCGCCACCGTGGAACTGCTGAGCTTTCTGCCGAGCGATTTCTTTCCGA

GCGTGCGTGATCTGCTGGATACCGCGAGCGCGCTGTATCGCGAAGCGCTGGAAAGCCCGGAACATTGTAGCCCGCA

CCATACCGCCCTGCGTCAGGCGATTCTGTGCTGGGGTGAACTGATGACCCTGGCGACCTGGGTTGGCAACAACCTG

TGCGATCCGGCGAGCCGCGATCTGGTTGTGAACTATGTGAATACCAACATGGGCCTGAAAATTCGTCAGCTGCTGT

GGTTTCATATCAGCTGCCTGACCTTTGGCCGCGAAACCGTGCTGGAATATCTGGTGAGCTTTGGCGTTTGGATCCG

TACCCCGCCGGCGTATCGTCCGCCGAATGCGCCGATTCTGAGCACCCTGCCGGAAACCACCGTTGTCGACAAGCTT

GCGGCCGCAAAGAAAAAGAAGAAGAAAAAGAAGAAGCTCGAGCACCACCACCACCACCAC

The PCR products are digested with the restriction enzyme DpnI at 37° C. for 1.5 hours to eliminate any un-mutated template. The digested products are run on a 1% agarose gel. The bands are excised and purified via gel extraction (Stratagene).

The PCR products are then transformed into E. coli BL21 (DE3) PlysS cells (Stratagene) and the resulting colonies are grown in 1×LB broth and the plasmid purified via mini-prep (Stratagene). The purified plasmids are then sequenced to confirm the change in nucleic acid sequence. This strategy can be applied to single amino acid changes or the deletion or insertion of multiple amino acid residues such as the removal of a poly-histidine tag (primers shown in Table 3).

TABLE 1

| Tail Mutant | Forward Primer (5' → 3') | Reverse Primer (5' → 3') |
| --- | --- | --- |
| K5 | CGACTCACTATAGGGGAATTGTGAGCGG (SEQ ID NO: 146) | GGCCTCGAGCTTCTTTTTCTTCTTTGCGGCCG CAAGCTTGTCGAC (SEQ ID NO: 147) |

TABLE 1-continued

| Tail Mutant | Forward Primer (5' → 3') | Reverse Primer (5' → 3') |
|---|---|---|
| K7 | CGACTCACTATAGGGGAATTGTGAGCGG (SEQ ID NO: 146) | GGCCTCGAGCTTCTTCTTTTTCTTCTTCTTTG CGGCCGCAAGCTTGTCGAC (SEQ ID NO: 148) |
| K9 | CGACTCACTATAGGGGAATTGTGAGCGG (SEQ ID NO: 146) | GGCCTCGAGCTTCTTCTTTTTCTTCTTCTTTT TCTTTGCGGCCGCAAGCTTGTCGAC (SEQ ID NO: 149) |
| K10 | CGACTCACTATAGGGGAATTGTGAGCGG (SEQ ID NO: 146) | GGCCTCGAGTTTCTTCTTCTTCTTCTTCTTCT TTTTCTTTGCGGCCGCAAGCTTGTCGAC (SEQ ID NO: 150) |
| K11 | CGACTCACTATAGGGGAATTGTGAGCGG (SEQ ID NO: 146) | GGCCTCGAGCTTCTTCTTTTTCTTCTTCTTTT TCTTCTTCTTTGCGGCCGCAAGCTTGTCGAC (SEQ ID NO: 151) |
| K13 | CGACTCACTATAGGGGAATTGTGAGCGG (SEQ ID NO: 146) | GGCCTCGAGCTTCTTCTTTTTCTTCTTCTTTT TCTTCTTCTTTTCTTTGCGGCCGCAAGCTTG TCGAC (SEQ ID NO: 152) |
| K20 | CGACTCACTATAGGGGAATTGTGAGCGG (SEQ ID NO: 146) | GGCCTCGAGCTTTTCTTCTTCTTCTTCTTCT TCTTCTTTTCTTCTTCTTCTTCTTCTTTT TTCTTTGCGGCCGCAAGCTTGTCGAC (SEQ ID NO: 153) |
| KA9 | CGACTCACTATAGGGGAATTGTGAGCGG (SEQ ID NO: 146) | GGCCTCGAGCTTCGCCTTAGCCTTCGCCTTAG CCTTTGCCTTCGCCTTAGCCTTTGCCTTTGCG GCCGCAAGCTTGTCGAC (SEQ ID NO: 154) |
| KG9 | CGACTCACTATAGGGGAATTGTGAGCGG (SEQ ID NO: 146) | (SEQ ID NO: 155) |
| K4-5 | CGACTCACTATAGGGGAATTGTGAGCGG (SEQ ID NO: 146) | GGCCTCGAGTTTCTTCTTCTTCTTCGGGCTCT GGCTCTTCTTTTTCTTTGCGGCCGCAAGCTTG TCGAC (SEQ ID NO: 156) |
| CP155 | CGACTCACTATAGGGGAATTGTGAGCGG (SEQ ID NO: 146) | ATTCTCGAGGCTGCGACCACGGCGACGCAC (SEQ ID NO: 157) |
| CP162 | CGACTCACTATAGGGGAATTGTGAGCGG (SEQ ID NO: 146) | ATTCTCGAGGCTCGGGGTACGACGGCGCGG (SEQ ID NO: 158) |
| CP170 | CGACTCACTATAGGGGAATTGTGAGCGG (SEQ ID NO: 146) | ATTCTCGAGGCTCTGGCTACGACGACGACGCG GGCTCGGGGT (SEQ ID NO: 159) |
| Linker 1 | CGACTCACTATAGGGGAATTGTGAGCGG (SEQ ID NO: 146) | GGCCTCGAGCTTCTTCTTTTTCTTCTTCTTTT TCTTGCCGGCGCTGCCCGCGCTGACAACGGTG GTTTCCGGCAG (SEQ ID NO: 160) |
| Linker 2 | CGACTCACTATAGGGGAATTGTGAGCGG (SEQ ID NO: 146) | GGCCTCGAGCTTCTTCTTTTTCTTCTTCTTTT TCTTGCCGGCGGTGCCCGCGGTGACAACGGTG GTTTCCGGCAG (SEQ ID NO: 161) |
| Linker 3 | CGACTCACTATAGGGGAATTGTGAGCGG (SEQ ID NO: 146) | GGCCTCGAGCTTCTTCTTTTTCTTCTTCTTTT TCTTGCCGGCGCCGCCCGCGCCGACAACGGTG GTTTCCGGCAG (SEQ ID NO: 162) |

TABLE 2

| Point Mutant | Forward Primer (5' → 3') | Reverse Primer (5' → 3') |
|---|---|---|
| F18H | AACTGCTGAGCCATCTGCCGAGCGATTT (SEQ ID NO: 163) | AAATCGCTCGGCAGATGGCTCAGCAGTT (SEQ ID NO: 176) |
| Y132A | TACCCCGCCGGCGGCTCGTCCGCCGAAT (SEQ ID NO: 164) | ATTCGGCGGACGAGCCGCCGGCGGGGTA (SEQ ID NO: 177) |

TABLE 2-continued

| Point Mutant | Forward Primer (5' → 3') | Reverse Primer (5' → 3') |
|---|---|---|
| Y132V | TACCCCGCCGGCGGTTCGTCCGCCGAAT (SEQ ID NO: 165) | ATTCGGCGGACGAACCGCCGGCGGGGTA (SEQ ID NO: 178) |
| Y132I | TACCCCGCCGGCGATTCGTCCGCCGAAT (SEQ ID NO: 166) | ATTCGGCGGACGAATCGCCGGCGGGGTA (SEQ ID NO: 179) |
| Y132F | TACCCCGCCGGCGTTTCGTCCGCCGAAT (SEQ ID NO: 167) | ATTCGGCGGACGAAACGCCGGCGGGGTA (SEQ ID NO: 180) |
| I139A | TCCGCCGAATGCGCCGGCTCTGAGCACCCT (SEQ ID NO: 168) | AGGGTGCTCAGAGCCGGCGCATTCGGCGGA (SEQ ID NO: 181) |
| S121C | TGGAATATCTGGTGTGCTTTGGCGTTT (SEQ ID NO: 169) | AAACGCCAAAGCACACCAGATATTCCA (SEQ ID NO: 182) |
| S141C | ATGCGCCGATTCTGTGCACCCTGCCGGAAA (SEQ ID NO: 170) | TTTCCGGCAGGGTGCACAGAATCGGCGCAT (SEQ ID NO: 183) |
| C48A | AGCCCGGAACATGCGAGCCCGCACCAT (SEQ ID NO: 171) | ATGGTGCGGGCTCGCATGTTCCGGGCT (SEQ ID NO: 184) |
| C61A | AGGCGATTCTGGCGTGGGGTGAACT (SEQ ID NO: 172) | AGTTCACCCCACGCCAGAATCGCCT (SEQ ID NO: 185) |
| C107A | TTTCATATCAGCGCGCTGACCTTTGGCCGCGA (SEQ ID NO: 173) | TCGCGGCCAAAGGTCAGCGCGCTGATATGAAA (SEQ ID NO: 186) |
| C77E D78S | TGGCAACAACCTGGAAAGCCCGGCGAGCCGCGA (SEQ ID NO: 174) | TCGCGGCTCGCCGGGCTTTCCAGGTTGTTGCCA (SEQ ID NO: 187) |
| C77E D78E | TTGGCAACAACCTGGAAGAACCGGCGAGCCGCGAT (SEQ ID NO: 175) | ATCGCGGCTCGCCGGTTCTTCCAGGTTGTTGCCAA (SEQ ID NO: 188) |

TABLE 3

| | Forward Primer (5' → 3') | Reverse Primer (5' → 3') |
|---|---|---|
| His Tag Removal | AAGAAAAAGAAGAAGTGAGATCCGGCT (SEQ ID NO: 189) | AGCAGCCGGATCTCACTTCTTCTTTTTCTT (SEQ ID NO: 190) |

Example 2

Various wild type and modified core proteins described herein can be expressed and purified according to Protocol 1 or Protocol 2 as follows:

Protocol 1:

A pET-11a vector containing the full-length HBV C-protein gene is transformed into *E. coli* DE3 cells and grown at 37° C. in LB media that is fortified with 2-4% glucose, trace elements and 200 μg/mL of carbenicillin. Protein expression is induced by the addition of 2 mM IPTG (isopropyl-beta-D-thiogalactopyranoside). Cells are harvested by pelleting after three hours of induction. SDS-PAGE is used to assess expression of C-protein.

Core protein is purified from *E. coli* by resuspending in a solution of 50 mM Tris-HCl, pH 7.4, 1 mM EDTA, 5 mM DTT, 1 mM AEBSF, 0.1 mg/mL DNase1 and 0.1 mg/mL RNase. Cells are then lysed by passage through a French pressure cell. The suspension is centrifuged at 26,000×G for one hour. The pellet is discarded and solid sucrose is added to the supernatant to a final concentration of 0.15 M and centrifuged at 100,000×G for one hour. The pellet is discarded and solid $(NH_4)_2SO_4$ is then added to reach a final concentration of 40% saturation. The mixture is stirred for one hour and then centrifuged for one hour at 26,000×G. The pellet is resuspended in a solution of 100 mM Tris-HCl at pH 7.5, 100 mM NaCl, 50 mM sucrose and 2 mM DTT (Buffer A) and loaded onto a Sepharose CL-4B (Pharmacia Biotech, Piscataway, N.J.) column (5 cm diameter×95 cm) equilibrated with Buffer A. The column is eluted at 2 mL/minute. Using this purification scheme, HBV viral capsids are separated from large aggregates and from soluble proteins of lower molecular weight. The fractions are pooled according to chromatographic profile and SDS-PAGE analysis. The solution is concentrated by ultrafiltration using Diaflo YM 100 ultrafitration membrane (Amicon, Beverly, Mass.) to about 10 mg/mL. Concentrated C-protein is dialyzed against 50 mM Tris-HCl, pH 7.5 and 0.15 M sucrose. The solution is then adjusted to pH 9.5 by adding 10N NaOH and urea to reach a final concentration of 3.5 M. The solution is then filtered using a Millex-HA 0.45 μm pore size filter unit (Millipore, Bedford, Mass.) and applied to a column (6.0 cm diameter×60 cm) of Superdex 75 (Pharmacia Biotech, Piscataway, N.J.) equilibrated with a solution consisting of 100 mM sodium bicarbonate, pH 9.5, and 2 mM DTT. The column is eluted at 5 mL/minute. The fractions containing dimeric protein as assessed by SDS-PAGE are pooled. These procedures can be used for the expression and purification of all core protein mutants. Alternately, the expression of this protein can be done in yeast cells according to methods well known to persons skilled in the art.

Protocol 2:

All protein constructs containing a C-terminal 6-histidine tag were purified as follows:

The pET vector containing the gene for K9 protein is kept in BL21 (DE3) PlysS cells for expression. The starter culture can be inoculated from a colony on a 1× Luria Broth (1×LB) agar plate or from a 10% glycerol stock, stored at –80° C. The 1×LB is autoclaved in a 2 L flask and cooled. 100 mg of ampicillin (Amp) is added to the 1×LB. A starter culture is inoculated and allowed to grow at 37° C. for up to 24 hours with shaking at 200 rpm.

Fifteen 2 L flasks with 0.8 L of 2× yeast-tryptone (2×YT) broth is autoclaved and 1 mL of 100 mg/mL Amp is added to each flask. 50 mL of starter culture is then added to each flask. The culture is incubated at 37° C., while shaking at 200 rpm until the optical density (OD) at 600 nm reaches 0.4-0.6. This process should take approximately 2 hours. When the OD reaches 0.4-0.6, the culture is induced with 1 mL of 1 M IPTG. Shaking is continued for 4 more hours until OD reaches 2.0 or greater. The cells are harvested by centrifuging in 500 mL centrifuge bottles at 11,300×G for 8 minutes. The bacterial pellets are transferred into two 50 mL conical tubes. Each tube is labeled with date/construct/prep number and frozen at –20° C.

Two 50 ml tubes (approximately 20 mL each) of cell paste are thawed. The following steps are applied to each tube. 40 mL of resuspension buffer (5 M urea, 50 mM $NaHCO_3$ (pH 9.5), 10 mM imidazole) is added into each tube. The cells are suspended by continuous pipetting and poured into a 400 mL beaker. More resuspension buffer is added until there is ~100 mL total cell resuspension in the beaker. The beaker containing resuspended cells is placed in an ice bath and sonicated for 5 minutes using a Branson probe sonifier (pulse mode at approximately 40% duty cycling and power setting of 5). The cell mixture is sonicated in several intervals and is allowed to rest on ice if it appears that the sample is heated to higher than room temperature. The cell lysate is diluted 2 fold to 200 mL total, and 200 µL of 100 mg/mL DNase is added to the suspension. This suspension is stirred on ice for 10 minutes. The sonication step is repeated for 5 more minutes while on ice. The lysate is transferred to six 50 mL plastic centrifuge tubes, and centrifuged at 32,000×g for 45 minutes. Supernatant is discarded.

For purification, a 50 mL $Ni^{2+}$-NTA agarose (Qiagen) column is washed and equilibrated in the resuspension buffer. 12 L of cells is lysed for each run of the column. The centrifuged lysate from 12 L of cells is combined and diluted to 500 mL with resuspension buffer. The centrifuged cell lysate is loaded onto the column, and the protein solution is allowed to sink to the top of the nickel matrix. 50 mL of resuspension buffer is passed through the column. An optional salt wash can be performed by washing the column with 250 mL of NaCl wash buffer (5 M urea, 50 mM $NaHCO_3$ (pH 9.5), 20 mM imidazole, 250 mM NaCl). This salt wash reduces the $A_{260}/A_{280}$ ratio of the final purified protein by a value of 0.1 A.U. The column is washed with 250 mL of wash buffer (5 M Urea, 50 mM $NaHCO_3$ (pH 9.5), 20 mM imidazole). Subsequently, 200 mL of elution buffer (5 M Urea, 2 mM $NaHCO_3$ (pH 9.5), 250 mM imidazole) is passed through the column. Fractions are collected at every 5 mL, and of these, which 5 to 8 fractions should contain protein.

The presence and/or concentration of protein is detected by measuring the absorbance of the fractions. SDS polyacrylamide gel electrophoresis (SDS PAGE) analysis is performed on the proteins to determine purity. Fractions containing protein are pooled, and transferred to dialysis tubing. Dialysis is performed in 4 L of storage buffer (5 M Urea, 2 mM $NaHCO_3$ (pH 9.5)) for at least 4 hours at 4° C. The protein can then be concentrated in an Amicon stirred cell concentrator (Millipore) to a final protein concentration of up to 75 mg/ml. A 12 L cell growth yields approximately 500 mg of pure protein. Pure dialyzed protein can be stored at –80° C. for 6-8 months.

Example 3

Figure 2:
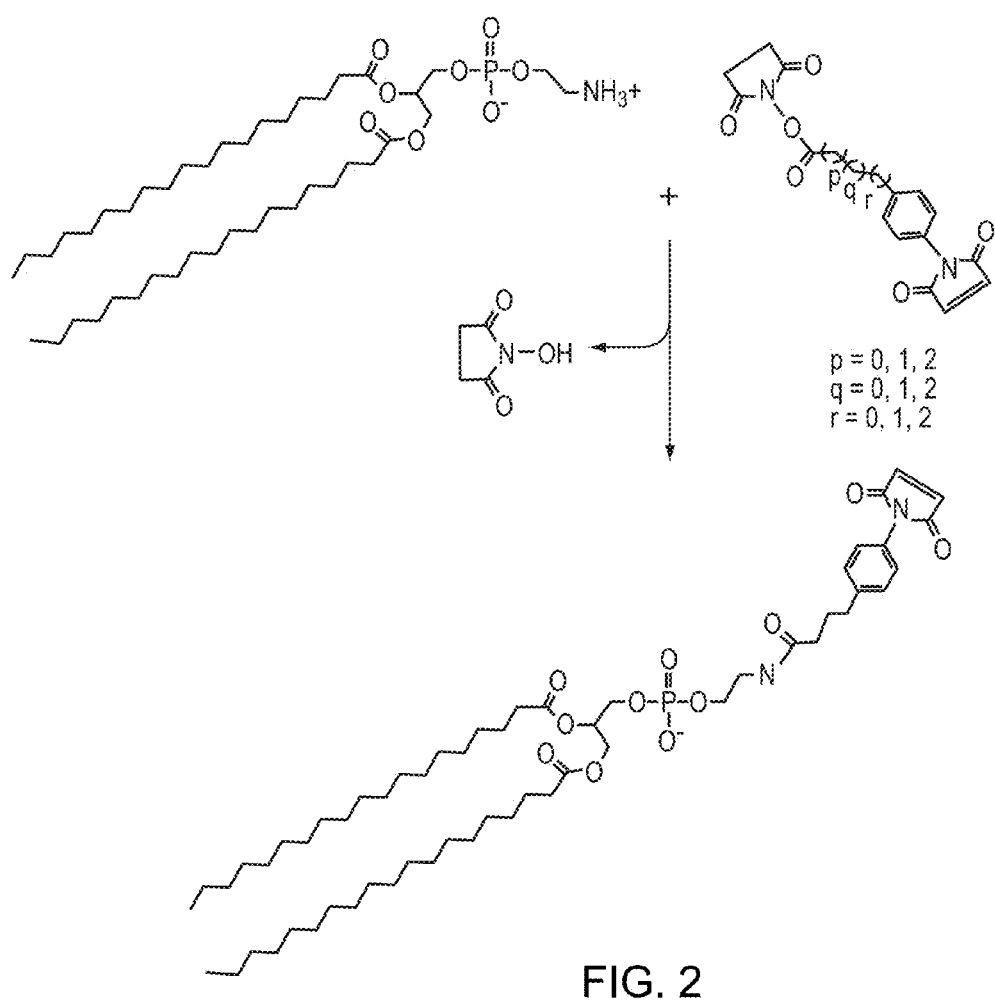
FIG. 2 is a schematic depicting phosphatidyl ethanolamine (PE) conjugation to an exemplary lipid linker moiety.

Conjugation of phospholipids via a SMPB (succinimidyl-4-(p-maleimidophenyl) butyrate) intermediate is depicted schematically in FIG. 2.

100 µmoles of phosphatidyl ethanolamine (PE) is dissolved in 5 mL of argon-purged, anhydrous methanol containing 100 µmoles of triethylamine (TEA). The solution is maintained under an argon or nitrogen atmosphere. The reaction can also be done in dry chloroform. 50 mg of SMPB (Pierce) is added to the PE solution and mixed well to dissolve.

The solution is maintained under an argon or nitrogen atmosphere while the reaction proceeds for 2 hours at room temperature. Methanol is removed from the reaction solution by rotary evaporation and the solids are redissolved in chloroform (5 mL). The water-soluble reaction by-products is extracted from the chloroform with an equal volume of 1% NaCl. Extraction is performed twice. The MPB-PE derivative is purified by chromatography on a column of silicic acid (Martin F J et al., Immunospecific targeting of liposomes to cells: A novel and efficient method for covalent attachment of Fab' fragments via disulfide bonds. Biochemistry, 1981; 20:4229-38). Chloroform is removed from the MBP-PE by rotary evaporation, and the derivative is stored at –20° C. under a nitrogen atmosphere until use.

Example 4

Figure 3:
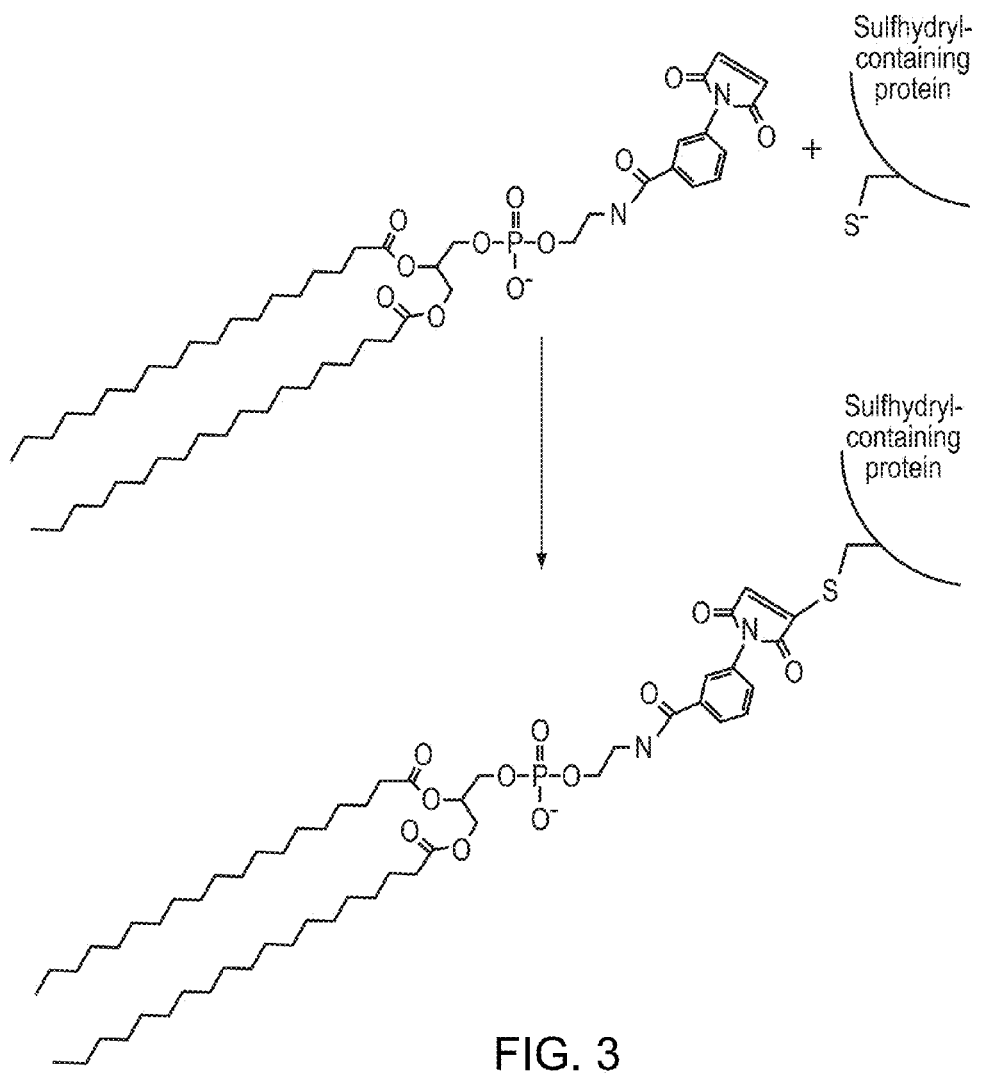
FIG. 3 is a schematic depicting conjugating a maleimide-containing linker to a sulfhydryl-containing protein.

Conjugation of a maleimide-containing linker to a sulfhydryl-containing protein is depicted schematically in FIG. 3.

The sulfhydryl-containing protein is dissolved in TRIS*HCl buffer (pH=8.0, 100 mM) to obtain a concentration of 1 mM). The solution is purged under a nitrogen or argon atmosphere for 20 minutes. The maleimide-containing linker is dissolved in the same buffer as above, and purged under a nitrogen or argon atmosphere for 20 minutes, to obtain a 10-fold molar excess.

The two solutions are combined and purged under a nitrogen or argon atmosphere for an additional 20 minutes. The reaction is allowed to proceed for 6 hours at room temperature.

Example 5

The instant example describes a general method for forming a therapeutic particle containing inhibitory dsRNA.

The protein is allowed to thaw to 25° C. The inhibitory dsRNA-containing solution is added to the protein solution at a molar ratio of 9.58:1 or 9.42:1 for non-modified or modified inhibitory dsRNA, respectively. The solution is mixed for 1 hour at 25° C. BME is added at a molar ratio of 3:1 to the protein to protect cysteine functional groups. This reaction is incubated for 1 hour at 25° C. A 2:1 volume ratio of 10 mM NaCl solution is added to reaction mixture containing protein and inhibitory dsRNA. The solution is kept in a water bath set to 25° C. for 48 hours.

To functionalize protein with maleimide-terminated lipid, 2× molar excess of PE-MAL (1,2-Dipalmitoyl-sn-Glycero-3-Phosphoethanolamine-N-[4-(p-maleimidophenyl)-butyramide] (Sodium Salt)) predissolved in 400 µL DMF (dimethylformamide) is added dropwise to the protein and inhibitory dsRNA-containing solution, and allowed to react for 10 minutes.

To make lipid coating material, cholesterol (Avanti Lipids, Alabaster, Ala., USA), HSPC (L-α-Phosphatidylcholine, Hydrogenated (Soy), Avanti Lipids, Alabaster, Ala., USA) and POPG (1-Palmitoyl-2-Oleoyl-sn-Glycero-3-[Phospho-rac-(1-glycerol)] (Sodium Salt), Avanti Lipids, Alabaster, Ala., USA) in dry power forms are premixed in a 3:1:1 molar ratio, respectively, in a glass beaker. The mixture is predissolved and homogenized with 2.0 mL of chloroform. Once homogenized, the chloroform is allowed to evaporate (20 to 30 minutes on a hot plate set to 50° C.). When dry, 0.5×PBS pH 9.5 (phosphate buffered saline with 5 mM $NaHCO_3$) is added to make the lipid coating material at a concentration of 2 mg/mL. This solution is sonicated for at least 3.0 min at 62° C.

The lipid coating material is added immediately after sonication to the solution containing functionalized protein and inhibitory dsRNA at a mass ratio of 5:1 protein:lipid coating material. The material is allowed to cool to 25° C.

The chimeric protein for forming the capsid is purified via FPLC (fast performance liquid chromatography) (Amersham Pharmacia). The large FPLC column (Pharmacia XK-16 16 mm×700 mm) is ran at 1.0 mL/min using 0.5×PBS pH 9.5 buffer as the mobile phase, and Sepharose CL-4B (Amersham Pharmacia) matrix as the stationary phase. Fractions containing therapeutic particles are collected and combined (typically eluting at 70 mL based on the stationary phase and column configuration described above). Protein concentration is determined using the Agilent 2100 Bioanalyzer system. Samples are diluted 1:1 with 0.5×PBS pH 9.5 and ran on a Protein 80 chip in triplicates as described by manufacturer.

Figure 33:
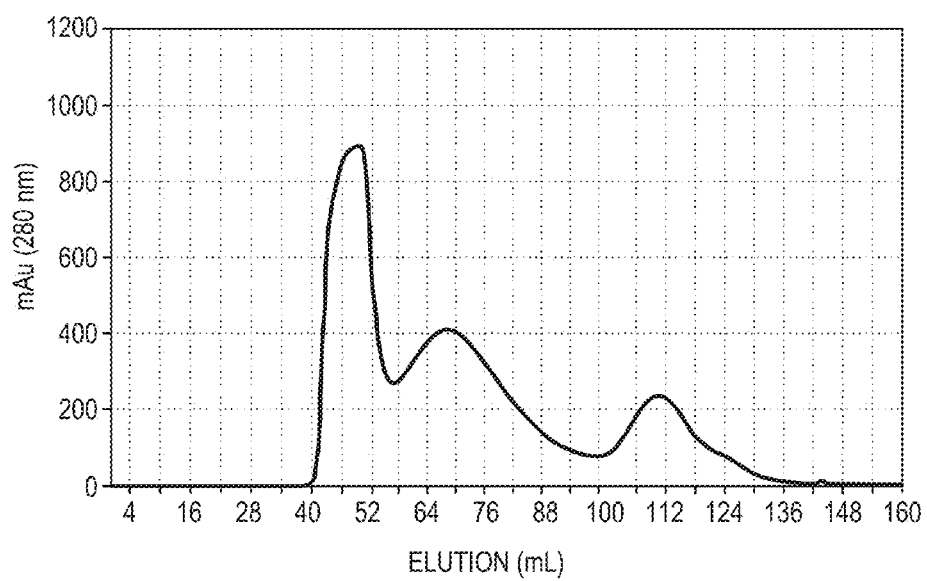
FIG. 33 depicts a chromatogram obtained by a purification method.
Figure 34:
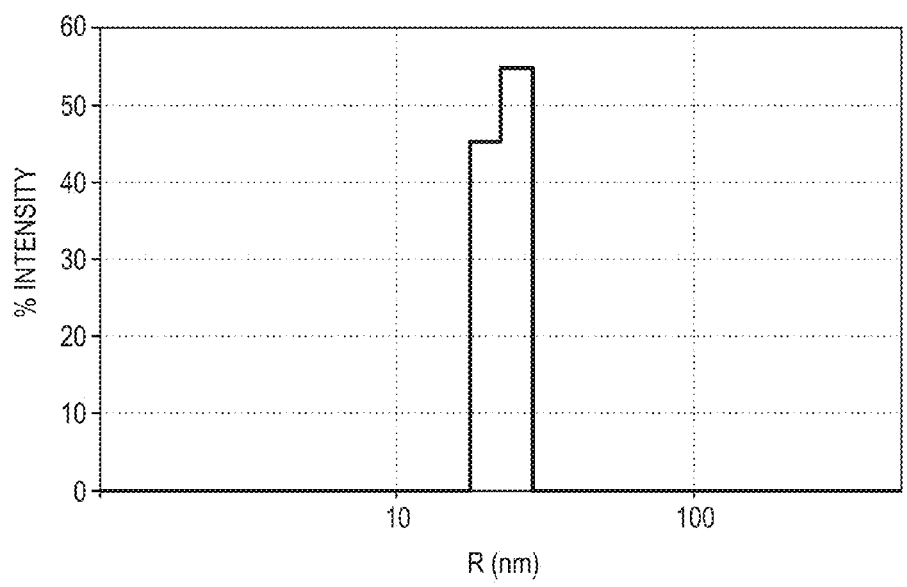
FIG. 34 depicts a particle size measurement.

An example of a chromatogram obtained by the purification method described above is shown in FIG. 33. An example of particle size measurement as determined by the instrument described above is shown in FIG. 34.

Example 6

The instant example describes two general methods for quantifying the inhibitory dsRNA contained within the therapeutic particle.

The first method describes SDS Extraction of inhibitory dsRNA from a therapeutic particle. A standard curve of inhibitory dsRNA is generated for concentrations of 175, 250, 350, 500, 700 nM; samples are prepared in triplicates. 100 µL of the therapeutic particle is mixed with 5 µL of 10% SDS solution. The solution is heated at 70° C. for 30 minutes and cooled to room temperature. 30 µL of a 75% glycerol stock is added to the particle/SDS solution. The lysed particles and the inhibitory dsRNA standards are run on a 15% urea-PAGE gel (Biorad 161-1135) at 230 V for 35 minutes in 1×TBE buffer. The gel is then stained with SYBR Green II (140 mL of water and 4 µL of stock SYBR Green II) on an orbiting platform for 30 minutes. The stained gel is scanned on a Typhoon Trio using 488 nm excitation with a 526 nm SP filter and the PMT set at 350 V. Using the Image Quant TL (V 7.0) software, the densitometry of the bands is measured and the concentration of the inhibitory dsRNA is determined using a standard curve.

The second method describes extraction using phenol/chloroform. A standard curve of inhibitory dsRNA is generated for concentrations of 175, 250, 350, 500, 700 nM; samples are prepared in triplicates. 100 µL of therapeutic particles are mixed with 100 µL of phenol:chloroform (95:5) solution. These solutions are vortexed for 5 minutes and spun at 13,000 g for 60 seconds. 50 µL of aqueous solution is mixed with 15 µL of a 75% glycerol stock. The lysed particles and the inhibitory dsRNA standards are run on a 15% urea-PAGE gel (Biorad 161-1135) at 230 V for 35 minutes in 1×TBE buffer. The gel is stained with SYBR Green II (140 mL of water and 4 µL of stock SYBR Green II) on an orbiting platform for 30 minutes. The stained gel is scanned on a Typhoon Trio using 488 nm excitation with a 526 nm SP filter and the PMT set at 350 V. Using the Image Quant TL (V 7.0) software, the densitometry of the bands is measured and the concentration of the inhibitory dsRNA is determined using a standard curve.

Example 7

The instant example describes two general methods for analyzing the lipid contained within the therapeutic particles.

The first example is a NMR-Analysis (dry extraction). 30 mL of the therapeutic particle is dried under vacuum in a speedvac. The resulting material is scraped into a 10 mL glass beaker. 3 mL of water and 3 mL of chloroform are added to the solids. This solution is sonicated for 20 seconds and the mixture is incubated for 30 minutes at room temperature. The solution is centrifuged and the chloroform layer is isolated and filtered through a glass plug. The chloroform is removed under vacuum and the NMR spectrum is measured of the material.

The second example is a NMR-Analysis (wet extraction). 30 mL of the therapeutic particles is mixed with 10 mL of chloroform. The solution is sonicated for 20 seconds and the mixture is incubated for 30 minutes at room temperature. The solution is centrifuged and the chloroform layer is isolated and filtered through a glass plug. The chloroform is removed under vacuum and the NMR spectrum is measured of the material.

Example 8

The instant example describes a general method for quantifying the protein contained within the therapeutic particle.

Protein analysis is done according to Agilent Protein 80 Assay Protocol (Protein 80 kit 5067-1515; protocol revision 04/2007). Samples are diluted 1:1 in 0.5× phosphate buffered saline (PBS, Fisher Scientific BP3994, 5 mM $NaHCO_3$, pH 9.5) and analyzed. The Chips are run on an Agilent 2100 Bioanalyzer and protein concentration is obtained.

Example 9

Targeting

To modify the antibodies, antibodies at a concentration of 4 mg/mL in 1×PBS buffer pH 7.4 are treated with 20 mole equivalents of Traut's reagent, 2-iminothiolane HCl, for 1 hour. The antibodies are purified via column chromatography (8×200 rnm) G-50 (Amersham Pharmacia) in 0.25×PBS buffer pH 7.4.

One mole equivalent of purified coated particle is treated with 200 mole equivalents of PE-maleimide lipid (1,2-Dipalmitoyl-sn-Glycero 3-Phosphoethanolamine-N-[4-(p-maleimidophenyl)-butyramide] (Sodium Salt)) (dissolved in DMF). Following 30 minutes of incubation, 1 mole equivalent of the particle is treated with 30 mole equivalents of the modified antibodies. The reaction is allowed to proceed overnight. Excess antibodies are removed via a packed column (16×200 mm) packed with Sepharose CL-4B matrix with the isocratic mobile phase (0.25×PBS pH7.4). This gives a typical yield of about 60% and has about 20-30 antibodies per particle as determined by SDS-PAGE gels.

Example 10

K9 Protein-RNA Complex Using Electrophoresis of Labeled Inhibitory dsRNA and K9 Protein Inhibitory dsRNA 3'-labeled with Dy547 is purchased from Dharmacon (Lafayette, Colo.). Labeled and unlabeled inhibitory dsRNA solutions are diluted to 4 µM in 4 M Urea, 10 mM Hepes, pH 8.15. The protein is labeled using 3 µM of the K9 protein incubated with 30 µM maleimido-cy5 (Pierce) in 4 M Urea, 10 mM Hepes, pH 8.15 for 1 hour. Labeled and unlabeled protein solutions are diluted to 3 µM in 4M Urea.

To allow the binding reaction to take place, 15 µL of the K9 protein is mixed with 5 µL inhibitory dsRNA and incubated for 10 minutes. Labeled and unlabeled RNA and protein are used in separate binding reactions. Samples are run on a 1.5% TAE-agarose gel for 35 minutes at 110 volts.

Figure 5:
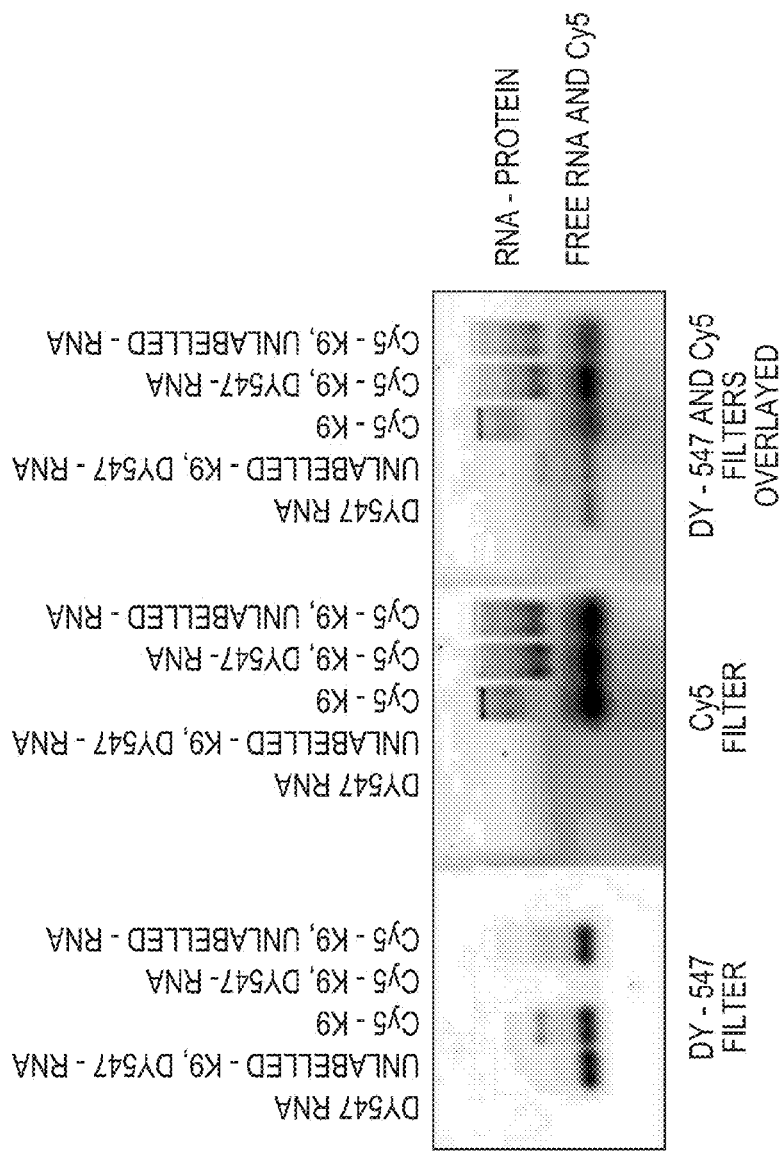
FIG. 5 depicts photographs of gels showing K9 protein-RNA complex.

A typhoon phosphoimager(GE) is used to visualize the cy5-only, DY547-only and cy5/DY547 labeled RNA protein complexes. Filters are employed to separately detect Dy547 (FIG. 5A) and cy5 (FIG. 5B) fluorescent labels. To image all fluorescence on the gel, cy5-filtered and dy547-filtered images are overlayed (FIG. 5C).

On a 1.5% agarose gel, a shifted band ("RNA-Protein") appears only when both RNA and K9 protein are present. Distinct fluorescent labeling shows that both RNA and protein migrate in this band, indicating that the K9 protein and inhibitory dsRNA form a complex in solution.

Example 11

Transmission Electron Microscopy and Dynamic Light Scattering

Figure 6:
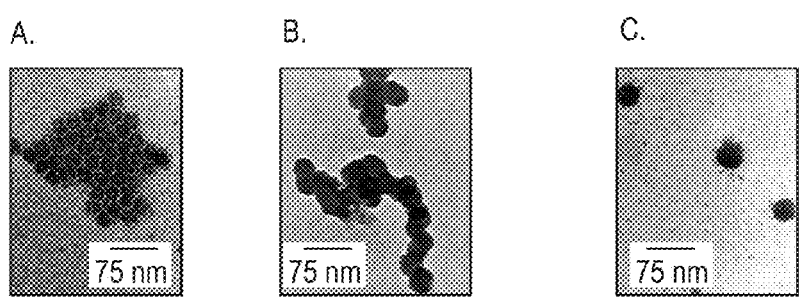
FIG. 6A is a photograph depicting negatively stained particles lacking a lipid layer at 200,000× magnification.
FIG. 6B is a photograph depicting lipid coated particles stained with 1% PTA at 200,000× magnification.
FIG. 6C is a photograph depicting lipid coated particles with surface attached anti-CD22 antibodies stained with 1% PTA at 200,000× magnification.

Transmission Electron microscopy (TEM) is a useful tool to examine the morphological characteristics of small (sub-micrometer) particles, including therapeutic particles. As shown in FIG. 6, the structural details and extensive surface topology of particles are best revealed by the use of negative staining procedures. The negative staining process involves surrounding particles with electron-dense chemicals thus revealing the structure, size, and surface topology of individual particles as the contrast between the stain (dark) and the specimen (light). One "drop" of particle (100 µg/ml) in PBS is placed on multiple formvar coated copper mesh TEM grids (Electron Microscopy Sciences) followed by one drop of 1% PTA solution (phosphotungstic acid in water, pH adjusted to 7.0 with 1N NaOH). After 2 minutes, excess liquid is blotted with filter paper. TEM grids are then allowed to air dry for approximately 10 minutes. Grids are then examined using standard transmission electron microscopy (TEM). Photographs are taken at multiple magnifications (5000×-1,000,000×) using an attached digital camera. Multiple particle constructs are used for these experiments, including particles with and without attached anti-CD22 antibodies as well as naked particles lacking a lipid coat.

Dynamic Light Scattering (DLS) is a useful tool to examine the size characteristics of small (sub-micrometer) particles in solution. Solutions of purified therapeutic particles are analyzed to validate that the predicted material is obtained. Results indicate that select fractions purified from a size exclusion column are in fact very monodispersed.

ELISA is a useful tool in determining the ability of the particles to bind various bioactive agents. Protein constructs (3 mg/ml) are mixed with 200 uM of RNA at a ratio of 6.25 protein dimers per RNA duplex and incubated for 15 minutes. This mixture is then diluted 1:1 with a buffer containing 30 mM Sodium, Hepes pH 7.5, and 60 mM NaCl in order to encapsulate RNA. Encapsulation is allowed to proceed overnight at room temperature. The samples are loaded on a 1.0% agarose gel containing ethidium bromide, run for 40 minutes at 100 Volts, and visualized on a Molecular Dynamics Typhoon imager.

Example 12

Assays

A. Fluorescent Particle Binding Assay (Anti-CD22 Targeted Vs. Non-Targeted Therapeutic Particles)

Figure 7:
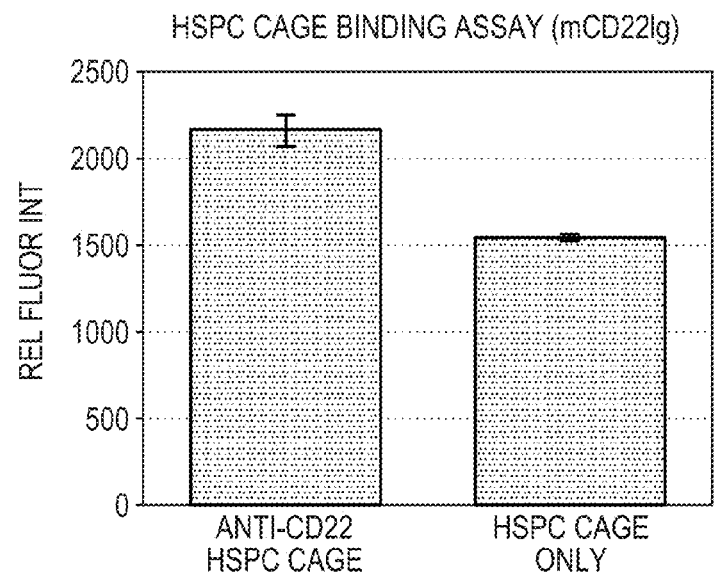
FIG. 7 depicts a bar graph showing the comparison of antibody targeted particle (anti-CD22 HSPC cage) and non-targeted particle (HSPC only) binding to mCD22Ig.

96-well ELISA plates are coated overnight with either 50 µL of mCD22Ig protein or 2% BSA (w/v) in 0.1 M borate buffered saline at a concentration of 50 ug/ml. Plates are washed 3 times in Tris buffered saline (TBS). All wells are then blocked with 2% BSA in TBS for 1 hour, followed by 3 TBS rinses. Anti-CD22 targeted particle constructs and non-targeted particle constructs (no antibody) containing 4% DiI embedded within the lipid coat are incubated in triplicates, at multiple concentrations, in buffer containing 2% BSA and 0.1% tween in TBS for 4 hours. Wells are rinsed 4 times in TBS and plates are read using a Typhoon Molecular Imager (Molecular Dynamics). Background wells contain mCD22Ig (from original plating) and TBS. The readings are conducted in TBS. FIG. 7 demonstrates that antibody-targeted, lipid-coated cages (anti-CD22 HSPC cages) bind to mCD22Ig 1.6 times better than lipid-coated non-targeted cages (HSPC cages), indicating that therapeutic particles are targeted with antibodies.

B. Particle Binding ELISA (Anti-CD22 Targeted vs. Non-targeted Therapeutic Particles)

96-well ELISA plates are coated overnight with either 50 µL of mCD22Ig protein or 2% BSA (w/v) in 0.1 M borate buffered saline at a concentration of 50 µg/ml. Plates are washed 3 times in Tris buffered saline (TBS). All wells are then blocked with 2% BSA in TBS for 1 hour, followed by 3 TBS rinses. Anti-CD22 targeted particle constructs and non-targeted particle constructs are incubated in triplicates, at multiple concentrations, in buffer containing 2% BSA and 0.1% tween in TBS for 4 hours. Wells are then rinsed 3 times in TBS followed by incubation with antibodies against (1) rabbit-anti HBV core protein (AbCam), (2) mouse anti-HBV core protein (GenTex), or (3) no antibody in 2% BSA and 0.1% tween in TBS for 1 hour. Wells are rinsed 3 times again in TBS followed by 1 hour incubation in (1) goat anti-rabbit conjugated to alkaline phosphatase, (2) goat anti-mouse Fc region conjugated to alkaline phosphatase, or (3) no antibodies in 2% BSA and 0.1% tween in TBS. All wells are rinsed 3 times in TBS, one time in PBS, and incubated in DDAO-phosphate (1:100,000) in PBS. Primary antibodies (rabbit-anti HBV core protein (AbCam) or mouse anti-HBV core protein (GenTex)) are omitted in background control wells.

Figure 8:
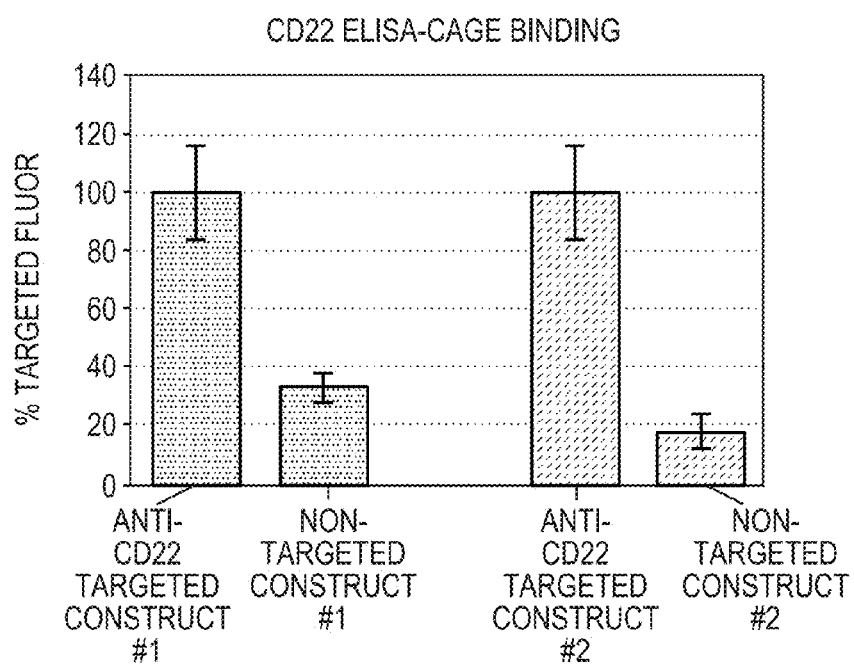
FIG. 8 depicts a bar graph comparing the binding to mCD22Ig of anti-CD22 targeted particles over that of non-targeted particles.

Readings are conducted using Cy5 excitation/emission settings on a Typhoon Molecular Imager. Anti-core protein antibodies are used to detect the presence of therapeutic particles. Non-targeted particle binding data are normalized to the % of anti-CD22 targeted particle binding. FIG. 8 demonstrates that anti-CD22 HSPC cages bind 3.3 times better than non-targeted cages, indicating that particles targeted with antibodies are specific for its respective receptor. Similar results are obtained with an ELISA assay that detects core proteins. In the core protein assay it is found that targeted particles bind 5.6 times better than non-targeted system.

Figure 9:
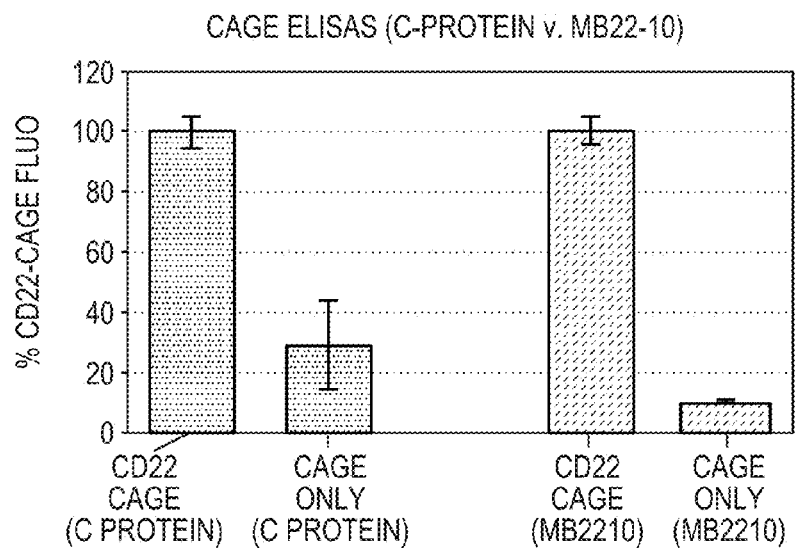
FIG. 9 depicts a bar graph showing two identical ELISA experiments demonstrating that significantly more anti-CD22 targeted particle binding to mCD22Ig than non-targeted particles.

Additional ELISA assays are conducted to measure the amount of mouse-anti CD22 antibody present on targeted cages versus non-targeted cages. Same protocol as above are used except for the omission of the primary antibodies. For these experiments, only goat anti-mouse Fc region specific antibodies are used to detect the presence of cages. DDAO-phosphate is used as the fluorescent substrate (see above) and all analyses are conducted in the same manner. Anti-core protein antibodies (blue columns) and goat-antimouse antibodies (red columns) are used to detect the presence of particles or anti-CD22 antibody on the surface of particles (respectively). Non-targeted particle binding data are normalized to the % of anti-CD22 targeted particle binding. FIG. 9 depicts that targeted particles bound 3.5 times better than non targeted particles, indicating antibodies are bound to the particle surface. In the mCD22Ig binding studies anti-CD22 HSPC cages bind 9 times better than non-targeted cages, again indicating that particles targeted with antibodies are specific for its respective receptor.

C. Fluorescent Cell Assays

Cell Growth

B Cell (BCLI and Ramos) and T cell lines (Jurkat and HH) are purchased from ATCC and grown at 37° C. (5% CO2) in RPMI medium with 10% fetal bovine serum, supplements and antibiotics. Cells grown under these conditions consistently exhibit "normal" growth characteristics. All cell experiments are conducted while cells are exhibiting log-phase growth characteristics.

Figure 10:
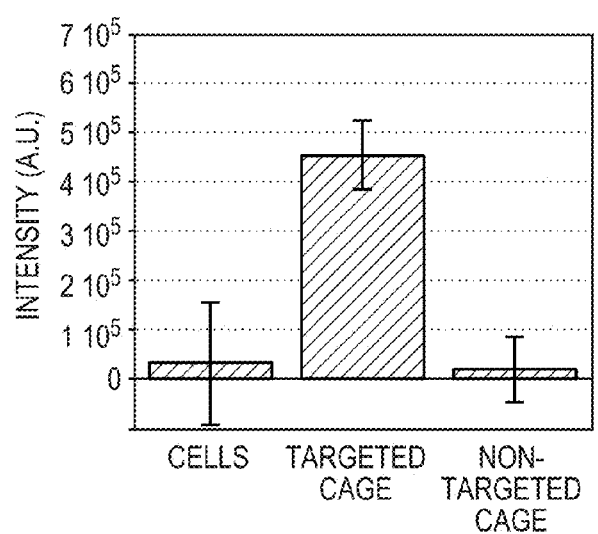
FIG. 10 depicts a bar graph showing anti-CD22 targeted particles bind to B Cells (Ramos cells) significantly better than non-targeted particles.

Anti-CD22 Targeted vs. Non-targeted Fluorescent Particle Binding to Cells 9 mL of Ramos cells (from cultures at a density of 1,000,000 cells/mL) are drawn from T75 culture flasks into 3 sterile 15 mL conical tubes (3 mL each), spun down, and re-suspended in 3 mL of complete RPMI medium. Cells are incubated with 3 mL (~60 nM) of fluorescent anti-CD22 targeted cages, non-targeted cages (both with 3% DiI embedded in the lipid coat), or an equal volume of "media only" at 37° C. at a concentration of 400,000 cages/cell for 2 hours. Cells are then spun down and rinsed 2 times in 5 mL of complete media. Cells are rinsed again 3 times in 5 mL sterile PBS, spun down and resuspended in 150 µl of PBS. To fix the cells, 150 µl of 2% paraformaldehyde is slowly added to the cells. Cells are allowed to fix for 10 minutes, and 100 µl of cell suspension is added to each well of a 96-well plate in triplicates. Plates are spun down using a clinical centrifuge. To detect fluorescence, a Typhoon Molecular Imager is used with Cy3 excitation/emission settings. Background fluorescence of "cells alone" is included for comparison. FIG. 10 demonstrates that the targeted particles are taken up by Ramos cells 3 times better than non targeted particles, indicating that targeting with antibodies for CD22 improves cellular up take of the therapeutic particles by B-cells.

Anti-CD22 Targeted vs. Non-targeted Fluorescent Particle Internalization

Adherent BCLI cells are plated onto glass coverslips (Fisher Scientific) in sterile 24-well tissue culture plates 12 hours prior to experimentation. Cells are allowed to grow to semi-confluency (cell density estimated at 200,000 cells/well) in complete RPMI media (see Cell Growth above). Prior to experiments, cells are rinsed with once with media and 500 µl of media is added to each well. Following experimental incubations (see below) adherent cells are rinsed once in media, 3 times in PBS, resuspended in 150 µl PBS. To fix the cells, 150 µl of 2% paraformaldehyde is slowly added to the tubes.

A total of 200,000 suspension cells (Ramos, Jurkat, and HH Cells) are added to sterile 24-well tissue culture plates. Media volumes are adjusted (upwards) to 500 µl Following experimental incubations (see below) suspension cells are sequentially pelleted and rinsed once in media and 3 times in PBS. Cells are then resuspended in 150 µl PBS. To fix the cells, 150 µl of 2% paraformaldehyde is slowly added to the tubes.

Figure 11A:
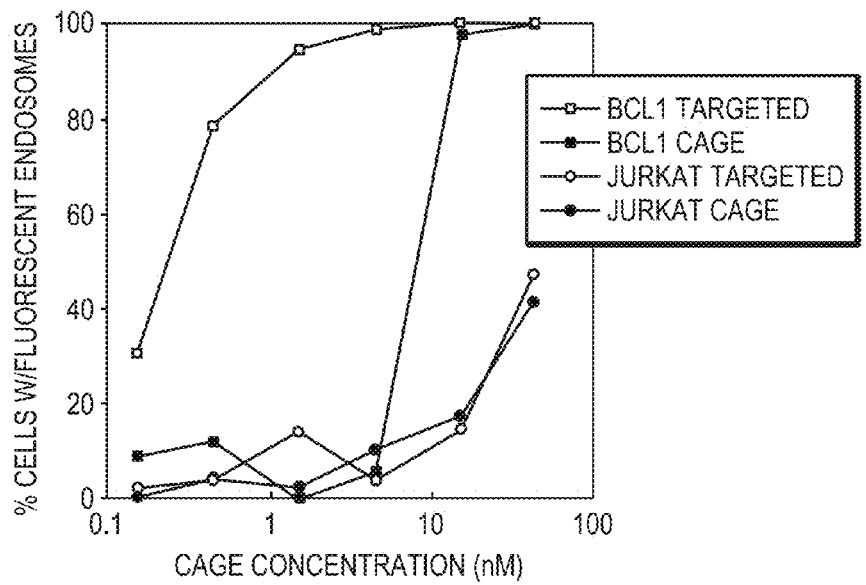
FIG. 11A is a line graph depicting that anti-CD22 targeted particles bind to B cells (BCL1) with more specificity than they bind to T Cells (Jurkat).
Figure 11B:
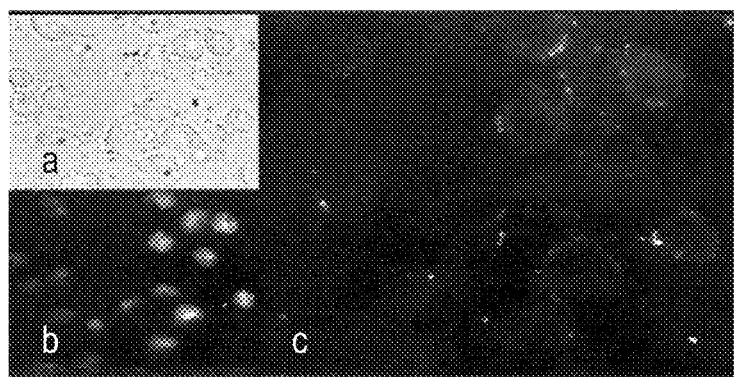
FIG. 11B is a photograph depicting a bright-field view of semi-confluent BCL1 cells (sub panel a), showing nuclei following counter stained with Hoechst 33342 (sub panel b) and showing internalized particles within all cells at 3 nm (sub panel c).
Figure 12A:
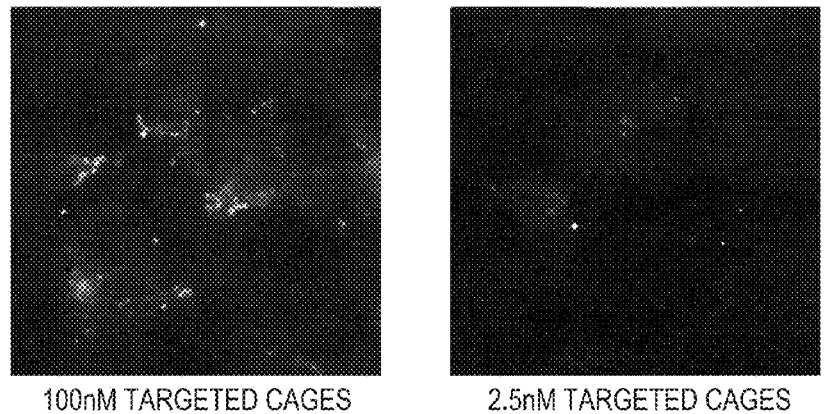
FIG. 12A shows photographs depicting the concentration-dependent (100 nM and 2.5 nM) internalization of anti-CD22 targeted particles and non-targeted particles in BCL1 cells.
Figure 12B:
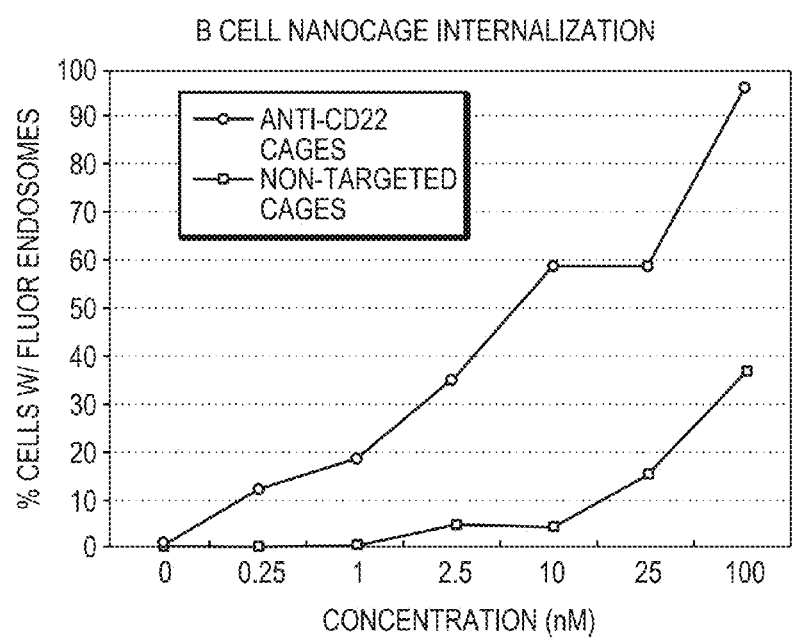
FIG. 12B is a line graph depicting the dose-response of anti-CD22 targeted particles and non-targeted particles in BCL1 cells.

For experimental incubations, cells (adherent and suspension) are incubated with fluorescent anti-CD22 targeted particles, non-targeted particles (both with 3% DiI embedded in the lipid coat), or an equal volume of "media only" at 37° C. at multiple particle concentrations [300,000 cages/cell (~30 nM), 100,000 cages/cell (~10 nM), 30,000 cages/cell (~3 nM), 10,000 cages/cell (~1 nM), 3000 cages/cell (~300 µM), and 1000 cages/cell (~100 µM)] in 500 µl media for 2 hours. Following rinses and fixation (see above), cells are cover-slipped in 5% n-propyl gallate in glycerol (w/v) and sealed under cover-slips using nail polish. Internalized fluorescent particles are quantified using standard fluorescence microscopy. Two-hundred cells are counted per coverslip and the percentage of cells with internalized particles is quantified. FIG. 11A depicts that non-targeted particles bind to both cell types with similar affinity at low concentrations, but binds better to B cells at higher concentrations. FIG. 11B depicts that targeted particle are preferentially internalized compared to non targeted particles. Further, the targeted particle is specific for B-cells only when compared to similar dosage concentration used in T-cell experiments. Hence, targeting of the particles significantly improves targeted cell uptake when compared to non-specific cells. FIG. 12A depicts the internalization of anti-CD22 targeted particles and non-targeted particles in BCLI cells at 100 nM and 2.5 nM dosages. FIG. 12B depicts that targeted particles are preferentially internalized compared to non targeted particles.

D. Competition Assay Using Anti-CD22 Targeted Particles in the Presence of "Free Anti-CD22"

Figure 13:
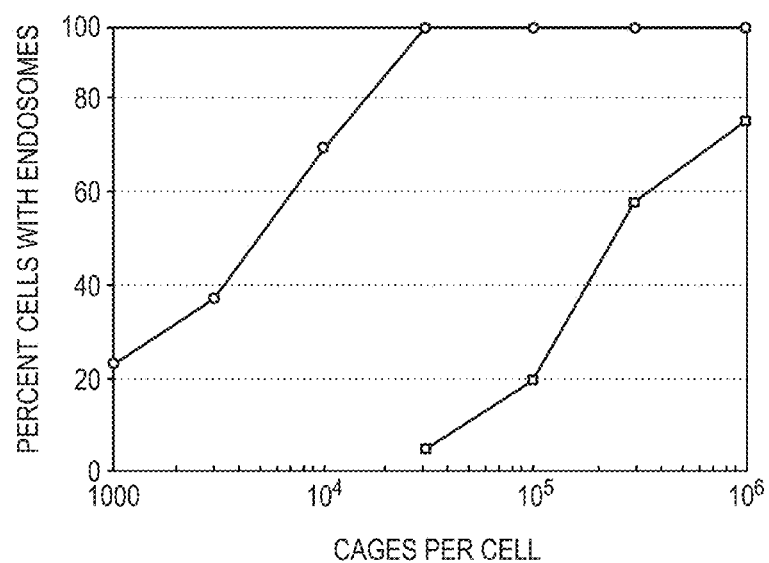
FIG. 13 is a line graph depicting that "free" anti-CD22 antibody containing preparations (pink) mixed with purified anti-CD22 targeted particles (yellow) results in a >100-fold shift in the dose-response relationship of particle internalization in B Cells.

Particle constructs are generated using standard procedures. Following antibody attachment to the particle, removal of free antibodies from the particles was not conducted. This results in the presence of free antibody (>10:1) in targeted particle preparations. Fluorescent internalization experiments are conducted using BCL1 cells and identical experimental conditions as stated above. Experimental incubations for this experiment included the comparison between identical concentrations of purified targeted particles and non-purified targeted particles. Particle concentrations for all experiments are determined by quantifying core protein concentration, so free antibody does not effect concentration calculations. Analysis of internalized particles in these experiments is identical to those mentioned above. FIG. 13 depicts that when targeted particles are incubated in the presence of free antibody, a ~1000 fold decrease in internalization is observed. FIG. 13 also depicts that targeted cages are being internalized through surface marker mediated internalization processes and are not internalized thru non specific endocytotic pathways.

Example 13

Capsid Stability Assay

The stability of capsids formed by core proteins with destabilizing and/or stabilizing mutations is assessed, and the relative stabilities of various capsids with that of the wild type capsid are compared.

Figure 14:
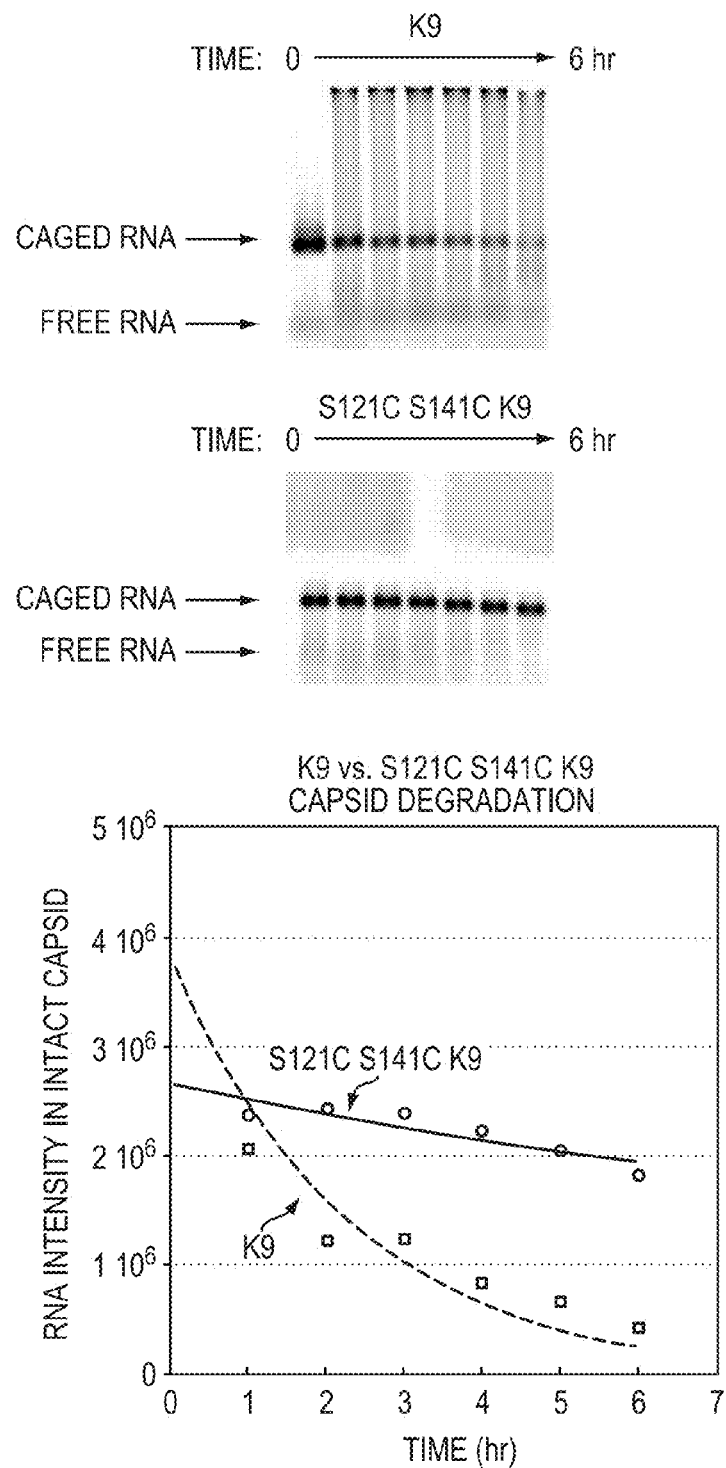
FIG. 14 depicts results from a capsid stability assay.

Capsids are formed in the presence of fluorescently-labeled RNA molecules. The core protein is incubated with the RNA at a ratio of 10:1 protein:RNA and then 70 mM NaCl is added at a 1:1 ratio to the protein/RNA mixture to initiate capsid formation. Capsid formation can be confirmed by light scattering and/or size-exclusion chromatography. The preformed capsids are incubated in 4M urea at a temperature of 55° C. to force degradation of the capsids. Aliquots of the capsids are taken at various time points and analyzed on a 1% agarose gel. The gel analysis reveals the amount of RNA that is present as free molecules or inside the intact capsid and as such serves as a gauge of intact capsid present at the various time points. The amount of RNA in the intact capsid band can be quantified by densitometry and plotted over time (see FIG. 14).

Example 14

Benzonase protection assays are performed to determine if a K9 core protein protects the encapsulated inhibitory dsRNA molecules from the benzonase nuclease.

Free RNA (50 nM) or core-protein encapsulated RNA (150 nM) is injected into IX benzonase cleavage buffer with varying amounts of benzonase (range=1.9 units/nmole to 945 units/nmole). A sample is prepared with no benzonase as a negative control. The mixture is incubated for 1 hour at room temperature. The samples are run on a 1.0% TAE-agarose gel containing ethidium bromide. The gel is imaged and the intensity of the RNA bands is determined.

Figure 15:
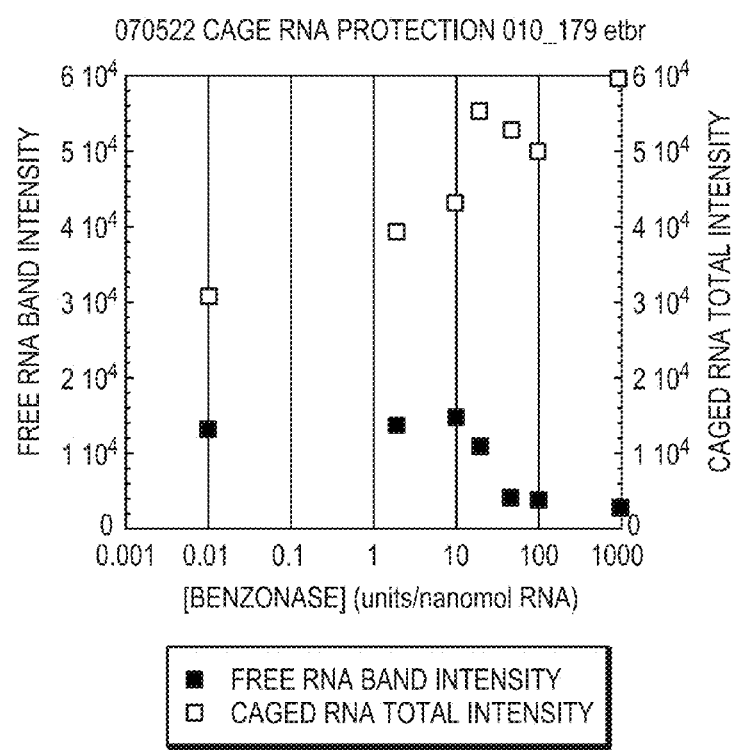
FIG. 15 is a quantitative representation of the results of a nuclease protection assay.

Free RNA band is degraded at about 20 units/nmol. RNA associated with the K9 core protein does not degrade at any nuclease concentrations tested, indicating that the RNA is effectively protected, as quantitated in FIG. 15. This assay shows that RNA is significantly protected against nuclease activity by encapsulation with K9 core protein.

Example 15

Serum Protection Assay

Degradation is compared to two control samples: free RNA and empty particles with RNA added after assembly. The second control is to determine whether particles protect RNA from serum degradation by some mechanism other than encapsulation.

Equal volumes of each RNA sample is mixed with human serum. The total volume of sample and serum is between 2-4 mL. Freeze several aliquots of sample and serum immediately for time zero time points, and place the remaining samples at 37° C. Multiple 50 µL aliquots are removed from samples at regular intervals, labeled and froze at −80° C. To process the samples, 10% SDS is added to achieve a final concentration of 0.7% SDS. The mixture is incubated at room temperature for 5 minutes. Samples are ran at 200 V for 30 minutes on a 1.0% TAE-agarose gel containing ethidium bromide. The lifetime of the RNAs is quantitated to determine the amount of protection.

Figure 16:
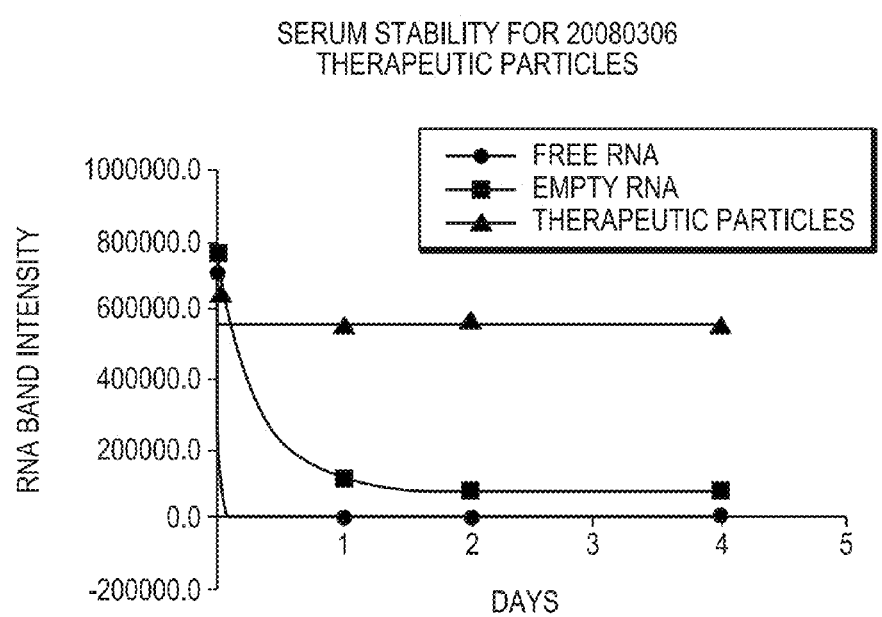
FIG. 16 is a quantitative representation of the results of a serum stability assay.

FIG. 16 demonstrates that the control samples are degraded by the first time point (1 day) while the particle-protected RNA survived without appreciable degradation for the duration of the experiment, 4 days. These results indicate that the particle protects the RNA cargo from serum degradation. Additional experiments indicate that RNA stability is achieved at 14 days without the degradation of the RNA payload. Free RNA, in the presence and absence of empty particle, is completely degraded by 1 day.

Example 16

The following assays determine the $K_d$, for K7, K9 and K11 constructs with fluorescent inhibitory dsRNA. The purpose of this study is to determine the affinity of a fluorescent inhibitory dsRNA construct for the HBV core protein mutants. Below is the sequence of fluorescent inhibitory dsRNA that was used in these experiments.

Siglo Cyclophilin B:

(SEQ ID NO: 191)
DY547-GGAAAGACUGUUCCAAAAAUUUUCCUUUCUGACAAGGUUUUU-P

A.

A solution of 20 nM fluorescent duplex (Siglo cycB, RNA from Dharmacon) in 10 mM Tris is referred to as f-RNA buffer. K9 protein stock is diluted to 6 µM in f-RNA buffer. The dilution is performed quickly on ice, so that particle assembly is less apt to form. Successive dilutions of K9 is made in f-RNA buffer. The RNA-protein dilutions are removed from ice and incubated at room temperature for 5 minutes.

The reactions are run on a gel under the following conditions: 15 µL of the samples in duplicates are loaded per lane on a 1.5% TAE-agarose gel. The gel is run at 200 V for 35 minutes and documented on a Molecular Dynamics Typhoon scanner.

Figure 17:
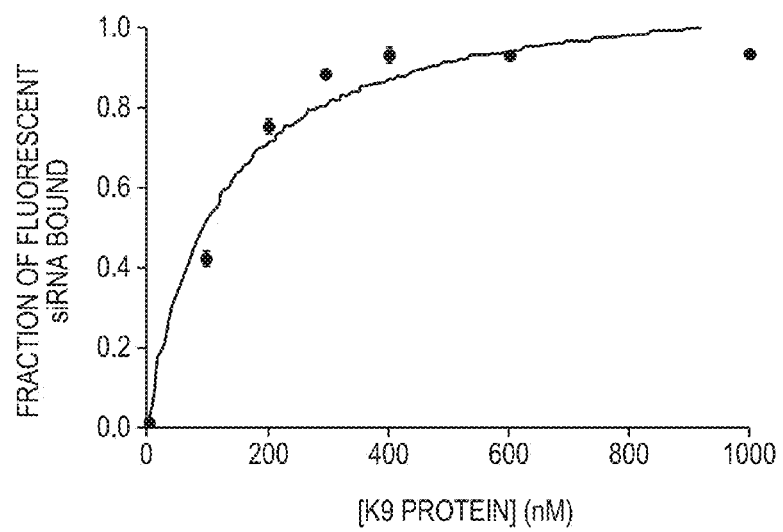
FIG. 17 is a line graph depicting the binding curve for K9 mutants.

FIG. 17 depicts that the fluorescent inhibitory dsRNA binds to K9 with a $K_d$ of 115 nM. This is a tight affinity, which is characteristic of RNA-protein interactions. This tight binding affinity is well below the concentrations of RNA and protein used for assembly of particles. Therefore, these data suggests that during assembly the RNA binding sites of K9 protein are saturated with RNA.

B.

A solution of 20 nM fluorescent duplex (Siglo cycB, RNA from Dharmacon) in 20 mM Sodium Bicarbonate, pH 9.5, is prepared. K7 and K11 protein stocks are diluted to 40 µM in the same buffer. A range of protein concentrations is generated by successively diluting the 40 µM protein in 20 mM Sodium Bicarbonate, pH 9.5. RNA and protein solutions are mixed 1:1 and allowed to bind at room temperature for 5 minutes. The final protein concentration in the binding reactions ranged three orders magnitude, from 20 µM to 20 nM. RNA loading buffer (xylene cyanol in 55% glycerol 20 mM Tris, pH 7.7) is added to the samples, and the samples are loaded on a 1.0% TAE-agarose gel (13 cm×16 cm) at 80 µL/lane. The gel is run at 180 V for 35 minutes and documented on a Molecular Dynamics Typhoon scanner.

Figure 18:
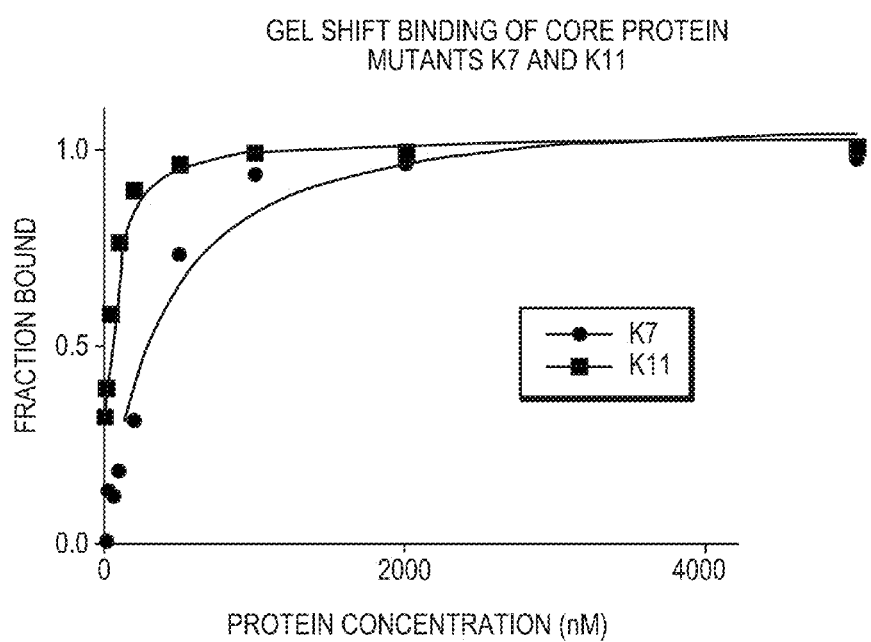
FIG. 18 is a line graph depicting the binding curves for K7 and K11 mutants.

FIG. 18 depicts that the fluorescent inhibitory dsRNA bound to K7 with a $K_d$ of 370 nM and to K11 with a $K_d$ of 69 nM. This is a tight affinity which is characteristic of RNA-protein interactions. The increase affinity observed for K11 relative to K9 and K7 is attributable to the larger number of cationic residues at the C-terminal end of this protein. As with the mutant K9, the affinity is high enough to fully saturate the RNA binding sites for both mutants during the process of particle assembly. Table 4 provides a summary of K7, K9, and K11 mutant binding conditions as well as the $K_d$ values.

TABLE 4

| Mutant | Affinity for SiGlo inhibitory dsRNA ($K_d$) | Conditions |
| --- | --- | --- |
| K7 | 370 nM | 20 mM NaHCO3, pH 9.5 |
| K9 | 115 nM | 20 mM Tris, pH 7.7 |
| K11 | 69 nM | 20 mM NaHCO3, pH 9.5 |

Example 17

The following examples demonstrate the ability of therapeutic particles to encapsulate inhibitory dsRNA, effectively delivering the encapsulated inhibitory dsRNA to a cell and the ability of the encapsulated inhibitory dsRNA to silence or down regulate the activity of a particular gene of interest.

A.

C166 cells stably expressing the enhanced green fluorescent protein (eGFP) are grown at 37° C., 5% CO2, in DMEM media with 10% fetal bovine serum and supplements. Cell stocks are grown in T25, T75, or T125 flasks and transferred to 24-well plates for experimentation. Cells are also grown on glass coverslips in 24-well plates when microscopy is to be performed. Cells grown under these conditions consistently exhibit "normal" growth characteristics and doubling times.

B. Lipid Particles Containing Red Fluorescent Inhibitory dsRNA Enter Cells

C166 cells are grown on glass coverslips in 24-well plates. Cells are plated onto coverslips 24 hours prior to the addition of lipid particles containing inhibitory dsRNA. 100 µl of lipid particles containing 3 nM final concentration of red-fluorescent inhibitory dsRNA directed against Cyclophilin B (SEQ ID NO: 191) are added to 1 mL of media and incubated at 37° C. for 4 hours. Control cells are incubated in 100 µl of PBS (no lipid particles present). Cells are rinsed 3 times in cold PBS and fixed in 1% paraformaldehyde in PBS. Hoescht 33342 (1:10,000) is added for the visualization of cell nuclei, and coverslips are mounted onto glass slides (cells facing down). Slides are visualized using standard fluorescence microscopy. Microscope settings are held constant for both experimental and control slides. Lipid particles containing red fluorescent inhibitory dsRNA enter eGFP-expressing C166 cells when incubated at 3 nM for 4 hours, thus staining these cells red.

Figure 19:
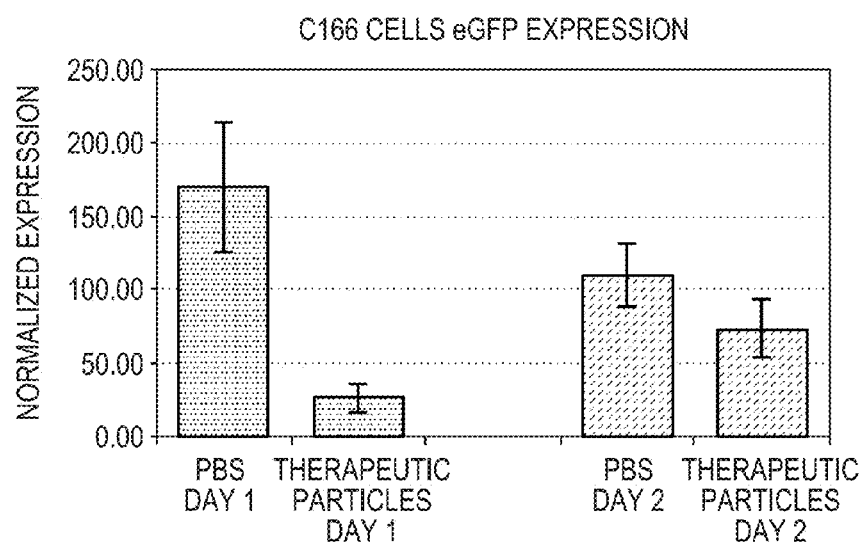
FIG. 19 depicts a bar graph showing the knock down eGFP mRNA expression using lipid coated particles containing inhibitory dsRNA directed against eGFP.

C. Lipid Particles Containing Inhibitory dsRNA Directed Against eGFP Inhibit eGFP mRNA Expression In Vitro C166 cells are grown on glass coverslips in 24-well plates. Cells are plated onto coverslips 24 hours prior to the addition of lipid particles. 250 µl of lipid particles containing inhibitory dsRNA directed against eGFP (eGFP-19) with the following sequences:

```
GCUGACCCUGAAGUUCAUC-dTdT    (SEQ ID NO: 192)

dTdT-CGACUGGGACUUCAAGUAG    (SEQ ID NO: 193)
``` are added to 1 mL of media and incubated at 37° C. for 24 and 48 hours. The final concentration of inhibitory dsRNA within the particle is 10 nM. Control cells are incubated in 250 µl of PBS (no lipid particles present). Cells are rinsed 3 times in cold PBS and homogenized using buffer RLT (Qiagen) with 0.1% BME. Three wells are used for each experimental condition at each time point. RNA is purified using the RNEasy kit (Qiagen) as recommended by the manufacturer, including an on-column DNAse digestion step. RNA is quantified on the Nanodrop (Thermofisher). 1 µg of total RNA is reverse transcribed using iScript reverse transcriptase (BioRad) as recommended by the manufacturer. Quantitative polymerase chain reactions (qPCR) are performed using cDNA, SybrGreen master mix (BioRad) as recommended by the manufacturer, and prequalified primer sets designed using Beacon Designer 6.0 (Premier Biosoft). eGFP gene inhibition is quantified using the ΔΔCt method by comparing eGFP expression levels in each sample to the geometric mean of 3 housekeeping genes in the same sample. All samples are run in triplicates. FIG. 19 depicts that lipid particles containing inhibitory dsRNA directed against eGFP entered cells and inhibited eGFP mRNA expression when incubated at 10 nM for 24 (84% knockdown) and 48 hours (33% knockdown).

D. Lipid Particles Containing Inhibitory dsRNA Directed Against eGFP Inhibit eGFP Protein Expression In Vitro.

C166 cells are grown on glass coverslips in 24-well plates. Cells are plated onto coverslips 24 hours prior to the addition of lipid particles. 100 µl of lipid particles red-fluorescent inhibitory dsRNA directed against eGFP (F-eGFP 19 with the following sequence:

```
DY547-GCUGACCCUGAAGUUCAUC-dTdT    (SEQ ID NO: 194)

dTdT-CGACUGGGACUUCAAGUAG          (SEQ ID NO: 193)
``` are added to 1 mL of media and allowed to sit at 37° C. for 18 hours. The final concentration of inhibitory dsRNA within the particle is 10 nM. Control cells are incubated in 100 µl of PBS (no lipid particles present). Cells are rinsed 3 times in cold PBS and fixed in 1% paraformaldehyde in PBS. Hoescht 33342 (1:10,000) is added for the visualization of cell nuclei, and coverslips are mounted onto glass slides (cells facing down) in 5% n-propyl gallate in glycerol. Slides are visualized using confocal microscopy. Microscope gain and PMT settings are held constant for both experimental and control conditions. Lipid particles containing red fluorescent inhibitory dsRNA directed against eGFP can enter cells and inhibit eGFP protein expression after an 18 hour incubation. eGFP (green) expression is reduced in cells incubated with lipid particles loaded with inhibitory dsRNA (red).

E. Lipid Particles Containing Inhibitory dsRNA Directed Against eGFP Inhibit eGFP mRNA Expression In Vivo.

Female C57BL/6-Tg(ACTb-eGFP)1Osb/J mice (~8 weeks old) are treated with 200 µl of lipid particles loaded with a total of ~620 ng inhibitory dsRNA (eGFP 19 of SEQ ID NO: 192 and SEQ ID NO: 193) through tail injections. The mice are sacrificed 24 or 48 hours later. 20 animals are injected with lipid particles loaded with inhibitory dsRNA, and 20 animals are injected with 200 µl of PBS alone. 16 animals are sacrificed from each group at 24-48 hours, and 4 animals from each group are sacrificed at 48 hours. RNA is harvested from the liver, kidney, heart, lung, spleen, and pancreas using RNA later storage solution (Ambion). RNA is purified from ~25 mg of tissue from each organ using the RNEasy total RNA purification kit and DNAse digestion is conducted on column. 1 µg of total RNA is reverse transcribed using the iScript reverse transcription kit. Equal amounts of cDNA are added to qPCR reactions. Levels of eGFP are normalized to the geometric mean of 3 housekeeping genes and percent inhibition is calculated using the ΔΔCt method. All qPCR samples are run in triplicates. Table 5 shows that lipid particles containing inhibitory dsRNA directed against eGFP inhibit eGFP mRNA expression in multiple organs in vivo. Percent of inhibition in multiple organs is calculated as described above after 24 hours (Day 1) and 48 hours (Day 2). N/A represents no inhibition.

TABLE 5

| Organ | Day 1 (% Knockdown) | Day 2 (% Knockdown) |
|---|---|---|
| Liver | 20 | 68 |
| Kidney | 64 | 14 |
| Heart | 41 | 32 |
| Lung | 25 | 23 |
| Spleen | 22 | 35 |
| Pancreas | N/A | 53 |

F. Lipid Particles Containing Inhibitory dsRNA Directed Against eGFP Inhibit eGFP Protein Expression In Vivo.

A female C57BL/6-Tg(ACTb-eGFP)1Osb/J mouse (~9 weeks old) is injected with 200 μL of lipid particles loaded with a total of ~40 ng siGlo-conjugated inhibitory dsRNA (F-eGFP 19 of SEQ ID NO: 194 and SEQ ID NO: 193). The mouse is sacrificed 24 hours later. A total of 1 animal received 200 μL lipid particles containing inhibitory dsRNA in PBS and 3 naive animals (female animals from the same litter) received no injection. Liver tissue is harvested and immediately placed in 4% paraformaldehyde in PBS and stored at 4° C. 16 μm frozen sections are cut at −20° C. on a cryostat, covers lipped in 5% n-propyl gallate in glycerol, and viewed using a confocal microscope. All PMT and gain settings are held constant for both experimental and control liver sections. Lipid particles containing red fluorescent inhibitory dsRNA directed against eGFP reduce eGFP protein expression in the mouse liver in vivo.

G. Lipid Particles Containing Inhibitory dsRNA Directed Against eGFP Knock Down eGFP Expression In Vivo.

For each mouse liver from the above experiment, 75 μg of tissue is homogenized and extracted in 1.5 mL of PBS-T using a Tissue Lyser (Qiagen). The extract is spun for 10 minutes at 12 g, 4° C. Supernatant is decanted into a fresh 2 mL tube. This centrifugation and decanting step is repeated to produce approximately 1 mL of clear liver protein extract. Liver protein extract is stored at −80° C.

Liver extract is diluted 1:1 with PBS and tested for protein concentration with a DC protein assay (BioRad) in a 96-well format. Final calculated protein concentrations are in the range of 2.5 to 3 mg/mL and vary from each other with a standard deviation of 0.2 mg/mL.

Figure 20:
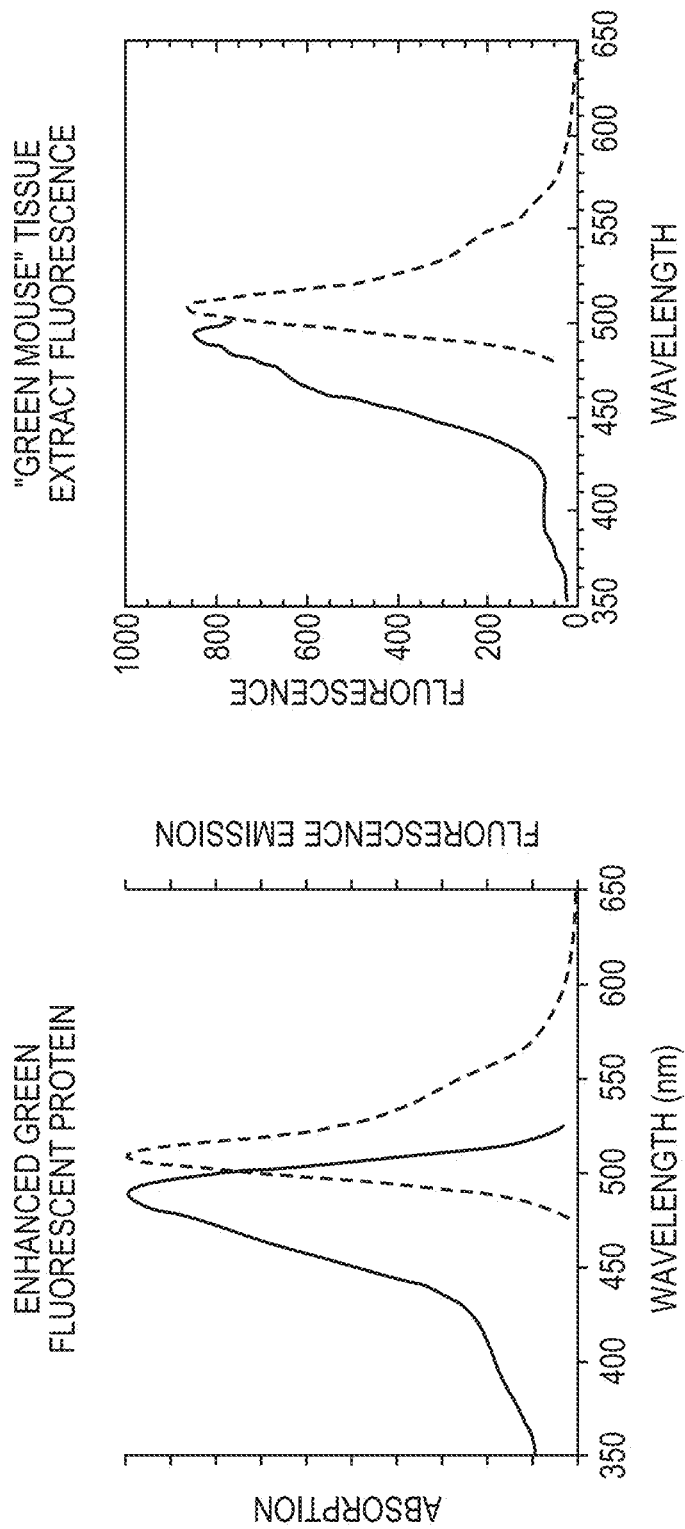
FIG. 20 depicts a fluorescent excitation and emission spectra for liver extracts match the corresponding spectra for EGFP.

Liver extracts are diluted 1:10 in PBS and tested for eGFP fluorescence on a fluorescent spectrophotometer. FIG. 20 depicts the fluorescent excitation and emission spectra for liver extracts which match the corresponding spectra for eGFP. To determine relative levels of eGFP fluorescence from individual liver extracts, 100 μL of 1:10 diluted extract is loaded into a 96 well plate and read on a Turner fluorescent plate reader. Each sample is read in duplicates. A standard curve for of 0 to 2 μM fluorescein is also generated from duplicate wells on the same plate.

Figure 21:
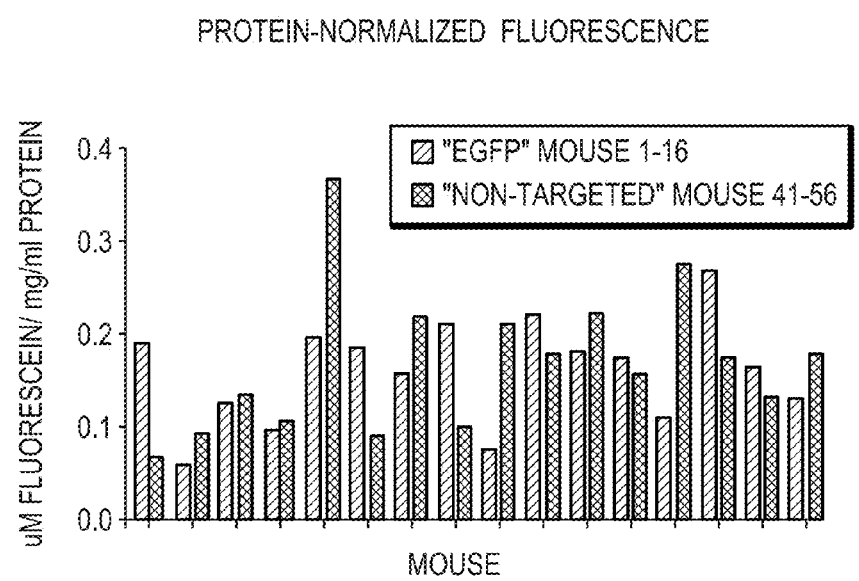
FIG. 21 depicts a bar graph showing that liver fluorescence values were normalized by the amount of protein and reported as μM Fluorescein equivalents per mg/mL protein.

FIG. 21 depicts the liver fluorescence values as normalized by the amount of protein and reported as μM Fluorescein equivalents per mg/mL protein. To determine inhibition, eGFP fluorescence is compared between livers treated with or without inhibitory dsRNA. At the 24 hour time point, there is a 6% inhibition for the inhibitory dsRNA treated liver when compared to controls (P-value of 0.34). For the 48-hour time point, there is a 36% inhibition for the inhibitory dsRNA treated liver when compared to controls (P-value of 0.035).

The results are consistent with a significant inhibition of eGFP protein expression at the 48 hour time point.

Example 18

To demonstrate in vitro knockdown of ApoB protein by ApoB2 loaded therapeutic particles, ApoA1 protein expression is monitored for normalization of protein expression. In both cases, ApoB and ApoA1, protein expression is quantified via ELISA.

HepG2 cells grown in HepG2 media are plated overnight on coated 96-well plates. The volume of cells per well is 100 uL. A therapeutic particle stock containing 171 nM ApoB2 inhibitory dsRNA is prepared at a ratio of 4.5 inhibitory dsRNA's per particle.

Cells are approximately 60% confluent at the beginning of the experiment. Media is replaced with HEPG2 media containing 20% stock therapeutic particles. Cells are incubated with particles or control (HepG2 containing 20% of vehicle) at 37° C. After 48 hours, the media is replaced with HepG2 media and allowed to incubate 24, 48 or 72 hours.

At the three time points for both particle-containing and control conditions, media from three wells are harvested for analysis of ApoB and ApoA1 levels.

Both ApoB and ApoA1 levels are detected by ELISA. For ELISA analysis of ApoB1, antibodies are immobilized on high binding polystyrene 96 well plates (Corning Costar cat#3590). The capturing antibody is Apolipoprotein B antibody B1G1 (cat# GTX27616), diluted 1:2000 in 0.1M sodium bicarbonate pH 9.6. To block further attachment to the plastic wells, PBS-BSA (PBS+10 mg/ml BSA) is applied. Samples are prepared in HepG2 conditioned media diluted 1:10 in PBS-0.1×BSA (PBS+1 mg/ml BSA). A standard is generated by serial dilution of an ApoB standard (Alerchek). The detection antibody is an ApoB-Horse Radish Peroxidase antibody conjugate (Genetex cat #GTX40047), diluted 1:1000 in PBS-BSA. Each well is measured in triplicates. Between capture antibody, block, sample, and detection antibody applications, wells are washed 3 times with 200 uL of PBST (PBS containing 0.1% TWEEN 20). HRP is detected with ULTRA-TMB reagent (Thermofisher).

For the ELISA analysis of ApoA1, an ApoA1 ELISA kit is purchased from Alerchek (cat# Cardiocheck Apolipoprotein A1) and used according to manufacturer's directions.

Figure 22:
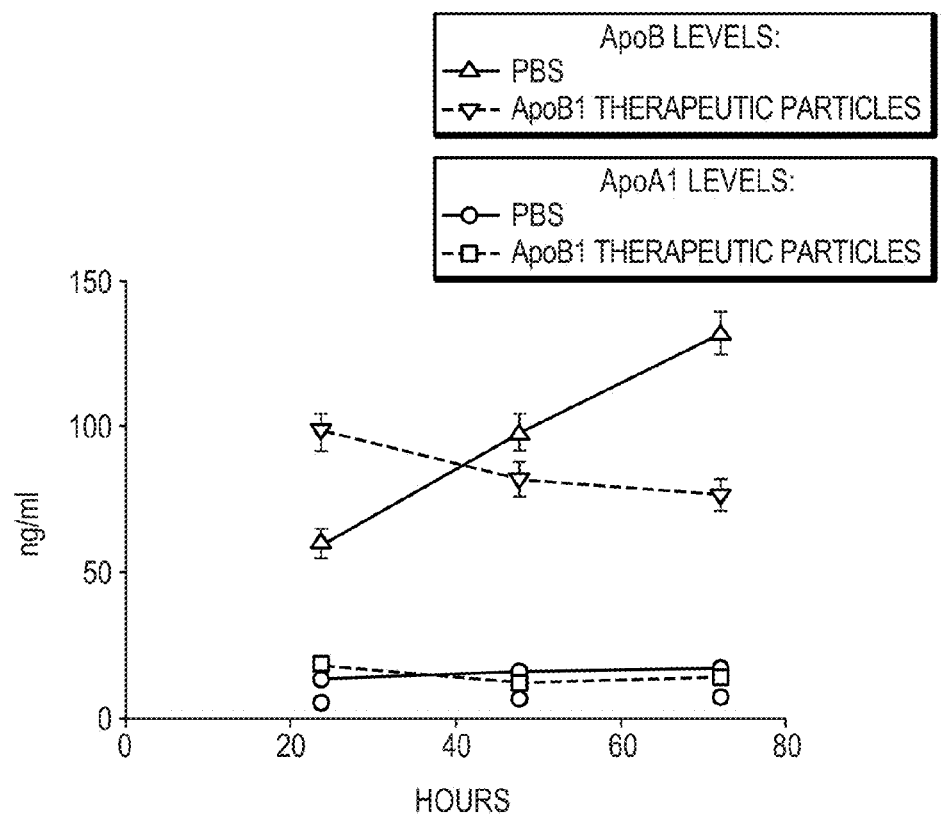
FIG. 22 depicts ApoA1 and ApoB levels at 24 hour, 48 hour and 72 hour time points.
Figure 23:
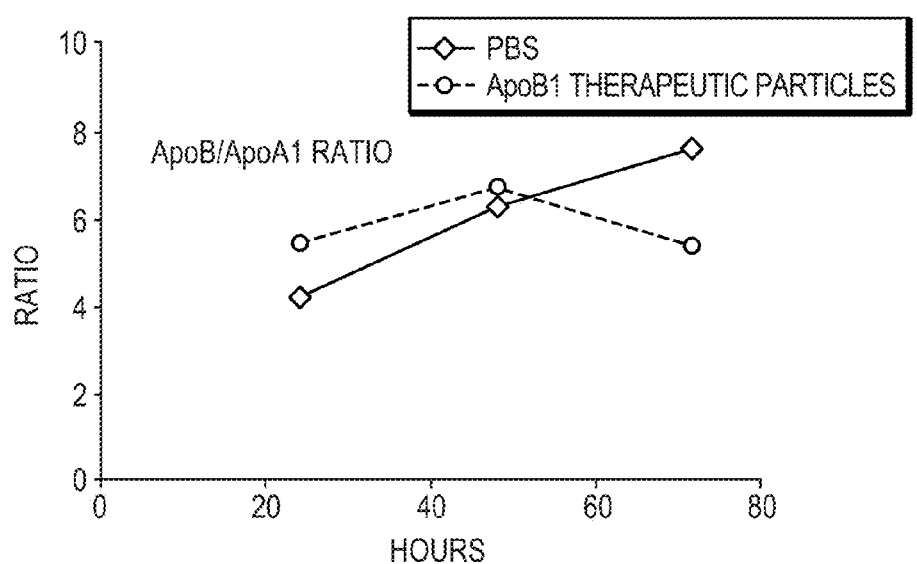
FIG. 23 depicts the ratio of ApoB to ApoA1 (ApoB/ApoA1) at 24 hour, 48 hour and 72 hour time points.

ApoA1 and ApoB levels are determined and graphed at the 24 hour, 48 hour and 72 hour time points (FIG. 22). The ratio of ApoB to ApoA1 (ApoB/ApoA1) is also graphed at these time points (FIG. 23). The maximum inhibition is seen at the 72 hour time point when the ApoB/ApoA1 ratio for particle-treated cells are 29% of the non-treated cells.

Example 19

Anti-CD22 Targeted Particles Loaded with Doxorubicin

B cells (Ramos), and T cells (Jurkat) are added to sterile 96-well plates containing 500,000 cells/ml in early log growth phase. Multiple concentrations (10 μM, 100 μM, 1 nM, 10 nM, and 100 nM) of both CD22-targeted particles and non-targeted particles loaded with doxorubicin are added to the cells along with complete media (see previously). Cells are assayed for viability using Typan Blue exclusion at multiple time points (12 hr, 24 Hr, 36 hr, 48 hr, 60 hr, and 72 hr). Cell viability is normalized to cell viability at the beginning of the experiments for each cell line and is expressed as a % of "normal". Cell density is also calculated and plotted across each time point for each concentration. All experiments at individual concentrations are conducted in triplicates for each time point.

Example 20

Anti-CD22 Targeted Particles Loaded with Doxorubicin are Evaluated for their Ability to Reduce Tumor Growth In Vivo Female athymic BALB/c nu/nu mice (Harlan Sprague-Dawley), 7-9 weeks of age are maintained on a normal diet ad libitum and under pathogen-free conditions. Raji or Ramos cells are harvested in logarithmic growth phase and 2.5–5.0× $10^6$ cells are injected subcutaneously into both sides of the abdomen of each mouse. Studies are initiated 3 weeks after implantation, when tumors are 100-300 $mm^3$. Experimental groups consist of untreated, doxorubicin alone, naked particles loaded with doxorubicin, and particles loaded with doxorubicin and coated with HB22.7.

Tumor volume is calculated by the formula for hemiellipsoids (DeNardo G L, Kukis D L, Shen S, et al., Clin Cancer Res 1997; 3:71-79). Initial tumor volume is defined as the volume on the day prior to treatment. Mean tumor volume is calculated for each group on each day of measurement; tumors that have completely regressed are considered to have a volume of zero. Tumor responses are categorized as follows: C, cure (tumor disappeared and did not regrow by the end of the 84 day study); CR, complete regression (tumor disappeared for at least 7 days, but later regrew); PR, partial regression (tumor volume decreased by 50% or more for at least 7 days, then regrew).

Differences in response among treatment groups are evaluated using the Kruskall Walis rank sum test with the response ordered as none, PR, CR, and Cure. Survival time is also evaluated using the Kruskall Walis test. Tumor volume is compared at 3 time points: month 1 (day 26-29), month 2 (day 55-58), and at the end of the study (day 84). If an animal is sacrificed due to tumor-related causes, the last volume is carried forward and used in the analysis of later time points. Analysis of variance is used to test for differences among treatment groups. P-values are two-tailed and represent the nominal p-values. Protection for multiple comparisons is provided by testing only within subsets of groups found to be statistically significantly different.

Example 21

ApoB Inhibition In Vitro Using Human HepG2 Cells

HepG2 cells (human hepatocellular carcinoma cell line-ATCC) are grown in DMEM with 10% fetal bovine serum, 2 mM l-glutamine, and penicillin/streptomycin at 37° C. and 5% $CO_2$. Cells are seeded in 96-well polyl-lysine coated plates at ~50,000 cells/well and allowed to settle overnight. The following day, when cells have reached >90% confluency, viral core protein particles as prepared as above, DharmaFECT, and PBS are to be added to cells. Particles and PBS are to be added at a volume of 25 ul to 75 ul of complete media for a total of 100 ul/well. All experimental conditions are performed using triplicate wells (n=3) of 96 well plates. ApoB inhibitory dsRNA (sense 5'-GUCAUCACACUGAAUACCAAU-3' (SEQ ID NO: 195) and antisense 5'-AUUGGUAUUCAGUGUGAUGACAC-3' (SEQ ID NO: 196)) are loaded in particles as described previously.

On Day 0 (24 hours after seeding cells on 96-well poly-1-lysine coated plastic plates), therapeutic particles and PBS are added to individual wells and incubated at 37° C. for 72 hours. After incubations are completed, media is removed from each well and 150 µl RLT lysis buffer (Qiagen) with b-mercaptoethanol (BME) is added to lyse the cells and stabilize RNA (as indicated by the manufacturer). Following lysis, the entire volume of lysate is added to 450 µl of RLT lysis buffer with BME for a total of 600 µl lysis solution. Total RNA is then purified from individual samples using Qiagen RNEasy columns on a QiaCube (Qiagen) automated RNA purification system as suggested by the manufacturer. Qiashredders and on-column DNase I (Qiagen) digestion steps are also conducted as suggested by the manufacturer (included in automated RNA preparation protocol). Following RNA purification, total RNA is quantified using a Nanodrop spectrophotometer (ThermoFisher) and equal amounts of RNA (as suggested by the manufacturer) are reverse transcribed for every sample within each experiment into cDNA using the iScript reverse transcriptase kit (BioRad). cDNA is then added to SybrGreen qPCR master mix (BioRad—as recommended by the manufacturer) and quantitative real-time qPCR (qPCR) is performed using the 96-well plate format on MyIQ real-time qPCR machines (BioRad). Included in all qPCR experiments are pre-designed and pre-validated primers for 3 housekeeping genes, glyceraldehydes-3-p-dehydrogenase (GAPDH), glucose phosphate isomerase (GPI), and hydroxymethylbilane synthase (HMBS), as well as pre-designed and pre-validated primers specific for the apolipoprotein B gene (ApoB). Standard thermal cycler protocols are used to perform qPCR reactions for a total of 40 cycles as suggested by the manufacturer. All qPCR data is analyzed using the $\Delta\Delta$Ct-based algorithm included in the BioRad iQ5 software package, which incorporates the normalization of ApoB mRNA expression to the geometric mean of the three housekeeping genes.

Figure 24:
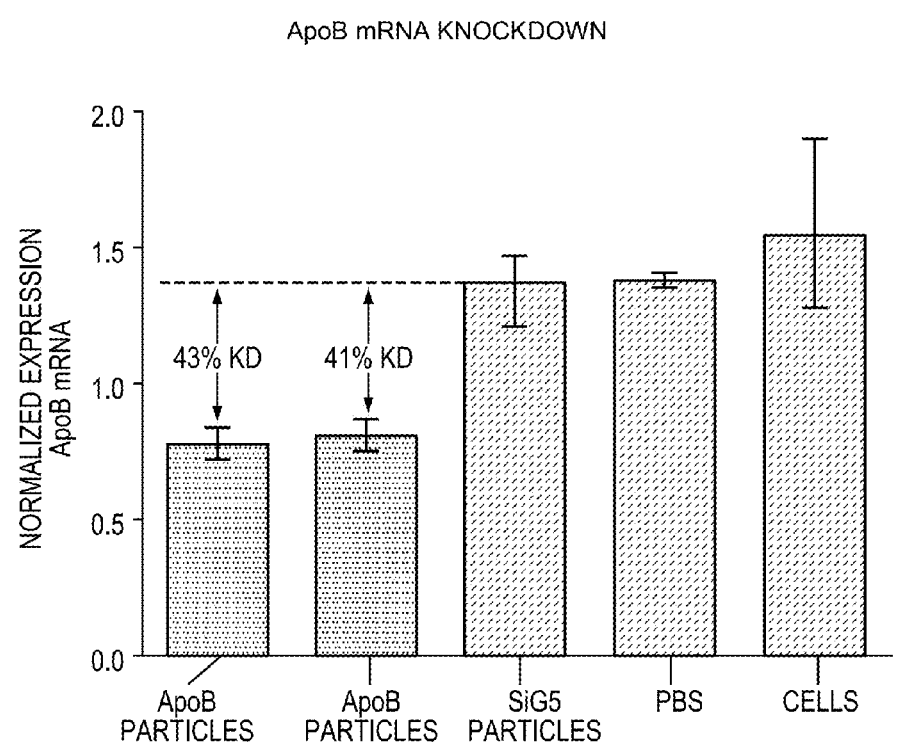
FIG. 24 depicts reduction in ApoB mRNA expression in HepG2 cells following a 72 hour incubation with 2 separate batches of chimeric therapeutic particles loaded with ApoB inhibitory dsRNA.

FIG. 24 indicates that ApoB mRNA expression is reduced in HepG2 cells following a 72 hour incubation with 2 separate batches of therapeutic particles loaded with ApoB inhibitory dsRNA, when compared to viral core particles loaded with SiGenome 5 inhibitory dsRNA (SiG5-Dharmacon/ThermoFisher), PBS, and media only (Cells). The percentage of ApoB mRNA inhibition reported on the graphs are compared with the expression value of ApoB mRNA in HepG2 cells incubated with viral core particles containing a commercially available control inhibitory dsRNA named SiGenome 5. The final inhibitory dsRNA concentration for ApoB viral core particles 1 is 650 nM/well, for viral core particles 2 is 550 nM/well, and for SiG5 viral core particles is 40 nM/well. Error bars denote standard deviation values.

Figure 25:
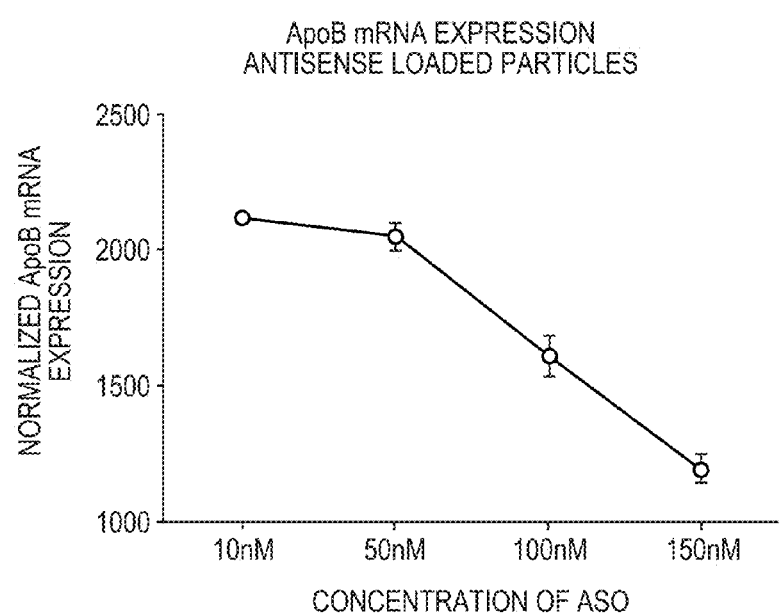
FIG. 25 depicts reduction in expression of ApoB mRNA in HepG2 cells as a concentration of chimeric therapeutic particles loaded with antisense DNA oligonucleotides increases.

FIG. 25 characterizes particles loaded with antisense DNA oligonucleotides (ASO) targeting the ApoB mRNA sequence. The results demonstrate ApoB mRNA inhibition when incubated on HepG2 cells for 72 hours (ASO antisense sequence 5'-mC*A*G*T*C*T*G*C*T*C*mG-3'; *=phosphorothioate linkages, m=2'-o-methyl ribose (SEQ ID NO: 197)). The graph demonstrates a decrease in the expression of ApoB mRNA in HepG2 cells as the concentration of viral core particles with ASO increases. Error bars denote standard deviation values.

Example 22

ApoB Inhibition In Vitro Using Mouse AML12 Cells

AML12 cells (mouse hepatocyte cell line-ATCC) are grown in DMEM with 10% fetal bovine serum, 2 mM 1-glutamine, insulin/transferring/selenium, and penicillin/streptomycin at 37° C. and 5% CO2 (as recommended by ATCC). Cells are seeded in 96-well plastic plates at ~50,000 cells/well and allowed to settle overnight. The following day, when cells reach >90% confluency, therapeutic particles and PBS are added to cells. Particles and PBS will be added at a volume of 25 μl to 75 μl of complete media for a total of 100 μl/well. All experimental conditions are performed using triplicate wells (n=3) of 96 well plates. ApoB inhibitory dsRNA has the following sequence: sense 5'-GUCAUCA-CACUGAAUACCAAU-3' (SEQ ID NO: 195) and antisense 5'-AUUGGUAUUCAGUGUGAUGACAC-3' (SEQ ID NO: 196)).

On Day 0 (24 hours after seeding cells on 96-well plastic plates), particles and PBS are added to individual wells and incubated at 37° C. for 72 and 96 hours. After incubations are complete, media is removed from each well and 150 μl RLT lysis buffer (Qiagen) with b-mercaptoethanol (BME) is added to lyse the cells and stabilize the RNA. Following lysis, the entire volume of lysate is added to 450 μl of RLT lysis buffer with BME for a total of 600 μl lysis solution. Total RNA is then purified from individual samples using Qiagen RNEasy columns on a QiaCube (Qiagen) automated RNA purification system. Qiashredders and on-column DNase I (Qiagen) digestion steps are also conducted (included in automated RNA preparation protocol).

Following RNA purification, total RNA is quantified using a Nanodrop spectrophotometer (ThermoFisher) and equal amounts of RNA are reverse transcribed for every sample within each experiment into cDNA using the iScript reverse transcriptase kit (BioRad).

cDNA is then added to SybrGreen qPCR master mix (Bio-Rad—as recommended by the manufacturer) and quantitative real-time qPCR (qPCR) is performed using the 96-well plate format on MyIQ real-time qPCR machines (BioRad). Included in all qPCR experiments are pre-designed and pre-validated primers for 3 housekeeping genes, glyceraldehydes-3-p-dehydrogenase (GAPDH), glucose phosphate isomerase (GPI), and hydroxymethylbilane synthase (HMBS), as well as pre-designed and pre-validated primers specific for the apolipoprotein B gene (ApoB). Standard thermal cycler protocols are used to perform qPCR reactions for a total of 40 cycles as suggested by the manufacturer. All qPCR data is analyzed using the ΔΔCt-based algorithm included in the BioRad iQ5 software package, which incorporates the normalization of ApoB mRNA expression to the geometric mean of the three housekeeping genes (GAPDH, GPI, and HMBS).

Figure 26:
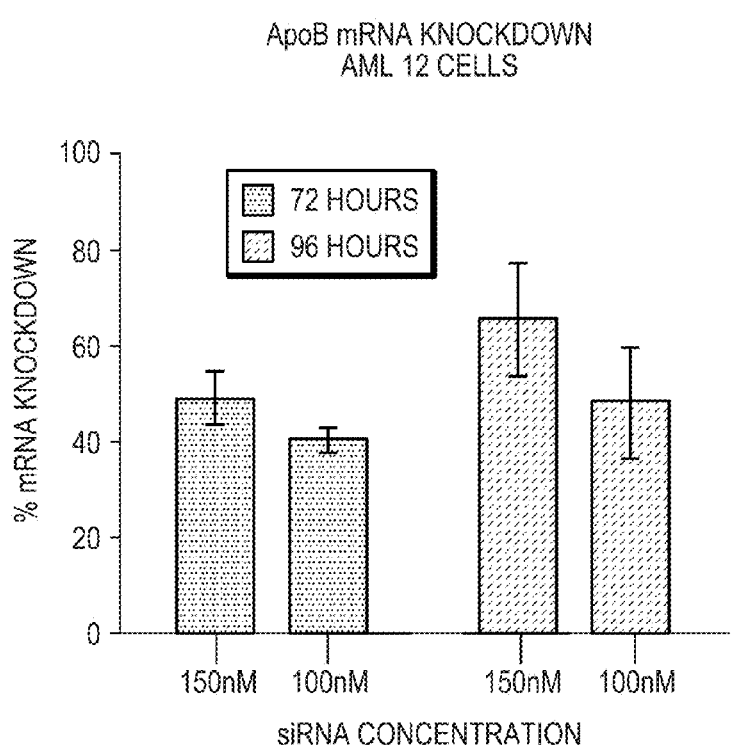
FIG. 26 depicts reduction in ApoB mRNA expression in AML12 cells following 72 and 96 hour incubations with chimeric therapeutic particles loaded with ApoB inhibitory dsRNA.

FIG. 26 demonstrates that ApoB mRNA expression is reduced in AML12 cells following 72 and 96 hour incubations with particles loaded with ApoB inhibitory dsRNA, when compared to PBS. The percentage of ApoB mRNA inhibition reported on the graphs are compared with the expression value of ApoB mRNA in AML12 cells incubated with PBS. ApoB particles inhibitory dsRNA concentrations are stated on the graph. Error bars denote standard deviation values.

Example 23

Factor VII Inhibition In Vitro Using Primary Mouse Hepatocytes

Cryopreserved mouse primary hepatocytes (Cellz Direct) are thawed and grown in William's Media with 10% fetal bovine serum (according to the manufacturer's protocol) at 37° C. and 5% CO2 for 24 hours. Thawed cells in suspension are then counted and plated at a density of 35,000 cells/well in 96-well collagen-1 coated plates (Becton Dickenson) using a proprietary mixture of media supplements (CellzDirect-Thawing/Plating Supplement Pack). Cells are allowed to settle and attach to the collagen-1 substrate for 48 hours as media is replaced after 24 and 48 hours. 48 hours after plating the cells, therapeutic particles, DharmaFECT, and PBS are added at a volume of 25 μl to 75 μl of complete media for a total of 100 μl/well. All experimental conditions are to be performed using triplicate wells (n=3) in 96 well plates. DharmaFECT transfection reagent #6 is used to transfect naked inhibitiory dsRNA into primary mouse hepatocytes as a positive control for mRNA knockdown. All DharmaFECT reagents are to be made up according to the manufacturer's suggested protocol and added at 100 μl/well, and all experiments are performed in triplicate. FVII inhibitory dsRNA, which has the following sequence: sense 5'-GGAUCAUCUCAAGUCUUACT*T-3' (SEQ ID NO: 198) and antisense 5'-GUAAGACUUGAGAUGAUCCT*T-3' (SEQ ID NO: 199); bold letters denote 2'-F-modified nucleotides and asterisks represent phosphorothioate linkages, as well as SiGenome 5, which has the following sequence: sense 5'-UGGUUUACAUGUCGACUAA-3' (SEQ ID NO: 200) are loaded into particles as described previously.

After incubations are completed, media is removed from each well and 150 μl RLT lysis buffer (Qiagen) with b-mercaptoethanol (BME) is added to lyse the cells and stabilize RNA. Following lysis, the entire volume of lysate is added to 450 μl of RLT lysis buffer with BME for a total of 600 μl lysis solution. Total RNA is then purified from individual samples using Qiagen RNEasy columns on a QiaCube (Qiagen) automated RNA purification system. Qiashredders and on-column DNase I (Qiagen) digestion steps are also conducted (included in automated RNA preparation protocol).

Following RNA purification, total RNA is quantified using a Nanodrop spectrophotometer (ThermoFisher) and equal amounts of RNA (as suggested by the manufacturer) are reverse transcribed for every sample within each experiment into cDNA using the iScript reverse transcriptase kit (Bio-Rad).

cDNA is then be added to SybrGreen qPCR master mix (BioRad—as recommended by the manufacturer) and quantitative real-time qPCR (qPCR) is performed using the 96-well plate format on MyIQ real-time qPCR machines (BioRad). Included in all qPCR experiments are pre-designed and pre-validated primers for 3 housekeeping genes, glyceraldehydes-3-p-dehydrogenase (GAPDH), Cyclophillin A, and tyrosine 3-monooxygenase/tryptophan 5-monooxygenase (YWHAZ), as well as pre-designed and pre-validated primers specific for the mouse Factor VII mRNA sequence. Standard thermal cycler protocols are used to perform qPCR reactions for a total of 40 cycles as suggested by the manufacturer. All qPCR data is analyzed using the ΔΔCt-based algorithm included in the BioRad iQ5 software package, which incorporates the normalization of FVII mRNA expression to the geometric mean of the three housekeeping genes mentioned above.

Figure 27:
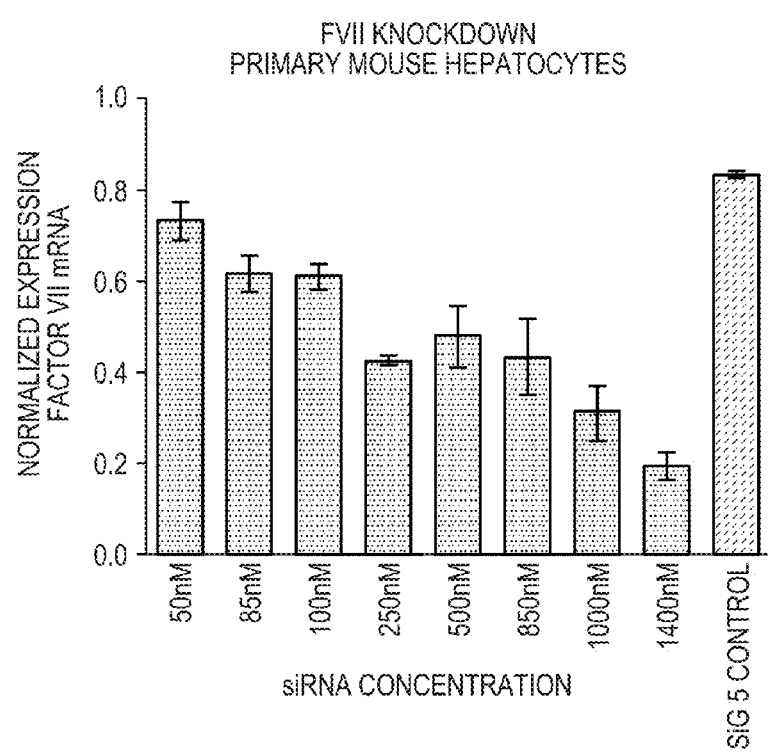
FIG. 27 depicts a dose response mRNA knockdown effect when chimeric therapeutic particles loaded with modified Factor VII inhibitory dsRNA is incubated on primary mouse hepatocytes for 72 hours.

FIG. 27 depicts particles loaded with modified Factor VII inhibitory dsRNA targeting the mouse FVII mRNA sequence. The results demonstrate a dose-dependent mRNA inhition when incubated on primary mouse hepatocytes for 72 hours. The graph demonstrates a decrease in the expression of FVII mRNA in hepatocytes as the concentration of inhibitory dsRNA—loaded particles increases. Error bars denote standard deviation values. SiGenome 5 control particles are incubated on cells at a concentration of 900 nM inhibitory dsRNA.

Figure 28:
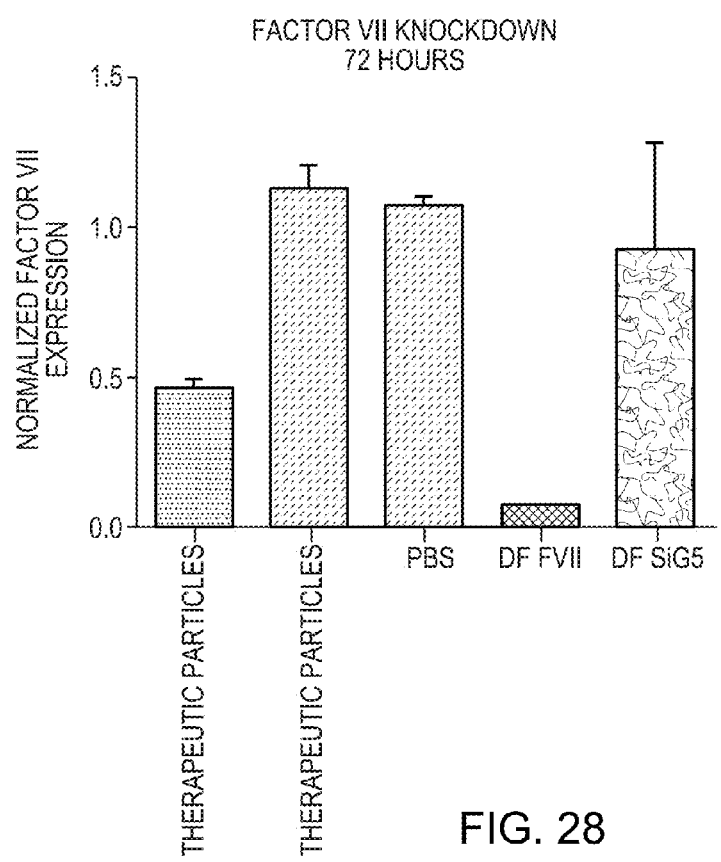
FIG. 28 depicts reduction in FVII mRNA expression in primary mouse hepatocytes following a 72 hours incubation with chimeric therapeutic particles.

FIG. 28 demonstrates that FVII mRNA expression is reduced in primary mouse hepatocytes following 72 hours of incubation with particles loaded with FVII inhibitory dsRNA, when compared to particles loaded with SiGenome 5 inhibitory dsRNA (SiG5-Dharmacon/ThermoFisher), and PBS. The final FVII inhibitory dsRNA concentration in the particles is 850 nM/well, and the final SiG5 inhibitory dsRNA concentration in the particles is 900 nM/well. DharmaFECT pre-incubated with FVII inhibitory dsRNA and incubated on cells at 100 nM for 72 hours also demonstrated FVII mRNA inhibition when compared with DharmeFECT pre-incubated with SiGenome 5 inhibitory dsRNA sequences. Error bars denote standard deviation values.

Figure 29:
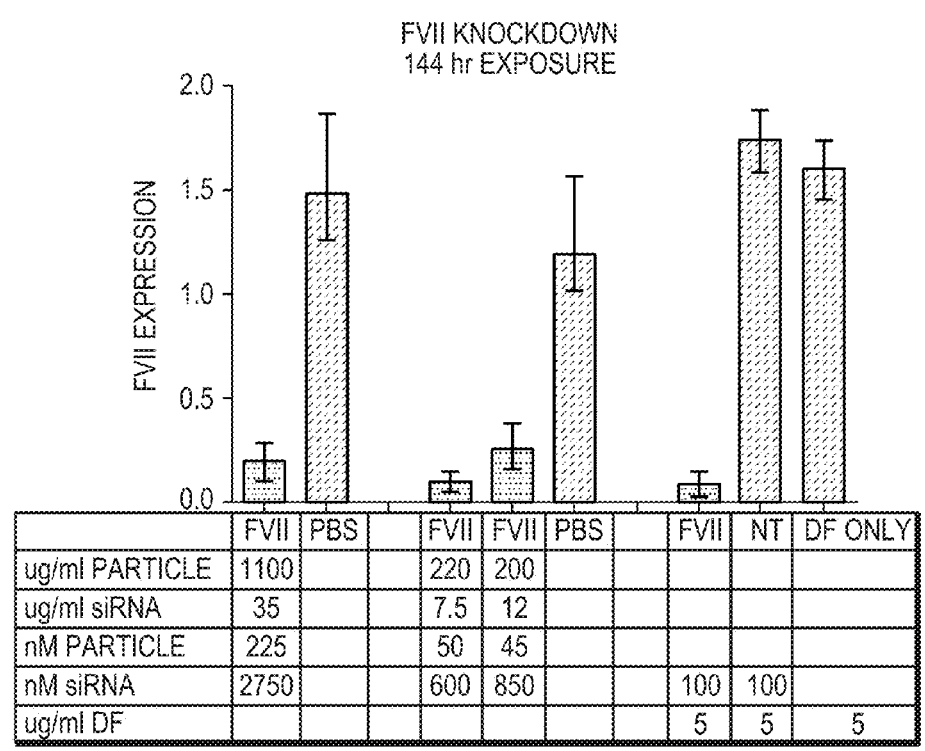
FIG. 29 depicts reduction in mRNA expression following dual exposure 144 hour incubation with chimeric therapeutic particles loaded with FVII inhibitory dsRNA.

FIG. 29 indicates results when cells are exposed to particles, PBS, or DharmaFECT for 144 hours. Media is replaced at 72 hours with fresh media containing particles, PBS, or DharmaFECT and incubated for an additional 72 hours (144 hours total). mRNA expression is reduced in primary mouse hepatocytes following a dual-exposure of 144 hour incubation with particles loaded with FVII inhibitory dsRNA when compared to PBS. The final FVII inhibitory dsRNA in the particles is 2750 nM/well, 600 nM/well, and 850 nM/well (same batch used in FIG. 28) as indicated in the figure. DharmaFECT pre-incubated with FVII inhibitory dsRNA and incubated on cells at 100 nM for 144 hours also demonstrated FVII mRNA inhibition when compared with DharmeFECT pre-incubated with SiGenome 5 inhibitory dsRNA sequences (NT) and also DharmaFECT with no inhibitory dsRNA (DF only). Error bars denote standard deviation values.

Example 24

Factor VII Inhibition In Vivo

A total of 48 female C57bl mice are injected intravenously in the tail vein with 200 μl of particles loaded with FVII inhibitory dsRNA at 0.5 mg/kg inhibitory dsRNA. The FVII inhibitory dsRNA has the following sequences: sense 5'-GGAUCAUCUCAAGUCUUACT*T-3' (SEQ ID NO: 198) and antisense 5'-GUAAGACUUGAGAUGAUCCT*T-3' (SEQ ID NO: 199); bold letters denote 2'-F-modified nucleotides and asterisks represent phosphrothioate linkages, and the SiGenome 5 inhibitory dsRNA, which has the sequence: sense 5'-UGGUUUACAUGUCGACUAA-3' (SEQ ID NO: 200) are loaded into particles as described previously. For the following study, six animals are sacrificed at 4 hours, 1 day, 3 days, 7 days, 10 days, 14 days, 21 days, and 28 days following injection and livers are removed and stored at 4° C. in RNA Later solution (Ambion) for subsequent mRNA purification and analysis. A total of 12 non-injected naïve animals are also sacrificed and livers are removed for use as control animals in this study. After the completion of the study, livers are removed from RNALater storage solution and 20 mg tissue samples are dissected, weighed and placed into 600 μl RLT lysis buffer (Qiagen) with b-mercaptoethanol (BME). Tissues are then lysed using a Tissue Lyser (Qiagen) at 30 hertz for 2 minutes. Total RNA is then purified from individual samples using Qiagen RNEasy columns on a QiaCube (Qiagen) automated RNA purification system as suggested by the manufacturer. Qiashredders and on-column DNase I (Qiagen) digestion steps are also conducted (included in automated RNA preparation protocol). Following RNA purification, total RNA is quantified using a Nanodrop spectrophotometer (ThermoFisher) and equal amounts of RNA (as suggested by the manufacturer) are reverse transcribed for every sample within each experiment into cDNA using the iScript reverse transcriptase kit (BioRad). cDNA is added to SybrGreen qPCR master mix (BioRad—as recommended by the manufacturer) and quantitative real-time qPCR (qPCR) is performed using the 96-well plate format on MyIQ real-time qPCR machines (BioRad). Included in all qPCR experiments are pre-designed and pre-validated primers for 3 housekeeping genes, glyceraldehydes-3-p-dehydrogenase (GAPDH), Cyclophillin A, and tyrosine 3-monooxygenase/tryptophan 5-monooxygenase (YWHAZ), as well as pre-designed and pre-validated primers specific for the mouse Factor VII mRNA sequence. Standard thermal cycler protocols are used to perform qPCR reactions for a total of 40 cycles as suggested by the manufacturer. All qPCR data is analyzed using the ΔΔCt-based algorithm included in the BioRad iQ5 software package, which incorporates the normalization of FVII mRNA expression to the geometric mean of the three selected housekeeping genes.

Figure 30:
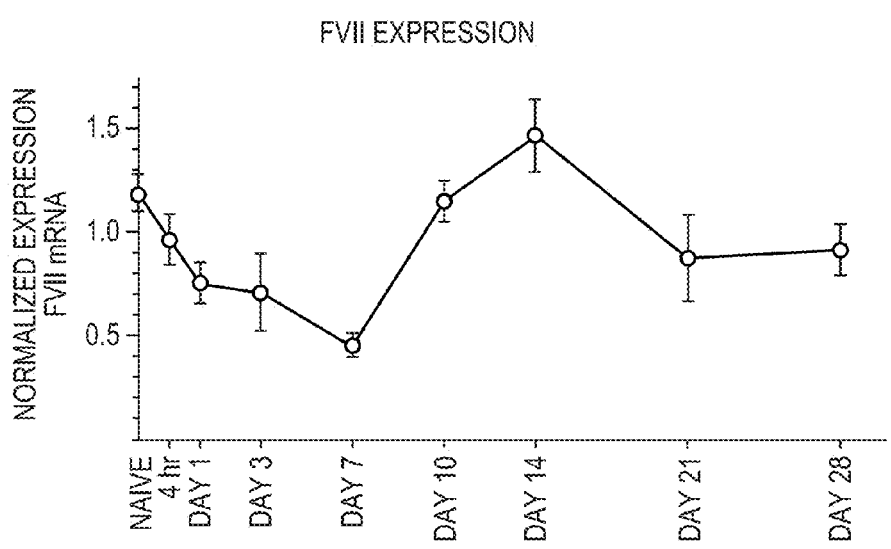
FIG. 30 depicts normalized FVII expression in mouse liver tissue following a single 200 ul injection of chimeric therapeutic particles loaded with FVII inhibitory dsRNA.

FIG. 30 depicts normalized FVII expression in mouse liver tissue. Animals are sacrificed at indicated time points (see above) following a single 200 μl injection of particles loaded with FVII inhibitory dsRNA at 0.5 mg/kg (n=6 animals at each time point for particles and n=12 for pre-dose time points). FVII expression is reduced in mouse liver tissue by 1 day following injection of particles and remained below the pre-dose level until returning to normal by Day 10.

Example 25

Angiotensinogen Inhibition in Mouse AML12 Cells

Mouse AML12 cells are grown in DMEM with 10% fetal bovine serum, insulin/transferring/selenium, 2 mM 1-glutamine, and penicillin/streptomycin at 37° C. and 5% CO2. Cells are seeded in 96-well plastic plates at ~50,000 cells/well and allowed to settle overnight. The following day, when cells have reached >90% confluency, therapeutic particles, DharmaFECT, and PBS are added to cells. Particles and PBS are added at a volume of 25 μl to 75 μl of complete media for a total of 100 μl/well. All experimental conditions were performed using triplicate wells (n=3) of 96 well plates. DharmaFECT transfection reagent #6 is used to transfect naked inhibitory dsRNA into HepG2 cells as a positive control. All DharmaFECT reagents are to be made up according to the manufacturer's suggested protocol and added at 100 μl/well, and all experiments are performed in triplicates. Angiotensinogen inhibitory dsRNA, which has the following sequence: sense 5'-UGUUGUUCAGAUUUGCCUCCG-CACC-3' (SEQ ID NO: 201) and antisense 5'-ACAA-CAAGUCUAAACGGAGGCGUGG-3' (SEQ ID NO: 202) and the SiGenome 5, which has the following sequence: sense 5'-UGGUUUACAUGUCGACUAA-3' (SEQ ID NO: 200) are loaded into particles as described previously.

On Day 0 (24 hours after seeding cells on 96-well poly-1-lysine coated plastic plates), therapeutic particles, PBS, and DharmaFECT are added to individual wells and incubated at 37° C. for 72 hours (unless indicated otherwise). After incubations are completed, media is removed from each well and 150 μl RLT lysis buffer (Qiagen) with b-mercaptoethanol (BME) is added to lyse the cells and stabilize the RNA. Following lysis, the entire volume of lysate is added to 450 μl of RLT lysis buffer with BME for a total of 600 μl lysis solution. Total RNA is purified from individual samples using Qiagen RNEasy columns on a QiaCube (Qiagen) automated RNA purification system. Qiashredders and on-column DNase I (Qiagen) digestion steps are also conducted (included in automated RNA preparation protocol). Following RNA purification, total RNA is quantified using a Nanodrop spectrophotometer (ThermoFisher) and equal amounts of RNA (as suggested by the manufacturer) are reverse transcribed for every sample within each experiment into cDNA using the iScript reverse transcriptase kit (BioRad). cDNA is added to SybrGreen qPCR master mix (BioRad—as recommended by the manufacturer) and quantitative real-time qPCR (qPCR) is performed using the 96-well plate format on MyIQ real-time qPCR machines (BioRad). Included in all qPCR experiments are pre-designed and pre-validated primers for 3 housekeeping genes, glyceraldehydes-3-p-dehydrogenase (GAPDH), Cyclophillin A, and tyrosine 3-monooxygenase/tryptophan 5-monooxygenase (YWHAZ), as well as pre-designed and pre-validated primers specific for angiotensinogen mRNA. Standard thermal cycler protocols are used to perform qPCR reactions for a total of 40 cycles as suggested by the manufacturer. All qPCR data is analyzed using the ΔΔCt-based algorithm included in the BioRad iQ5 software package, which incorporates the normalization of angiotensinogen mRNA expression to the geometric mean of the three housekeeping genes, GAPDH, Cyclophilin A, and YWHAZ.

Figure 31:
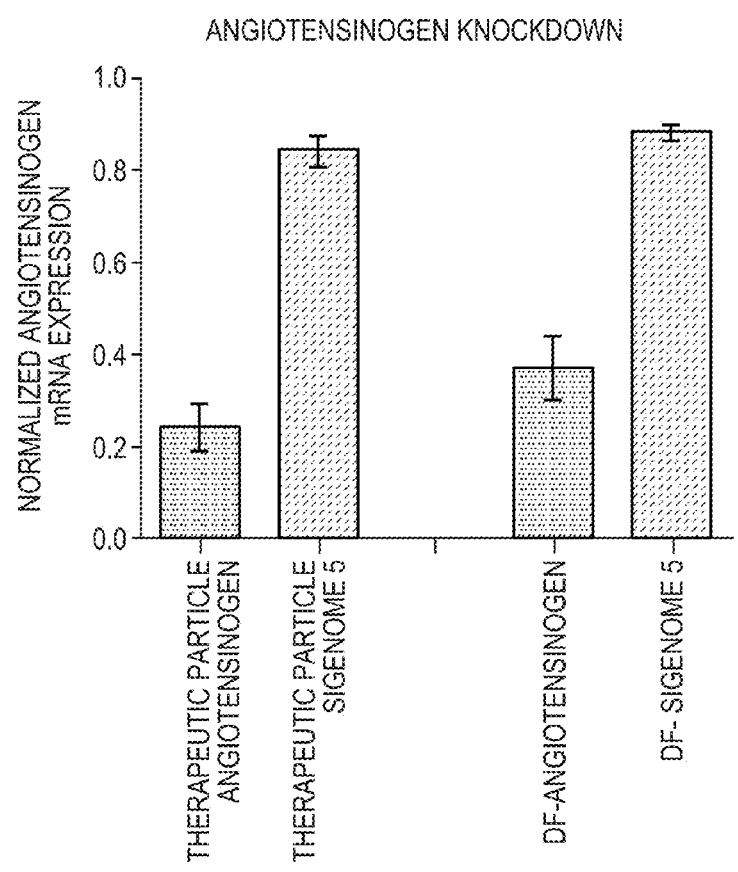
FIG. 31 depicts the reduction in angiotensinogen mRNA expression in mouse AML12 cells following a 72 hour incubation with chimeric therapeutic particles.

FIG. 31 indicates angiotensinogen mRNA expression is reduced in mouse AML12 cells following 72 hours of incubation with therapeutic particles loaded with angiotensinogen inhibitory dsRNA, when compared to particles loaded with SiGenome 5 inhibitory dsRNA (SiG5-Dharmacon/ThermoFisher). The final angiotensinogen inhibitory dsRNA concentration within the particles is 900 nM/well, and the final SiG5 inhibitory dsRNA concentration within the particles is 900 nM/well. DharmaFECT pre-incubated with Angiotensinogen inhibitory dsRNA (see above for sequence) and incubated on cells at 100 nM for 72 hours also demonstrated angiotensinogen mRNA inhibition when compared with DharmeFECT pre-incubated with SiGenome 5 inhibitory dsRNA sequences at 100 nM (see above for sequence). Error bars denote standard deviation values.

Figure 32:
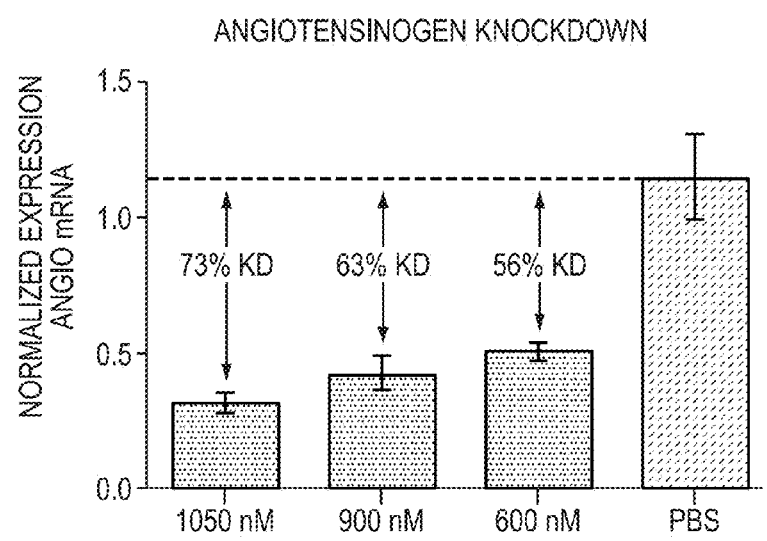
FIG. 32 depicts a dose dependent angiotensinogen mRNA knockdown effect when chimeric therapeutic particles are incubated on AML12 cells for 72 hours.

FIG. 32 depicts particles loaded with angiotensinogen inhibitory dsRNA targeting the mouse angiotensinogen mRNA sequence. The results demonstrate a dose-dependent mRNA inhibition effect for the 3 concentrations tested when incubated on AML12 cells for 72 hours. The graph demonstrates a decrease in the expression of Angiotensinogen mRNA in the mouse hepatocyte cell line as the concentration of inhibitory dsRNA—loaded particles increases. Percentage of inhibition is calculated against the normalized expression of angiotensinogen mRNA in well incubated with PBS. Error bars denote standard deviation values.

Example 26

Endotoxin Levels

Endotoxin measurement is based on the *Limulus Amebocyte* Lysate Pyrogent Plus Single Test Kit (Lonza, US License No. 1701, Catalog No. N289-06). The endotoxin vial is reconstituted with 1.0 ml of LAL reagent water (Lonza #W50-640) and vertexed for at least 15 minutes. Endotoxin is diluted with the LAL reagent water to a concentration of 1EU/ml. For a positive control, 0.25 ml of an endotoxin standard that contains twice the labeled minimum sensitivity is used. For a negative control, 0.23 ml of LAL reagent water is used.

Five sample serial dilutions are prepared in duplicates, beginning with a 1:4 diluation and end with a 1:64 dilution of sample:LAL reagent water. 0.25 ml of each sample is added to the test vial. Mix the samples by tilting and gently swirling the vial until the contents are in solution. Each vial of sample is incubated for 60 minutes (+/−2 minutes) at 37° C. (+/−1° C.). At the end of the incubation period, each vial is carefully removed and inverted 180 degrees. A positive reaction is characterized by the formation of a firm gel that remains intact momentarily when the tube is inverted, which should be observed in the positive sample control vial. A negative test is characterized by the absence of solid clot after inversion. The lysate may show an increase in turbidity or viscosity. This is considered a negative result.

The endotoxin concentration is calculated by the multiple of the lysate sensitivity and the geometric mean of the endpoint:

(Anti $\log_{10}$(Mean($\log_{10}$ Endpoint1;$\log_{10}$ Endpoint2)))$^{-1}$×lysate sensitivity.

Results from an endotoxin analysis of mFVII-containing therapeutic particles are shown below in Table 6. The results indicate that there is no endotoxin contamination in the therapeutic particles.

TABLE 6

| Tube Number | Sample | Dilution Factor | Result |
|---|---|---|---|
| 1 | Endotoxin standard | 1:4 | + |
| 2 | Endotoxin standard | 1:4 | + |
| 3 | LAL water | N/A | − |
| 4 | LAL water | N/A | − |
| 5 | mFVII CS | 1:4 | − |
| 6 | mFVII CS | 1:4 | − |
| 7 | mFVII CS | 1:8 | + |
| 8 | mFVII CS | 1:8 | − |
| 9 | mFVII CS | 1:16 | − |
| 10 | mFVII CS | 1:16 | − |
| 11 | mFVII CS | 1:32 | − |
| 12 | mFVII CS | 1:32 | − |
| 13 | mFVII CS | 1:64 | − |
| 14 | mFVII CS | 1:64 | − |

Sensitivity calculation:

(Anti $\log_{10}$(Mean($\log_{10}$ 0.125;$\log_{10}$ 1)))$^{-1}$×0.06EU/mL=0.170EU/mL

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.
US20060292174; US20070269370; U.S. Ser. No. 12/082,154

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The terms "a" and "an" and "the" used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

What is claimed is:

1. A chimeric therapeutic comprising a modified viral core protein and a therapeutic agent, wherein the modified viral core protein is selected from the group consisting of CP155 (SEQ ID NO: 50), CP162 (SEQ ID NO: 52), and CP170 (SEQ ID NO: 54).

2. The chimeric therapeutic of claim 1, wherein said therapeutic agent is bound to said modified viral core protein.

3. The chimeric therapeutic of claim 1, wherein said modified viral core protein is further mutated such that at least one amino acid is independently selected from the group consisting of asparagine 21, alanine 21, valine 21, alanine 27, isoleucine 27, valine 60, and leucine 97.

4. The chimeric therapeutic of claim 3, wherein said modified viral core protein has at least one amino acid selected from the group consisting of phenylalanine 23, aspartic acid 29, threonine 33, leucine 37, valine 120, valine 124, arginine 127, tyrosine 132, glutamic acid 77, aspartic acid 78 and alanine 80 changed to a cysteine.

5. The chimeric therapeutic of claim 1, wherein said therapeutic agent is a nucleic acid, a protein, or a small molecule.

6. A therapeutic composition comprising:
   a particle formed from a plurality of chimeric therapeutics of claim 1, wherein said particle, optionally, further comprises a coating; and
   a pharmaceutically acceptable excipient,
   wherein said particle comprises 180 or 240 viral core proteins.

7. The therapeutic composition of claim 6, wherein the particle is a modified icosahedral.

8. The therapeutic composition of claim 6, wherein the coating comprises one or more lipid molecules.

* * * * *